United States Patent
Xu et al.

(10) Patent No.: US 10,214,512 B2
(45) Date of Patent: Feb. 26, 2019

(54) FACTOR XIA INHIBITORS

(71) Applicant: MERCK SHARP & DOHME CORP., Rahway, NJ (US)

(72) Inventors: Jiayi Xu, Edison, NJ (US); Amjad Ali, Freehold, NJ (US); Wei Zhou, Scotch Plains, NJ (US); Ying-Duo Gao, Holmdel, NJ (US); Scott D. Edmondson, Concord, MA (US); Eric Mertz, Christianburg, VA (US); Santhosh F. Neelamkavil, Edison, NJ (US); Weiguo Liu, Princeteon, NJ (US); Wanying Sun, Edison, NJ (US); Dong-Ming Shen, Edison, NJ (US); Bart Harper, New York, NY (US); Cheng Zhu, Edison, NJ (US); Thomas Bara, Scotch Plains, NJ (US); Yeon-Hee Lim, Psicataway, NJ (US); Meng Yang, Westfield, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/771,538

(22) PCT Filed: Oct. 24, 2016

(86) PCT No.: PCT/US2016/058362
§ 371 (c)(1),
(2) Date: Apr. 27, 2018

(87) PCT Pub. No.: WO2017/074832
PCT Pub. Date: May 4, 2017

(65) Prior Publication Data
US 2018/0339977 A1    Nov. 29, 2018

Related U.S. Application Data

(60) Provisional application No. 62/248,075, filed on Oct. 29, 2015.

(51) Int. Cl.
| C07D 471/08 | (2006.01) |
| C07D 471/18 | (2006.01) |
| C07D 401/14 | (2006.01) |
| A61P 7/02 | (2006.01) |
| C07D 487/08 | (2006.01) |
| C07D 413/14 | (2006.01) |
| C07D 401/04 | (2006.01) |

(52) U.S. Cl.
CPC ............. *C07D 401/14* (2013.01); *A61P 7/02* (2018.01); *C07D 401/04* (2013.01); *C07D 413/14* (2013.01); *C07D 471/08* (2013.01); *C07D 487/08* (2013.01)

(58) Field of Classification Search
None
See application file for complete search history.

(56) References Cited

U.S. PATENT DOCUMENTS

| 7,262,210 | B2 | 8/2007 | Kreutter et al. | |
| 7,829,584 | B2 | 11/2010 | Player et al. | |
| 2010/0173899 | A1 | 7/2010 | Pinto et al. | |
| 2014/0038969 | A1* | 2/2014 | Yang | C07D 401/04 514/248 |
| 2014/0163002 | A1* | 6/2014 | Lam | C07D 471/06 514/210.18 |
| 2014/0221338 | A1* | 8/2014 | Pinto | C07D 487/08 514/210.18 |
| 2015/0203492 | A1* | 7/2015 | Yang | C07D 401/04 514/43 |
| 2016/0096839 | A1* | 4/2016 | Dilger | C07D 471/18 514/248 |
| 2016/0347757 | A1* | 12/2016 | Neelamkavil | C07D 487/08 |
| 2017/0057961 | A1* | 3/2017 | Dilger | C07D 487/08 |
| 2018/0162821 | A1* | 6/2018 | Corte | C07D 225/06 |

OTHER PUBLICATIONS

International Search Report and Written Opinion for PCT/US2016/058362 dated Dec. 27, 2016; 8 pages.

* cited by examiner

*Primary Examiner* — Nyeemah A Grazier
(74) *Attorney, Agent, or Firm* — Nicole M. Beeler; John C. Todaro

(57) ABSTRACT

The present invention provides a compound of Formula (I) and pharmaceutical compositions comprising one or more said compounds, and methods for using said compounds for treating or preventing thromboses, embolisms, hypercoagulability or fibrotic changes. The compounds are selective Factor XIa inhibitors or dual inhibitors of Factor XIa and plasma Kallikrein.

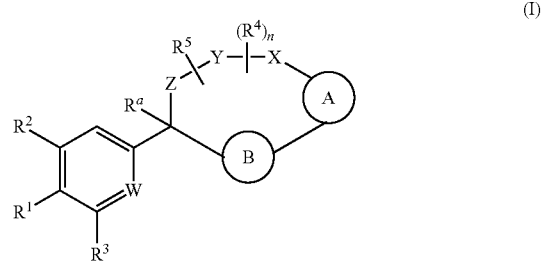

14 Claims, No Drawings

FACTOR XIA INHIBITORS

CROSS REFERENCE TO RELATED APPLICATIONS

This application is a U.S. National Phase application under 35 U.S.C. § 371 of PCT Application No. PCT/US 2016/058362 filed Oct. 24, 2016, which claims priority from U.S. Ser. No. 62/248,075 filed Oct. 29, 2015.

BACKGROUND OF THE INVENTION

Factor XIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel, blocking circulation and inducing a heart attack or stroke. Thromboembolic disorders are the largest cause of mortality and disability in the industrialized world.

Blood clotting is a process of control of the blood stream essential for the survival of mammals. The process of clotting, and the subsequent dissolution of the clot after wound healing has taken place, commence after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting factors V, VIII, IX, X, XI and XII and also prekallikrein, high molecular weight kininogen, calcium ions and phospholipids from platelets. The activation of factor XIa is a central point of intersection between the two pathways of activation of clotting. Factor XIa has an important role in blood clotting.

Coagulation is initiated when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma Kallikrein further activates factor XII, leading to an amplification of contact activation. Alternatively, the serine protease polylcarboxylpeptidase can activate plasma Kallikrein complexed with high molecular weight kininogen in a multiportion complex formed on the surface of cells and matrices (Shariat-Madar et al., Blood, 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact Activation Pathway", Hemostasis and Thrombosis, pp. 103-122, Lippincott Williams & Wilkins (2001); Schmaier, A. H., "Contact Activation", Thrombosis and Hemorrhage, pp. 105-128 (1998)). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., J Exp. Med., 202:271-281 (2005); Kleinschmitz et al., J Exp. Med., 203:513-518 (2006)). The fact that factor XI is downstream from factor XIIa, combined with the identical phenotype of the XII and XI deficient mice suggest that the contact activation system could play a major role in factor XI activation in vivo.

Plasma Kallikrein is a zymogen of a trypsin-like serine protease and is present in plasma. The gene structure is similar to that of factor XI. Overall, the amino acid sequence of plasma Kallikrein has 58% homology to factor XI. Proteolyticactivation by factor XIIa at an internal I 389-R390 bond yields a heavy chain (371 amino acids) and a light chain (248 amino acids). The active site of plasma Kallikrein is contained in the light chain. The light chain of plasma Kallikrein reacts with protease inhibitors, including alpha 2 macroglobulin and C1-inhibitor. Interestingly, heparin significantly accelerates the inhibition of plasma Kallikrein by antithrombin III in the presence of high molecular weight kininogen (HMWK). In blood, the majority of plasma Kallikrein circulates in complex with HMWK. Plasma Kallikrein cleaves HMWK to liberate bradykinin. Bradykinin release results in increase of vascular permeability and vasodilation (for review, Coleman, R., "Contact Activation Pathway", Hemostasis and Thrombosis, pp. 103-122, Lippincott Williams & Wilkins (2001); Schmaier A. H., "Contact Activation", Thrombosis and Hemorrhage, pp. 105-128 (1998)).

Patients presenting genetic deficiency on C1-esterase inhibitor suffer from hereditary angioedema (HAE), a lifelong disease that results in intermittent swelling throughout the body, including the hands, feet, face, throat, genitals and gastrointestinal tract. Analysis of blisters arising from acute episodes have been shown to contain high levels of plasma Kallikrein, and treatment with a protein-based reversible plasma Kallikrein inhibitor, Ecallantide (Kalbitor), has been approved by the FDA for the treatment of acute attacks of HAE (Schneider, L, et al., J. Allergy Clin. Immunol., 120: p. 416 (2007)).

Additionally, the plasma Kallikrein-kinin system is abnormally abundant in patients diagnosed with advanced diabetic macular edema (DME). Recent publications have shown that plasma Kallikrein contributes to observed retinal vascular leakage and dysfunction in diabetic rodent models (A. Clermont, et al., Diabetes, 60:1590 (2011)), and that treatment with a small molecule plasma Kallikrein inhibitor ameliorated the observed retinal vascular permeability and other abnormalities related to retinal blood flow.

Factor XIa inhibitor compounds are described in WO2014160592, WO2013022814, WO 2013022814, WO 2013022818, WO 2013055984, WO2013056034, WO2013056060, WO2013118805. WO2013093484. WO2002042273, WO2002037937, WO2002060894, WO2003015715, WO2004002405, US20040180855, WO2004080971, WO2004094372, U.S.20050228000, U.S.20050282805, WO2005123680, U.S.20090036438, U.S.20120088758, U.S.20060074103, WO2006062972, WO2006076246, U.S.20060154915, U.S.20090062287, U.S.20060183771, WO2007070818, WO2007070816, WO2007070826, WO2008076805, WO2008157162, WO2009114677, WO2011100402, and WO2011100401.

SUMMARY OF THE INVENTION

The present invention relates to compounds of Formula I:

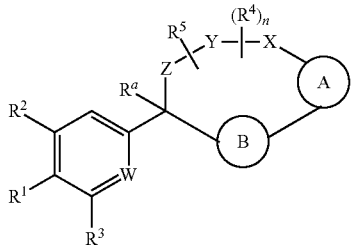

and pharmaceutically acceptable salts thereof. The compounds of Formula I are selective Factor XIa inhibitors or dual inhibitors of Factor XIa and plasma Kallikrein, and as such may be useful in the treatment, inhibition or amelioration of one or more disease states that could benefit from inhibition of Factor XIa or plasma Kallikrein, including thromboses, embolisms, hypercoagulability or fibrotic changes. The compounds of this invention could further be used in combination with other therapeutically effective agents, including but not limited to, other drugs useful for the treatment of thromboses, embolisms, hypercoagulability or fibrotic changes. The invention furthermore relates to processes for preparing compounds of Formula I, and pharmaceutical compositions which comprise compounds of Formula I and pharmaceutically acceptable salts thereof.

DETAILED DESCRIPTION OF THE INVENTION

The present invention relates to compounds of Formula I:

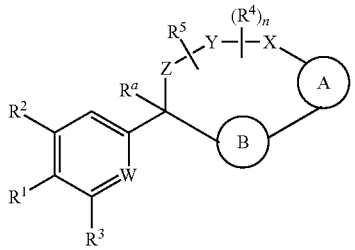

wherein Ⓐ
is aryl or heteroaryl, which is optionally substituted with one to three groups independently selected from the group consisting of halo, oxo, cyano, $R^6$, $OR^6$, $C(O)OR^6$, $C_{1-3}$ alkyl-$C(O)OR^6$, $NR^6R^7$, $NH_3^+$, $C_{1-3}$ alkyl-$NR^7R^8$, $NHC(O)R^6$, $NHC(O)OR^6$, $NHC(O)OC_{3-6}$ cycloalkyl, $NHC(O)O$—$C_{1-3}$ alkyl-$OR^7$, $NHC(O)O$—$C_{1-3}$ alkyl-$C(O)OH$, $C_{1-3}$ alkyl-$NHC(O)OR^7$, $NHC(O)NR^7R^8$, $NHSO_2R^6$, $C(O)NR^7R^8$, $CH_2C(O)NR^7R^8$ and $NHCONH$—$C_{1-3}$ alkyl-heterocyclyl;

Ⓑ
is aryl or heteroaryl, which is optionally substituted with one to three groups independently selected from the group consisting of halo, cyano, oxido, oxo, cyclopropyl, $R^6$, $OR^6$, $C(O)OR^6$, $C_{1-3}$ alkyl-$C(O)OR^6$, $C(O)NR^6R^7$ and $NR^6R^7$;

W is N or $N^+O^-$;

Y—X is —$C(O)NR^6$—, —$C(O)O$—, —$CHC(O)OR^7$—$NR^6$—, —$CR^6R^7$—$C(O)NR^6$—, —$CHC(O)R^7$—$NR^6$—, —$CHC(O)OR^7$—$CH_2$—, —$CHC(O)NR^6R^7$—$NR^6$—, —$CHCR^6R^7OR^8$—$NR^6$—, —$CHCR^6R^7$—$NR^6R^7$—$NR^6$—, —$OC(O)NR^6$—, —$NR^6C(O)NR^6$— or —$SO_2NR^6$—;

Z is $C_{3-8}$ alkylene or $C_{3-8}$ alkenylene, wherein one or two of the carbon atoms in said alkylene and alkenylene may be replaced with O, $NR^6$, C=O, $C(O)NR^6$, $NR^6C(O)$, S, SO or $SO_2$;

$R^1$ is aryl, heteroaryl, $C_{3-6}$ cycloalkyl or heteroalkyl, wherein said aryl, heteroaryl, cycloalkyl and heterocyclyl groups are optionally substituted with one to four substituents independently selected from the group consisting of halo, nitro, cyano, oxo, $R^6$, $OR^6$, $C(O)R^6$, $C(O)OR^6$, $NR^6R^7$, $C_{1-3}$ alkyl-$NR^6R^7$, $NHC(O)R^7$, $NHC(O)OR^7$, $C(NH)NR^6R^7$, $C_{3-6}$ cycloalkyl and heteroaryl (which is optionally substituted with halo, cyano, cyclopropyl, $C(O)OH$, $C(O)NR^6R^7$ or $R^6$);

$R^2$ is hydrogen, cyano, halo, $R^6$ or $OR^6$;

$R^3$ is hydrogen, cyano, halo, $R^6$ or $OR^6$;

each $R^4$ is independently $C_{1-6}$ alkyl, $CO_2R^6$, $COR^6$ or $CONR^7R^8$, wherein said alkyl is optionally substituted with one to three halo;

$R^5$ is hydrogen, halo or $C_{1-6}$ alkyl;

or one of $R^4$ and $R^5$ can be taken together with the atoms between them to form a 3 to 6 membered ring;

each $R^6$ is independently hydrogen or $C_{1-6}$ alkyl, which is optionally substituted with one to three groups independently selected from the group consisting of halo and hydroxy;

each $R^7$ is independently hydrogen, $C_{1-6}$ alkyl, heteroaryl or heterocyclyl, wherein said alkyl group is optionally substituted with one to three groups independently selected from the group consisting of halo and hydroxy;

each $R^8$ is independently hydrogen or $C_{1-6}$ alkyl;

$R^a$ is hydrogen, hydroxy or $O(C_{1-6}$ alkyl);

n is an integer between zero and three;

or a pharmaceutically acceptable salt thereof.

An embodiment of the present invention relates to compounds of Formula I:

I wherein

Ⓐ is aryl or heteroaryl, which is optionally substituted with one to three groups independently selected from the group consisting of halo, cyano, $R^6$, $OR^6$, $C(O)OR^6$, $C_{1-3}$ alkyl-C(O)OR$^6$, $NR^6R^7$, $NH_3^+$, $C_{1-3}$ alkyl-NR$^7$R$^8$, NHC(O)R$^6$, NHC(O)OR$^6$, NHC(O)OC$_{3-6}$ cycloalkyl, NHC(O)O—C$_{1-3}$ alkyl-OR$^7$, NHC(O)O—C$_{1-3}$ alkyl-C(O)OH, C$_{1-3}$ alkyl-NHC(O)OR$^7$, NHC(O)NR$^7$R$^8$, NHSO$_2$R$^6$, C(O)NR$^7$R$^8$, CH$_2$C(O)NR$^7$R$^8$ and NHCONH—C$_{1-3}$ alkyl-heterocyclyl;

Ⓑ is aryl or heteroaryl, which is optionally substituted with one to three groups independently selected from the group consisting of halo, cyano, oxo, $R^6$, $OR^6$, $C(O)OR^6$, $C_{1-3}$ alkyl-C(O)OR$^6$, C(O)NR$^6$R$^7$ and NR$^6$R$^7$;

W is N or N$^+$O$^-$;

Y—X is —C(O)NR$^6$—, —C(O)O—, —CHC(O)R$^7$—NR$^6$—, —CR$^6$R$^7$—C(O)NR$^6$—, —CHC(O)R$^7$—NR$^6$—, —CHC(O)NR$^6$R$^7$—NR$^6$—, —CHCR$^6$R$^7$OR$^8$—NR$^6$—, —CHCR$^6$R$^7$—NR$^6$R$^7$—NR$^6$—, —OC(O)NR$^6$—, —NR$^6$C(O)NR$^6$— or —SO$_2$NR$^6$—;

Z is $C_{3-8}$ alkylene or $C_{3-8}$ alkenylene, wherein one or two of the carbon atoms in said alkylene and alkenylene may be replaced with O, NR$^6$, C=O, C(O)NR$^6$, NR$^6$C(O), S, SO or SO$_2$;

R$^1$ is aryl, heteroaryl, $C_{3-6}$ cycloalkyl or heteroalkyl, wherein said aryl, heteroaryl, cycloalkyl and heterocyclyl groups are optionally substituted with one to three substituents independently selected from the group consisting of halo, nitro, cyano, oxo, R$^6$, OR$^6$, C(O)R$^6$, C(O)OR$^6$, NR$^6$R$^7$, C$_{1-3}$ alkyl-NR$^6$R$^7$, NHC(O)R$^7$, NHC(O)OR$^7$, C(NH)NR$^6$R$^7$, C$_{3-6}$ cycloalkyl and heteroaryl (which is optionally substituted with halo, cyano, C(O)NR$^6$R$^7$ or R$^6$);

R$^2$ is hydrogen, cyano, halo, R$^6$ or OR$^6$;

R$^3$ is hydrogen, cyano, halo, R$^6$ or OR$^6$;

R$^4$ is C$_{1-6}$ alkyl, CO$_2$R$^6$, COR$^6$ or CONR$^7$R$^8$, wherein said alkyl is optionally substituted with one to three halo;

R$^5$ is hydrogen, halo or C$_{1-6}$ alkyl;

or R$^4$ and R$^5$ can be taken together with the atoms between them to form a 3 to 6 membered ring;

R$^6$ is hydrogen or C$_{1-6}$ alkyl, which is optionally substituted with one to three groups independently selected from the group consisting of halo and hydroxy;

R$^7$ is hydrogen, C$_{1-6}$ alkyl, heteroaryl or heterocyclyl, wherein said alkyl group is optionally substituted with one to three groups independently selected from the group consisting of halo and hydroxy;

R$^8$ is hydrogen or C$_{1-6}$ alkyl;

R$^a$ is hydrogen, hydroxy or O(C$_{1-6}$ alkyl);

n is an integer between zero and three;

or a pharmaceutically acceptable salt thereof.

An embodiment of the present invention relates to compounds of Formula Ia:

Ia wherein

Ⓐ is aryl or heteroaryl, which is optionally substituted with one to three groups independently selected from the group consisting of halo, oxo, cyano, R$^6$, OR$^6$, C(O)OR$^6$, C$_{1-3}$ alkyl-C(O)OR$^6$, NR$^6$R$^7$, NH$_3^+$, C$_{1-3}$ alkyl-NR$^7$R$^8$, NHC(O)R$^6$, NHC(O)OR$^6$, NHC(O)OC$_{3-6}$ cycloalkyl, NHC(O)O—C$_{1-3}$ alkyl-OR$^7$, NHC(O)O—C$_{1-3}$ alkyl-C(O)OH, C$_{1-3}$ alkyl-NHC(O)OR$^7$, NHC(O)NR$^7$R$^8$, NHSO$_2$R$^6$, C(O)NR$^7$R$^8$, CH$_2$C(O)NR$^7$R$^8$ and NHCONH—C$_{1-3}$ alkyl-heterocyclyl;

Ⓑ is aryl or heteroaryl, which is optionally substituted with one to three groups independently selected from the group consisting of halo, cyano, oxido, oxo, cyclopropyl, R$^6$, OR$^6$, C(O)OR$^6$, C$_{1-3}$ alkyl-C(O)OR$^6$, C(O)NR$^6$R$^7$ and NR$^6$R$^7$;

R$^1$ is aryl, heteroaryl, C$_{3-6}$ cycloalkyl or heteroalkyl, wherein said aryl, heteroaryl, cycloalkyl and heterocyclyl groups are optionally substituted with one to four substituents independently selected from the group consisting of halo, nitro, cyano, oxo, R$^6$, OR$^6$, C(O)R$^6$, C(O)OR$^6$, NR$^6$R$^7$, C$_{1-3}$ alkyl-NR$^6$R$^7$, NHC(O)R$^7$, NHC(O)OR$^7$, C(NH)NR$^6$R$^7$, C$_{3-6}$ cycloalkyl and heteroaryl (which is optionally substituted with halo, cyano, cyclopropyl, C(O)OH, C(O)NR$^6$R$^7$ or R$^6$);

R$^2$ is hydrogen, cyano, halo, R$^6$ or OR$^6$;

R$^3$ is hydrogen, cyano, halo, R$^6$ or OR$^6$;

R$^4$ is C$_{1-6}$ alkyl, CO$_2$R$^6$, COR$^6$ or CONR$^7$R$^8$, wherein said alkyl is optionally substituted with one to three halo;

R$^6$ is hydrogen or C$_{1-6}$ alkyl, which is optionally substituted with one to three groups independently selected from the group consisting of halo and hydroxy;

R$^7$ is hydrogen or C$_{1-6}$ alkyl, which is optionally substituted with one to three groups independently selected from the group consisting of halo and hydroxy;

R$^8$ is hydrogen or C$_{1-6}$ alkyl;

R$^a$ is hydrogen, hydroxy or O(C$_{1-6}$ alkyl);

n is an integer between zero and three;

or a pharmaceutically acceptable salt thereof.

An embodiment of the present invention relates to compounds of Formula Ib:

Ib

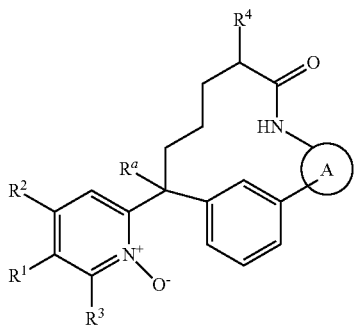

wherein

Ⓐ is aryl or heteroaryl, which is optionally substituted with one to three groups independently selected from the group consisting of halo, cyano, $R^6$, $OR^6$, $C(O)OR^6$, $C_{1-3}$ alkyl-C(O)OR$^6$, $NR^6R^7$, $NH_3^+$, $C_{1-3}$ alkyl-NR$^7R^8$, NHC(O)R$^6$, NHC(O)OR$^6$, NHC(O)OC$_{3-6}$ cycloalkyl, NHC(O)O—C$_{1-3}$ alkyl-OR$^7$, NHC(O)O—C$_{1-3}$ alkyl-C(O)OH, C$_{1-3}$ alkyl-NHC(O)OR$^7$, NHC(O)NR$^7R^8$, NHSO$_2$R$^6$, C(O)NR$^7R^8$, CH$_2$C(O)NR$^7R^8$ and NHCONH—C$_{1-3}$ alkyl-heterocyclyl;

Ⓑ is aryl or heteroaryl, which is optionally substituted with one to three groups independently selected from the group consisting of halo, cyano, oxo, $R^6$, $OR^6$, $C(O)OR^6$, $C_{1-3}$ alkyl-C(O)OR$^6$, C(O)NR$^6R^7$ and NR$^6R^7$;

$R^1$ is aryl, heteroaryl, $C_{3-6}$ cycloalkyl or heteroalkyl, wherein said aryl, heteroaryl, cycloalkyl and heterocyclyl groups are optionally substituted with one to three substituents independently selected from the group consisting of halo, nitro, cyano, oxo, $R^6$, $OR^6$, $C(O)R^6$, $C(O)OR^6$, $NR^6R^7$, $C_{1-3}$ alkyl-NR$^6R^7$, NHC(O)R$^7$, NHC(O)OR$^7$, C(NH)NR$^6R^7$, $C_{3-6}$ cycloalkyl and heteroaryl (which is optionally substituted with halo, cyano, C(O)NR$^6R^7$ or $R^6$);

$R^2$ is hydrogen, cyano, halo, $R^6$ or $OR^6$;

$R^3$ is hydrogen, cyano, halo, $R^6$ or $OR^6$;

$R^4$ is $C_{1-6}$ alkyl, $CO_2R^6$, $COR^6$ or $CONR^7R^8$, wherein said alkyl is optionally substituted with one to three halo;

$R^6$ is hydrogen or $C_{1-6}$ alkyl, which is optionally substituted with one to three groups independently selected from the group consisting of halo and hydroxy;

$R^7$ is hydrogen or $C_{1-6}$ alkyl, which is optionally substituted with one to three groups independently selected from the group consisting of halo and hydroxy;

$R^8$ is hydrogen or $C_{1-6}$ alkyl;

$R^a$ is hydrogen, hydroxy or $O(C_{1-6}$ alkyl);

n is an integer between zero and three;

or a pharmaceutically acceptable salt thereof.

In an embodiment of the invention, Ⓐ is phenyl, dihydroquinlinyl or pyrazolyl, which is optionally substituted with one to three groups independently selected from the group consisting of halo, oxo, cyano, $R^6$, $OR^6$, $C(O)OR^6$, $NR^6R^7$, NHC(O)OR$^6$, NHC(O)O—C$_{1-3}$ alkyl-OR$^7$ and NHC(O)O—C$_{1-3}$ alkyl-C(O)OH. In a class of the invention, Ⓐ is phenyl, which is optionally substituted with one to three groups independently selected from the group consisting of halo, C(O)OR$^6$, NHC(O)OR$^6$ and NR$^6R^7$. In a subclass of the invention, Ⓐ is phenyl, which is optionally substituted with one to three groups independently selected from the group consisting of fluoro, C(O)OH, NHC(O)OH and NHC(O)OCH$_3$. In an embodiment of the invention, Ⓑ is a selected from the group consisting of phenyl, pyrrolyl, pyrazolyl, imidazolyl, triazolyl, pyridinyl, pyridinyl N-oxide, pyridazinyl, pyrimidinyl, pyrazinyl and triazinyl, wherein said groups are optionally substituted with one to three groups independently selected from the group consisting of halo, oxido, $R^6$ and cyclopropyl. In a class of the invention, Ⓑ is a selected from the group consisting of phenyl, imidazolyl, pyridinyl and pyrimidinyl, wherein said groups are optionally substituted with one to three groups independently selected from the group consisting of halo, oxido, $R^6$ and cyclopropyl. In a subclass of the invention, Ⓑ is phenyl, which is optionally substituted with halo. In another class of the invention, Ⓑ is imidazolyl, which is optionally substituted with methyl. In another subclass of the invention, Ⓑ is pyridinyl, which is optionally substituted with halo. In another subclass of the invention, Ⓑ is pyridinyl, which is optionally substituted with oxido. In another subclass of the invention, Ⓑ is pyrimidinyl, which is optionally substituted with halo.

In an embodiment of the invention, Y—X is C(O)NR$^6$. In a class of the embodiment, Y—X is C(O)NH. In another embodiment of the invention, Y—X is CHC(O)OR$^7$—NR$^6$—. In a class of the embodiment, Y—X is CHC(O)OH—NH. In an embodiment of the invention, Y—X is CHC(O)NR$^6R^7$—NR$^6$. In a class of the embodiment, Y—X is CHC(O)NH(CH$_3$)—NH. In an embodiment of the invention, Y—X is CHC(O)OR$^7$—NR$^6$.

In an embodiment of the invention, Z is $C_{3-8}$ alkylene.

In an embodiment of the invention, W is $N^+O^-$. In another embodiment of the invention, W is N.

In an embodiment of the invention, $R^1$ is aryl, which optionally is substituted with one to four substituents independently selected from the group consisting of chloro, fluoro, iodo, methyl, cyclopropyl, OCF$_3$, OCF$_2$, CF$_3$, CF$_2$, and heteroaryl (which is optionally substituted with halo, cyano, cyclopropyl, C(O)OH, methyl, CF$_3$ or CF$_2$). In a class of the embodiment, $R^1$ is phenyl, which optionally is substituted with one to three substituents independently selected from the group consisting of halo, $C_{3-6}$ cycloalkyl and tetrazolyl.

In an embodiment of the invention, $R^2$ is hydrogen.

In an embodiment of the invention, $R^3$ is hydrogen.

In an embodiment of the invention, $R^4$ is $C_{1-6}$ alkyl. In a class of the invention, $R^4$ is methyl.

In an embodiment of the invention, $R^5$ is hydrogen. In another embodiment of the invention, $R^5$ is halo. In a class of the invention, $R^5$ is fluoro. In another embodiment of the invention, $R^5$ is $C_{1-6}$ alkyl. In a class of the invention, $R^5$ is methyl.

In an embodiment of the invention, n is zero. In another embodiment of the invention, n is one. In another embodiment of the invention, n is two. In another embodiment of the invention, n is three.

In an embodiment of the invention, $R^a$ is hydrogen or hydroxy. In a class of the invention, $R^a$ is hydrogen. In another class of the invention, $R^a$ is hydroxy.

Reference to the preferred classes and subclasses set forth above is meant to include all combinations of particular and preferred groups unless stated otherwise.

Specific embodiments of the present invention include, but are not limited to the compounds identified herein as Examples 1 to 172, or pharmaceutically acceptable salts thereof.

Also included within the scope of the present invention is a pharmaceutical composition which is comprised of a compound of Formula I, Formula Ia or Formula Ib as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

The invention also includes compositions for inhibiting loss of blood platelets, inhibiting formation of blood platelet aggregates, inhibiting formation of fibrin, inhibiting thrombus formation, inhibiting embolus formation, treating inflammatory disorders, treating diabetic retinopathy and treating hereditary angioedema in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

The invention also includes compositions for preventing or treating unstable angina, refractory angina, myocardial infarction, transient ischemic attacks, atrial fibrillation, thrombotic stroke, embolic stroke, deep vein thrombosis, disseminated intravascular coagulation, ocular buildup of fibrin, and reocclusion or restenosis of recanalized vessels, in a mammal, comprising a compound of the invention in a pharmaceutically acceptable carrier. These compositions may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

Compounds of the invention are Factor XIa inhibitors and may have therapeutic value in, for example, preventing coronary artery disease. The compounds are selective Factor XIa inhibitors or dual inhibitors of Factor XIa and plasma Kallikrein.

It will be understood that, as used herein, references to the compounds of structural Formula I, Formula Ia and Formula Ib are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Also included are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-di ethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

If the compounds of Formula I, Formula Ia or Formula Ib simultaneously contain acidic and basic groups in the molecule the invention also includes, in addition to the salt forms mentioned, inner salts or betaines (zwitterions).

The present invention encompasses all stereoisomeric forms of the compounds of Formula I, Formula Ia and Formula Ib. Unless a specific stereochemistry is indicated, the present invention is meant to comprehend all such isomeric forms of these compounds. Centers of asymmetry that are present in the compounds of Formula I, Formula Ia and Formula Ib can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. When a particular configuration is depicted, that enantiomer (either (R) or (S), at that center) is intended. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the transform as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I, Formula Ia or Formula Ib or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

When any variable (e.g. $R^4$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" (with one or more substituents) should be understood as meaning that the group in question is either unsubstituted or may be substituted with one or more substituents.

Furthermore, compounds of the present invention may exist in amorphous form and/or one or more crystalline forms, and as such all amorphous and crystalline forms and mixtures thereof the compounds of Formula I, Formula Ia and Formula Ib are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Reference to the compounds of this invention as those of a specific formula or embodiment, e.g., Formula I, Formula Ia or Formula Ib or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO⁻ depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

Except where noted herein, the terms "alkyl" and "alkylene" are intended to include both branched- and straight-chain saturated aliphatic hydrocarbon groups having the specified number of carbon atoms. Commonly used abbreviations for alkyl groups are used throughout the specification, e.g. methyl, may be represented by conventional abbreviations including "Me" or $CH_3$ or a symbol that is an extended bond as the terminal group, e.g.

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. For example, the structures

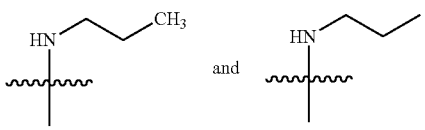

have equivalent meanings. $C_{1-4}$ alkyl includes n-, iso-, sec- and t-butyl, n- and isopropyl, ethyl and methyl. If no number is specified, 1-4 carbon atoms are intended for linear or branched alkyl groups.

Except where noted herein, the term "alkenylene" is intended to include both branched- and straight-chain unsaturated aliphatic hydrocarbon groups having the specified number of carbon atoms and containing at least one carbon-to-carbon double bond.

Except where noted, the term "cycloalkyl" means a monocyclic or bicyclic saturated aliphatic hydrocarbon group having the specified number of carbon atoms. For example, "cycloalkyl" includes cyclopropyl, cyclobutyl, cyclopentyl, cyclohexyl, and so on.

Except where noted, the term "halogen" or "halo" means fluorine, chlorine, bromine or iodine.

Except where noted, the term "heteroaryl", as used herein, represents a stable monocyclic or bicyclic ring system of up to 10 atoms in each ring, wherein at least one ring is aromatic, and at least one ring contains from 1 to 4 heteroatoms selected from the group consisting of O, N and S. Bicyclic heteroaryl ring systems include fused ring systems, where two rings share two atoms, and spiro ring systems, where two rings share one atom. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, tetrahydroquinoline and 3-oxo-3,4dihydro-2N-benzo[b][1,4]thiazine. If the heteroaryl contains nitrogen atoms, it is understood that the corresponding N-oxides thereof are also encompassed by this definition.

Except where noted, the term "heterocycle" or "heterocyclyl" as used herein is intended to mean a stable nonaromatic monocyclic or bicyclic ring system of up to 10 atoms in each ring, unless otherwise specified, containing from 1 to 4 heteroatoms selected from the group consisting of O, N, S, SO, or $SO_2$. Bicyclic heterocyclic ring systems include fused ring systems, where two rings share two atoms, and spiro ring systems, where two rings share one atom. "Heterocyclyl" therefore includes, but is not limited to the following: piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

Except where noted, the term "aryl" is intended to mean any stable monocyclic or bicyclic carbon ring of up to 12 atoms in each ring, wherein at least one ring is aromatic. Examples of such aryl elements include phenyl, naphthyl, tetrahydronaphthyl and indanyl.

"Celite®" (Fluka) diatomite is diatomaceous earth, and can be referred to as "Celite".

Except where noted herein, structures containing substituent variables such as variable "R" below:

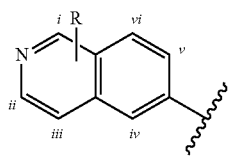

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

Except where noted herein, bicyclic ring systems include fused ring systems, where two rings share two atoms, and spiro ring systems, where two rings share one atom.

The invention also relates to medicaments containing at least one compound of the Formula I, Formula Ia or Formula Ib and/or of a pharmaceutically acceptable salt of the compound of the Formula I, Formula Ia or Formula Ib and/or an optionally stereoisomeric form of the compound of the Formula I, Formula Ia or Formula Ib or a pharmaceutically acceptable salt of the stereoisomeric form of the compound of Formula I, Formula Ia or Formula Ib, together with a pharmaceutically suitable and pharmaceutically acceptable vehicle, additive and/or other active substances and auxiliaries.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, humans, sheep, horses, cattle, pigs, dogs, cats, rats, and mice.

Factor XIa or dual Factor XIa/plasma Kallikrein inhibition are useful not only in the anticoagulant therapy of individuals having thrombotic conditions, but are useful whenever inhibition of blood coagulation is required such as to prevent coagulation of stored whole blood and to prevent coagulation in other biological samples for testing or storage. Thus, the Factor XIa or dual Factor XIa/plasma Kallikrein inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention may be useful for treating or preventing venous thromboembolism (e.g., obstruction or occlusion of a vein by a detached thrombus; obstruction or occlusion of a lung artery by a detached thrombus), cardiogenic thromboembolism (e.g., obstruction or occlusion of the heart by a detached thrombus), arterial thrombosis (e.g., formation of a thrombus within an artery that may cause infarction of tissue supplied by the artery), atherosclerosis (e.g., arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention may be useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention may be useful for maintaining patency in arteriovenous cannulas.

Examples of atherosclerosis include arteriosclerosis.

The compounds of the invention may also be Kallikrein inhibitors and especially useful for treatment of hereditary angioedema.

Examples of devices that come into contact with blood include vascular grafts, stents, orthopedic prosthesis, cardiac prosthesis, and extracorporeal circulation systems.

The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible.

The invention also relates to a process for the production of a medicament, which comprises bringing at least one compound of the Formula (I) into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the Factor XIa inhibitors or dual Factor XIa/plasma Kallikrein inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the Factor XIa inhibitors or dual Factor XIa/plasma Kallikrein inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the Factor XIa inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/mL, e.g. 0.1 mg/mL, 0.3 mg/mL, and 0.6 mg/mL, and administered in amounts per day of between 0.01 mL/kg patient weight and 10.0 mL/kg patient weight, e.g. 0.1 mL/kg, 0.2 mL/kg, 0.5 mL/kg. In one example, an 80 kg patient, receiving 8 mL twice a day of an intravenous formulation having a concentration of active ingredient of 0.5 mg/mL, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

Compounds of the Formula I, Formula Ia and Formula Ib can be administered both as a monotherapy and in combination with other therapeutic agents, including antithrombotics (anticoagulants and platelet aggregation inhibitors), thrombolytics (plasminogen activators), other profibrinolytically active substances, hypotensives, blood sugar regulators, lipid-lowering agents and antiarrhythmics.

The Factor XIa inhibitors or dual Factor XIa/plasma Kallikrein inhibitors can also be co-administered with suitable anticoagulants, including, but not limited to, other Factor XIa inhibitors, thrombin inhibitors, thrombin receptor antagonists, factor VIIa inhibitors, factor Xa inhibitors, factor IXa inhibitors, factor XIIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors. Factor XIa inhibitors may be administered first following thrombus formation, and tissue plasminogen activator or other plasminogen activator is administered thereafter.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of the invention, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g., olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, eplerenone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., a mLodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazosin, prazosin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pra mLintide acetate; inhibitors of glucose uptake, such as sodium-glucose transporter (SGLT) inhibitors and its various isoforms, such as SGLT-1, SGLT-2 (e.g., ASP-1941, TS-071, BI-10773, tofogliflozin, LX-4211, canagliflozin, dapagliflozin, ertugliflozin, ipragliflozin and remogliflozin), and SGLT-3; or with other drugs beneficial for the prevention or the treatment of the above-mentioned diseases including but not limited to diazoxide; and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of Factor XIa inhibitors or Factor XIa/plasma Kallikrein inhibitors of the invention in combination with other suitable anti-platelet agents, anticoagulation agents, or thrombolytic agents may be the same as those doses of Factor XIa inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e., prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds is preferably, but not necessarily, a synergistic combination. Synergy, as described for example by Chou and Talalay, Adv. Enzyme Regul. 1984, 22, 27-55, occurs when the effect (in this case, inhibition of the desired target) of the compounds when administered in combination is greater than the additive effect of each of the compounds when administered individually as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claims.

For purposes of this specification, the following abbreviations have the indicated meanings:
Ac Acetyl
ACN acetonitrile
AcOH or HOAc acetic acid
aq aqueous
Bn benzyl
Boc or BOC tert-butoxycarbonyl
Bu butyl
Bz benzoyl
cBu cyclobutyl
Cbz benyzloxycarbonyl
cPr cyclopropyl
DAST (diethylamino)sulfur trifluoride
dba dibenzylideneacetone
DCE 1,2-dichloroethane
DCM dichloromethane
DEA diethanolamine
DIBAL or Dibal-H diisobutylaluminum hydride
DIEA or Hünig's base N,N-diisopropylethylamine
DMA 1,2-dimethylacetamide DMAP 4-dimethylaminopyridine
DMF dimethylformamide
DMP Dess-Martin periodinane (1,1,1-triacetoxy)-1,1-dihydro-1,2-benziodoxol-3(1H)-one
DMSO dimethyl sulfoxide
dppf 1,1'-bis(diphenylphosphino)ferrocene
dtbpf 1,1'-bis(di-tert-butylphosphino)ferrocene
EDC 1-ethyl-3-(3-dimethylaminopropyl)carbodiimide
ESI electrospray ionization
Et ethyl
EtOH ethanol
EtOAc ethyl acetate
g grams
h hour
HATU N,N,N',N'-tetramethyl-O-(7-azabenzotriazol-1-yl)uranium hexafluorophosphate
HMDS 1,1,1,3,3,3-hexamethyldisilazane
HOBt 1-hydroxybenzotriazole
HPLC high-performance liquid chromatography
IPA isopropanol
iPr isopropyl
LCMS liquid chromatography mass spectrometry
LDA lithium diisopropylamide
LHMDS, LiHMDS lithium bis(trimethylsilyl) amide
mCPBA m-choroperoxybenzoic acid
Me methyl
MeOH methanol
mg milligrams
min minute
μL microliters
mL milliliters
mmol millimoles
MOM methoxymethyl
MS mass spectrometry
MTBE methyl tert-butyl ether
NCS N-chlorosuccinimide
NMR nuclear magnetic resonance spectroscopy
Ph phenyl
PMB p-methoxybenzyl
Pr propyl
ROESY Rotating-frame Overhauser SpectroscoPY
rac racemic mixture
RT or rt (ambient, about 25° C.)
SEM 2-(trimethylsilyl)ethoxy)methyl
SEM-Cl (2-(chloromethoxy)ethyl)trimethylsilane
SFC supercritical fluid chromatography
TBAF tert-butyl ammonium fluoride
TBS or TBDMS tert-butyldimethyl silyl
TBSCl tert-butyldimethylsilyl chloride
TBDPS tert-butyldiphenylsilyl
TBDPSCl tert-butyldiphenylsilyl chloride
tBu tert-butyl
tBu X-phos 2-di-tert-butylphosphino-2',4',6'-triisopropylbiphenyl
TEA triethylamine (Et$_3$N)
Tf trifloromethanesulfonic anhydride
TFA trifluoroacetic acid
TFAA trifluoroacetic anhydride
THF
TLC thin layer chromatography
TMS trimethylsilyl
Tris tris(hydroxymethyl)aminomethane
Ts toluenesulfonyl (tolyl)
TSA p-toluenesulfonic acid
X-PHOS 2-dicyclohexylphosphino-2',4',6'-triisopropylbiphenyl
Xantphos 4,5-bis(diphenylphosphino)-9,9-dimethylxanthene
Zhan catalyst 1,3-Bis(2,4,6-trimethylphenyl)-4,5-dihydroimidazol-2-ylidene[2-(i-propoxy)-5-(N,N-imethylaminosulfonyl) phenyl]methyleneruthenium(II) dichloride Also, TLC is thin layer chromatography; Ts is tosyl; UV is ultraviolet; W is watts; wt. % is percentage by weight; x g is times gravity; α$_D$ is the specific rotation of polarized light at 589 nm; ° C. is degrees Celsius; % w/v is percentage in weight of the former agent relative to the volume of the latter agent.

"Human FXIa Ki (nm)" is Human Factor XIa Ki (nm).

Analytical Reverse Phase Hplc Mass Spectrometry Conditions:

LC1: Column: Waters Xterra™ (Waters Technologies Corporation, Wilmington, Del.) MS C-18, 3.5 μm, 3.0×50 mm, Temperature: 50° C.; Eluent: 10:90 to 98:2 v/v acetonitrile/water$^+$0.05% TFA over 3.75 min. Flow Rate: 1.0 mL/min, Injection 10 μL; Detection: PDA, 200-600 nm; MS: range 150-750 amu; positive ion electrospray ionization LC2: Column: Waters Xterra™ (Waters Technologies Corporation, Wilmington, Del.) IS C-18, 3.5 μm, 2.1×20 mm, Temperature: 50° C., Eluent: 5:95 to 95:5 v/v acetonitrile/water$^+$0.05% TFA over 1.75 min, Flow Rate: 1.5 mL/min, Injection 5 μL, Detection: PDA, 200-600 nm, MS: range 150-750 amu; positive ion electrospray ionization LC3: Column: Waters Xterra™ (Waters Technologies Corporation, Wilmington, Del.) IS C-18, 3.5 μm, 2.1×20 mm, Temperature: 50° C., Eluent: 5:95 to 95:5 v/v acetonitrile/water$^+$0.05% TFA over 3.00 min, Flow Rate: 1.5 mL/min, Injection 5 μL, Detection: PDA, 200-600 nm, MS: range 150-750 amu; positive ion electrospray ionization LC4: Column: Waters Xterra™ (Waters Technologies Corporation, Wilmington, Del.) IS C-18, 3.5 μm, 3.0×50 mm, Temperature: 50° C., Eluent: 10:90 to 98:2 v/v acetonitrile/water$^+$0.05% TFA over 1.25 min, Flow Rate: 1.5 mL/min, Injection 5 μL, Detection: PDA, 200-600 nm, MS: range 150-750 amu; positive ion electrospray ionization LC5: Column: Sunfire™ (Waters Technologies Corporation, Wilmington, Del.)C-18, 5 μm, 4.6×100 mm, Temperature: 50° C., Eluent: 10:90 to 98:2 v/v acetonitrile/water$^+$0.1% formic acid over 1.25 min, Flow Rate: 1.5 mL/min, Injection 5 μL, Detection: PDA, 200-600 nm, MS: range 150-750 amu; positive and negative ion electrospray ionization LC6: Column: Agilent ZORBAX™ (E. I. Du Pont de Nemours and Company, Wilmington, Del.) SB-YMC-Actus Pro C18, 3.5 m, 2.1×50 mm, Temperature: 50° C., Eluent: 10:90 to 100:0 v/v acetonitrile/water 0.05% TFA over 4.00 min, Flow Rate: 0.8 mL/min, Injection 1 μL, Detection: PDA, 200-400 nm, MS: range 100-1000 amu; positive ion electrospray ionization General Schemes Compounds of the present invention may be prepared using conventional techniques or according to the methodology outlined in the following general synthetic schemes.

Multiple embodiments of the present invention are summarized in Scheme 1 which depicts the preparation of compounds I and II from intermediate 1a, synthesized from the Negishi cross coupling reaction of two readily available compounds in the presence of a catalyst such as tetrakis(triphenylphosphine)palladium(0) in a solvent such as tetrahydrafuran at elevated temperatures. Allylation of intermediate 1b by a base such as lithium diisopropylamide and allyl bromide affords intermediate 1b. Intermediate 1d is prepared by a palladium catalyzed Suzuki-Miyaura coupling of intermediate 1b and a boronate or boronic acid 1c in the presence of a precatalyst such as chloro(2-dicyclohexyl-phosphino-2',4',6'-tri-i-propyl-1,1'-biphenyl)[2-(2-amino-ethyl)phenyl] palladium(II) methyl-tert-butyl ether adduct and a base such as potassium phosphate in a mixture of water and another solvent such as THF or dioxane at elevated temperatures. Protection of the hydroxyl group of intermediate 1d by a protection group such as a tert-butyl-diphenylsilyl group followed by an amide coupling of 1e with 3-butenoic acid or a substituted 3-butenoic acid leads to intermediate 1f. Intramolecular olefin metathesis of 1f mediated by a catalyst such as Zhan catalyst-1B in a solvent such as toluene or dichloroethane at ambient or elevated temperatures closes the ring; deprotection in situ or after workup provides intermediate 1g. Transformation of the phenol to a phenyl triflate 1h followed by another palladium catatlyzed Suzuki-Miyaura coupling with a boronate or boronic acid affords compound I. Alternatively, compound I can be synthesized by a one-pot-two-step transformation of the triflate 1h to a boronic acid in the presence of a palladium catalyst followed by a subsequent Suzuki-Miyaura coupling with an aryl halide or triflate. A final oxidization of compound I by an oxidant such as mCPBA, peracetic acid or oxone in a solvent such as acetic acid or dichloromethane at ambient temperature finishes pyridine N-oxide II.

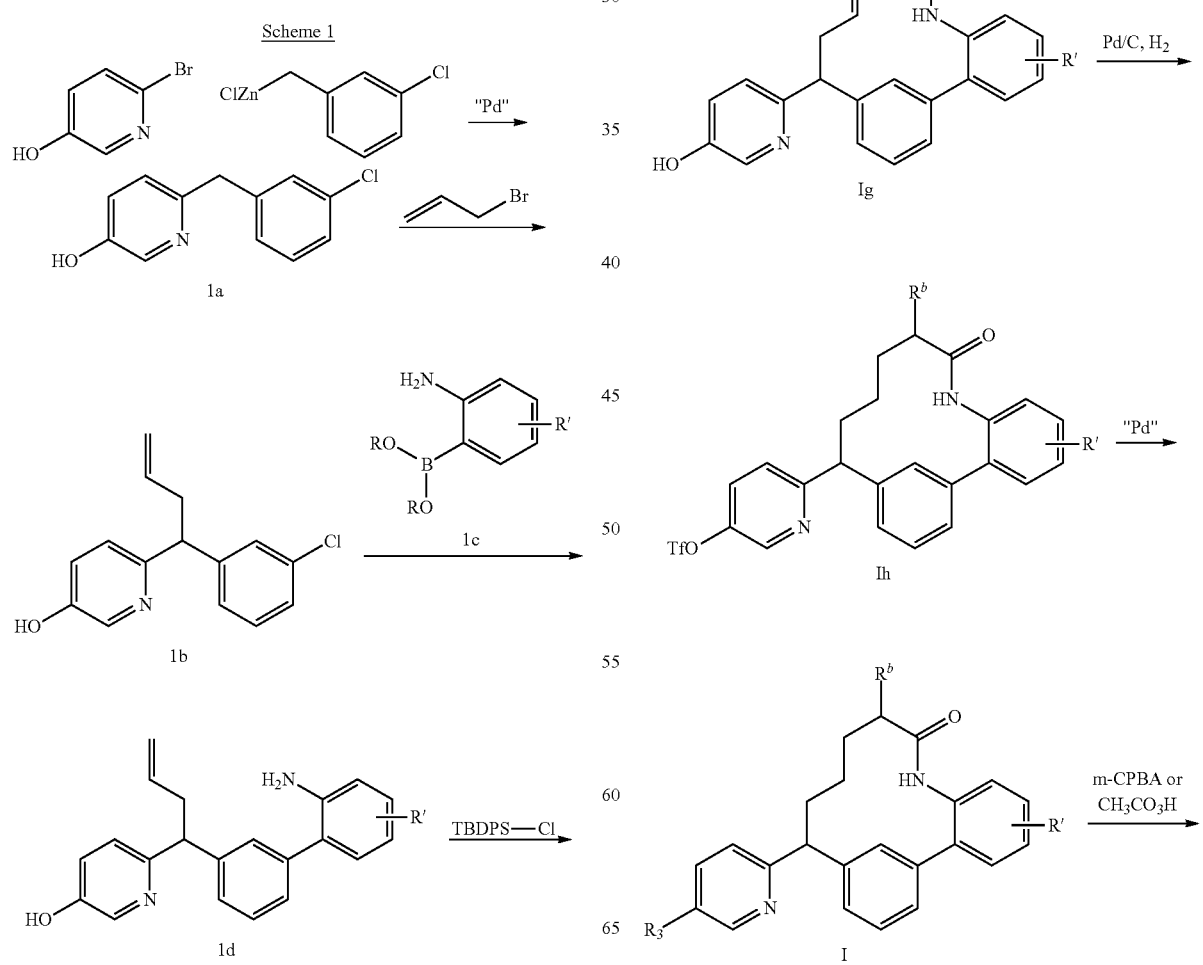
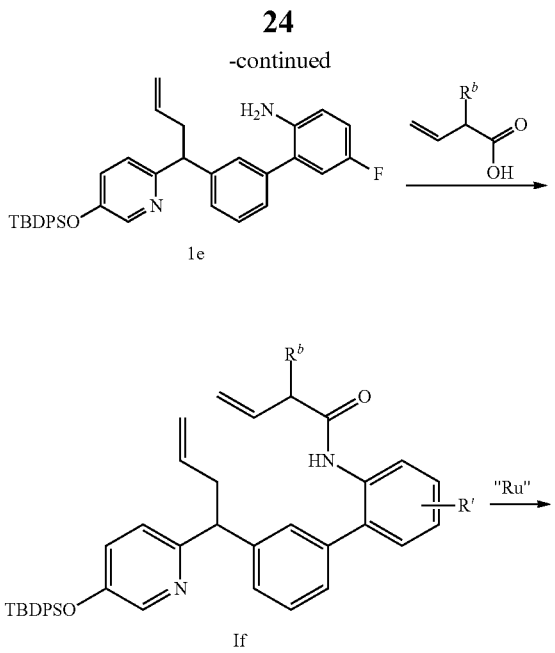

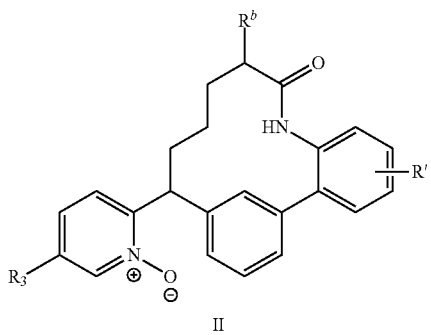

II

Representative macrocycles with an imidazole B ring of this invention can be prepared as shown in Scheme 2. Deprotonation of para-methoxybenzyl protected 2-methyl-5-hydroxypyridine 2a with a base such as lithium diisopropylamide followed by quenching with diethyl carbonate affords ester 2b. Allylation of 2b in the presence of a base and allyl bromide, followed by saponification by a base such as lithium hydroxide generates carboxylic acid 2d. Reaction of 2d with an alpha-bromo ketone 2e mediated by a base such as cesium carbonate in a solvent such as DMF provides intermediate 2f. Condensation of 2f with excess amount of ammonium acetate in a solvent such as toluene or a mixed solvent of toluene and acetic acid at elevated temperatures affords imidazole 2g. Protection of the imidazole NH with a SEM group and conversion of the bromo to an amino group employing a copper precatalyst such as copper (I) iodide and a ligand such as L-proline gives intermediate 2i. The synthesis of III is accomplished by following the subsequent steps described in Scheme 1.

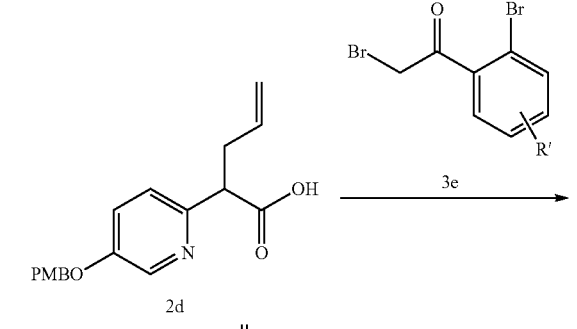

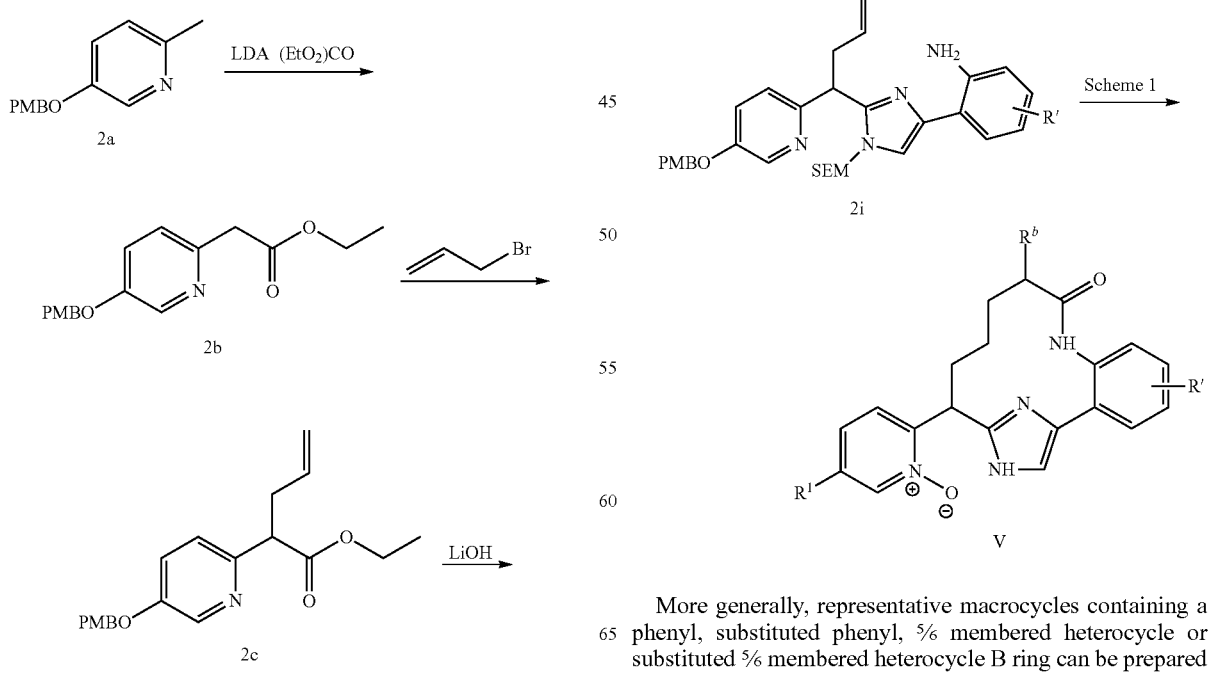

More generally, representative macrocycles containing a phenyl, substituted phenyl, 5/6 membered heterocycle or substituted 5/6 membered heterocycle B ring can be prepared as shown in Scheme 3. Suzuki-Miyaura coupling of intermediate ketone 3a with a boronic acid or ester 3b in the presence of a palladium precatalyst such as PdCl$_2$(dppf) and a base such as potassium phosphate in a mixed solvent of water and dioxane or THF at elevated temperatures provide 3c. Amide bond formation between 3c and (4-carboxybutyl) triphenylphosphonium bromide mediated by a peptide coupling reagent such as HATU affords 3d, which upon treatment with excess equivalents of a base such as LHMDS in a solvent such as THF at a concentration equal or lower than about 0.02 M at rt provides 3e. Selective hydrogenation of the alkene in the presence of a chloropyridine moiety catalyzed by either Raney nickel or vanadium contaminated platinum on carbon gives 3f. The synthesis of compound III is accomplished by the subsequent Suzuki-Miyaura coupling of 3f with a boronic acid or ester. Alternatively, 3f can be converted to a boronic acid or ester, which reacts with an aryl halide or triflate in the presence of a catalyst to afford compound III. In cases where X$_2$ is an alkoxyl group, it is transformed to the corresponding triflate before the Suzuki-Miyaura coupling. Oxidation of IV to N-oxide V is described in Scheme 3.

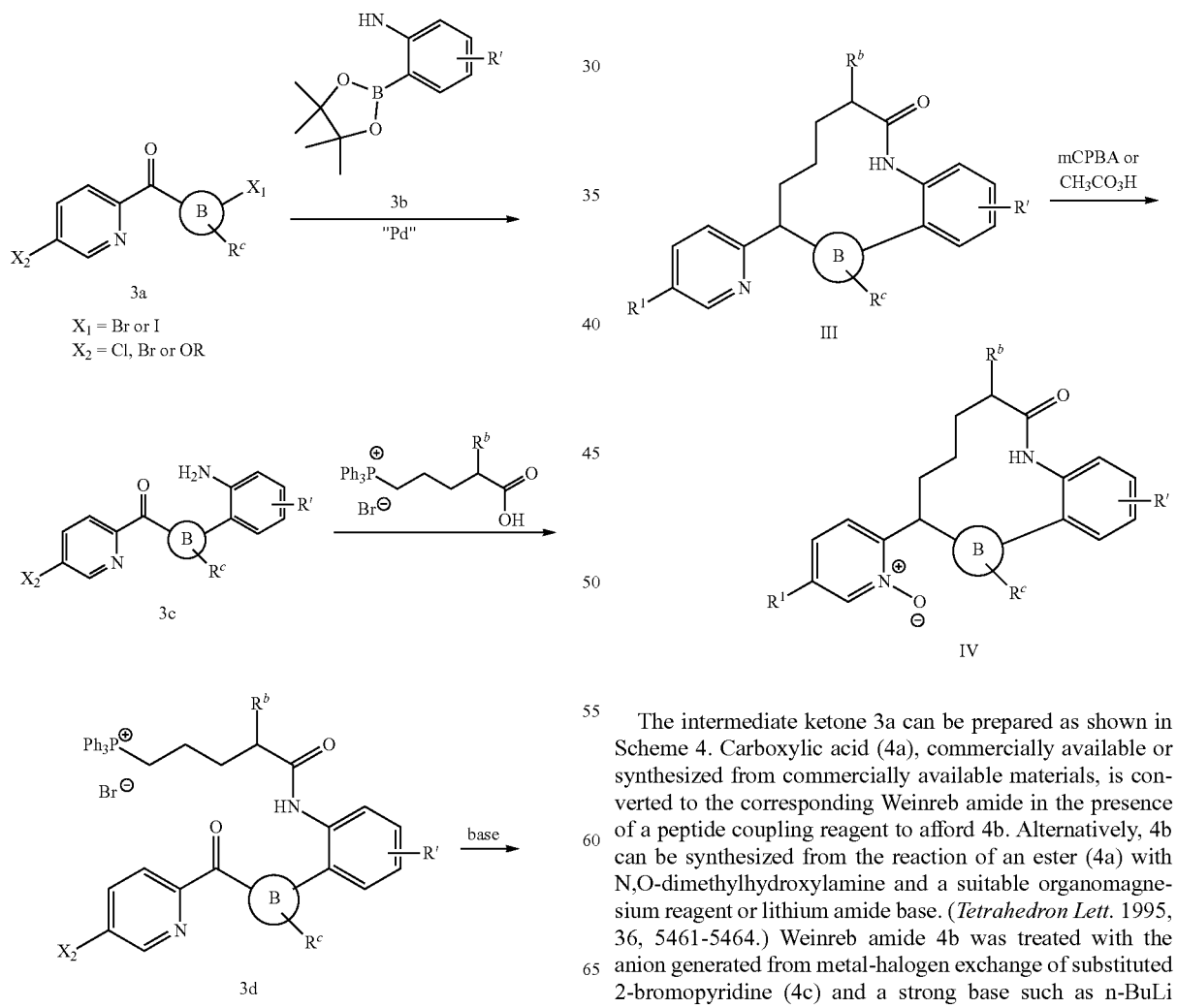

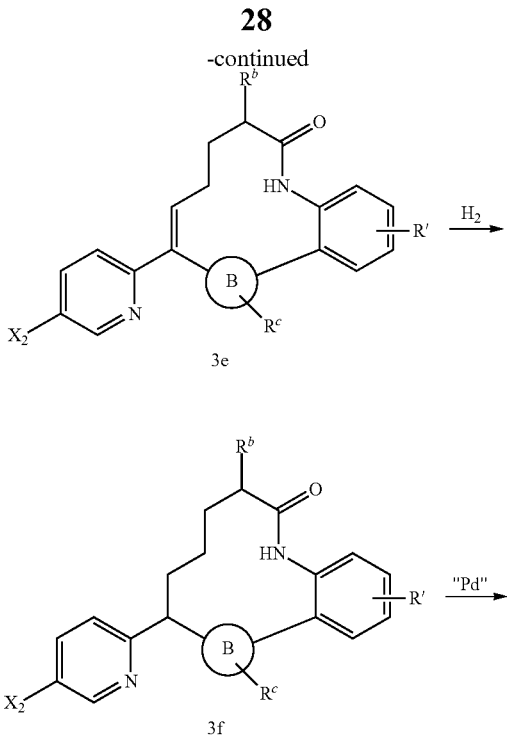

The intermediate ketone 3a can be prepared as shown in Scheme 4. Carboxylic acid (4a), commercially available or synthesized from commercially available materials, is converted to the corresponding Weinreb amide in the presence of a peptide coupling reagent to afford 4b. Alternatively, 4b can be synthesized from the reaction of an ester (4a) with N,O-dimethylhydroxylamine and a suitable organomagnesium reagent or lithium amide base. (*Tetrahedron Lett.* 1995, 36, 5461-5464.) Weinreb amide 4b was treated with the anion generated from metal-halogen exchange of substituted 2-bromopyridine (4c) and a strong base such as n-BuLi provides the corresponding ketone 3a.

Scheme 4

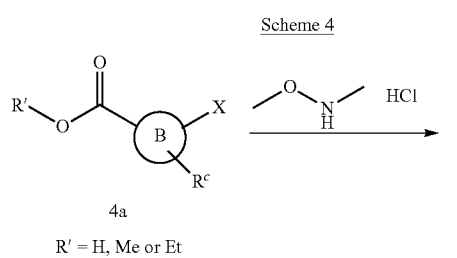

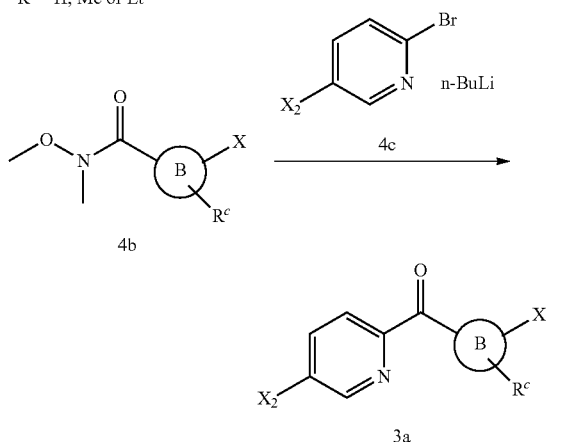

Alternatively, ketone 3a can be made from the reaction of the Weinreb amide of a 4-substituted picolinic acid (5b) with an organometallic nucleophile (5a) generated by deprotonation or metal-halogen exchange of the corresponding arene or heterarene with an organometallic base such as n-BuLi (Scheme 5).

Scheme 5

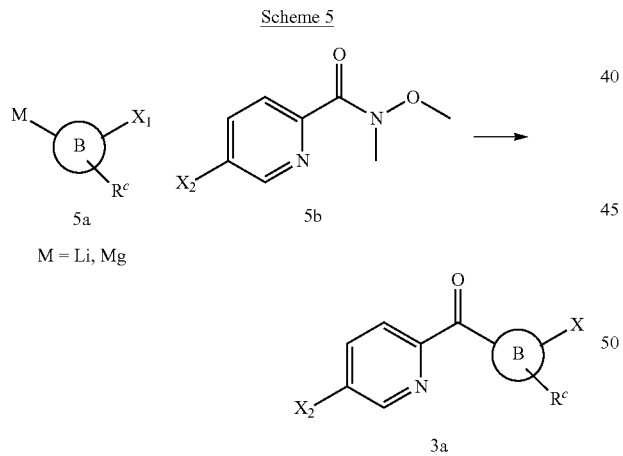

In another embodiment of the invention, macrocycles with general structures V and VI can be prepared from intermediate 1d as shown in Scheme 6. Reaction of aniline 1d with ethyl 2-oxoacetate and allyltributyltin in the presence of a mild acid such as maleic acid (Zhao et. al., Synthesis 2006, 19, 3189.) affords 6a. Protection of the hydroxyl group with TBDPS followed by a ring closure metathesis reaction catalyzed by a ruthenium catalyst such as Zhan's catalyst and removal of TBDPS protection provides 6c. Hydrogenation of 6c and conversion of the hydroxyl group to a triflate afford 6e. Suzuki-Miyaura coupling of 6e with a boronic acid or ester gives intermediate 6f. Protection of the aniline with a trifluoroacetyl group followed by oxidation of pyridine by an oxidant such as mCPBA or peracetic acid affords pyridine N-oxide 6h. The treatment of 6h with a base such as lithium hydroxide in a mixed solvent of water, methanol and THF at elevated temperature causes hydrolysis of the ethyl ester and removal of the trifluoroacetyl protection on the aniline to afford amino acid V. Compound VI can be prepared by coupling of V with an amine in the presence of a peptide coupling reagent such as HATU.

Scheme 6

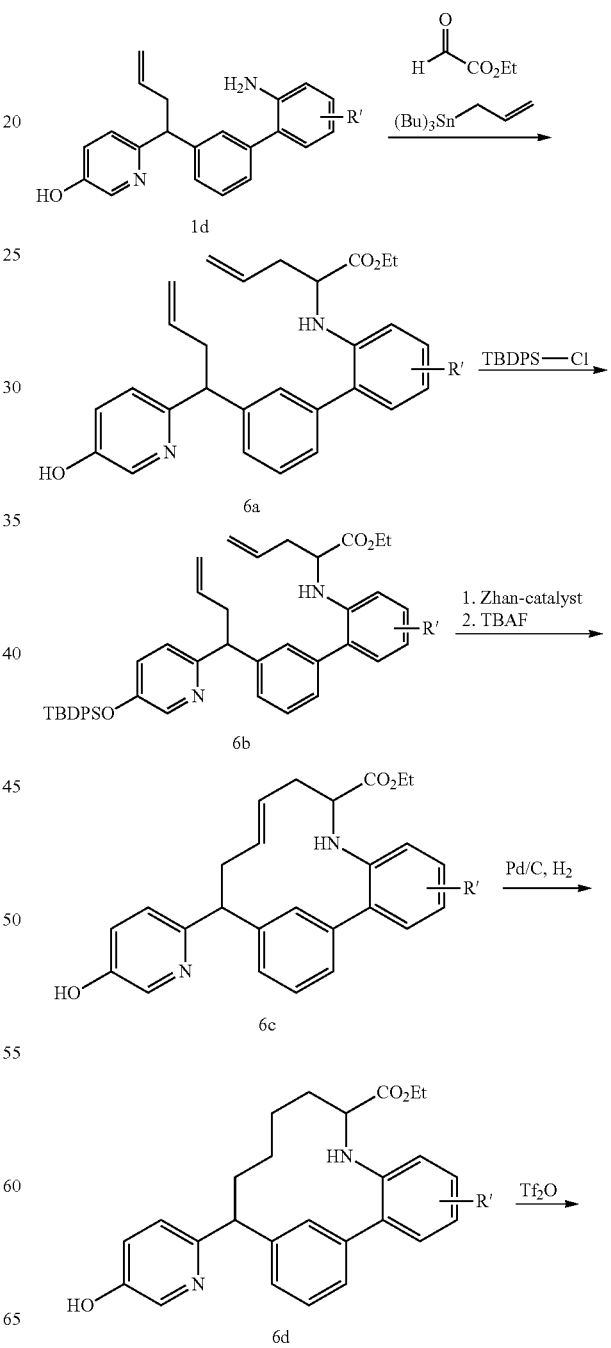

-continued

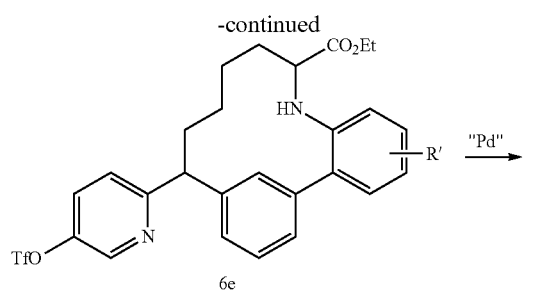
6e

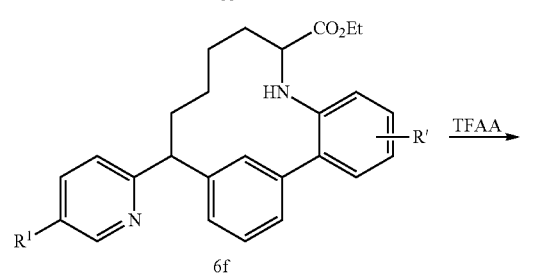
6f

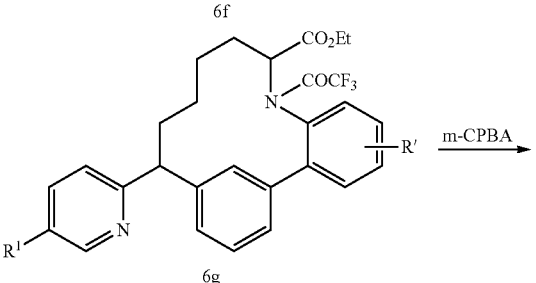
6g

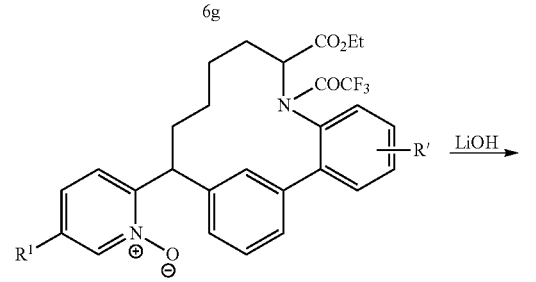
6h

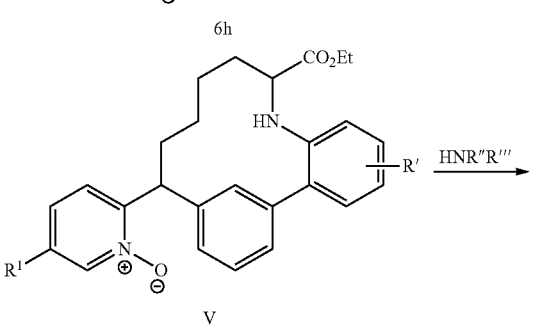
V

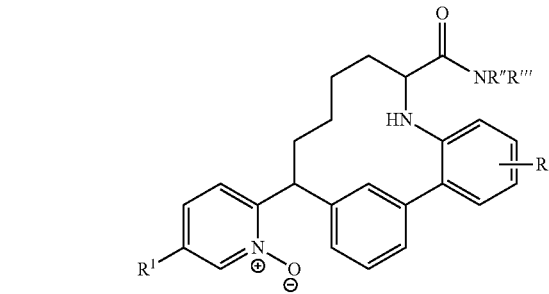
VI

Separation of diastereomers can be carried out at various stages in the preparation of the desired final compounds; however, it is typically carried out on the final products using supercritical fluid chromatography (SFC). Separation of enantiomers is achieved by SFC employing various chiral columns. The absolute configuration is assigned either directly by X-ray co-crystal structures or by comparison of the FXIa Ki values between one pair of enantiomers based on the assumption that compounds with certain configuration are more potent than their corresponding enantiomer.

Preparative thin layer chromatography (PTLC) was performed on 20×20 cm plates (500 µm-1500 µm thick silica gel). Flash column chromatography was conducted on ISCO flash chromatography systems using columns pre-packed with silica gel, eluting with hexanes/ethyl acetate or DCM/MeOH gradient unless noted otherwise.

INTERMEDIATES

Intermediate 1

6-(1-(3-Chlorophenyl)but-3-en-1-yl)pyridin-3-ol

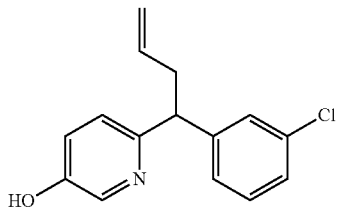 [SMILES: C=CCC(c1cccc(Cl)c1)c1ccc(O)cn1]

Step A: 6-(3-Chlorobenzyl)pyridin-3-ol: To a clean, dry 500 mL round bottom flask charged with a magnetic stirring bar was added 2-bromo-5-hydroxypyridine (4.2 g, 24.14 mmol) and tetrakis(triphenylphosphine)palladium(0) (2.79 g, 2.414 mmol). It was sealed by a rubber septum and purged with nitrogen three times. To the flask was transferred THF (degassed, 100 mL) through a cannula and it was stirred to form a solution. To the solution was transferred 3-chlorobenzylzinc chloride (0.5 M in THF, 100 mL, 50.0 mmol) through a cannula. The flask was merged into a pre-heated oil bath at 65° C. and stirred for 4 h. It was allowed to cool to rt and aged overnight. The reaction was quenched with ammonium chloride (50 mL) and brine (50 mL). The mixture was extracted with ethyl acetate (100 mL). The organic layer was separated and dried over sodium sulfate, filtered and concentrated. The residue was triturated in DCM (50 mL), filtered and rinsed with DCM (2×10 mL) to afford the title compound. MS (ES+) m/z: 220 (M+H).

Step B: 5-(2-Chloro-5-nitrophenyl)dihydrofuran-2(3H)-one: To a solution of 6-(3-chlorobenzyl)pyridin-3-ol (1.4 g, 6.37 mmol) in THF (40 mL) at −78° C. was added a solution of LDA (2 M in THF, 8.60 mL, 17.21 mmol). The reaction was stirred for 10 min and a solution of allyl bromide (0.56 mL, 6.47 mmol) in THF (5 mL) was added dropwise. The resulting mixture was stirred for 30 min and was allowed to warm to rt with stirring over 3 h. It was quenched with saturated aqueous ammonium chloride and the mixture was extracted with ethyl acetate (3×30 mL). The combined organic layers were washed with brine and dried over sodium sulfate, filtered and concentrated under reduced pressure. The residue was purified by flash column chromatography on silica gel (eluting with 0-50% ethyl acetate in hexane) to give the title compound. MS (ES+) m/z: 260 (M+H).

Intermediate 2

(3-Bromophenyl)(5-chloropyridin-2-yl)methanone

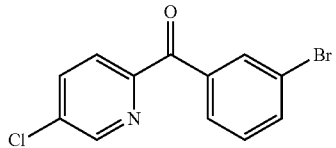 [SMILES: O=C(c1cccc(Br)c1)c1ccc(Cl)cn1]

Step A: 3-Bromo-N-methoxy-N-methylbenzamide: To a mixture of 3-bromobenzoic acid (40 g, 199 mmol), N,O-dimethylhydroxylamine hydrochloride (23.29 g, 239 mmol) and triethylamine (83 mL, 597 mmol) in dichloromethane (398 mL) at 0° C. was added EDC (49.6 g, 259 mmol). The mixture was stirred for 5 min and was allowed to warm to rt with stirring over 2 h. It was sequentially washed with hydrochloric acid (1 M, 100 mL), aqueous sodium bicarbonate (saturated, 100 mL) and brine. The organic layer was separated and dried over anhydrous magnesium sulfate. It was filtered and the filtrate was concentrated under reduced pressure to give the title compound. MS (ES+) m/z: 246, 248 (M+H).

Step B: (3-Bromophenyl)(5-chloropyridin-2-yl)methanone: To a stirred solution of 2-bromo-5-chloropyridine (21.68 g, 113 mmol) in anhydrous toluene (512 mL) at −78° C. was added n-butyllithium (2.5 M in hexane) (49.0 mL, 123 mmol) dropwise over a period of 1 h by a syringe pump. The mixture was stirred at −78° C. for 90 min. A solution of 3-bromo-N-methoxy-N-methylbenzamide (25 g, 102 mmol) in anhydrous toluene (80 mL) was added to the mixture over a period of 30 min by a syringe pump. The resulting mixture was stirred at −78° C. for another 2 h and was warmed to 0° C. A solution of hydrochloric acid (1 M, 100 mL) was added to the reaction and stirred for 20 min. The pH of the mixture was adjusted to about 9 by addition of aqueous sodium bicarbonate (saturated). The mixture was extracted with ethyl acetate (2×200 mL). The combined organic layers were washed with brine (100 mL), dried over sodium sulfate, filtered and the filtrate was concentrated under reduced pressure. The residue was purified by flash column chromatography on silica gel (eluting with EtOAc/hexane=9:1 v/v) to afford the title compound. MS (ES+) m/z: 296, 298 (M+H).

Intermediate 3

(5-Chloropyridin-2-yl)(3-(4,4,5,5-tetramethyl-1,3,2-dioxaborolan-2-yl)phenyl)methanone

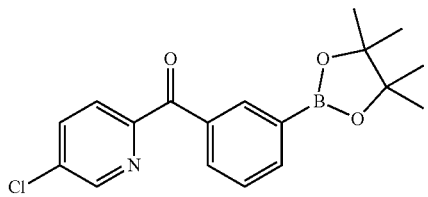 [SMILES: CC1(C)OB(c2cccc(C(=O)c3ccc(Cl)cn3)c2)OC1(C)C]

A mixture of (3-bromophenyl)(5-chloropyridin-2-yl)methanone (4.00 g, 13.48 mmol), bis(pinacolato)diboron (4.10 g, 16.20 mmol), potassium acetate (2.00 g, 20.00 mmol) and Pd(dppf)Cl₂ (1.00 g, 1.35 mmol) in dioxane (60 mL) was stirred at 85° C. for 4.5 h. It was quenched with aqueous ammonium chloride (saturated, 50 mL) and extracted with EtOAc (50 mL×3). The organic layer washed with brine (100 mL), dried over sodium sulfate, filtered and concentrated. The residue was purified by column chromatography on silica gel (eluting with petroleum ether:ethyl acetate=50:1 to 10:1) to give the title compound. ¹H NMR (400 MHz, CDCl₃): δ 8.61 (s, 1H), 8.33 (s, 1H), 8.06-7.95 (m., 3H), 7.82 (d, J=8.4 Hz, 1H), 7.44 (t, J=7.2 Hz, 1H), 1.28 (s, 12H).

Intermediate 4

(3-bromo-5-fluorophenyl)(5-chloropyridin-2-yl)methanone

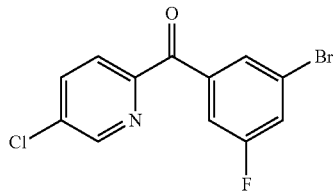 [SMILES: O=C(c1cc(F)cc(Br)c1)c1ccc(Cl)cn1]

The title compound was prepared from 3-bromo-5-fluorobenzoic acid by the procedure described in the synthesis of Intermediate 2. MS (ES+) m/z: 314, 316 (M+H); ¹H NMR (400 MHz, CDCl₃): δ 8.69 (d, J=1.8 Hz, 1H), 8.02-8.14 (m, 2H), 7.92 (dd, J=2.2, 8.4 Hz, 1H), 7.81 (d, J=8.6 Hz, 1H), 7.49 (d, J=7.7 Hz, 1H).

Intermediate 5

2-Bromo-1-(2-bromo-5-fluorophenyl)ethan-1-one

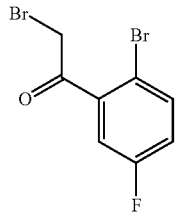 [SMILES: O=C(CBr)c1cc(F)ccc1Br]

To a stirred solution of 1-(2-bromo-5-fluorophenyl)ethanone (5 g, 23.04 mmol) and HBr (48% w/w aqueous, 0.2 mL, 1.768 mmol) in diethyl ether (50 mL) at 0° C. was added bromine (1.2 mL, 23.29 mmol) dropwise. The mixture was stirred at rt for 2 h. It was transferred into a separatory funnel and washed with water (50 mL). The aqueous layer was extracted with diethyl ether (100 mL). The combined organic layers were dried over sodium sulfate, filtered and concentrated. The residue was purified by flash column chromatography on silica gel (eluting with 0-20% ethyl acetate in hexane) to give the title compound.

Intermediate 6

(3-Bromo-4-fluorophenyl)(5-chloropyridin-2-yl)methanone

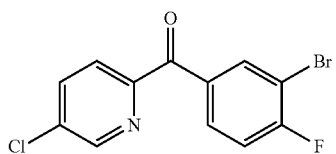 [SMILES: O=C(c1ccc(F)c(Br)c1)c1ccc(Cl)cn1]

The title compound was prepared from 3-bromo-4-fluorobenzoic acid by the procedure described in the synthesis of Intermediate 2. MS (ES$^+$) m/z: 314, 316 (M+H); $^1$H NMR (400 MHz, CDCl$_3$): δ 8.79 (d, J=2.0 Hz, 1H), 8.29 (dd, J=1.6, 7.0 Hz, 1H), 8.20 (dd, J=2.2, 8.4 Hz, 1H), 8.04 (d, J=8.2 Hz, 2H), 7.53 (t, J=8.6 Hz, 1H).

Intermediate 7

(3-Bromo-4,5-difluorophenyl)(5-chloropyridin-2-yl)methanone

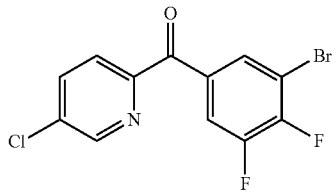 [SMILES: O=C(c1cc(F)c(F)c(Br)c1)c1ccc(Cl)cn1]

Intermediate 7 was prepared from 3-bromo-4,5-difluorobenzoic acid by the procedure described in the synthesis of Intermediate 2. MS (ES$^+$) m/z: 332, 334 (M+H).

Intermediate 8

(2-Bromopyridin-4-yl)(5-chloropyridin-2-yl)methanone

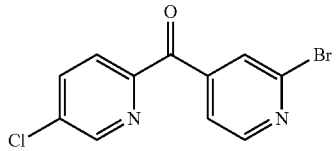 [SMILES: O=C(c1ccnc(Br)c1)c1ccc(Cl)cn1]

Step A: (2-Bromopyridin-4-yl)(5-chloropyridin-2-yl)methanol: A solution of 2-bromo-5-chloropyridine (3.41 g, 17.74 mmol) in 10 mL of anhydrous THF at −78° C. under nitrogen was added to a solution of n-butyllithium (2.5 M in hexane, 7.10 mL, 17.74 mmol) in anhydrous THF (50 mL) dropwise. The reaction mixture was stirred for 15 min and a solution of 2-bromopyridine-4-carboxaldehyde (3.0 g, 16.13 mmol) in 20 mL of THF was added in one portion. It was stirred for 10 min and the dry ice-acetone bath was replaced with an ice-water batch. The reaction was stirred at 0° C. for 30 min and then quenched with saturated aqueous ammonium chloride. The mixture was extracted with ethyl acetate. The organic layer was separated, dried over sodium sulfate, filtered and concentrated under reduced pressure. The residue was purified by flash column chromatography on silica gel (eluting with 0-100% ethyl acetate in hexane) to afford the title compound. MS (ES$^+$) m/z: 299, 301 (M+H).

Step B: (2-Bromopyridin-4-yl)(5-chloropyridin-2-yl)methanone: A solution of (2-bromopyridin-4-yl)(5-chloropyridin-2-yl)methanol (1.3 g, 4.34 mmol) in DCM (40 mL) was stirred with manganese dioxide (3.77 g, 43.4 mmol) at rt for 1 h. The reaction mixture was filtered through a pad of Celite and the solid cake was rinsed with 10% methanol in DCM (100 mL). The filtrate was concentrated to give the title compound. MS (ES$^+$) m/z: 297, 299 (M+H).

Alternatively, Intermediate 8 was prepared from 2-bromoisonicotinic acid by the procedure described in the synthesis of Intermediate 2. MS (ES$^+$) m/z: 297, 299 (M+H); $^1$H NMR (400 MHz, CDCl$_3$): δ 8.68 (d, J=1.8 Hz, 1H), 8.56 (d, J=4.9 Hz, 1H), 8.14 (d, J=8.4 Hz, 1H), 8.10 (s, 1H), 7.93 (dd, J=8.4, 2.2 Hz, 1H), 7.85 (d, J=4.9 Hz, 1H).

Intermediate 9

(2-Bromo-5-fluoropyridin-4-yl)(5-chloropyridin-2-yl)methanone

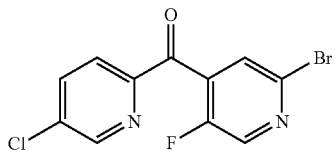 [SMILES: O=C(c1ccc(Cl)cn1)c1cc(Br)ncc1F]

Step A: (2-Bromo-5-fluoropyridin-4-yl)(5-chloropyridin-2-yl)methanol: To a solution of 2,4-dibromo-5-fluoropyridine (7.53 g, 29.5 mmol) in 100 mL of toluene at −78° C. was added dropwise a solution of n-butyllithium (2.5 M, 7 mL, 17.50 mmol). It was stirred for 15 min and to the solution was added a solution of 5-chloropicolinaldehyde (3.8 g, 26.8 mmol) in 30 mL of toluene by a syringe. The mixture was stirred for 1 h and it was allowed to warm to 0° C. before it was quenched with saturated aqueous ammonium chloride. The mixture was extracted with ethyl acetate. The organic layer washed with brine, dried over sodium sulfate, filtered and concentrated to afford the title compound (as a mixture of two regio-isomers in 9:1 ratio in favor of the desired isomer). It was used without purification. MS (ES$^+$) m/z: 317, 319 (M+H).

Step B: (2-Bromo-5-fluoropyridin-4-yl)(5-chloropyridin-2-yl)methanone: A solution of the above product (3.8 g, 10.77 mmol) in DCM (50 mL) was stirred with manganese dioxide (9.36 g, 108 mmol) at rt for 2 h. The solids were removed by filtration through a pad of Celite and rinsed with 10% ammonia in MeOH (7 N)/DCM (3×50 mL). The filtrate was concentrated and the residue was dissolved in 20% ammonia in MeOH (7 N)/DCM and was purified by flash column chromatography on silica gel (eluting with 0-2% ammonia in MeOH (7 N)/DCM) to afford the title compound. MS (ES$^+$) m/z: 315, 317 (M+H); $^1$H NMR (400 MHz, CDCl$_3$): δ 8.80 (d, J=2.0 Hz, 1H), 8.63 (s, 1H), 8.26 (dd, J=2.0, 8.5 Hz, 1H), 8.18 (d, J=8.5 Hz, 1H), 7.97 (d, J=4.5 Hz, 1H).

Intermediate 10

(4-Bromopyridin-2-yl)(5-chloropyridin-2-yl)methanone

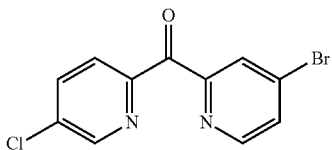 [SMILES: O=C(c1ccc(Cl)cn1)c1cc(Br)ccn1]

The title compound was prepared from 2,4-dibromopyridine by the procedure described in the synthesis of Intermediate 9. The product was purified by flash column chromatography on silica gel (eluting with 0-5% NH$_3$ in methanol (7 N) in DCM) to give the title compound. MS (ES$^+$) m/z: 297, 299 (M+H).

Intermediate 11

(5-Chloropyridin-2-yl)(5-fluoro-4-iodopyridin-2-yl)methanone

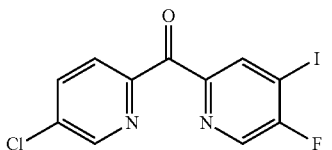 [SMILES: O=C(c1ccc(Cl)cn1)c1cc(I)c(F)cn1]

Step A: (5-Chloropyridin-2-yl)(5-fluoropyridin-2-yl)methanone: The title compound was prepared from 2-bromo-5-fluoropyridine by the procedure described in the synthesis of Intermediate 9. MS (ES$^+$) m/z: 237.0 [M+H].

Step B: (5-Chloropyridin-2-yl)(5-fluoro-4-iodopyridin-2-yl)methanol: To a solution of (5-chloropyridin-2-yl)(5-fluoropyridin-2-yl)methanone (3.00 g, 12.68 mmol) in THF (30 mL) at −78° C. was added a solution of LDA (2 M in THF, 8.24 mL, 16.48 mmol). It was stirred for 30 min and iodine (3.86 g, 15.21 mmol) was added in one portion. The mixture was stirred at −78° C. for 2 h and quenched with saturated aqueous ammonium chloride (20 mL). It was extracted with ethyl acetate (100 mL×3). The combined organic layers were washed with brine (200 mL), dried over anhydrous sodium sulfate, filtered, and concentrated under reduced pressure. The residue was purified by flash column chromatography on silica gel (eluting with EtOAc:petroleum ether=1:8 to 1:5 v/v) to give the title compound. MS (ES$^+$) m/z: 365.0 [M+H].

Step C: (5-Chloropyridin-2-yl)(5-fluoro-4-iodopyridin-2-yl)methanone: To a solution of (5-chloropyridin-2-yl)(5-fluoro-4-iodopyridin-2-yl)methanol (580 mg, 1.591 mmol) in DCM (6 mL) was added manganese(IV) oxide (1383 mg, 15.91 mmol). The mixture was stirred at rt for 12 h. The solids were removed by filtration through a pad of Celite and rinsed with DCM (30 ML). The filtrate was concentrated in vacuo to give the title compound. MS (ES$^+$) m/z: 363.0 [M+H].

Intermediate 12

(3-Bromophenyl)(5-chloro-4-methoxypyridin-2-yl)methanone

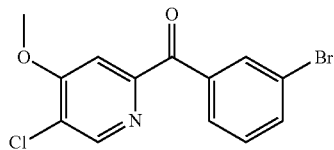 [SMILES: COc1cc(C(=O)c2cccc(Br)c2)ncc1Cl]

Step A: 2-Bromo-5-chloro-4-methoxypyridine: To a solution of 2-bromo-5-chloropyridin-4-ol (7.80 g, 37.40 mmol) in DCM (30 mL) and MeOH (3 mL) was added TMS-diazomethane (94 mL, 187 mmol, 2 M in hexane) at 0° C. The reaction mixture was stirred at 25° C. for 12 h. Solid precipitations were removed by filtration through a pad of Celite. The filtrate was concentrated under reduced pressure and the residue was purified by flash column chromatography (SiO$_2$, petroleum ether:EtOAc=1:0-3:1) to give the title compound. $^1$H NMR (400 MHz, CDCl$_3$): δ 8.19 (s, 1H), 7.00 (s, 1H), 3.94 (s, 3H).

Step B: (3-Bromophenyl)(5-chloro-4-methoxypyridin-2-yl)methanone: To a stirred solution of 2-bromo-5-chloro-4-methoxypyridine (5.50 g, 24.72 mmol) in toluene (200 mL) at −78° C. was added a solution of n-BuLi (10.88 mL, 27.20 mmol, 2.5 M in hexane). The resulting mixture was stirred at −78° C. for 1 h, before the addition of 3-Bromo-N-methoxy-N-methylbenzamide (7.24 g, 29.70 mmol). The mixture was stirred for 16 h while the temperature was allowed to rise to rt. It was quenched with saturated aqueous ammonium chloride (100 mL) and extracted with EtOAc (100 mL×3). The combined organic layers were washed with brine (200 mL), dried over anhydrous sodium sulfate, filtered, and concentrated under reduced pressure. The residue was purified by flash column chromatography (SiO$_2$, petroleum ether:EtOAc=50:1-5:1) to give the title compound. MS (ESI) m/z 325.9, 327.9 (M+H); $^1$H NMR (400 MHz, CDCl$_3$): δ 8.53 (s, 1H), 8.21 (s, 1H), 8.01 (d, J=7.8 Hz, 1H), 7.70 (d, J=8.2 Hz, 1H), 7.66 (s, 1H), 7.35 (t, J=7.8 Hz, 1H), 4.05 (s, 3H).

Intermediate 13

(6-Bromo-5-fluoropyridin-2-yl)(5-chloropyridin-2-yl)methanone

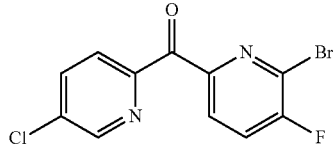 [SMILES: O=C(c1ccc(Cl)cn1)c1ccc(F)c(Br)n1]

The title compound was prepared from 6-bromo-5-fluoropicolinic acid by the procedure described in the synthesis of Intermediate 2. MS (ES$^+$) m/z: 315, 317 (M+H); $^1$H NMR (400 MHz, CDCl$_3$): δ 8.79 (d, J=2.0 Hz, 1H), 8.29 (dd, J=1.6, 7.0 Hz, 1H), 8.20 (dd, J=2.2, 8.4 Hz, 1H), 8.04 (d, J=8.2 Hz, 2H), 7.53 (t, J=8.6 Hz, 1H).

Intermediate 14

(5-Chloropyridin-2-yl)(6-chloropyrimidin-4-yl)methanone

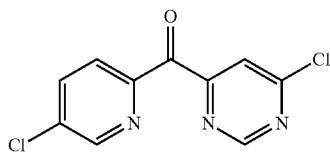 [SMILES: O=C(c1ccc(Cl)cn1)c1cc(Cl)ncn1]

Step A: 6-Chloropyrimidine-4-carbonyl chloride: To a solution of 6-hydroxypyrimidine-4-carboxylic acid (2.00 g, 14.28 mmol) and oxalyl dichloride (1.81 g, 14.28 mmol) in EtOAc (30 mL) at 0° C. was added a few drops of DMF (0.5 mL, 6.46 mmol). The mixture was stirred at 80° C. for 16 h. It was cooled to rt and concentrated under reduced pressure to give the title compound.

Step B: 6-Chloro-N-methoxy-N-methylpyrimidine-4-carboxamide: To a solution of 6-chloropyrimidine-4-carbonyl chloride (26.60 g, 150 mmol) and N,O-dimethylhydroxylamine hydrochloride (17.59 g, 180 mmol) in DCM (300 mL) at 0° C. was added DIEA (52.50 mL, 301 mmol). The reaction mixture was allowed to warm to rt and stirred for 16 h. It was diluted with water (200 mL) and extracted with DCM (300 mL×4). The combined organic layers were dried over sodium sulfate, filtered and concentrated under reduced pressure. The residue was purified by flash column chromatography (SiO$_2$, petroleum ether:EtOAc=5:1) to give the title compound as an oil. MS (ESI) m/z 202.1 (M+H); $^1$H NMR (400 MHz, CDCl$_3$): δ 9.03 (s, 1 H), 7.58 (brs, 1 H), 3.74 (s, 3 H), 3.37 (s, 3 H).

Step C: (5-Chloropyridin-2-yl)(6-chloropyrimidin-4-yl)methanone: A solution of n-BuLi (39.9 mL, 100 mmol, 2.5 M in hexane) was added to a stirred solution of 2-bromo-5-chloropyridine (19.18 g, 100 mmol) in toluene (150 mL) at −78° C. The mixture was stirred for 0.5 h, then a solution of 5-chloro-N-methoxy-N-methylpicolinamide (10 g, 49.80 mmol) in toluene (50 mL) was added. The mixture was stirred at −78° C. for 1 h. It was quenched with saturated ammonium chloride (200 mL) and extracted with EtOAc (100 mL×3). The combined organic layers were dried over sodium sulfate, filtered and concentrated. The residue was purified by flash column chromatography (SiO$_2$, petroleum ether:EtOAc=12:1 to 10:1) to give the title compound. MS (ESI) m/z 254.0 (M+H), $^1$H NMR (400 MHz, CDCl$_3$): δ 9.16 (s, 1 H), 8.68 (d, J=1.6 Hz, 1 H), 8.18 (d, J=8.6 Hz, 1 H), 7.89-7.99 (m, 2 H).

Intermediate 15

(5-Bromopyridin-2-yl)(4-iodo-1-((2-(trimethylsilyl)ethoxy)methyl)-1H-imidazol-2-yl)methanone

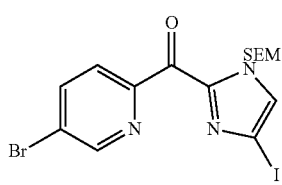 [SMILES: C[Si](C)(C)CCOCn1cc(I)nc1C(=O)c1ccc(Br)cn1]

Step A: 4-Iodo-1-((2-(trimethylsilyl)ethoxy)methyl)-1H-imidazole: To a suspension of NaH (4.21 g, 105 mmol, 60% wt) in DMF (200 mL) at 0° C. was added 4-iodo-1H-imidazole (17 g, 88 mmol) in small portions. It was stirred for 1 h and SEM-Cl (16.07 g, 96 mmol) was added to the reaction. The mixture was stirred at rt for 12 h and poured into ice-water (200 mL). The mixture was extracted with EtOAc (100 mL×3). The combined organic layers were washed with water (3×50 mL), dried over sodium sulfate, filtered and concentrated under reduced pressure. The residue was purified by flash column chromatography on silica gel (eluting with petroleum ether:EtOAc=10:1 to 3:1 v/v) to afford the title compound. MS (ES$^+$) m/z: 325 (M+H).

Step B: 5-Bromo-N-methoxy-N-methylpicolinamide: To a solution of 5-bromopicolinic acid (15 g, 74.3 mmol) in DCM (200 mL) at 0° C. was added EDC (21.35 g, 111 mmol), N,O-dimethylhydroxylamine hydrochloride (10.86 g, 111 mmol) and pyridine (15.01 mL, 186 mmol). The mixture was stirred at rt for 16 h and concentrated under reduced pressure. The residue was diluted with EtOAc (250 mL) and washed with 1N HCl (50 mL) and then brine. The organic layer was dried over sodium sulfate, filtered and concentrated under reduced pressure to give the title compound, which was used in next step without further purification. MS (ES$^+$) m/z: 245, 247 (M+H).

Step C: (5-Bromopyridin-2-yl)(4-iodo-1-((2-(trimethylsilyl)ethoxy)methyl)-1H-imidazol-2-yl)methanone: To a solution of 4-iodo-1-((2-(trimethylsilyl)ethoxy)methyl)-1H-imidazole (15.88 g, 49.0 mmol) in THF (100 mL) at −78° C. was added dropwise a solution of LDA (26.5 mL, 53.0 mmol, 2 M in THF). The reaction was stirred for 1 h and a solution of 5-bromo-N-methoxy-N-methylpicolinamide (10 g, 40.8 mmol) in THF (20 mL) was added dropwise. The resulting mixture was stirred at −78° C. for 1 h and it was quenched with saturated aqueous ammonium chloride (10 mL). The mixture was extracted with EtOAc (150 mL). The organic layer washed with brine, dried over sodium sulfate, filtered and concentrated under reduced pressure. The residue was purified by flash column chromatography on silica gel (eluting with petroleum ether:EtOAc=10:1 v/v) to give the title compound. $^1$H NMR (400 MHz, CDCl$_3$): δ 8.85 (s, 1H), 8.23 (m, 1H), 8.02 (m, 1H), 7.52 (s, 1H), 5.81 (s, 2H), 3.65 (m, 2H), 0.96 (m, 2H), −0.01 (s, 9H).

Intermediate 16

(5-Chloropyridin-2-yl)(4-iodo-5-methyl-1-((2-(trimethylsilyl)ethoxy)methyl)-1H-imidazol-2-yl)methanone

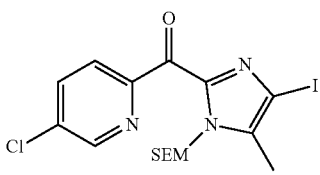 [SMILES: Cc1c(I)nc(C(=O)c2ccc(Cl)cn2)n1COCC[Si](C)(C)C]

Step A: 4-Iodo-5-methyl-1H-imidazole: A solution of 4-methyl-1H-imidazole (5.4 g, 65.8 mmol) and iodine (16.69 g, 65.8 mmol) in dioxane (51 ml) was treated with NaOH (132 ml, 132 mmol) for 1 h. Most organic solvent was removed under reduced pressure. It was neutralized by saturated ammonium chloride and extracted with ethyl acetate (2×100 mL). The combined organic layers were washed with brine, dried over sodium sulfate, filtered and concentrated. The residue was triturated in 50 mL of diethyl ether and aged for 10 min. The white solids were collected by filtration and dried under vacuum to give the title compound.

Step B: 4-Iodo-5-methyl-1-((2-(trimethylsilyl)ethoxy)methyl)-1H-imidazole: A solution of 5-iodo-4-methyl-1H-imidazole (4.42 g, 21.25 mmol) in DMF (24 ml) at 0° C. was added NaH (60% wt, 1.020 g, 25.5 mmol). It was stirred for 15 min and was added SEM-Cl (4.52 ml, 25.5 mmol). The mixture was stirred for 30 min and warmed to rt stirring for another 30 min. The reaction was quenched with saturated aqueous ammonium chloride (50 mL) and extracted with ethyl acetate (2×100 mL). The combined organic layers were washed with water (3×100 mL), brine (100 mL), dried over sodium sulfate, filtered and concentrate under reduced pressure. The residue was purified by flash column chromatography on silica gel (eluting with 0-5% 7 N $NH_3$ in MeOH/DCM) to give the title compound. MS (ESI) m/z 338.9; $^1$H NMR ($CDCl_3$, 500 MHz): δ 7.47 (s, 1H), 5.20 (s, 2H), 3.45 (t, J=8.0 Hz, 2 H), 2.24 (s, 3 H), 0.88 (t, J=8.0 Hz, 2H), −0.03 (s, 9 H). Structures were confirmed by ROESY 5-Iodo-4-methyl-1-((2-(trimethylsilyl)ethoxy)methyl)-1H-imidazole was isolated as a side product.

Step C: (5-Chloropyridin-2-yl)(4-iodo-5-methyl-1-((2-(trimethylsilyl)ethoxy)methyl)-1H-imidazol-2-yl)methanone: To a solution of 4-iodo-5-methyl-1-((2-(trimethylsilyl)ethoxy)methyl)-1H-imidazole (1 g, 2.96 mmol) in 10 mL of anhydrous THF at −78° C. was added a solution of LDA (2 M in THF/heptane/ethylbenzene) (1.8 ml, 3.60 mmol). It was stirred for 10 min and a solution of 5-chloro-N-methoxy-N-methylpicolinamide (0.712 g, 3.55 mmol) in 5 mL of THF was added. The mixture was stirred for 30 min and warmed to 0° C. stirring for 30 min. It was quenched with sat. aq. ammonium chloride and extracted with ethyl acetate (2×50 mL). The combined organic layers were dried over sodium sulfate, filtered and concentrated. The residue was purified by flash column chromatography on silica gel (eluting with 0-4% methanol in DCM, gradient) to give the title compound. MS (ESI) m/z 477.8.

Intermediate 17

(2-Bromo-1-((2-(trimethylsilyl)ethoxy)methyl)-1H-imidazol-4-yl)(5-chloropyridin-2-yl)methanone

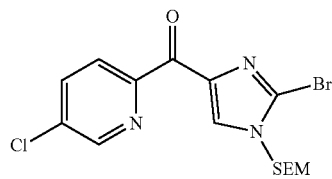 [SMILES: C[Si](C)(C)CCOCn1cc(C(=O)c2ccc(Cl)cn2)nc1Br]

Step A: 2-Bromo-1-((2-(trimethylsilyl)ethoxy)methyl)-1H-imidazole: To a stirred solution of 2-bromo-1H-imidazole (1 g, 6.80 mmol) in DMF (15 mL) was added NaH (0.272 g, 6.80 mmol, 60% wt) at 0° C. under nitrogen. The mixture was stirred at 0° C. for 1 h. To the resulting mixture was added SEM-Cl (1.207 mL, 6.80 mmol) and it was stirred at 20° C. for another 1 h. It was quenched carefully with water (15 mL) at 0° C. and the mixture was extracted with EtOAc (20 mL×4). The combined organic layers were dried over sodium sulfate, filtered and concentrated under reduced pressure. The residue was purified by flash column chromatography on silica gel (eluting with petroleum ether:ethyl acetate=3:1 v/v) to give the title compound. MS ($ES^+$) m/z: 277, 279 (M+H)

Step B: (2-Bromo-1-((2-(trimethylsilyl)ethoxy)methyl)-1H-imidazol-5-yl)(5-chloropyridin-2-yl)methanol: To a stirred solution of 2-bromo-1-((2-(trimethylsilyl)ethoxy)methyl)-1H-imidazole (15.53 g, 56.0 mmol) in THF (100 mL) at −78° C. cooled by a dry ice-acetone bath, a solution of LDA (30.2 mL, 60.3 mmol, 2 M in THF) was added under nitrogen. The mixture was stirred at −78° C. for 1 h, then 5-chloropicolinaldehyde (6.1 g, 43.1 mmol) was added into the reaction solution dropwise. After addition the bath was removed and the reaction was allowed to warm to rt and stirred for another 2 h. It was quenched with saturated aqueous ammonium chloride (100 mL) and the mixture was extracted with EtOAc (100 mL×4). The combined organic layers were dried over sodium sulfate, filtered and concentrated under reduced pressure. The residue was purified by flash column chromatography on silica gel (eluting with petroleum ether:EtOAc=1:1 v/v) to give the title compound. MS ($ES^+$) m/z: 418, 420 (M+H).

Step C: (2-Bromo-1-((2-(trimethylsilyl)ethoxy)methyl)-1H-imidazol-5-yl)(5-chloropyridin-2-yl)methanone: To a stirred solution of oxalyl dichloride (5.71 g, 45.0 mmol) in DCM (150 mL) was added DMSO (6.76 g, 87 mmol) at −78° C. under nitrogen. The mixture was stirred for 1 h, then (2-bromo-1-((2-(trimethylsilyl)ethoxy)methyl)-1H-imidazol-5-yl)(5-chloropyridin-2-yl)methanol (14.5 g, 34.6 mmol) was added through a syringe. The mixture was stirred at −78° C. for 1 h and TEA (19.30 mL, 138 mmol) was added. The reaction mixture was allowed to warm to rt and stirred for 12 h. It was quenched with ice water (100 mL) and extracted with EtOAc (100 mL×4). The combined organic layers were dried over sodium sulfate, filtered and concentrated under reduced pressure. The residue was purified by flash column chromatography on silica gel (eluting with petroleum ether:EtOAc=3:1 v/v) to give the title compound. MS ($ES^+$) m/z: 416, 418 (M+H).

Step D: (2-Bromo-1H-imidazol-5-yl)(5-chloropyridin-2-yl)methanone: To a degassed solution of (2-bromo-1-((2-(trimethylsilyl)ethoxy)methyl)-1H-imidazol-5-yl)(5-chloropyridin-2-yl)methanone (15 g, 36.0 mmol) in DCM (150 mL) at 0° C. was added TFA (30 mL, 389 mmol) under nitrogen. The resulting mixture was stirred at rt for 2 h. It was concentrated in vacuo to give the title compound, which was used for the next step without further purification. MS ($ES^+$) m/z: 286, 288 (M+H).

Step E: (2-Bromo-1-((2-(trimethylsilyl)ethoxy)methyl)-1H-imidazol-5-yl)(5-chloropyridin-2-yl)methanone: To a degassed solution of (2-bromo-1H-imidazol-5-yl)(5-chloropyridin-2-yl)methanone (10.3 g, 35.9 mmol) and SEM-Cl (8.3 mL, 46.7 mmol) in DCM (150 mL), DIEA (18.8 mL, 108 mmol) was added at 0° C. under nitrogen. The resulting mixture was stirred at 25° C. for 12 h. It was diluted with water (100 mL) and extracted with EtOAc (200 mL×4). The combined organic layers were dried over sodium sulfate, filtered and concentrated under reduced pressure. The residue was purified by flash column chromatography on silica gel (eluting with petroleum Intermediate 18

4-fluoro-2-(4,4,5,5-tetramethyl-1,3,2-dioxaborolan-2-yl)aniline

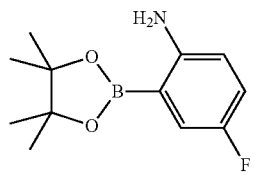 [SMILES: CC1(C)OB(c2cc(F)ccc2N)OC1(C)C]

The title compound was prepared by a modified procedure reported in the literature (Org. Lett., 2014, 16, 2916-2919). A mixture of 2-bromo-4-fluoroaniline (20 g, 105 mmol), PdCl$_2$(PPh$_3$)$_2$(7.39 g, 10.53 mmol), 4,4,5,5-tetramethyl-1,3,2-dioxaborolane (40.4 g, 316 mmol) and Et$_3$N (58.7 mL, 421 mmol) in dioxane (400 mL) was stirred at 110° C. for 16 h under nitrogen atmosphere. It was cooled to rt and poured into a saturated aqueous solution of ammonium chloride (300 mL). The mixture was extracted with DCM (300 mL). The organic layer was separated, dried over sodium sulfate, and filtered. The filtrate was concentrated and the residue was purified by flash column chromatography on silica gel (eluting with EtOAc/petroleum ether=10:90 v/v) to give the title compound. $^1$H NMR (400 MHz, CDCl$_3$): δ 7.25 (m, 1H), 6.92 (m, 1H), 6.54 (m, 1H), 4.42 (brs, 2H), 1.34 (s, 12H).

Intermediate 19 methyl (3-amino-4-(4,4,5,5-tetramethyl-1,3,2-dioxaborolan-2-yl)phenyl)carbamate

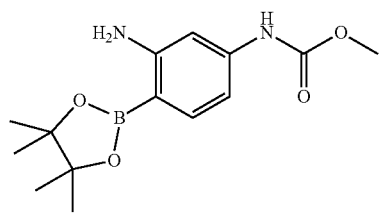

Step A: Methyl (4-bromo-3-nitrophenyl)carbamate: To a stirred mixture of 4-bromo-3-nitroaniline (11 g, 50.7 mmol) in anhydrous THF (230 mL) cooled by an ice-water bath was added NaH (60% wt in mineral oil, 2.43 g, 60.8 mmol) in small portions. The mixture was stirred for 10 min and methyl chloroformate (4.49 mL, 65.9 mmol) was added dropwise. The reaction mixture was stirred overnight while the bath temperature was allowed to warm to rt. It was cooled to 0° C. and quenched carefully with water (8 mL). The mixture was diluted with brine (100 mL) and extracted with ethyl acetate (2×100 mL). The organic layer was separated, dried over anhydrous magnesium sulfate, filtered and concentrated under reduced pressure to give the title compound. $^1$H NMR (500 MHz, CDCl$_3$): δ 8.05 (d, 1H), 7.66 (d, 1H), 7.48 (d, 1H), 6.86 (s, 1H), 3.84 (s, 3H).

Step B: Methyl (3-amino-4-bromophenyl)carbamate: To a stirred mixture of methyl (4-bromo-3-nitrophenyl)carbamate (14.3 g, 52.0 mmol) and ammonium chloride (8.34 g, 156 mmol) in ethanol (195 mL)-water (65.0 mL) was added iron powder (8.71 g, 156 mmol). The mixture was stirred at 80° C. for 3 h. It was cooled to rt and diluted with dichloromethane (300 mL). The mixture was filtered through a pad of Celite. The filtrate was transferred to a separatory funnel and extracted with dichloromethane (2×80 mL). The combined organic layers were washed with brine (150 mL), dried over anhydrous magnesium sulfate, filtered and concentrated under reduced pressure. The residue was purified by flash column chromatography on silica gel (eluting with EtOAc/hexane=1/1 v/v) to give the title compound. MS (ES$^+$) m/z: 245, 247 (M+H).

Step C: Methyl (3-amino-4-(4,4,5,5-tetramethyl-1,3,2-dioxaborolan-2-yl)phenyl)carbamate: A mixture of bis(pinacolato)diboron (4.14 g, 16.32 mmol), methyl (3-amino-4-bromophenyl)carbamate (2.00 g, 8.16 mmol), potassium acetate (2.403 g, 24.48 mmol) and 1,1'-bis(diphenylphosphino)ferrocene-palladium(II)dichloride dichloromethane complex (0.666 g, 0.816 mmol) in a round bottom flask charged with a magnetic stirring bar was vacuumed and backfilled with nitrogen three times. Degassed dioxane (40.8 mL) was added subsequently and the resulting mixture was stirred at 100° C. under nitrogen for 4 h. It was cooled to rt and diluted with ethyl acetate (100 mL). The mixture washed with water (50 mL). The organic layer was separated and dried over anhydrous magnesium sulfate, filtered and concentrated under reduced pressure. The residue was purified by flash column chromatography on silica gel (eluting with EtOAc/hexane=30% v/v) to give the title compound. MS (ES$^+$) m/z: 293 (M+H).

Intermediate 20 methyl 4-amino-3-(4,4,5,5-tetramethyl-1,3,2-dioxaborolan-2-yl)benzoate

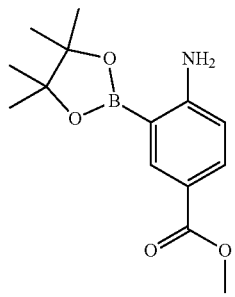

The title compound was prepared from methyl 4-amino-3-bromobenzoate by the procedure described in the synthesis of Intermediate 19 Step C. MS (ES$^+$) m/z: 278 (M+H).

Intermediate 21 tert-butyl (3-amino-4-(4,4,5,5-tetramethyl-1,3,2-dioxaborolan-2-yl)phenyl)carbamate

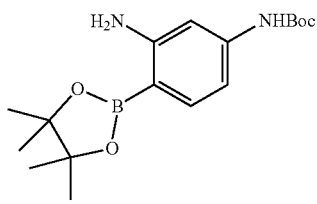 [SMILES: CC(C)(C)OC(=O)Nc1ccc(B2OC(C)(C)C(C)(C)O2)c(N)c1]

Step A: tert-Butyl (4-bromo-3-nitrophenyl)carbamate: To a stirred mixture of 4-bromo-3-nitroaniline (20 g, 92 mmol), DMAP (5.63 g, 46.1 mmol) and Boc$_2$O (24.14 g, 111 mmol) in THF (300 mL) at 0° C. DIEA (23.82 g, 184 mmol) was added. The mixture was stirred at rt for 16 h. Hydrochloric acid (1 M, 200 mL) was added to the reaction and the mixture was extracted with ethyl acetate (3×200 mL). The combined organic fractions were washed with aqueous sodium bicarbonate (saturated, 2×200 mL), dried over sodium sulfate, filtered and the solvent was evaporated under reduced pressure. The residue was purified by flash column chromatography on silica gel (eluting with petroleum ether:EtOAc=10:1 v/v) to give the title compound.

Step B: tert-Butyl (3-amino-4-bromophenyl)carbamate: To a round bottom flask were added tert-butyl (4-bromo-3-nitrophenyl)carbamate (10 g, 31.5 mmol), EtOH (200 mL), water (40 mL), ammonium hydrochloride (16.87 g, 315 mmol) and iron powder (17.61 g, 315 mmol). The reaction mixture was stirred at 80° C. for 2 h and it was allowed to cool to rt. The mixture was filtered through a pad of Celite and the filtrate was concentrated under reduced pressure. The residue was diluted with water (100 mL) and was extracted with ethyl acetate(200 mL×3). The combined organic layers were dried over sodium sulfate, filtered and concentrated under reduced pressure to give the title compound, which was used without further purification.

Step C: tert-Butyl (3-amino-4-(4,4,5,5-tetramethyl-1,3,2-dioxaborolan-2-yl)phenyl)carbamate: A mixture of tert-butyl (3-nitro-4-(4,4,5,5-tetramethyl-1,3,2-dioxaborolan-2-yl)phenyl)carbamate (28.50 g, 78.00 mmol) and Pd—C (2.50 g, 2.35 mmol) in MeOH (300 mL) was stirred at 25° C. for 2 h under H$_2$ atmosphere. The mixture was filtered and the filter cake washed with methanol (500 mL). The filtrate was concentrated under reduced pressure to give the title compound. MS (ESI) m/z: 335 [M+H]. $^1$H NMR (400 MHz, CDCl$_3$): δ 7.48 (d, J=8.0 Hz, 1H), 6.92 (brs, 1H), 6.41 (dd, J=2.0, 8.0 Hz, 2H), 4.78 (brs, 2H), 1.50 (s, 9H), 1.32 (s, 12H).

Intermediate 22 ethyl (3-amino-4-(4,4,5,5-tetramethyl-1,3,2-dioxaborolan-2-yl)phenyl)carbamate

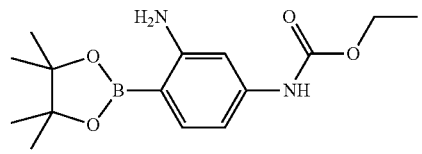 [SMILES: CCOC(=O)Nc1ccc(B2OC(C)(C)C(C)(C)O2)c(N)c1]

The title compound was prepared from by the procedure described in the synthesis of Intermediate 19. The product was purified by flash column chromatography on silica gel (eluting with petroleum ether:EtOAc=15:1 to 5:1) to give the title compound. MS (ESI) m/z 307.1 (M+H); $^1$H NMR (400 MHz, CDCl$_3$): δ 7.52 (d, J=8.2 Hz, 1H), 6.92 (brs, 1H), 6.58-6.41 (m, 2H), 4.79 (brs, 2H), 4.21 (q, J=7.0 Hz, 2H), 1.33 (s, 12H), 1.25 (t, J=7.0 Hz, 3H).

Intermediate 23 methyl (5-amino-4-bromo-2-fluorophenyl)carbamate

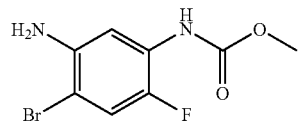

Step A: Methyl (4-bromo-2-fluoro-5-nitrophenyl)carbamate: To a solution of 4-bromo-2-fluoro-5-nitroaniline (4.40 g, 18.72 mmol) in THF (100 mL) was added DIEA (9.81 mL, 56.20 mmol) and methyl chloroformate (5.31 g, 56.20 mmol). The mixture was stirred at 25° C. for 15 h. Most solvent was removed; the residue was added EtOAc (100 mL) and washed with brine (50 mL×2), dried over sodium sulfate, filtered and concentrated. The residue was purified by flash column chromatography on silica gel (eluting with petroleum ether:EtOAc=20:1-10:1) to give the title compound. $^1$H NMR (400 MHz, CDCl$_3$): δ 8.80 (d, J=5.9 Hz, 1H), 7.46 (d, J=9.8 Hz, 1H), 6.99 (brs, 1H), 3.84 (s, 3H).

Step B: Methyl (5-amino-4-bromo-2-fluorophenyl)carbamate: To a solution of methyl (4-bromo-2-fluoro-5-nitrophenyl)carbamate (3.70 g, 12.63 mmol) in EtOH (60 mL) and water (20 mL) was added iron (1.41 g, 25.30 mmol) and ammonium chloride (2.70 g, 50.50 mmol). The mixture was stirred at 30° C. for 16 h. The reaction mixture was filtered and the filtrate was concentrated under reduced pressure. The residue was added EtOAc (100 mL) and washed with brine (50 mL×2), dried over sodium sulfate, filtered and concentrated. The residue was purified by flash column chromatography on silica gel (eluting with petroleum ether:EtOAc=15:1) to give the title compound. MS (ESI) m/z 263, 265 (M+H); $^1$H NMR (400 MHz, CDCl$_3$): δ 7.62 (brs, 1H), 7.14 (d, J=10.2 Hz, 1H), 6.77 (brs, 1H), 3.97 (brs, 2H), 3.78 (s, 3H).

Intermediate 24

(4-carboxypentyl)triphenylphosphonium bromide

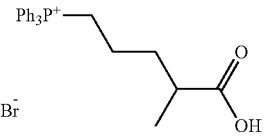

Step A: Diethyl 2-(3-bromopropyl)-2-methylmalonate: To a stirred suspension of sodium hydride (12.63 g, 316 mmol, 60% wt) in THF (200 mL) under nitrogen was added a solution of diethyl 2-methylmalonate (50 g, 287 mmol) in THF (50 mL) at 0° C. It was stirred for 0.5 h and 1,3-dibromopropane (87 g, 431 mmol) was added. The reaction was heated to 70° C. and stirred for another 3 h. It was cooled to 0° C. and carefully quenched with water. It was extracted with EtOAc (100 mL×3). The combined organic layers were washed with brine (100 mL), dried over sodium sulfate, filtered and concentrated. The residue was purified by flash column chromatography on silica gel (eluting with petroleum ether:ethyl acetate=100:1 to 30:1) to give the title compound. MS: (ESI) m/z 295.2, 297.2 (M+H).

Step B: 5-Bromo-2-methylpentanoic acid: To a stirred solution of diethyl 2-(3-bromopropyl)-2-methylmalonate (48 g, 163 mmol) in acetic acid (55 mL) was added hydrogen bromide (52.60 g, 650 mmol). The mixture was stirred at 120° C. for 15 h. It was cooled to rt and concentrated under reduced pressure. The residue was added water (50 mL) and extracted with DCM (70 mL×3) and the organic layer washed with brine (30 mL), dried over sodium sulfate and filtered. The filtrate was concentrated to give the title compound.

Step C: (4-Carboxypentyl)triphenylphosphonium bromide: To a stirred solution of 5-bromo-2-methylpentanoic acid (29 g, 149 mmol) in toluene (260 mL) was added triphenylphosphine (46.80 g, 178 mmol). Then the mixture was stirred at 120° C. under N₂ for 16 h. It was cooled to rt and transferred to a separatory funnel. The toluene layer was separated out and the product layer washed with hot toluene (30 mL×5). It was separated and purified by flash column chromatography on silica gel (eluting with DCM:MeOH=20:1) to give the title compound. MS: (ESI) m/z 377.1 (M+H). ¹H NMR (400 MHz, CDCl₃): δ 7.81-7.76 (m, 9H), 7.72-7.69 (m, 6H), 4.07-3.98 (m, 1H), 3.32-3.16 (m, 2H), 2.03-1.98 (m, 1H), 1.75-1.64 (m, 3H), 1.09 (d, J=6.4 Hz, 3H).

Intermediate 25

5-((1-phenyl-1H-tetrazol-5-yl)sulfonyl)pentanoic acid

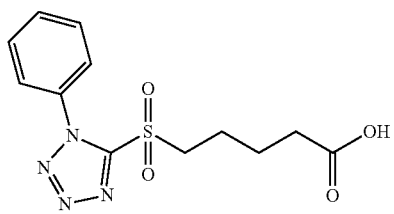 [SMILES: O=C(O)CCCCS(=O)(=O)c1nnnn1-c1ccccc1]

Step A: Ethyl 5-((1-phenyl-1H-tetrazol-5-yl)thio)pentanoate: To a solution of 1-phenyl-1H-tetrazole-5-thiol (38 g, 213 mmol) and ethyl 5-bromopentanoate (49.00 g, 235 mmol) in acetone (40 mL) was added K₂CO₃ (29.50 g, 213 mmol). The mixture was stirred for 3 h and it was filtered through a pad of Celite. The filtrate was concentrated under reduced pressure and the residue was purified by flash column chromatography on silica (petroleum ether:ethyl acetate from 100:1 to 10:1) to give the title compound. MS: (ESI) m/z 307.0 (M+H).

Step B: 5-((1-Phenyl-1H-tetrazol-5-yl)thio)pentanoic acid: To a stirred solution of ethyl 5-((1-phenyl-1H-tetrazol-5-yl)thio)pentanoate (65 g, 212 mmol) in THF (200 mL) and water (160 mL) was added LiOH (20.32 g, 849 mmol). The mixture was stirred at rt for 16 h. Aqueous HCl (1 N) was added to adjust pH to 5. The mixture was extracted with ethyl acetate (500 mL×2). The combined organic layers were dried over sodium sulfate, filtered and the filtrate was concentrated to give the title compound. MS: (ESI) m/z 279.0 (M+H).

Step C: 5-((1-Phenyl-1H-tetrazol-5-yl)sulfonyl)pentanoic acid: To a stirred solution of 5-((1-phenyl-1H-tetrazol-5-yl)thio)pentanoic acid (26 g, 93 mmol) in EtOH (100 mL) was added ammonium molybdate tetrahydrate (11.55 g, 9.34 mmol) at 0° C. The mixture was stirred for 5 min, then hydrogen peroxide (635 g, 5605 mmol) was added slowly. The mixture was stirred at 40° C. for 16 h. It was extracted with DCM (200 mL×2). The combined organic layers were washed with aqueous Na₂SO₃ (0.5 M, 200 mL), dried over sodium sulfate and filtered. The filtrate was concentrated to give the title compound. MS: (ESI) m/z 311.0 (M+H). ¹H NMR (400 MHz, CDCl₃): δ 7.51-7.68 (m, 5H), 3.67-3.75 (m, 2H), 2.39 (t, J=7.2 Hz, 2H), 1.93-2.04 (m, 2H), 1.79 (q, J=7.4 Hz, 2H).

Intermediate 26

5-(benzo[d]thiazol-2-ylsulfonyl)pentanoic acid

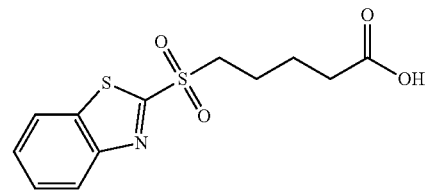 [SMILES: O=C(O)CCCCS(=O)(=O)c1nc2ccccc2s1]

The title compound was prepared from benzo[d]thiazole-2-thiol by the procedure described in the synthesis of Intermediate 25. MS: (ESI) m/z 300.0 (M+H); ¹H NMR (400 MHz, CDCl₃): δ 8.20 (d, J=7.8 Hz, 1H), 8.01 (d, J=8.2 Hz, 1H), 7.55-7.66 (m, 2H), 3.48-3.58 (m, 2H), 2.38 (t, J=7.2 Hz, 2H), 1.89-2.00 (m, 2H), 1.75-1.84 (m, 2H).

Intermediate 27

5-(benzo[d]thiazol-2-ylsulfonyl)-2,2-dimethylpentanoic acid

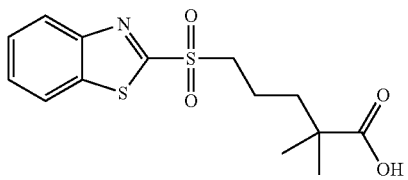 [SMILES: CC(C)(CCCS(=O)(=O)c1nc2ccccc2s1)C(=O)O]

Step A: Methyl 5-(benzo[d]thiazol-2-ylthio)-2-methylpentanoate: To a solution of methyl 5-(benzo[d]thiazol-2-ylthio)pentanoate (120 g, 426 mmol) in THF (1500 mL) at −78° C. was added a solution of LDA (299 mL, 597 mmol, 2 M in THF) dropwise. The reaction was stirred for 0.5 h before iodomethane (78 mL, 1258 mmol) was added. It was stirred for another 2 h and quenched with saturated aqueous ammonium chloride (500 mL). The mixture was allowed to warm to rt and extracted with EtOAc (800 mL×2). The combined organic layers were dried over sodium sulfate and concentrated under reduced pressure. The residue was purified by flash column chromatography on silica (petroleum ether:EtOAc from 20:1 to 10:1, gradient) to give the title compound. $^1$H NMR (400 MHz, CDCl$_3$) δ 7.82 (dd, J=1.1, 8.1 Hz, 1H), 7.71 (dd, J=1.2, 8.0 Hz, 1H), 7.37 (ddd, J=1.2, 7.2, 8.2 Hz, 1H), 7.23-7.28 (m, 1H), 3.59-3.66 (m, 3H), 3.26-3.34 (m, 2H), 2.46-2.50 (m, 1H), 1.77-1.84 (m, 3H), 1.56-1.61 (m, 1H), 1.14 (d, J=7.0 Hz, 3H).

Step B: Methyl 5-(benzo[d]thiazol-2-ylthio)-2,2-dimethylpentanoate: To a solution of methyl 5-(benzo[d]thiazol-2-ylthio)-2-methylpentanoate (3 g, 10.16 mmol) in THF (45 mL) at −78° C. was added solution of LDA (6.60 mL, 13.20 mmol, 2 M in THF) dropwise. The reaction was stirred for 0.5 h before iodomethane (2.51 mL, 40.30 mmol) was added. It was stirred for 0.5 h and quenched with saturated aqueous ammonium chloride (30 mL). The mixture was allowed to warm to rt and extracted with EtOAc (50 mL×2). The combined organic layers were dried over sodium sulfate and concentrated under reduced pressure to give the title compound.

Step C: 5-(Benzo[d]thiazol-2-ylthio)-2,2-dimethylpentanoic acid: To a solution of methyl 5-(benzo[d]thiazol-2-ylthio)-2,2-dimethylpentanoate (5.50 g, 17.77 mmol) in THF (55 mL) and water (55 mL) was added LiOH (3.41 g, 142 mmol) at 20° C. The mixture was stirred for 72 h and HCl (1 M) was added to adjust pH to 5. The mixture was extracted with EtOAc (50 mL×2). The combined organic layers were dried over sodium sulfate and filtered. The filtrate was concentrated to give the title compound, which was used to the next step directly without further purification. MS (ESI) m/z 296.2 (M+H).

Step D: 5-(Benzo[d]thiazol-2-ylsulfonyl)-2,2-dimethylpentanoic acid: To a solution of 5-(benzo[d]thiazol-2-ylthio)-2,2-dimethylpentanoic acid (4.90 g, 16.59 mmol) in EtOH (5 mL) at 0° C. was added ammonium molybdate tetrahydrate (2.05 g, 1.66 mmol). The mixture was stirred for 5 min, and hydrogen peroxide (113 g, 995 mmol) was added slowly. The mixture was stirred at 15° C. for 12 h. Water (80 mL) was added, and the mixture was extracted with EtOAc (50 mL×3). The combined organic layers were washed with saturated sodium thiosulfate (80 mL), dried over sodium sulfate and filtered. The filtrate was concentrated under reduced pressure to give the title compound. MS (ESI) m/z 328.0 (M+H); $^1$H NMR (400 MHz, CDCl$_3$) δ 8.24-8.19 (m, 1H), 8.02 (d, J=7.3 Hz, 1H), 7.67-7.58 (m, 2H), 3.55-3.47 (m, 2H), 2.04-1.80 (m, 2H), 1.79-1.62 (m, 2H), 1.25-1.15 (m, 6H).

Intermediate 28

1-(3-(benzo[d]thiazol-2-ylsulfonyl)propyl)cyclopropane-1-carboxylic acid

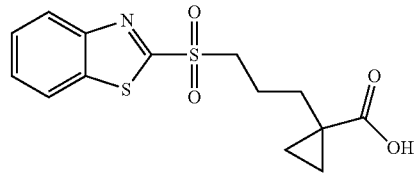 [SMILES: O=C(O)C1(CCCS(=O)(=O)c2nc3ccccc3s2)CC1]

Step A: tert-Butyl 1-(3-bromopropyl)cyclopropanecarboxylate: To a solution of diisopropylamine (12.52 g, 124 mmol) in THF (300 mL) was added n-BuLi (49.5 mL, 124 mmol, 2.5M in hexane) slowly at −10° C. After the addition was completed, the mixture was stirred at −10° C. for 0.5 h and cooled to −70° C. To the reaction mixture was added dropwise tert-butyl cyclopropanecarboxylate (16 g, 113 mmol) followed by 1,3-dibromopropane (45.4 g, 225 mmol). After addition, the reaction mixture was gradually warmed to 25° C. for 3 h. It was quenched with saturated aqueous ammonium chloride solution (150 mL), and extracted with EtOAc (150 mL×3). The combined organic fractions were washed with brine (20 mL), dried over sodium sulfate, filtered and the solvent was evaporated. The crude compound was purified by column chromatography on silica gel (petroleum ether:ethyl acetate=100:1) to give the title compound.
$^1$H NMR (400 MHz, CDCl$_3$): δ 3.40 (t, J=6.7 Hz, 2H), 2.25 (d, J=6.7 Hz, 2H), 1.55-1.60 (m, 2H), 1.42 (s, 9H), 0.73-0.76 (m, 2H), 0.62 (dd, J=1.8, 2.7 Hz, 2H).

Step B: tert-Butyl 1-(3-(benzo[d]thiazol-2-ylthio)propyl)cyclopropanecarboxylate: To a solution of benzo[d]thiazole-2-thiol (2.67 g, 15.96 mmol) and tert-butyl 1-(3-bromopropyl)cyclopropanecarboxylate (4 g, 6.08 mmol, 40% purity) in acetone (30 mL) was added K$_2$CO$_3$ (4.20 g, 30.4 mmol) at 25° C. After addition, the mixture was stirred for 2 h. Solids were removed by filtration through a pad of Celite. The filtrate was concentrated under reduced pressure. The residue was purified by column chromatography on silica gel (petroleum ether:EtOAc from 20:1 to 10:1) to the title compound. MS (ESI) m/z 350.0 (M+H).

Step C: 1-(3-(Benzo[d]thiazol-2-ylthio)propyl)cyclopropanecarboxylic acid: To a stirred solution of tert-butyl 1-(3-(benzo[d]thiazol-2-ylthio)propyl)cyclopropanecarboxylate (5.5 g, 15.74 mmol) in EtOAc (40 mL) was added a solution of HCl in ethyl acetate (4 M, 40 mL, 40 mmol). The mixture was stirred 25° C. for 2 h. It was concentrated under reduced pressure. The residue was triturated with 80 mL petroleum ether. The solids were filtered and rinsed with petroleum ether (20 mL×2) to give the title compound, which was used into the next step without further purification. MS (ESI) m/z 294.0 (M+H).

Step D: 1-(3-(Benzo[d]thiazol-2-ylsulfonyl)propyl)cyclopropanecarboxylic acid: A solution of 1-(3-(benzo[d]thiazol-2-ylthio)propyl)cyclopropanecarboxylic acid (4 g, 13.63 mmol) in THF (60 mL) at 0° C. was added ammonium molybdate tetrahydrate (1.685 g, 1.363 mmol). The mixture was stirred for 5 min, then hydrogen peroxide (15.46 g, 136 mmol) was added slowly into the mixture. The mixture was stirred at 25° C. for 16 h and it was quenched with aqueous sodium thiosulfate (100 mL, 50% solution). The mixture was extracted with EtOAc (70 mL×3). The combined organic layers were washed with brine (40 mL), dried over sodium sulfate and filtered. The filtrate was concentrated under reduced pressure to give the title compound, which was used to the next step without further purification. MS (ESI) m/z 348.1 (M+Na); $^1$H NMR (400 MHz, CDCl$_3$): δ 8.17-8.23 (m, 1H), 7.97-8.04 (m, 1H), 7.53-7.66 (m, 2H), 3.40-3.57 (m, 2H), 2.01-2.15 (m, 2H), 1.61-1.73 (m, 2H), 1.24-1.32 (m, 2H), 0.74-0.81 (m, 1H), 0.74-0.81 (m, 1H).

Intermediate 29

5-(benzo[d]thiazol-2-ylsulfonyl)-4-methylpentanoic acid

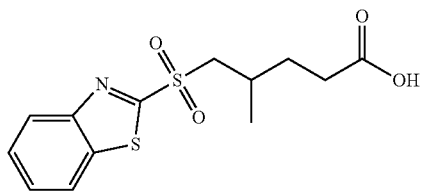 [SMILES: CC(CCC(=O)O)CS(=O)(=O)c1nc2ccccc2s1]

Step A: 1,3-Dibromo-2-methylpropane: 2-Methylpropane-1,3-diol (10 g, 111 mmol) was added slowly to tribromophosphine (21.08 mL, 222 mmol) at 0° C. After addition, the mixture was stirred at 80° C. for 18 h. The reaction mixture was cooled to rt and poured into a cooled aqueous solution of sodium carbonate (2.0 L) at 0° C. The mixture was extracted with DCM (500 mL×3). The combined organic layers were washed with brine (500 mL), dried over sodium sulfate, filtered and concentrated. The residue was purified by flash column chromatography on silica gel (eluting with petroleum ether) to give the title compound. $^1$H NMR (CDCl$_3$, 400 MHz): δ 3.56-3.49 (m, 2H), 3.49-3.42 (m, 2H), 2.24-2.12 (m, 1H), 1.15 (d, J=6.8 Hz, 3H).

Step B: Triethyl 4-bromo-3-methylbutane-1,1,1-tricarboxylate: A mixture of triethyl methanetricarboxylate (12 g, 51.7 mmol), 1,3-dibromo-2-methylpropane (13.39 g, 62.0 mmol) and K$_2$CO$_3$ (7.86 g, 56.8 mmol) in DMF (130 mL) was stirred at 80° C. for 18 h. It was cooled to rt and quenched with water (300 mL). The mixture was extracted with EtOAc (150 mL×2). The combined organic layers were washed with brine (150 mL), dried over sodium sulfate, filtered and concentrated. The residue was purified by flash column chromatography on silica gel (EtOAc in petroleum ether=0% to 2%, gradient) to give the title compound. $^1$H NMR (CDCl$_3$, 400 MHz): δ 4.25 (q, J=7.1 Hz, 6H), 3.51-3.42 (m, 1H), 3.41-3.32 (m, 1H), 2.42-2.31 (m, 1H), 2.22-2.07 (m, 2H), 1.29 (t, J=7.0 Hz, 9H), 1.08 (d, J=6.5 Hz, 3H).

Step C: 5-Bromo-4-methylpentanoic acid: To a solution of triethyl 4-bromo-3-methylbutane-1,1,1-tricarboxylate (8.5 g, 23.15 mmol) in AcOH (60 mL) was added HBr (18.73 g, 93 mmol). The mixture was stirred for 18 h at 120° C. under nitrogen. It was cooled to rt and concentrated under reduced pressure. The residue was added EtOAc (150 mL) and washed with brine (100 mL×3). The organic layer was dried over sodium sulfate, filtered and concentrated under reduced pressure to give the title compound.

Step D: Methyl 5-bromo-4-methylpentanoate: To a solution of 5-bromo-4-methylpentanoic acid (4.7 g, 24.10 mmol) in MeOH (50 mL) was slowly added concentrated H$_2$SO$_4$ (0.642 mL, 12.05 mmol). The mixture was heated to reflux under nitrogen for 18 h. It was cooled to rt and diluted with water (50 mL). The pH of the solution was adjusted to 7-8 by addition of aqueous sodium bicarbonate. The mixture was extracted with EtOAc (30 mL×3). The combined organic layers were washed with brine (50 mL×2), dried over sodium sulfate, filtered and concentrated under reduced pressure to give the title compound.

Step E: Methyl 5-(benzo[d]thiazol-2-ylthio)-4-methylpentanoate: A mixture of methyl 5-bromo-4-methylpentanoate (4.2 g, 20.09 mmol), benzo[d]thiazole-2-thiol (5.04 g, 30.1 mmol) and K$_2$CO$_3$ (4.16 g, 30.1 mmol) in acetonitrile (100 mL) was stirred at 25° C. for 18 h. It was quenched with water (300 mL) and extracted with EtOAc (100 mL×3). The combined organic layers were washed with brine (150 mL), dried over sodium sulfate, filtered and concentrated. The residue was purified by column chromatography on silica gel (EtOAc in petroleum ether=0%-6%, gradient) to give the title compound. MS (ESI) m/z: 296.1 (M+H);

Step F: 5-(Benzo[d]thiazol-2-ylthio)-4-methylpentanoic acid: To a solution of methyl 5-(benzo[d]thiazol-2-ylthio)-4-methylpentanoate (5.28 g, 17.87 mmol) in THF (80 mL) was added an aqueous solution of LiOH (2 N, 13.40 mL, 26.8 mmol). It was stirred for 3 h and diluted with water (200 mL). The pH of the solution was adjusted to 4-5 by addition of aqueous HCl (1 N). The mixture was extracted with EtOAc (80 mL×3). The combined organic layers were washed with brine (120 mL), dried over sodium sulfate, filtered and concentrated to give the title compound.

Step G: 5-(Benzo[d]thiazol-2-ylsulfonyl)-4-methylpentanoic acid: To a stirred mixture of 5-(benzo[d]thiazol-2-ylthio)-4-methylpentanoic acid (5.03 g, 17.88 mmol) in THF (50 mL) and water (25 mL) at 0° C. was added oxone (29.1 g, 47.4 mmol). The mixture was stirred at rt overnight. It was diluted with ice-water (100 mL) and quenched with saturated aqueous sodium thiosulfate. The mixture was extracted with DCM (150 mL×3). The combined organic layers were washed with brine (200 mL), dried over sodium sulfate, filtered and concentrated under reduced pressure to give the title compound. MS (ESI) m/z: 314.0 (M+H); $^1$H NMR (CDCl$_3$, 400 MHz): δ 8.21 (dd, J=1.3, 7.6 Hz, 1H), 8.05-7.99 (m, 1H), 7.68-7.56 (m, 2H), 3.57 (dd, J=5.0, 14.3 Hz, 1H), 3.40 (dd, J=7.6, 14.4 Hz, 1H), 2.44-2.30 (m, 3H), 1.96-1.84 (m, 1H), 1.75-1.61 (m, 1H), 1.17 (d, J=4.0 Hz, 3H).

Intermediate 30 cis-2-(2-((benzo[d]thiazol-2-ylsulfonyl)methyl)cyclopropyl)acetic acid

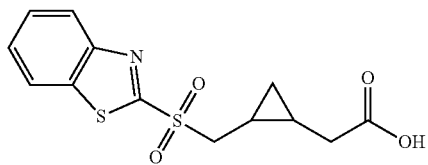 [SMILES: O=C(O)CC1CC1CS(=O)(=O)c1nc2ccccc2s1]

Step A: Benzyl 2-diazoacetate: To a stirred biphasic mixture of benzyl 2-aminoacetate hydrochloride (10 g, 49.6 mmol) in 1:1 water/DCM (166 ml) at 0° C. under nitrogen was added dropwise a solution of sodium nitrite (6.84 g, 99 mmol) in water (6 mL). The resulting mixture was stirred for 1.5 h at 0° C. then warmed to rt overnight. It was diluted with sodium bicarbonate (saturated, 100 mL) and extracted with dichloromethane (100 mL×3). The combined organic layers were dried over magnesium sulfate, filtered and concentrated under reduced pressure. The residue was purified by flash column chromatography on silica gel (eluting with 3:1 EtOAc/EtOH and hexane, 0 to 30%, gradient) to afford the title compound. MS (ES+) m/z: 208.1 (M+32).

Step B: cis-Benzyl 2-(2-(tert-butoxy)-2-oxoethyl)cyclopropane-1-carboxylate and trans-benzyl 2-(2-(tert-butoxy)-2-oxoethyl)cyclopropane-1-carboxylate: To a stirred solution of tert-butyl but-3-enoate (3.5 g, 24.61 mmol) and rhodium (II) acetate (1.088 g, 4.92 mmol) in DCM (35.2 ml) under nitrogen was added dropwise benzyl 2-diazoacetate (4.77 g, 27.1 mmol) and allowed to continue stirring overnight. The resulting solution was filtered over a pad of Celite and the filtrate was concentrated under reduced pressure. The residue was purified by flash column chromatography on silica gel (eluting with 3:1 EtOAc/EtOH and hexane, 0 to 20%, gradient) to afford the title compounds. Isomer A (cis, faster eluting) MS (ES+) m/z: 313.1 (M+Na). Isomer B (trans, slower eluting) MS (ES+) m/z: 313.1 (M+Na).

Step C: cis-2-(2-(tert-Butoxy)-2-oxoethyl)cyclopropane-1-carboxylic acid: A mixture of cis-Benzyl 2-(2-(tert-butoxy)-2-oxoethyl)cyclopropane-1-carboxylate (1.22 g, 4.20 mmol) and palladium on carbon catalyst (0.447 g, 0.420 mmol) in MeOH (21 ml) was stir under atmospheric pressure of hydrogen for 7 h at which point it was filtered over a pad of Celite. The filtrate was evaporated under reduced pressure to afford the title compound. MS (ES+) m/z: 201.1 (M+H).

Step D: cis-tert-Butyl 2-(2-(hydroxymethyl)cyclopropyl)acetate: To a solution of cis-2-(2-(tert-butoxy)-2-oxoethyl)cyclopropane-1-carboxylic acid (704 mg, 3.52 mmol) in THF (35.2 ml) with stirring under an atmosphere of nitrogen was slowly added the borane (1 M in THF, 8.79 ml, 8.79 mmol). It was allowed to progress for 6 h at which point the solution was cooled to 0° C. and water (250 uL) was added followed by MeOH (5 mL) until bubbling stopped. The solution was evaporated under reduced pressure. The residue was purified by normal phase chromatography (gradient elution with 3:1 EtOAc/EtOH and hexane, 0 to 40%, gradient) to afford the title compound. MS (ES+) m/z: 187.1 (M+H).

Step E: cis-Butyl 2-(2-(bromomethyl)cyclopropyl)acetate: To a stirred mixture of cis-tert-butyl 2-(2-(hydroxymethyl)cyclopropyl)acetate (322 mg, 1.729 mmol) in DCM (14.40 ml) was added triphenylphosphine (680 mg, 2.59 mmol) followed by carbon tetrabromide (860 mg, 2.59 mmol). It stirred for 24 h at which point the mixture was evaporated under reduced pressure. After the addition of acetone (50 mL) the solid was filtered off and the filtrate was evaporated under reduced pressure to afford the title compound, which was used without purification. MS (ES+) m/z: 193.0 (M-56).

Step F: cis-tert-Butyl 2-(2-((benzo[d]thiazol-2-ylthio)methyl)cyclopropyl)acetate: A mixture of benzo[d]thiazole-2-thiol (434 mg, 2.59 mmol) and potassium carbonate (359 mg, 2.59 mmol) was stirred in acetone (6.92 mL) under nitrogen for 10 min. A solution of cis-butyl 2-(2-(bromomethyl)cyclopropyl)acetate (431 mg, 1.730 mmol) in acetone (6.9 ml) was added and the reaction was allowed to proceed overnight. The solids were filtered off and the filtrate was evaporated under reduced pressure. The residue was purified by flash column chromatography on silica gel (eluting with 3:1 EtOAc/EtOH and hexane, 0 to 5%, gradient) to afford the title compound. MS (ES+) m/z: 336.1 (M+H).

Step G: cis-2-(2-((Benzo[d]thiazol-2-ylthio)methyl)cyclopropyl)acetic acid: A solution of cis-tert-butyl 2-(2-((benzo[d]thiazol-2-ylthio)methyl)cyclopropyl)acetate (300 mg, 0.894 mmol) in 1:1 DCM/TFA (17.88 mL) was stirred for 1 h. Most solvent was evaporated under reduced pressure to give the title compound, which was used without purification. MS (ES+) m/z: 280.0 (M+H).

Step H: cis-2-(2-((Benzo[d]thiazol-2-ylsulfonyl)methyl)cyclopropyl)acetic acid: To a stirred solution of cis-2-(2-((benzo[d]thiazol-2-ylthio)methyl)cyclopropyl)acetic acid (215 mg, 0.770 mmol) in THF (14.7 mL) was added a solution of oxone (1419 mg, 2.309 mmol) in water (7.3 mL) and allowed to continue overnight. The mixture was quenched with sodium sulfite (saturated, 125 mL) and then extracted with EtOAc (100 mL). The aqueous solution was again extracted with 3:1 chloroform/IPA (100 mL×2). The combined organic layers were dried over magnesium sulfate, filtered and concentrated under reduced pressure. The resulting residue was further dried under vacuum for 6 h to give the title compound. MS (ES+) m/z: 311.9 (M+H).

Intermediate 31 trans-2-(2-((benzo[d]thiazol-2-ylsulfonyl)methyl)cyclopropyl)acetic acid

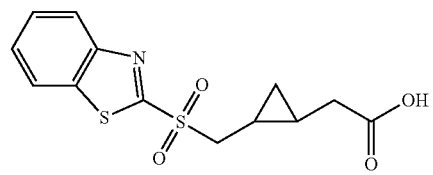 [SMILES: O=C(O)CC1CC1CS(=O)(=O)c1nc2ccccc2s1]

Intermediate 30 was prepared from trans-benzyl 2-(2-(tert-butoxy)-2-oxoethyl)cyclopropane-1-carboxylate by the procedure described in the synthesis of Intermediate 29. MS (ES+) m/z: 311.9 (M+H).

Intermediate 32

2-(3-chloro-2,6-difluorophenyl)-4,4,5,5-tetramethyl-1,3,2-dioxaborolane

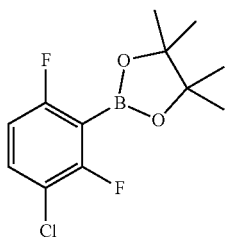 [SMILES: CC1(C)OB(c2c(F)ccc(Cl)c2F)OC1(C)C]

To a solution of 1-chloro-2,4-difluorobenzene (10 g, 67.3 mmol) in anhydrous THF (150 mL) was added n-butyl-lithium (2.5 M in hexane, 26.9 mL, 67.3 mmol) dropwise at −78° C. In this period, the temperature was controlled below −65° C. After addition, the mixture was stirred at −78° C. for another 1.5 h. To the mixture dropwise 2-isopropoxy-bispinacolatodiboron (25.05 g, 135 mmol) was added. The resulting reaction mixture was allowed to warm to rt (25° C.) and stirred for 16 h. The mixture was quenched with water (50 mL), filtered and the filtrate was concentrated under reduced pressure. The residue was extracted with EtOAc (150 mL×2). The combined organic layers were dried over sodium sulfate, filtered and concentrated under reduced pressure. The residue was triturated in petroleum ether (100 mL) for 1 h. The solids were collected by filtration to afford the title compound. $^1$H NMR (400 MHz, CD$_3$OD): δ 7.02-6.93 (m, 1H), 6.53 (t, J=8.0 Hz, 1H), 1.09 (s, 12H).

Intermediate 33

4-chloro-2-(4,4,5,5-tetramethyl-1,3,2-dioxaborolan-2-yl)aniline

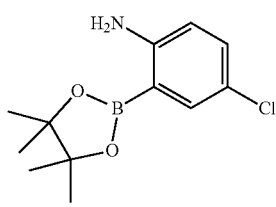 [SMILES: CC1(C)OB(c2cc(Cl)ccc2N)OC1(C)C]

The title compound was prepared from 2-bromo-4-chloroaniline by the procedure described in the synthesis of Intermediate 18. MS (ESI) m/z: 254 [M+H].

Intermediate 34

2-bromo-4-chloro-1-(trifluoromethoxy)benzene

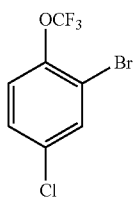

To a stirred solution of 5-chloro-2-(trifluoromethoxy)aniline (1.00 g, 4.73 mmol) in acetonitrile (60 mL) and water (6 mL) was added copper(II) bromide (1.48 g, 6.62 mmol). And isopentyl nitrite (0.95 g, 8.13 mmol). The mixture was stirred at 70° C. for 1 h. It was cooled to rt and quenched with water (200 mL). The mixture was extracted with DCM (60 mL×2). The combined organic layers were washed with brine (60 mL), dried over sodium sulfate, filtered and concentrated. The residue was purified by flash column chromatography on silica gel (eluting with petroleum ether) to give the title compound. $^1$H NMR (400 MHz, CDCl$_3$): δ 7.58 (d, J=2.2 Hz, 1H), 7.29-7.22 (m, 1H), 7.19 (s, 1H).

Intermediate 35

2-bromo-4-chloro-1-(difluoromethoxy)benzene

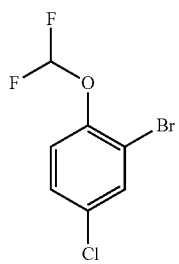

To a stirred mixture of 2-bromo-4-chlorophenol (500 mg, 2.41 mmol) and KOH (2.71 g, 48.2 mmol) in acetonitrile (15 mL) and water (15 mL) under nitrogen at −78° C. was added diethyl (bromodifluoromethyl)phosphonate (1.29 g, 4.82 mmol). The mixture was allowed to warm to rt and stirred for 30 min. Water (20 mL) was added and the mixture was extracted with petroleum ether (100 mL). The organic fraction washed with brine (100 mL), dried over sodium sulfate, filtered and the solvent was evaporated under reduced pressure to give the title compound. $^1$H NMR (400 MHz, CDCl$_3$): δ 7.61 (s, 1H), 7.28 (dd, J=2.3, 9.0 Hz, 1H), 7.15 (brd, J=9.0 Hz, 1H), 6.49 (t, J=73.2 Hz, 1H).

Intermediate 36

2-bromo-1-(difluoromethoxy)-3-fluorobenzene

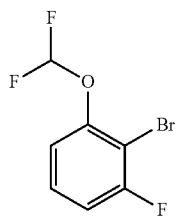

To a stirred mixture of 2-bromo-3-fluorophenol (6.00 g, 31.40 mmol) in DMF (30 mL) was added K$_2$CO$_3$ (5.21 g, 37.70 mmol) and sodium 2-chloro-2,2-difluoroacetate (5.75 g, 37.70 mmol) in one portion and the mixture was stirred at 70° C. for 15 h under N$_2$. Water (100 mL) was added and the mixture was extracted with petroleum ether (100 mL×2). The combined organic fractions were washed with brine, dried over sodium sulfate, filtered and the solvent was evaporated under reduced pressure to give the title compound, which was used directly. $^1$H NMR (400 MHz, CDCl$_3$): δ 7.34-7.23 (m, 1H), 7.07-6.94 (m, 2H), 6.54 (t, J=73.0 Hz, 1H).

Intermediate 37

2-bromo-1-(difluoromethyl)-3-fluorobenzene

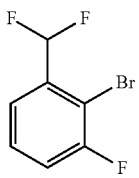

To a stirred mixture of 2-bromo-3-fluorobenzaldehyde (2.00 g, 9.85 mmol) in DCM (70 mL) under N$_2$ atmosphere was added DAST (1.65 mL, 12.31 mmol) at 0° C. The mixture was stirred for 1 h, then it was allowed to warm to 25° C. stirring for another 1 h. Aqueous saturated NaHCO$_3$ (50 mL) was added and the mixture was extracted with DCM (100 mL×2). The combined organic fractions were dried over sodium sulfate, filtered and the solvent was evaporated under reduced pressure. The residue was purified by flash column chromatography on silica gel (eluting with eluted with 0-5% EtOAc in petroleum ether) to give the title compound. $^1$H NMR (400 MHz, CDCl$_3$): δ 7.50-7.36 (m, 2H), 7.25 (t, J=8.2 Hz, 1H), 6.92 (t, J=60.0 Hz, 1H).

Intermediate 38

2-bromo-1-(difluoromethoxy)-3,4-difluorobenzene

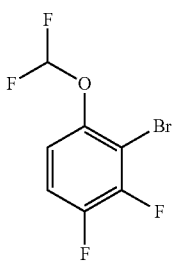 [SMILES: Fc1ccc(OC(F)F)c(Br)c1F]

Step A: 1,2-Difluoro-4-(methoxymethoxy)benzene: To a stirred mixture of 3,4-difluorophenol (5.00 g, 38.40 mmol) in DCM (80 mL) at −10° C. was added DIEA (13.43 mL, 77 mmol), then MOM-Cl (5.84 mL, 77.00 mmol) dropwise. The mixture was warmed to 20° C. and stirred for 16 h. Aqueous ammonium chloride (saturated, 100 mL) was added and the mixture was extracted with DCM (150 mL×2). The combined organic fractions were washed with aqueous HCl (1M, 100 mL), dried over sodium sulfate, filtered and the solvent was evaporated under reduced pressure. The residue was purified by flash column chromatography on silica gel (eluting with petroleum ether:EtOAc=20:1) to give the title compound. $^1$H NMR (400 MHz, CDCl$_3$): δ 7.10-7.01 (m, 1H), 6.89 (ddd, J=2.9, 6.7, 11.9 Hz, 1H), 6.74 (dtd, J=1.8, 3.2, 9.1 Hz, 1H), 5.14 (s, 2H), 3.49 (s, 3H).

Step B: 2-Bromo-3,4-difluoro-1-(methoxymethoxy)benzene: To a stirred mixture of 1,2-difluoro-4-(methoxymethoxy)benzene (5.20 g, 29.90 mmol) in THF (80 mL) was added n-BuLi (14.33 mL, 35.80 mmol, 2.5 M in hexane) dropwise at −78° C. The mixture was stirred for 60 min at −78° C. followed by the addition of Br$_2$ (1.85 mL, 35.80 mmol). The mixture was stirred for another 1 h and aqueous ammonium chloride (saturated, 100 mL) was added. The mixture was extracted with DCM (200 mL×2). The combined organic fractions were washed with brine (200 mL×2), dried over sodium sulfate, filtered and the solvent was evaporated under reduced pressure to give the title compound.

Step C: 2-Bromo-3,4-difluorophenol: To a stirred mixture of 2-bromo-3,4-difluoro-1-(methoxymethoxy)benzene (7.00 g, 27.70 mmol) in THF (40 mL) was added aqueous HCl (46.10 mL, 277 mmol, 6 M). The mixture was stirred at 25° C. for 16 h quenched with water (100 mL). The mixture was extracted with diethyl ether (200 mL×2). The combined organic fractions were washed with brine (200 mL×2), dried over sodium sulfate, filtered and the solvent was evaporated under reduced pressure to give the title compound.

Step D: 2-bromo-1-(difluoromethoxy)-3,4-difluorobenzene: To a stirred mixture of 2-bromo-3,4-difluorophenol (6.30 g, 25.60 mmol) and potassium hydroxide (28.80 g, 512 mmol) in acetonitrile (100 mL) and water (100 mL) was added diethyl (bromodifluoromethyl)phosphonate (13.68 g, 51.20 mmol). The mixture was stirred at 25° C. for 30 min and was quenched with water (200 mL). The mixture was extracted with diethyl ether (500 mL×2). The combined organic fractions were washed with brine (500 mL×2), dried over sodium sulfate, filtered and the solvent was evaporated under reduced pressure. The residue was purified by flash column chromatography on silica gel (eluting with petroleum ether) to give the title compound. $^1$H NMR (400 MHz, CDCl$_3$): δ 7.17 (dt, J=8.3, 9.2 Hz, 1H), 7.07-7.00 (m, 1H), 6.51 (t, J=72.0 Hz, 1H).

Intermediate 39

4-chloro-3-fluoro-2-(4,4,5,5-tetramethyl-1,3,2-dioxaborolan-2-yl)aniline

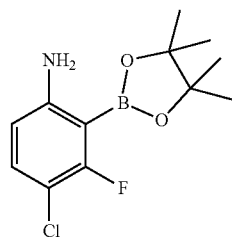 [SMILES: CC1(C)OB(c2c(N)ccc(Cl)c2F)OC1(C)C]

The title compound was prepared from 2-bromo-4-chloro-3-fluoroaniline by the procedure described in the synthesis of Intermediate 19 Step C. MS (ES$^+$) m/z: 272 (M+H).

Intermediate 40

(5-chloropyridin-2-yl)(5-fluoro-4-iodopyridin-2-yl)methanone

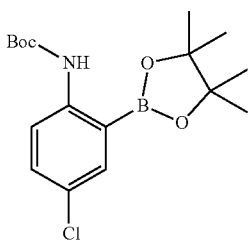 [SMILES: CC(C)(C)OC(=O)Nc1ccc(Cl)cc1B1OC(C)(C)C(C)(C)O1]

To a solution of Intermediate 33 (6.00 g, 23.67 mmol) in toluene (80 mL) was added Boc$_2$O (16.48 mL, 71.0 mmol) and TEA (16.49 mL, 118 mmol). The mixture was stirred at 80° C. under nitrogen for 13 h. It was cooled to rt and quenched with water (80 mL). It was extracted with EtOAc (3×80 mL). The combined organic layers were dried over sodium sulfate, and filtered. The filtrate was concentrated in vacuo. The residue was purified by flash column chromatography on silica gel (eluting with 10% EtOAc/petroleum ether, gradient) to give the title compound. $^1$H NMR (400 MHz, CDCl$_3$): δ 8.62 (s, 1H), 8.15 (d, J=8.8 Hz, 1H), 7.66 (d, J=2.4 Hz, 1H), 7.34 (dd, J=2.4, 8.8 Hz, 1H), 1.52 (s, 9H), 1.36 (s, 12H).

Intermediate 41

5-(4-chloro-2-(4,4,5,5-tetramethyl-1,3,2-dioxaborolan-2-yl)phenyl)oxazole

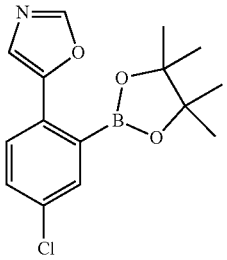 [SMILES: CC1(C)OB(c2cc(Cl)ccc2-c2cnco2)OC1(C)C]

Step A: 2-Bromo-4-chloro-N-methoxy-N-methylbenzamide: To a round bottom flask were added 2-bromo-4-chlorobenzoic acid (10 g, 42.5 mmol), DCM (150 mL), HATU (19.38 g, 51.0 mmol), N,O-dimethylhydroxylamine hydrochloride (12.43 g, 127 mmol) and triethylamine (29.6 mL, 212 mmol). The reaction mixture was stirred for 18 h at rt. The mixture was quenched with water (200 mL) and extracted with DCM (100 mL×3). The combined organic layers were dried over anhydrous sodium sulfate, filtered and the filtrate was concentrated in vacuo. The residue was purified by flash column chromatography on silica gel (eluting with petroleum ether:EtOAc=10:1 v/v) to give the title compound. MS (ES$^+$) m/z: 278, 280 [M+H].

Step B: 2-Bromo-4-chlorobenzaldehyde: To a solution of 2-bromo-4-chloro-N-methoxy-N-methylbenzamide (11 g, 39.5 mmol) in anhydrous THF (150 mL) was added diisobutylaluminum hydride (1 M in toluene, 71.1 mL, 71.1 mmol) dropwise at −78° C. The reaction mixture was stirred for 1 h and was quenched with saturated potassium sodium tartrate solution (300 mL). The mixture was stirred for 20 min and filtered through a pad of Celite. The filtrate was extracted with ethyl acetate (200 mL×3). The combined organic layers were dried over anhydrous sodium sulfate, filtered and the filtrate was concentrated in vacuo to the title compound. It was used in the next step without further purification.

Step C: 5-(2-Bromo-4-chlorophenyl)oxazole: To a round bottom flask were added 2-bromo-4-chlorobenzaldehyde (8.00 g, 36.5 mmol), MeOH (200 mL), 1-((isocyanomethyl)sulfonyl)-4-methylbenzene (10.68 g, 54.7 mmol) and K$_2$CO$_3$ (15.11 g, 109 mmol). The mixture was stirred at 70° C. for 3 h. The mixture was concentrated in vacuo and water (200 mL) was added. The mixture was extracted with ethyl acetate (150 mL×3). The combined organic layers were dried over anhydrous sodium sulfate, filtered and the filtrate was concentrated under reduced pressure. The residue was purified by flash column chromatography on silica gel (eluting with 0-10% ethyl acetate/petroleum ether) to give the title compound. MS (ES$^+$) m/z: 258, 260 [M+H].

Step D: 5-(4-Chloro-2-(4,4,5,5-tetramethyl-1,3,2-dioxaborolan-2-yl)phenyl)oxazole: The title compound was prepared from 5-(2-bromo-4-chlorophenyl)oxazole by the procedure described in the synthesis of Intermediate 19. MS (ES$^+$) m/z: 306 [M+H].

Intermediate 42

1-(4-chloro-2-(trimethylstannyl)phenyl)-4-(difluoromethyl)-1H-1,2,3-triazole

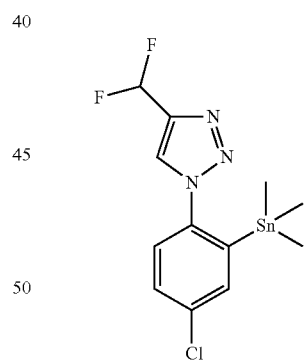

Step A: 1-Azido-2-bromo-4-chlorobenzene: To a suspension of 2-bromo-4-chloroaniline (5 g, 24.22 mmol) in HCl (36.5% wt, 30 mL, 365 mmol) and water (100 mL) at −5° C., a solution of sodium nitrite (1.838 g, 26.6 mmol) in water (10 mL) was added dropwise. The mixture was stirred at −5° C. for 1 h, and the suspension turn into a clear solution. A solution of sodium azide (1.732 g, 26.6 mmol) in water (10 mL) was added dropwise to the reaction. Solids precipitated out from the solution during the addition. It was stirred at −5° C. for 0.5 h. The mixture was extracted with ethyl acetate (70 mL×3). The combined organic layers were washed with saturated aqueous sodium bicarbonate (20 mL), water (40 mL) and brine (50 mL) sequentially. The organic layer was dried over anhydrous sodium sulfate, filtered and concentrated under reduced pressure to give the title compound.

Step B: (1-(2-Bromo-4-chlorophenyl)-1H-1,2,3-triazol-4-yl)methanol: To a round bottom flask were added 1-azido-2-bromo-4-chlorobenzene (5 g, 21.51 mmol), prop-2-yn-1-ol (2.412 g, 43.0 mmol), sodium (R)-2-((S)-1,2-dihydroxyethyl)-4-hydroxy-5-oxo-2,5-dihydrofuran-3-olate (2.130 g, 10.75 mmol), copper(II) sulfate (1.716 g, 10.75 mmol), THF (60 mL) and water (60 mL). The reaction mixture was stirred at 100° C. under nitrogen for 6 h. It was cooled to rt and filtered through a pad of Celite. The filtrate was concentrated in vacuo. Water (100 mL) was added to the residue and the mixture was extracted with ethyl acetate (3×50 mL). The combined organic layers were dried over anhydrous sodium sulfate, filtered and concentrated in vacuo. The residue was purified by flash column chromatography on silica gel (eluting with 0-40% EtOAc/petroleum ether) to give the title compound. MS (ESI) m/z: 288, 290 [M+H].

Step C: 1-(2-Bromo-4-chlorophenyl)-1H-1,2,3-triazole-4-carbaldehyde: To a round bottom flask were added (1-(2-bromo-4-chlorophenyl)-1H-1,2,3-triazol-4-yl)methanol (5 g, 12.48 mmol), DCM (100 mL) and manganese(IV) oxide (10.85 g, 125 mmol). The reaction mixture was stirred at 25° C. for 18 h. The mixture was filtered and concentrated under reduced pressure. The residue was purified by flash column chromatography on silica gel (eluting with 0-20% EtOAc/petroleum ether, 40 min, dry loaded) to give the title compound. MS (ESI) m/z: 286, 288 [M+H].

Step D: 1-(2-Bromo-4-chlorophenyl)-4-(difluoromethyl)-1H-1,2,3-triazole: To a solution of 1-(2-bromo-4-chlorophenyl)-1H-1,2,3-triazole-4-carbaldehyde (1.6 g, 5.58 mmol) in DCM (20 mL) was added DAST (1.476 mL, 11.17 mmol). The resulting mixture was stirred at 20° C. for 2 h and quenched with saturated aqueous sodium bicarbonate (20 mL) and water (50 mL). The mixture was extracted with DCM (3×20 mL). The combined organic layers were dried over anhydrous sodium sulfate, filtered and concentrated under reduced pressure to give the title compound, which was used in next step without further purification. MS (ESI) m/z: 308, 310 [M+H].

Step E: 1-(4-Chloro-2-(trimethylstannyl)phenyl)-4-(difluoromethyl)-1H-1,2,3-triazole: To a solution of 1-(2-bromo-4-chlorophenyl)-4-(difluoromethyl)-1H-1,2,3-triazole (1.8 g, 4.38 mmol) and 1,1,1,2,2,2-hexamethyldistannane (4.30 g, 13.13 mmol) in toluene (30 mL) was added tetrakis(triphenylphosphine)palladium(0) (1.011 g, 0.875 mmol). The mixture was stirred at 120° C. under nitrogen for 18 h. It was cooled to rt and filtered through a pad of Celite. The filtrate was concentrated under reduced pressure. The residue was purified by flash column chromatography on silica gel (eluting with 0-10% EtOAc/petroleum ether) to give the title compound. MS (ESI) m/z: 394 [M+H].

Intermediate 43

1-(2-bromo-4-chlorophenyl)-4-cyclopropyl-1h-1,2,3-triazole

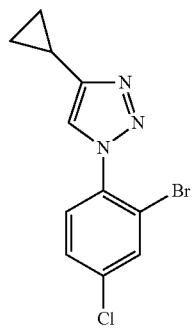 [SMILES: Clc1ccc(-n2cc(C3CC3)nn2)c(Br)c1]

To a stirred mixture of 1-azido-2-bromo-4-chlorobenzene (660 mg, 2.84 mmol) in toluene (12 mL) was added cyclopropylacetylene (0.360 mL, 4.26 mmol); the mixture was stirred at 110° C. for overnight. The reaction mixture was cooled to rt and concentrated under reduced pressure. The residue was purified by flash column chromatography on silica gel (eluting with 20-50% EtOAc/hexane) to give the title compound. MS (ES⁺) m/z: 298, 300 (M+H).

Intermediate 44

1-(4-chloro-2-iodophenyl)-4-(difluoromethyl)-1H-1,2,3-triazole

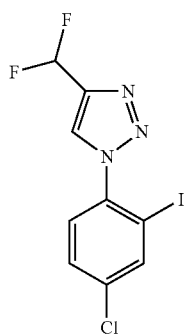 [SMILES: FC(F)c1cn(-c2ccc(Cl)cc2I)nn1]

Step A: 1-Azido-4-chloro-2-iodobenzene: To a solution of 4-chloro-2-iodoaniline (10 g, 39.5 mmol) in ethyl acetate (80 mL) and water (10 mL) in an ice-water bath, was added HCl (37%, 22.03 mL, 268 mmol) dropwise. The resulting mixture was stirred for 10 minutes. To the solution was added a solution of sodium nitrite (2.132 mL, 67.1 mmol) in water (15 mL) over 10 min. The mixture was stirred for 30 min; and a solution of sodium azide (4.36 g, 67.1 mmol) in water (16 mL) was added slowly. The mixture was stirred in an ice-water bath and allowed to warm to rt overnight. The mixture was diluted with water (100 mL) and extracted with ethyl acetate (2×200 mL). The combined organic layers were washed subsequently with water (150 mL), aqueous sodium bicarbonate (saturated, 150 mL) and brine (100 mL), dried (MgSO₄), filtered. The solvent was evaporated under reduced pressure. The residue was purified by flash column chromatography on silica gel (eluting with 0-5% ethyl acetate in hexane) to give the title compound.

Step B: (1-(4-Chloro-2-iodophenyl)-1H-1,2,3-triazol-4-yl) methanol: To a mixture of 1-azido-4-chloro-2-iodobenzene (5.0 g, 17.9 mmol), propagyl alcohol (1.003 g, 17.89 mmol) in DMF (44.7 mL) was added cupric sulfate (1 M) (3.58 mL, 3.58 mmol) and sodium ascorbate (1 M) (3.58 mL, 3.58 mmol) subsequently. The reaction mixture was stirred at 50° C. overnight. It was cooled to rt and diluted with water (50 mL) and extracted with ethyl acetate (2×100 mL). The combined organic layers were washed with water (2×50 mL) and aqueous sodium bicarbonate (40 mL). The organic layer was separated, dried over MgSO$_4$ and filtered. The filtrate was evaporated under reduced pressure. The residue was triturated in 10% MeOH/DCM and aged for 30 min. The solids were collected by filtration and air dried to give the title compound. MS (ES$^+$) m/z: 336 (M+H).

Step C: 1-(4-Chloro-2-iodophenyl)-1H-1,2,3-triazole-4-carbaldehyde: Dess-Martin periodinane (6.92 g, 16.31 mmol) was added to a stirred mixture of (1-(4-chloro-2-iodophenyl)-1H-1,2,3-triazol-4-yl)methanol (4.56 g, 13.59 mmol) in dichloromethane (68.0 mL) at rt. The mixture was stirred for 90 min and was quenched with a mixture of aqueous sodium thiosulfate (saturated, 50 mL) and aqueous sodium bicarbonate (saturated, 50 mL). The mixture was extracted with dichloromethane (2×50 mL). The combined organic layers were washed with brine (saturated, 100 mL), dried (Na$_2$SO$_4$) and filtered. The filtrate was concentrated under reduced pressure and the residue was purified by flash column chromatography on silica gel (eluting with 0-25% ethyl acetate in hexane) to give the title compound. MS (ES$^+$) m/z: 333 (M+H).

Step D: 1-(4-chloro-2-iodophenyl)-4-(difluoromethyl)-1H-1,2,3-triazole: To a solution of 1-(4-chloro-2-iodophenyl)-1H-1,2,3-triazole-4-carbaldehyde (1.5 g, 4.50 mmol) in dichloromethane (30.0 mL) at 0° C. was added diethylaminosulfur trifluoride (2.90 g, 17.99 mmol). The reaction mixture was allowed to warm to rt and stirred for 2 h. The mixture was diluted with dichloromethane (30 mL) and quenched with aqueous sodium bicarbonate (saturated, 30 mL). The organic layer was separated and washed with brine (30 mL), dried over MgSO$_4$, filtered. The filtrate was concentrated under reduced pressure. The residue was the residue was purified by flash column chromatography on silica gel (eluting with 1:3 ethyl acetate/hexane) to give the title compound. MS (ES$^+$) m/z: 356 (M+H).

Intermediate 45

1-(2-bromo-4-chlorophenyl)-4-chloro-1H-1,2,3-triazole

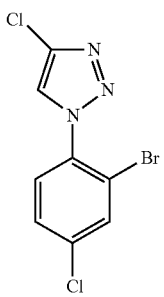 [SMILES: Clc1ccc(-n2cc(Cl)nn2)c(Br)c1]

Step A: 1-(2-Bromo-4-chlorophenyl)-4-(tributylstannyl)-1H-1,2,3-triazole: To a stirred solution of 1-azido-2-bromo-4-chlorobenzene (660 mg, 2.84 mmol) in toluene (12 mL) was added tributylstannylacetylene (1073 mg, 3.41 mmol) and the mixture was stirred at 110° C. for overnight. The reaction mixture was cooled to rt and concentrated under reduced pressure. The residue was purified by flash column chromatography on silica gel (eluting with 5-20% ethyl acetate in hexane) to afford the title compound.

Step B: 1-(2-Bromo-4-chlorophenyl)-4-chloro-1H-1,2,3-triazole: To a stirred solution of 1-(2-bromo-4-chlorophenyl)-4-(tributylstannyl)-1H-1,2,3-triazole (1.0 g, 1.826 mmol) in acetonitrile (15 mL) was added NCS (0.366 g, 2.74 mmol). The reaction mixture was stirred at 60° C. for overnight. It was cooled to rt and concentrated under reduced pressure. The residue was purified by flash column chromatography on silica gel (eluting with 20% ethyl acetate in hexane) to give the title compound. MS (ES$^+$) m/z: 292, 294 (M+H).

Intermediate 46

1-(2-bromo-4-chlorophenyl)-4-(trifluoromethyl)-1H-1,2,3-triazole

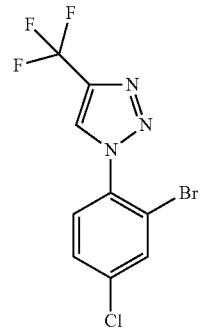

Excess amount of 3,3,3-trifluoropropyne was bubbled into a stirred mixture of 1-azido-2-bromo-4-chlorobenzene (4.0 g, 17.21 mmol) and copper(I) oxide (0.246 g, 1.721 mmol) in acetonitrile (43.0 mL) at rt for 30 min. The mixture was stirred overnight and concentrated under reduced pressure. The residue was purified by flash column chromatography on silica gel (eluting with 20% ethyl acetate in hexane) to give the title compound. MS (ES$^+$) m/z: 326, 328 (M+H).

Intermediate 47

1-(2-bromo-4-chlorophenyl)-1H-pyrazole

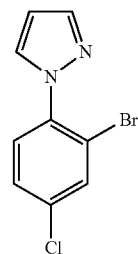 [SMILES: Clc1ccc(-n2cccn2)c(Br)c1]

To a stirred mixture of 2-bromo-4-chloro-1-fluorobenzene (6.00 g, 28.60 mmol) in DMF (30 mL) was added 1H-pyrazole (2.15 g, 31.50 mmol) and Cs$_2$CO$_3$ (23.33 g, 71.60 mmol) at rt. The mixture was stirred at 100° C. for 15 h. It was cooled to rt and quenched with aqueous ammonium chloride (saturated, 30 mL). The mixture was extracted with EtOAc (20 mL×3). The combined organic fractions were washed with brine (saturated, 20 mL), dried over sodium sulfate, filtered and the solvent was evaporated under reduced pressure. The residue was purified by flash column chromatography on silica gel (eluting with petroleum ether:EtOAc=10:1) to give the title compound. $^1$H NMR (400 MHz, CDCl$_3$): δ 7.83 (d, J=2.5 Hz, 1H), 7.77-7.65 (m, 2H), 7.54-7.38 (m, 2H), 6.55-6.45 (m, 1H).

Intermediate 48

1-(2-bromo-4-chlorophenyl)-4-methyl-1H-pyrazole

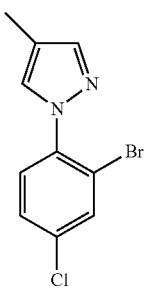

The title compound was prepared from 4-methyl-1H-pyrazole by the procedure described in the synthesis of Intermediate 47. $^1$H NMR (400 MHz, CDCl$_3$): δ 7.69 (d, J=2.2 Hz, 1H), 7.59 (d, J=0.8 Hz, 1H), 7.55 (s, 1H), 7.46-7.41 (m, 1H), 7.40-7.35 (m, 1H), 2.17 (s, 3H).

Intermediate 49

1-(2-bromo-4-chlorophenyl)-4-(trifluoromethyl)-1H-pyrazole

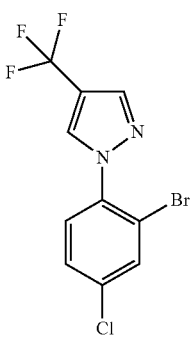

The title compound was prepared from 4-(trifluoromethyl)-1H-pyrazole by the procedure described in the synthesis of Intermediate 47. MS (ES$^+$) m/z: 325, 327 (M+H).

Intermediate 50

1-(4-chloro-3-fluoro-2-iodophenyl)-4-(trifluoromethyl)-1H-pyrazole

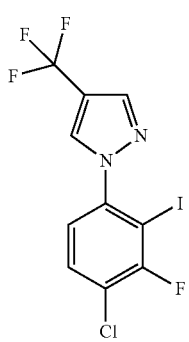 [SMILES: Fc1c(Cl)ccc(-n2cc(C(F)(F)F)cn2)c1I]

The title compound was prepared from 4-(trifluoromethyl)-1H-pyrazole and 1-chloro-2,4-difluoro-3-iodobenzene by the procedure described in the synthesis of Intermediate 47. MS (ESI) m/z 391.1 (M+H); $^1$H NMR (400 MHz, CDCl$_3$): δ 7.96-8.03 (m, 1H), 7.82 (s, 1H), 7.45-7.57 (m, 1H), 7.14-7.26 (m, 1H).

Intermediate 51

1-(2-bromo-4-chlorophenyl)-1H-pyrazole-4-carbonitrile

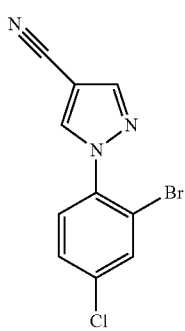 [SMILES: N#Cc1cnn(-c2ccc(Cl)cc2Br)c1]

The title compound was prepared from 1H-pyrazole-4-carbonitrile by the procedure described in the synthesis of Intermediate 47. MS (ES$^+$) m/z: 282, 284 (M+H).

Intermediate 52

5-chloro-2-(1-(difluoromethyl)-1H-pyrazol-4-yl)phenyl trifluoromethanesulfonate

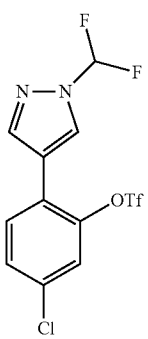 [SMILES: O=S(=O)(Oc1cc(Cl)ccc1-c1cnn(C(F)F)c1)C(F)(F)F]

Step A: 5-Chloro-2-(1-(difluoromethyl)-1H-pyrazol-4-yl)phenol: 1-(difluoromethyl)-4-(4,4,5,5-tetramethyl-1,3,2-dioxaborolan-2-yl)-1H-pyrazole (282 mg, 1.157 mmol), 2-bromo-5-chlorophenol (200 mg, 0.964 mmol) and 1,1'-bis(diphenylphosphino)ferrocene-palladium(II)dichloride dichloromethane complex (79 mg, 0.096 mmol) were mixed in a pressure release vial, degassed and backfilled with nitrogen (3×). Dioxane (6 mL) and potassium phosphate tribasic (3M aqueous) (1 mL) were added subsequently. The reaction mixture was stirred at 80° C. for 3 h. It was cooled to rt and purified by flash column chromatography on silica gel (eluting with 50% ethyl acetate in hexane) to give the title compound. MS (ES$^+$) m/z: 245 (M+H).

Step B: 5-Chloro-2-(1-(difluoromethyl)-1H-pyrazol-4-yl)phenyl trifluoromethanesulfonate: To a mixture of 5-chloro-2-(1-(difluoromethyl)-1H-pyrazol-4-yl)phenol (90 mg, 0.368 mmol) and Hunig's Base (0.193 mL, 1.104 mmol) in dichloromethane (2 mL) at 0° C. was added trifluoromethanesulfonic anhydride (1M in DCM) (0.552 mL, 0.552 mmol) dropwise. The mixture was stirred at rt for 3 h. The residue was purified by flash column chromatography on silica gel (eluting with 50% ethyl acetate in hexane) to give the title compound. MS (ES$^+$) m/z: 377 (M+H).

Intermediate 53 methyl (3-amino-4-bromo-5-fluorophenyl)carbamate

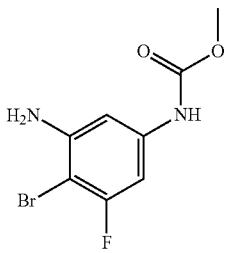

Step A: 2-Fluoro-4,6-dinitrophenol: To a stirred solution of 2-fluorophenol (10 g, 89 mmol) in DCM (100 mL) at 0° C. was added nitric acid (10.48 mL, 223 mmol) dropwise. The resulting mixture was stirred at 25° C. for 2 h. It was quenched with aqueous NaOH (2 M) to adjust pH to 5. It was diluted with water (100 mL), extracted with EtOAc (100 mL×5). The combined organic layers were washed with brine (200 mL), dried over sodium sulfate, filtered and concentrated under reduced pressure to give the title compound.

Step B: 2-Bromo-1-fluoro-3,5-dinitrobenzene: To a stirred solution of 2-fluoro-4,6-dinitrophenol (16 g, 79 mmol) in DMF (40 mL) and toluene (300 mL) was added PBr$_3$ (11.20 mL, 119 mmol) dropwise. The resulting mixture was stirred at 110° C. for 1 h. It was cooled to rt, diluted with EtOAc (200 mL) and transferred into a separatory funnel. It washed with water (100 mL×3), dried over sodium sulfate, filtered and concentrated to give the title compound.

Step C: 4-Bromo-3-fluoro-5-nitroaniline: A stirred solution of 2-bromo-1-fluoro-3,5-dinitrobenzene (18 g, 67.90 mmol) in AcOH (400 mL, 6987 mmol) was added iron (11.38 g, 204 mmol) in small portions. The mixture was stirred for 1 h at rt and it was quenched with aqueous NaOH (2 M) to adjust pH to 8. It was diluted with water (200 mL), extracted with EtOAc (500 mL×3), washed with brine (500 mL), dried over sodium sulfate, filtered and concentrated under reduced pressure. The residue was purified by flash column chromatography on silica (petroleum:EtOAc=100:1 to 3:1) to give the title compound. $^1$H NMR (400 MHz, CDCl$_3$): δ 6.93 (s, 1H), 6.62 (dd, J=2.7, 9.8 Hz, 1H), 4.15 (brs, 2H).

Step D: Methyl (4-bromo-3-fluoro-5-nitrophenyl)carbamate: To a stirred solution of 4-bromo-3-fluoro-5-nitroaniline (12 g, 35.70 mmol) and DIEA (18.73 mL, 107 mmol) in DCM (250 mL) at 0° C. as added methyl chloroformate (8.44 mL, 107 mmol) dropwise. The mixture was stirred at 25° C. for 15 h. Water (30 mL) was added and the mixture was extracted with EtOAc (200 mL×3). The combined organic fractions were washed with brine (200 mL), dried over sodium sulfate, filtered and the solvent was evaporated under reduced pressure. The residue was purified by flash column chromatography on silica (petroleum ether:EtOAc=100:1 to 3:1) to give the title compound. $^1$H NMR (400 MHz, CDCl$_3$): δ 7.69 (s, 1H), 7.64 (d, J=9.7 Hz, 1H), 7.02 (brs, 1H), 3.82 (s, 3H).

Step E: Methyl (3-amino-4-bromo-5-fluorophenyl)carbamate: To a solution of methyl (4-bromo-3-fluoro-5-nitrophenyl)carbamate (9.50 g, 29.20 mmol) in EtOH (90 mL) and water (30 mL) was added iron (3.26 g, 58.4 mmol), ammonium chloride (6.24 g, 117 mmol) and the mixture was stirred at 90° C. for 2 h. It was cooled to rt and filtered through a pad of Celite. The solids were washed with EtOH (20 mL×2) and water (50 mL). The filtrate was extracted with EtOAc (100 mL×3). The combined organic fractions were washed with brine (100 mL), dried over sodium sulfate, filtered and the solvent was evaporated under reduced pressure to give the title compound. $^1$H NMR (400 MHz, CDCl$_3$): δ 6.74 (brs, 1H), 6.57 (d, J=11.7 Hz, 2H), 4.25 (brs, 2H), 3.76 (s, 3H).

Intermediate 54

1-(4-chloro-3-fluoro-2-iodophenyl)-4-(trifluoromethyl)-1H-1,2,3-triazole

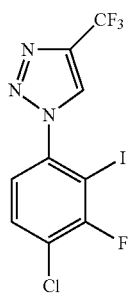 [SMILES: Fc1c(Cl)ccc(-n2cc(C(F)(F)F)nn2)c1I]

Step A: 1-Azido-4-chloro-3-fluoro-2-iodobenzene: To a solution of 4-chloro-3-fluoro-2-iodoaniline (300 mg, 1.105 mmol) in EtOAc (6.9 mL) was added to a solution of HCl (37% wt, 2.3 mL, 27.8 mmol) in water (6.9 mL) at 0° C. The resulting mixture was stirred for 10 minutes. To this suspension was added a solution of sodium nitrite (84 mg, 1.216 mmol) in water (0.5 mL) over three minutes. The reaction was stirred for 30 min. A solution of sodium azide (79 mg, 1.216 mmol) in 0.5 mL water was added slowly to the above reaction mixture. The mixture was then stirred in an ice-water bath under nitrogen and allowed to warm to rt overnight. The mixture was extracted with ethyl acetate (2×30 mL). The combined organic fractions were washed with brine (30 mL) and dried over sodium sulfate, filtered and the solvent was evaporated under reduced pressure to give the title compound.

Step B: 1-(4-Chloro-3-fluoro-2-iodophenyl)-4-(trifluoromethyl)-1H-1,2,3-triazole: 3,3,3-Trifluoropropyne (104 mg, 1.105 mmol) was bubbled into a stirred mixture of 1-azido-4-chloro-3-fluoro-2-iodobenzene (329 mg, 1.105 mmol) and copper(I) oxide (15.81 mg, 0.111 mmol) in acetonitrile (2.8 mL) for 10 min. Then reaction vessel was capped and sealed. The reaction mixture was stirred at rt overnight. The mixture was concentrated under reduced pressure. The residue was purified by flash column chromatography on silica gel (eluting with 0-10% ethyl acetate in hexane) to give the title compound. MS (ES$^+$) m/z: 391.6 (M+H).

Intermediate 55 methyl (3-amino-4-(2-(5-bromopicolinoyl)-1-((2-(trimethylsilyl)ethoxy)methyl)-1H-imidazol-4-yl)phenyl)carbamate

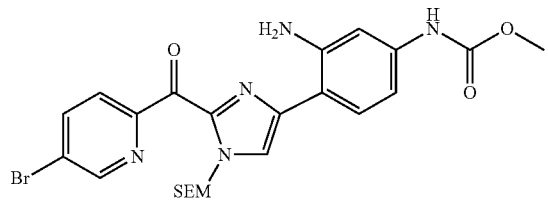 [SMILES: COC(=O)Nc1ccc(-c2cn(COCC[Si](C)(C)C)c(C(=O)c3ccc(Br)cn3)n2)c(N)c1]

To a mixture of Intermediate 15 (40 g, 79 mmol), Intermediate 19 (25.3 g, 87 mmol), tetrakis(triphenylphosphine)palladium(0) (4.55 g, 3.94 mmol), DMF (354 mL) and potassium phosphate tribasic (50.1 g, 236 mmol) was stirred at 60° C. for 3.5 h. It was cooled to rt and most solvent was removed under reduced pressure. The residue was diluted with ethyl acetate (200 mL) and washed with water (3×100 mL), then brine (100 mL). The organic layer was dried over sodium sulfate, filtered and concentrated under reduced pressure. The residue was purified by flash column chromatography on silica gel (eluting with 0-60% EtOAc/hexane, gradient) to give the title compound. MS (ES$^+$) m/z: 546, 548 [M+H].

Intermediate 56 methyl (3-amino-4-(2-(5-bromopicolinoyl)-1-((2-(trimethylsilyl)ethoxy)methyl)-1H-imidazol-4-yl)phenyl)carbamate

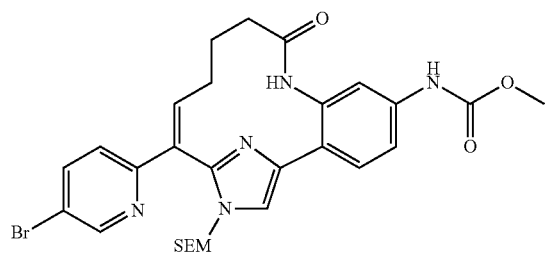 [SMILES: COC(=O)Nc1ccc2c(c1)NC(=O)CCC/C=C(/c1ccc(Br)cn1)c1nc-2cn1COCC[Si](C)(C)C]

Step A: (5-((2-(2-(5-Bromopicolinoyl)-1-((2-(trimethylsilyl)ethoxy)methyl)-1H-imidazol-4-yl)-5-((methoxycarbonyl)amino)phenyl)amino)-5-oxopentyl)triphenylphosphonium bromide: To a mixture of Intermediate 55 (36.5 g, 66.8 mmol), (4-carboxybutyl)triphenylphosphonium bromide (32.6 g, 73.5 mmol) in DCM (230 mL) were added DIEA (35.0 mL, 200 mmol) and HATU (30.5 g, 80 mmol). The mixture was stirred at rt for 2 h and the reaction mixture was purified by flash column chromatography on silica gel (eluting with 0-6% MeOH/DCM, gradient) to give the title compound. MS (ES$^+$) m/z: 890, 892 [M+H].

Step B: Methyl ((12Z,8Z)-9-(5-bromopyridin-2-yl)-4-oxo-11-((2-(trimethylsilyl)ethoxy)methyl)-11H-3-aza-1(4,2)-imidazola-2(1,2)-benzenacyclononaphan-8-en-2$^4$-yl)carbamate: To a solution of (5-((2-(2-(5-Bromopicolinoyl)-1-((2-(trimethylsilyl)ethoxy)methyl)-1H-imidazol-4-yl)-5-((methoxycarbonyl)amino)phenyl)amino)-5-oxopentyl)triphenylphosphonium bromide in degassed THF (3000 mL) at 0° C. was added cesium carbonate (50 g, 153 mmol). The mixture was stirred at rt for 16 h. The solids were removed by filtration and the filtrate was concentrated under reduced pressure. The residue slurry was added 100 mL of diethyl ether and 20 mL of water and aged for 1 h. Solids were collected by filtration and rinsed with diethyl ether (2×50 mL) to give the title compound. MS (ES$^+$) m/z: 612, 614 [M+H]; $^1$H NMR (CDCl$_3$, 400 MHz): δ 8.65 (d, J=2.0 Hz, 1H), 7.92 (s, 1H), 7.84 (dd, J=2.1, 8.2 Hz, 1H), 7.49 (d, J=8.3 Hz, 1H), 7.33 (d, J=8.5 Hz, 1H), 7.24 (s, 1H), 6.93-6.84 (m, 1H), 5.31 (s, 1H), 3.82-3.71 (m, 5H), 3.32-3.23 (m, 2H), 1.62 (m, 4H), 0.95-0.83 (m, 2H), 0.77 (t, J=8.2 Hz, 2H), −0.06 (s, 9H).

Intermediate 57 methyl ((1²Z,8Z)-9-(5-bromopyridin-2-yl)-5-methyl-4-oxo-1¹-((2-(trimethylsilyl)ethoxy)methyl)-1¹H-3-aza-1(4,2)-imidazola-2(1,2)-benzenacyclononaphan-8-en-2⁴-yl)carbamate

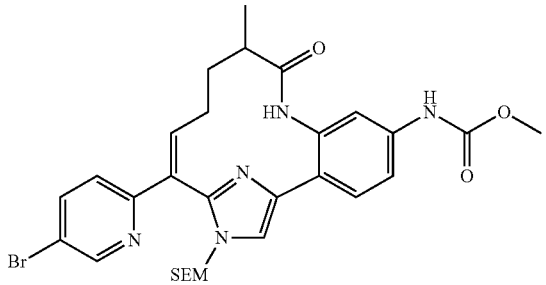 [SMILES: COC(=O)Nc1ccc2c(c1)NC(=O)C(C)CC/C=C(/c1ccc(Br)cn1)c1nc-2cn1COCC[Si](C)(C)C]

Step A: (5-((2-(2-(5-Bromopicolinoyl)-1-((2-(trimethylsilyl)ethoxy)methyl)-1H-imidazol-4-yl)-5-((methoxycarbonyl)amino)phenyl)amino)-4-methyl-5-oxopentyl)triphenylphosphonium bromide: To a stirred mixture of Intermediate 55 (5.00 g, 9.15 mmol), (4-carboxypentyl)triphenylphosphonium bromide (4.18 g, 9.15 mmol) and DIEA (15.98 mL, 91 mmol) in DCM (50 mL) was added 2,4,6-tripropyl-1,3,5,2,4,6-trioxatriphosphinane 2,4,6-trioxide (11.64 g, 18.30 mmol) at 30° C. The mixture was stirred at 30° C. for 16 h. It was diluted with water and extracted with EtOAc (100 mL×2). The combined organic layers were washed with brine (50 mL×2), dried over sodium sulfate, filtered and the solvent was evaporated under reduced pressure. The residue was purified by flash column chromatography on silica (DCM:CH₃OH=50:1) to give the title compound. MS (ESI) m/z 904.2, 906.2 (M-Br).

Step B: Methyl ((1²z,8z)-9-(5-bromopyridin-2-yl)-5-methyl-4-oxo-1¹-((2-(trimethylsilyl)ethoxy)methyl)-1¹H-3-aza-1(4,2)-imidazola-2(1,2)-benzenacyclononaphan-8-en-2⁴-yl)carbamate: The title compound was prepared by the procedure described in the synthesis of Intermediate 56 Step B. The product was purified by flash column chromatography on silica (petroleum ether:EtOAc=10:1 to 2:1, gradient) to give the title compound. MS (ESI) m/z 626.2, 628.2 (M+H).

EXAMPLES

Example 1 (racemate), 1-a and 1-b 9-(5-(5-chloro-2-(1H-tetrazol-1-yl)phenyl)pyridin-2-yl)-2⁵-fluoro-3-aza-1(1,3),2(1,2)-dibenzenacyclononaphan-4-one

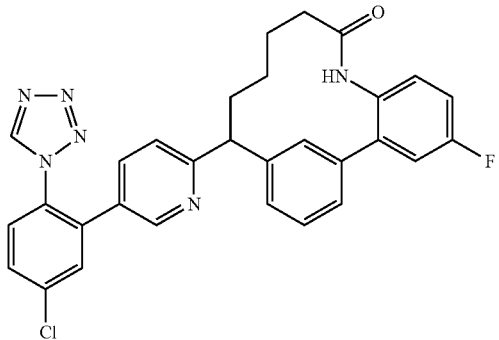 [SMILES: O=C1CCCCC(c2ccc(-c3cc(Cl)ccc3-n3cnnn3)cn2)c2cccc(c2)-c2cc(F)ccc2N1]

1A: 6-(1-(2'-Amino-5'-fluoro-[1,1'-biphenyl]-3-yl)but-3-en-1-yl)pyridin-3-ol 6-(3-Chlorobenzyl)pyridin-3-ol (5.00 g, 19.25 mmol), methyl (3-amino-4-(4,4,5,5-tetramethyl-1,3,2-dioxaborolan-2-yl)phenyl)carbamate (5.48 g, 23.10 mmol), Pd-Xphos precatalyst (0.796 g, 0.963 mmol) and degassed dioxane (77 mL) were added to a 500 mL round bottom flask charged with a magnetic stirring bar. To the mixture was added a degassed aqueous solution of potassium phosphate (3 M, 19.3 mL, 57.8 mmol). The mixture was stirred in an oil bath at 80° C. for 4 h and was cooled to rt. The mixture was extracted with ethyl acetate (2×100 mL). The combined organic layers were dried over sodium sulfate, filtered and concentrated under reduced pressure. The residue was purified by flash column chromatography on silica gel (eluting with 0-100% ethyl acetate in hexane) to give the title compound. MS (ES⁺) m/z: 335 (M+H).

1B: 3'-(1-(5-((tert-Butyldiphenylsilyl)oxy)pyridin-2-yl)but-3-en-1-yl)-5-fluoro-[1,1'-biphenyl]-2-amine To a solution of 1A (550 mg, 1.645 mmol) and TEA (0.48 mL, 3.44 mmol) in DCM (5 mL), TBDPS-Cl (0.5 mL, 1.946 mmol) was added at rt. The reaction mixture was stirred for 1 h and it was directly purified by flash column chromatography on silica gel (eluting with 0-50% ethyl acetate in hexane) to give the title compound. MS (ES⁺) m/z: 573 (M+H).

1C: N-(3'-(1-(5-((tert-Butyldiphenylsilyl)oxy)pyridin-2-yl)but-3-en-1-yl)-fluoro-[1,1'-biphenyl]-2-yl)but-3-enamide To a stirred mixture of but-3-enoic acid (0.588 mL, 6.91 mmol), 1B (3.3 g, 5.76 mmol) and Hunig's base (10.06 mL, 57.6 mmol) in dichloromethane (28.8 mL), 2,4,6-tripropyl-1,3,5,2,4,6-trioxatriphosphorinane-2,4,6-trioxide (50% in ethyl acetate, 7.33 g, 11.52 mmol) was added. The mixture was stirred at rt for 1 h. It was diluted with DCM (20 mL), washed with aqueous sodium bicarbonate (saturated, 15 mL), dried over MgSO₄, filtered and the solvent was evaporated under reduced pressure. The residue was purified by flash column chromatography on silica gel (eluting with EtOAc/hexane=30% v/v) to give the title compound. MS (ES⁺) m/z: 641 (M+H).

1D: (E)-9-(5-((tert-Butyldiphenylsilyl)oxy)pyridin-2-yl)-2⁵-fluoro-3-aza-1(1,3),2(1,2)-dibenzenacyclononaphan-6-en-4-one

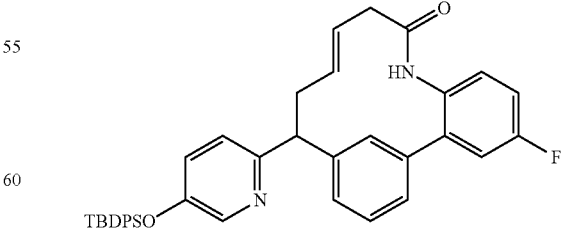

Degassed toluene (281 mL) was added to a mixture of 1C (3.6 g, 5.62 mmol), Zhan catalyst-1B (0.824 g, 1.123 mmol) and p-toluenesulfonic acid monohydrate (0.855 g, 4.49 mmol) in a 500 mL round bottom flask under nitrogen. The mixture was stirred at 50° C. overnight. The mixture was cooled to rt and diluted with dichloromethane (400 mL). The solution washed with aqueous sodium bicarbonate (saturated, 100 mL), dried (MgSO$_4$), filtered and the solvent was evaporated under reduced pressure. The residue was purified by flash column chromatography (eluting with 0-40% ethyl acetate in hexane) to give the title compound. MS (ES$^+$) m/z: 613 (M+H).

1E: $2^5$-Fluoro-9-(5-hydroxypyridin-2-yl)-3-aza-1(1,3),2(1,2)-dibenzenacyclononaphan-4-one

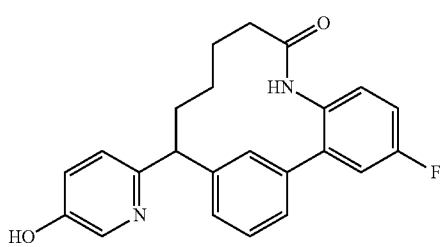 [SMILES: O=C1CCCCC(c2ccc(O)cn2)c2cccc(c2)-c2cc(F)ccc2N1]

A mixture of 1D (600 mg, 0.979 mmol), Pd(OH)$_2$ (20 wt % on carbon, 68.7 mg, 0.098 mmol) and methanol (9.8 mL) was stirred at rt under a hydrogen balloon for 16 h. The mixture was filtered through a pad of Celite and the filtrate was concentrated under reduced pressure. The crude product dissolved in THF (9.4 mL) was treated with TBAF (1 M in THF, 1.9 mL, 1.9 mmol). The mixture was stirred at rt for 1 h, then it was quenched with ammonium chloride (10 mL) and extracted with ethyl acetate. The organic layer was dried over sodium sulfate, filtered and concentrated under reduced pressure. The residue was purified by flash column chromatography on silica gel (eluting with EtOH-EtOH (3:1)/hexane) to give the title compound. MS (ES$^+$) m/z: 377 (M+H).

1F: 6-($2^5$-Fluoro-4-oxo-3-aza-1(1,3),2(1,2)-dibenzenacyclononaphane-9-yl)pyridin-3-yl trifluoromethanesulfonate

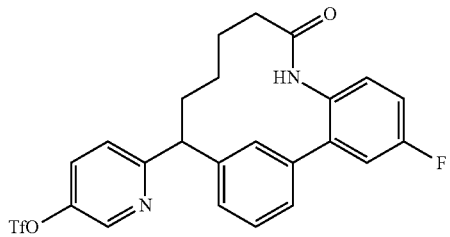 [SMILES: O=C1CCCCC(c2ccc(OS(=O)(=O)C(F)(F)F)cn2)c2cccc(c2)-c2cc(F)ccc2N1]

To a stirred mixture of 1E (350 mg, 0.930 mmol) and Hunig's Base (487 μL, 2.79 mmol) in DCM (9.3 mL) was added Tf$_2$O (1 M in DCM, 1.4 mL, 1.4 mmol). The mixture was stirred at rt for 2 h. The mixture was diluted with dichloromethane (10 mL), washed with aqueous sodium bicarbonate (saturated, 10 mL), dried (MgSO$_4$), filtered and the solvent was evaporated under reduced pressure. The residue was purified by flash column chromatography on silica gel (eluting with EtOAc/hexane) to give the title compound. MS (ES$^+$) m/z: 509 (M+H).

1G: 9-(5-(2-Amino-5-chlorophenyl)pyridin-2-yl)-$2^5$-fluoro-3-aza-1(1,3),2(1,2)-dibenzenacyclononaphan-4-one

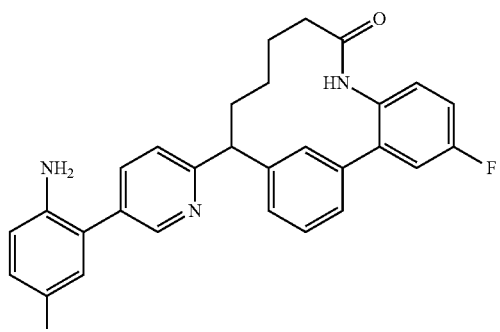

To a microwave vial charged with a magnetic stirring bar was added 1F (100 mg, 0.197 mmol), [1,1'-bis(diphenylphosphino)ferrocene]dichloropalladium(II) (32.1 mg, 0.039 mmol), 4-chloro-2-(4,4,5,5-tetramethyl-1,3,2-dioxaborolan-2-yl)aniline (59.8 mg, 0.236 mmol), CsF (90.0 mg, 0.590 mmol) and degassed dioxane (2.4 mL). The vial was sealed and the mixture was stirred in an oil bath at 100° C. for 2 h. The mixture was cooled to rt and purified by flash column chromatography on silica gel (eluting with EtOAc-EtOH (3:1)/hexane) to give the title compound. MS (ES$^+$) m/z: 486 (M+H).

Example 1

9-(5-(5-Chloro-2-(1H-tetrazol-1-yl)phenyl)pyridin-2-yl)-$2^5$-fluoro-3-aza-1(1,3),2(1,2)-dibenzenacyclononaphan-4-one Example 1-a (S)-9-(5-(5-Chloro-2-(1H-tetrazol-1-yl)phenyl)pyridin-2-yl)-$2^5$-fluoro-3-aza-1(1,3),2(1,2)-dibenzenacyclononaphan-4-one Example 1-b (R)-9-(5-(5-Chloro-2-(1H-tetrazol-1-yl)phenyl)pyridin-2-yl)-$2^5$-fluoro-3-aza-1(1,3),2(1,2)-dibenzenacyclononaphan-4-one A solution of 1G (95 mg, 0.195 mmol), sodium azide (38.1 mg, 0.586 mmol) and trimethyl orthoformate (65 μl, 0.586 mmol) in acetic acid (1 mL) was stirred at 90° C. for 2 h and cooled to rt. It was diluted with ethyl acetate (20 mL) and washed with sodium bicarbonate and then brine. The organic layer was dried over sodium sulfate, filtered and concentrated under reduced pressure. The residue was purified by flash column chromatography on silica gel (eluting with EtOAc-EtOH (3:1) in hexane) to give the title compound. MS (ES$^+$) m/z: 539 (M+H).

The racemate was separated by chiral reverse phase SFC (OJ, 21×250 mm, 40% MeOH-MeCN (2:1)/CO$_2$, 60 mL/min, 100 bar, 35° C.) to give Example 1-a (faster eluting) and Example 1-b (slower eluting). The absolute configuration was assigned based on biological data and X-ray structures of close analogues. MS (ES$^+$) m/z: 539

(M+H); ¹H NMR (500 MHz, CDCl₃): δ 8.40 (s, 1 H); 8.32 (s, 1 H); 7.55-7.63 (m, 3 H); 7.46-7.50 (m, 2 H); 7.42 (t, J=7.7 Hz, 1 H); 7.17-7.23 (m, 3 H); 7.07-7.12 (m, 3 H); 6.71 (s, 1 H); 4.15 (t, J=7.7 Hz, 1 H); 2.25-2.29 (m, 2 H); 2.14 (t, J=6.9 Hz, 2 H); 1.72-1.78 (m, 1 H); 1.44-1.47 (m, 2 H); 0.99 (d, J=6.4 Hz, 1H).

Example 2-a (S) 5-(5-chloro-2-(1H-tetrazol-1-yl)phenyl)-2-(2⁵-fluoro-4-oxo-3-aza-1(1,3),2(1,2)-dibenzenacyclononaphane-9-yl)pyridine 1-oxide

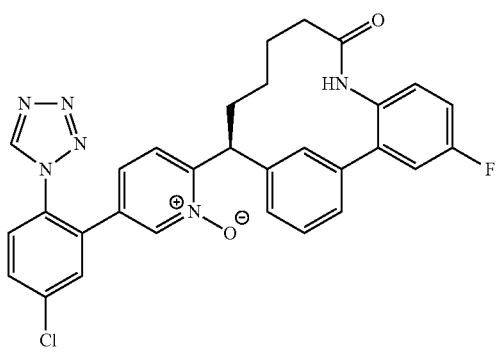 [SMILES: O=C1CCCC[C@H](c2ccc(-c3cc(Cl)ccc3-n3cnnn3)c[n+]2[O-])c2cccc(c2)-c2cc(F)ccc2N1]

To a solution of Example 1-a (35 mg, 0.065 mmol) in DCM (1 mL) was added m-CPBA (22.4 mg, 0.13 mmol). The reaction mixture was stirred at rt for 3 h. It was directly purified by flash column chromatography on silica gel (eluting with EtOAc-EtOH (3:1)/hexane) to give the desired product. MS (ES⁺) m/z: 555 (M+H); ¹H NMR (500 MHz, DMSO-d₆): δ 9.68 (s, 1 H); 9.53 (s, 1 H); 8.20 (s, 1 H); 7.89 (s, 1 H); 7.83 (s, 2 H); 7.60 (s, 1 H); 7.50 (d, J=8.3 Hz, 1 H); 7.32-7.37 (m, 2 H); 7.21-7.28 (m, 3 H); 6.95 (d, J=8.3 Hz, 1 H); 6.88 (d, J=7.6 Hz, 1 H); 4.56 (d, J=12.8 Hz, 1H); 2.27 (t, J=9.6 Hz, 1 H); 1.82-2.04 (m, 4 H); 1.47 (m, 1 H); 1.20 (m, 1 H); 1.05 (t, J=7.2 Hz, 1H).

Example 2-b (R) 5-(5-chloro-2-(1H-tetrazol-1-yl)phenyl)-2-(2⁵-fluoro-4-oxo-3-aza-1(1,3),2(1,2)-dibenzenacyclononaphane-9-yl)pyridine 1-oxide

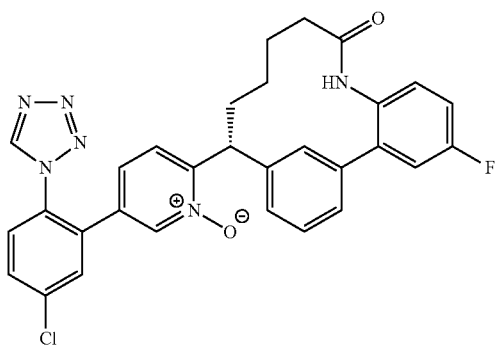 [SMILES: O=C1CCCC[C@@H](c2ccc(-c3cc(Cl)ccc3-n3cnnn3)c[n+]2[O-])c2cccc(c2)-c2cc(F)ccc2N1]

Example 2-b was prepared from Example 1-b by the procedure described in Example 2-a. MS (ES⁺) m/z: 555 (M+H); ¹H NMR (500 MHz, DMSO-d₆): δ 9.68 (s, 1 H); 9.53 (s, 1 H); 8.20 (s, 1 H); 7.89 (s, 1 H); 7.83 (s, 2 H); 7.60 (s, 1 H); 7.50 (d, J=8.3 Hz, 1 H); 7.32-7.37 (m, 2 H); 7.21-7.28 (m, 3 H); 6.95 (d, J=8.3 Hz, 1 H); 6.88 (d, J=7.6 Hz, 1 H); 4.56 (d, J=12.8 Hz, 1H); 2.27 (t, J=9.6 Hz, 1 H); 1.82-2.04 (m, 4 H); 1.47 (m, 1 H); 1.20 (m, 1 H); 1.05 (t, J=7.2 Hz, 1H).

Example 3 (racemate), 3-a, 3-b, 3-c and 3-d 5-(5-chloro-2-(1H-tetrazol-1-yl)phenyl)-2(2⁵-fluoro-5-methyl-4-oxo-3-aza-1(1,3),2(1,2)-dibenzenacyclononaphane-9-yl)pyridine 1-oxide

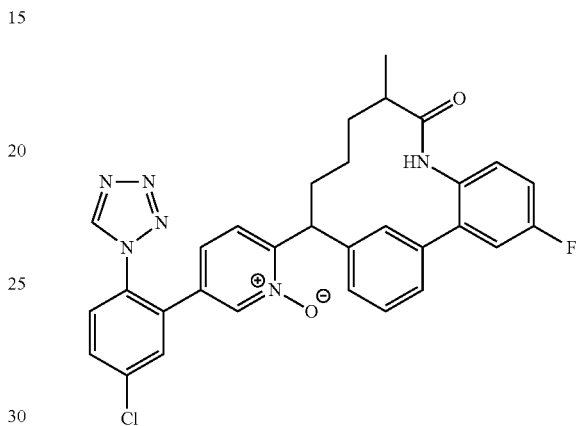

Example 3 was prepared by the procedures described in Example 1 and 2 by replacing but-3-enoic acid with 2-methylbut-3-enoic acid in the synthesis of 1C.

The four diastereomers were separated by chiral reverse phase HPLC (IC-H, 4.6×250 mm, 50% MeOH/CO₂, 2.4 mL/min, 100 bar, 40° C.). The absolute configuration was assigned based on X-ray and ¹HNMR spectroscopic data.

Example 3-a 5-(5-chloro-2-(1H-tetrazol-1-yl)phenyl)-2-((5R,9R)-2⁵-fluoro-5-methyl-4-oxo-3-aza-1(1,3),2(1,2)-dibenzenacyclononaphane-9-yl)pyridine 1-oxide

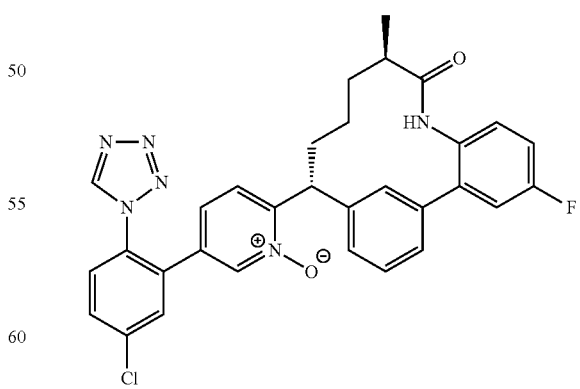

Example 3-a was isolated as peak 1. MS (ES⁺) m/z: 569 (M+H); ¹H NMR (500 MHz, DMSO): δ 9.67 (s, 1H), 9.40 (s, 1H), 8.20 (s, 1H), 7.89 (s, 1H), 7.82-7.84 (m, 2H), 7.63 (d, J=8.3 Hz, 1H), 7.56 (s, 1H), 7.31-7.39 (m, 2H), 7.19-7.26

(m, 3H), 6.97 (d, J=8.3 Hz, 1H), 6.78 (d, J=7.6 Hz, 1H), 4.49 (dd, J=13.0, 3.6 Hz, 1H), 2.29 (d, J=9.3 Hz, 1H), 1.94 (m, 1H); 1.70 (t, J=11.7 Hz, 2H), 1.25 (m, 3H); 1.09 (d, J=6.8 Hz, 3H).

Example 3-b 5-(5-chloro-2-(1H-tetrazol-1-yl)phenyl)-2-((5S,9S)-2⁵-fluoro-5-methyl-4-oxo-3-aza-1(1,3),2(1,2)-dibenzenacyclononaphane-9-yl)pyridine 1-oxide

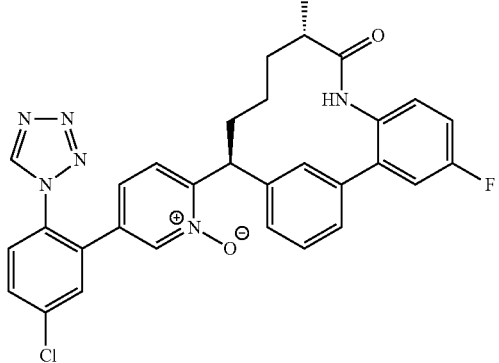

Example 3-b was isolated as peak 2. MS (ES⁺) m/z: 569 (M+H); ¹H NMR (500 MHz, DMSO): δ 9.67 (s, 1H), 9.40 (s, 1H), 8.20 (s, 1H), 7.89 (s, 1H), 7.82-7.84 (m, 2H), 7.63 (d, J=8.3 Hz, 1H), 7.56 (s, 1H), 7.31-7.39 (m, 2H), 7.19-7.26 (m, 3H), 6.97 (d, J=8.3 Hz, 1H), 6.78 (d, J=7.6 Hz, 1H), 4.49 (dd, J=13.0, 3.6 Hz, 1H), 2.29 (d, J=9.3 Hz, 1H), 1.95 (m, 1H); 1.70 (t, J =11.7 Hz, 2H), 1.25 (m, 3H); 1.09 (d, J=6.8 Hz, 3H).

Example 3-c 5-(5-Chloro-2-(1H-tetrazol-1-yl)phenyl)-2-((5S,9R)-2⁵-fluoro-5-methyl-4-oxo-3-aza-1(1,3),2(1,2)-dibenzenacyclononaphane-9-yl)pyridine 1-oxide

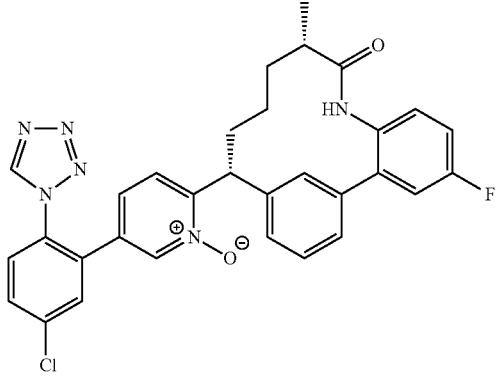 [SMILES: C[C@H]1CCC[C@@H](c2ccc(-c3cc(Cl)ccc3-n3cnnn3)c[n+]2[O-])c2cccc(c2)-c2cc(F)ccc2NC1=O]

Example 3-c was isolated as peak 3. MS (ES⁺) m/z: 569 (M+H); ¹H NMR (500 MHz, DMSO): δ 9.65 (s, 1H), 9.51 (s, 1H), 8.19 (s, 1H), 7.87 (s, 1H), 7.79-7.83 (m, 2H), 7.63 (s, 1H), 7.29-7.37 (m, 3H), 7.21 (d, J=6.7 Hz, 2H), 6.96 (d, J=7.6 Hz, 1H), 6.88 (d, J=8.3 Hz, 1H), 4.60 (m, 1H), 1.85 (br s, 4H), 1.18-1.36 (m, 3H), 0.92 (d, J=6.8 Hz, 3H).

Example 3-d 5-(5-Chloro-2-(1H-tetrazol-1-yl)phenyl)-2-((5R,9S)-2⁵-fluoro-5-methyl-4-oxo-3-aza-1(1,3),2(1,2)-dibenzenacyclononaphane-9-yl)pyridine 1-oxide

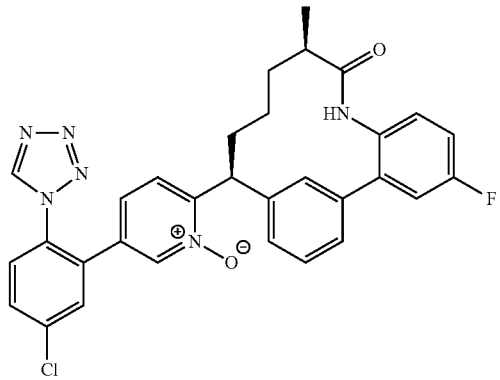 [SMILES: C[C@@H]1CCC[C@H](c2ccc(-c3cc(Cl)ccc3-n3cnnn3)c[n+]2[O-])c2cccc(c2)-c2cc(F)ccc2NC1=O]

Example 3-d was isolated as peak 4. MS (ES⁺) m/z: 569 (M+H); ¹H NMR (500 MHz, DMSO): δ 9.65 (s, 1H), 9.51 (s, 1H), 8.19 (s, 1H), 7.87 (s, 1H), 7.79-7.83 (m, 2H), 7.63 (s, 1H), 7.29-7.37 (m, 3H), 7.21 (d, J=6.7 Hz, 2H), 6.96 (d, J=7.6 Hz, 1H), 6.88 (d, J=8.3 Hz, 1H), 4.60 (m, 1H), 1.85 (br s, 4H), 1.18-1.36 (m, 3H), 0.92 (d, J=6.8 Hz, 3H).

Example 4 (racemate), 4-a and 4-b 2-(2⁵-Carboxy-4-oxo-3-aza-1(1,3),2(1,2)-dibenzenacyclononaphane-9-yl)-5-(5-chloro-2-(1H-tetrazol-1-yl)phenyl)pyridine 1-oxide

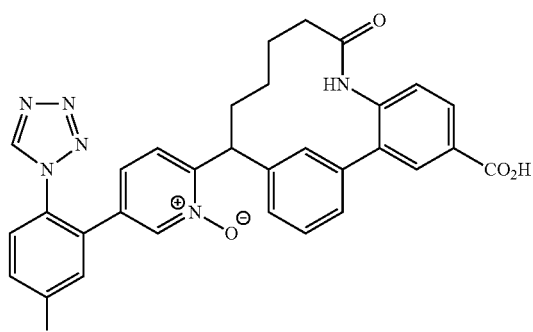

4A: Methyl 4-oxo-9-(5-(((trifluoromethyl)sulfonyl)oxy)pyridin-2-yl)-3-aza-1(1,3),2(1,2)-dibenzenacyclononaphane-2⁵-carboxylate

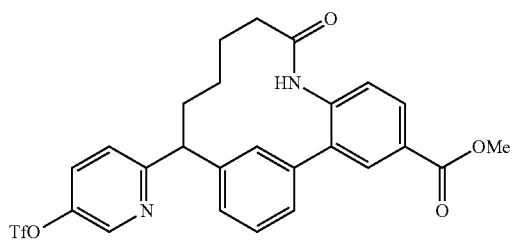 [SMILES: COC(=O)c1ccc2c(c1)-c1cccc(c1)C(c1ccc(OS(=O)(=O)C(F)(F)F)cn1)CCCCC(=O)N2]

4A was prepared by the same synthetic route as the synthesis of 1F employing Intermediate 1 and Intermediate 20 as the starting materials. MS (ES+) m/z: 549 (M+H).

4B: Methyl 9-(5-(2-amino-5-chlorophenyl)pyridin-2-yl)-4-oxo-3-aza-1(1,3),2(1,2)-dibenzenacyclononaphane-2⁵-carboxylate

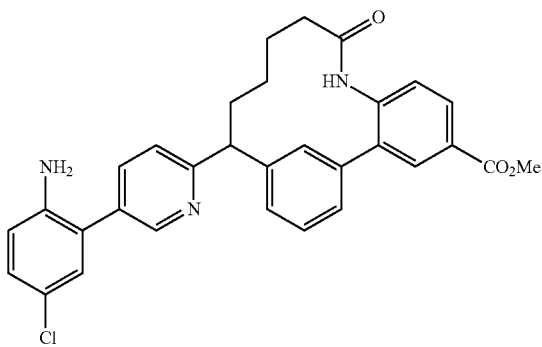 [SMILES: COC(=O)c1ccc2c(c1)-c1cccc(c1)C(c1ccc(-c3cc(Cl)ccc3N)cn1)CCCCC(=O)N2]

4B was prepared from 4A by the procedure described in the synthesis of 1G MS (ES+) m/z: 526 (M+H).

4C: 9-(5-(2-Amino-5-chlorophenyl)pyridin-2-yl)-4-oxo-3-aza-1(1,3),2(1,2)-dibenzenacyclononaphane-2⁵-carboxylic acid

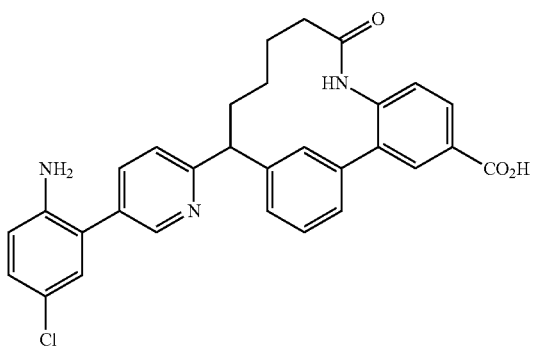 [SMILES: Nc1ccc(Cl)cc1-c1ccc(C2CCCCC(=O)Nc3ccc(C(=O)O)cc3-c3cccc2c3)nc1]

To a solution of 4B (80 mg, 0.152 mmol) in MeOH (760 μl) and THF (760 μl) was added an aqueous solution of sodium hydroxide (3 M, 152 μl, 0.456 mmol). The mixture was stirred at rt overnight and was neutralized with HCl (1 M) to pH 5. The mixture was concentrated under reduced pressure and dried under vacuum. The residue was used without further purification. MS (ES+) m/z: 512 (M+H).

4D: 9-(5-(5-Chloro-2-(1H-tetrazol-1-yl)phenyl)pyridin-2-yl)-4-oxo-3-aza-1(1,3),2(1,2)-dibenzenacyclononaphane-2⁵-carboxylic acid

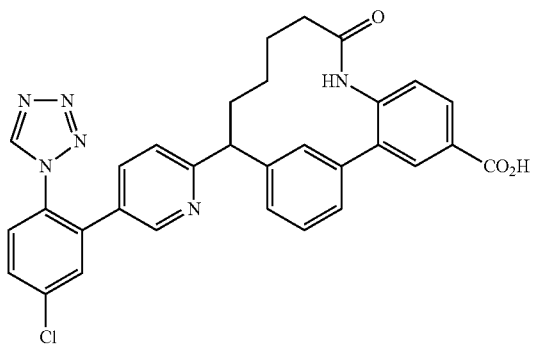 [SMILES: O=C1CCCCC(c2ccc(-c3cc(Cl)ccc3-n3cnnn3)cn2)c2cccc(c2)-c2cc(C(=O)O)ccc2N1]

4D was prepared from 4C by the procedure described in the synthesis of 1H. MS (ES+) m/z: 565 (M+H).

Example 4

To a solution of 4D (73 mg, 0.129 mmol) in DCM (1 mL) was added m-CPBA (96 mg, 0.388 mmol). The resulting solution was stirred at rt for 2 h. Solids were precipitated. It was filtered and the solids were washed with DCM (5 mL) to give the title compound. MS (ES+) m/z: 565 (M+H).

A racemic sample of Example 4 was subjected to chiral separation (Whelk 30×250 mm, 60% MeOH (0.2% NH₄OH)/CO₂, 70 mL/min, 100 bar, 35° C.). The fractions of both enantiomers were collected separately and concentrated under reduced pressure. The residue from the slower eluent was concentrated and neutralized by one drop of 5% citric acid solution and two drops of KH₂PO₄, before it was purified by flash column chromatography on silica gel (eluting with 0-20% methanol in DCM) to give Example 4-a. MS (ES+) m/z: 581 (M+H); ¹H NMR (500 MHz, DMSO-d₆): 13.05 (br s, 1H), 9.73-9.75 (m, 1H), 9.66 (s, 1H), 8.18 (m, 1H), 8.03 (s, 1H), 7.88-7.93 (m, 2H), 7.78-7.81 (m, 2H), 7.58 (m, 1H), 7.52 (d, 1H), 7.28-7.39 (m, 3H), 6.94 (t, 1H), 6.87 (d, 1H), 4.55 (d, 1H), 2.32 (t, 1H), 1.91-1.99 (m, 2H), 1.80 (br s, 1H), 1.47 (br s, 1H), 1.23 (br s, 1H), 1.02 (m, 1H).

The residue from the faster eluent was dissolved in 2 mL of 50% DCM/methanol and added two drops of 1 M KH₂PO₄ and one drop of 5% citric acid solution. The mixture was purified by flash column chromatography on silica gel (eluting with 0-20% methanol in DCM) to give Example 4-b. MS (ES+) m/z: 581 (M+H).

Example 5 (racemate), 5-a and 5-b 2-(2⁵-carboxy-4-oxo-3-aza-1(1,3),2(1,2)-dibenzenacyclononaphane-9-yl)-5-(3-chloro-2-fluoro-6-(1H-tetrazol-1-yl)phenyl)pyridine 1-oxide

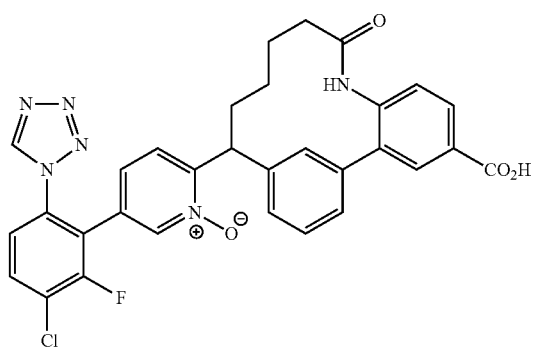 [SMILES: O=C1CCCCC(c2ccc(-c3c(-n4cnnn4)ccc(Cl)c3F)c[n+]2[O-])c2cccc(c2)-c2cc(C(=O)O)ccc2N1]

Example 5 was prepared by the procedures described in the synthesis of Example 4. MS (ES+) m/z: 599 (M+H).

A racemic sample of Example 5 was subjected to chiral separation by SFC (OD-H, 2×25 cm, 30% MeOH (NH₄OH)/CO₂, 100 bar, 60 mL/min, 35° C.) to give Example 5-a (faster eluting) and Example 5-b (slower eluting). MS (ES+) m/z: 599 (M+H).

Example 6 (racemate), 6-a and 6-b 5-(5-Chloro-2-(1H-tetrazol-1-yl)phenyl)-2-($2^4$-((methoxycarbonyl)amino)-4-oxo-3-aza-1(1,3),2(1,2)-dibenzenacyclononaphane-9-yl)pyridine 1-oxide

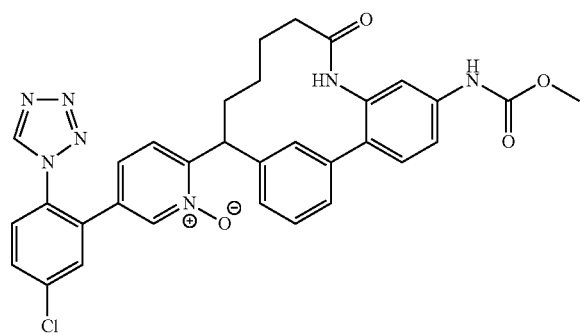 [SMILES: COC(=O)Nc1ccc2c(c1)NC(=O)CCCCC(c1ccc(-c3cc(Cl)ccc3-n3cnnn3)c[n+]1[O-])c1cccc-2c1]

6A: 6-($2^4$-((Methoxycarbonyl)amino)-4-oxo-3-aza-1(1,3),2(1,2)-dibenzenacyclononaphane-9-yl)pyridin-3-yl trifluoromethanesulfonate

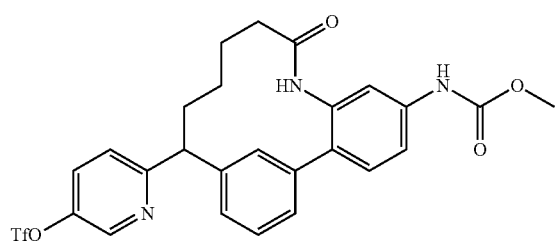 [SMILES: COC(=O)Nc1ccc2c(c1)NC(=O)CCCCC(c1ccc(OS(=O)(=O)C(F)(F)F)cn1)c1cccc-2c1]

6A was prepared by the same synthetic route as the synthesis of 1F employing Intermediate 1 and Intermediate 19 as the starting materials. MS (ES$^+$) m/z: 564 (M+H).

Example 6

Example 6 was prepared from 6A following the synthetic route described in the synthesis of Example 1 and Example 2. MS (ES$^+$) m/z: 610 (M+H).

A racemic sample of Example 6 was subjected to chiral separation by SFC (IC, 30×250 mm, 80% 2:1 MeOH:MeCN/CO$_2$, 70 mL/min, 100 bar, 35° C.) to give Example 6-a (slower eluting) and Example 6-b (faster eluting). MS (ES$^+$) m/z: 610 (M+H); $^1$H NMR (500 MHz, DMSO-d$_6$): δ 9.81 (s, 1H), 9.66 (s, 1H), 9.55 (s, 1H), 8.19 (d, 1H), 7.88 (d, 1H), 7.79-7.83 (m, 2H), 7.56 (s, 1H), 7.47 (d, 2H), 7.41 (d, 1H), 7.29 (m, 2H), 7.19 (d, 1H), 6.92 (m, 1H), 6.79 (d, 1H), 4.53 (d, 1H), 3.68 (s, 3H), 2.28 (m, 1H), 1.94 (m, 2H), 1.78 (m, 2H), 1.46 (m, 1H), 1.21 (m, 1H), 1.02 (m, 1H).

Example 7-a and 7-b 5-(5-chloro-3-fluoro-2-(1H-tetrazol-1-yl)phenyl)-2-($2^5$-fluoro-4-oxo-3-aza-1(1,3),2(1,2)-dibenzenacyclononaphane-9-yl)pyridine 1-oxide

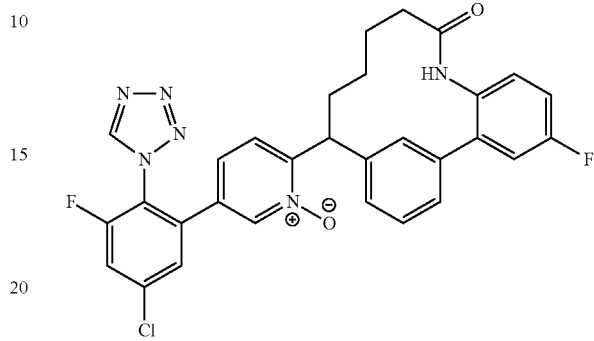

7A: 9-(5-(2-Amino-5-chloro-3-fluorophenyl)pyridin-2-yl)-$2^5$-fluoro-3-aza-1(1,3),2(1,2)-dibenzenacyclononaphan-4-one To a vial was added a mixture of 1F (110 mg, 0.216 mmol), potassium acetate (42.5 mg, 0.433 mmol), bis(pinacolato)diboron (71.4 mg, 0.281 mmol), and chloro(2-dicyclohexylphosphino-2',4',6'-triisopropyl-1,1'-biphenyl)[2-(2-aminoethyl)phenyl]palladium(II) (15.98 mg, 0.022 mmol). It was degassed and backfilled with nitrogen three times. Degassed dioxane (2.4 mL) was added subsequently, and the resulting mixture was stirred at 100° C. for 1 h. The mixture was cooled to rt. A solution of 2-bromo-4-chloro-6-fluoroaniline (72.8 mg, 0.324 mmol) and chloro(2-dicyclohexylphosphino-2',4',6'-triisopropyl-1,1'-biphenyl)[2-(2-aminoethyl)phenyl]palladium(II) (15.98 mg, 0.022 mmol) in degassed dioxane (1 mL) was added, followed by the addition of aqueous potassium phosphate tribasic (3 M, 0.22 mL, 0.66 mmol). The reaction mixture was stirred at 100° C. for 1 h. It was allowed to cool to rt and purified directly by fast flash column chromatography (eluting with EtOAc-EtOH (3:1)/Hexane=40% v/v) to give the title compound. MS (ES$^+$) m/z: 504 (M+H).

7B: 9-(5-(5-Chloro-3-fluoro-2-(1H-tetrazol-1-yl)phenyl)pyridin-2-yl)-$2^5$-fluoro-3-aza-1(1,3),2(1,2)-dibenzenacyclononaphan-4-one

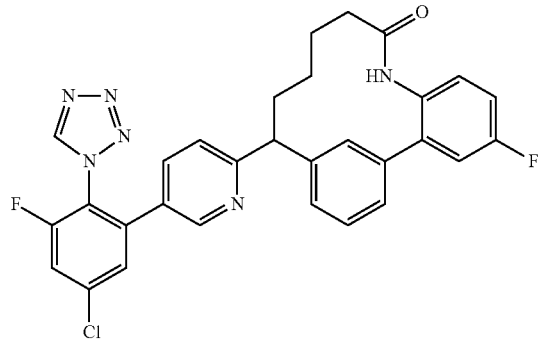 [SMILES: O=C1CCCCC(c2ccc(-c3cc(Cl)cc(F)c3-n3cnnn3)cn2)c2cccc(c2)-c2cc(F)ccc2N1]

To a stirred mixture of 7A (36 mg, 0.071 mmol) and trimethyl orthoformate (7.58 mg, 0.071 mmol) in acetic acid (1 mL), sodium azide (4.64 mg, 0.071 mmol) was added. The mixture was stirred at 90° C. for 2 h. It was cooled to rt and was concentrated under reduced pressure. The residue was purified by flash column chromatography on silica gel (eluting with EtOAc-EtOH (3:1)/Hexane=30% to 70% v/v) to give the title compound. MS (ES$^+$) m/z: 557 (M+H).

Example 7 m-CPBA (11.15 mg, 0.065 mmol) was added to a stirred mixture of 7B (18 mg, 0.032 mmol) in dichloromethane (1 mL). The mixture was stirred at rt overnight and was directly purified by flash column chromatography on silica gel (eluting with EtOAc-EtOH (3:1)/Hexane=30 to 100% v/v) to give the racemic compound. MS (ES$^+$) m/z: 573 (M+H).

A racemic sample of Example 7 was subjected to chiral separation by SFC (IC, 21×250 mm, 50% MeOH:MeCN (2:1)/CO$_2$, 60 mL/min, 100 bar, 35° C.) to give Example 7-a (faster eluting) and Example 7-b (slower eluting). MS (ES$^+$) m/z: 573 (M+H); $^1$H NMR (500 MHz, CH$_3$OH-d$_4$): δ 9.46 (s, 1H), 8.25 (s, 1H), 7.79 (d, 1H), 7.68 (s, 1H), 7.64 (s, 1H), 7.58 (d, 1H), 7.37 (t, 1H), 7.21-7.30 (m, 4H), 7.14 (m, 1H), 6.89 (d, 1H), 4.68 (t, 1H), 2.38 (t, 1H), 2.11 (t, 1H), 1.98 (m, 2H), 1.91 (d, 1H), 1.56 (m, 1H), 1.38 (m, 1H), 1.23 (m, 1H). By using the procedures described above, and appropriate starting materials, the following compounds were synthesized and characterized by LC/MS.

| Ex | Structure | Name | MS (M + 1) |
|---|---|---|---|
| 8 | 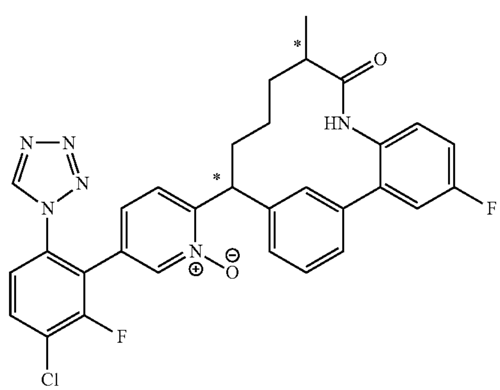 [SMILES: CC1CCCC(c2ccc(-c3c(-n4cnnn4)ccc(Cl)c3F)c[n+]2[O-])c2cccc(c2)-c2cc(F)ccc2NC1=O] | 5,5-(3-chloro-2-fluoro-6-(1h-tetrazol-1-yl)phenyl)-2-($2^5$-fluoro-5-methyl-4-oxo-3-aza-1(1,3),2(1,2)-dibenzenacyclononaphane-9-yl)pyridine 1-oxide | 587 |
| 9 | 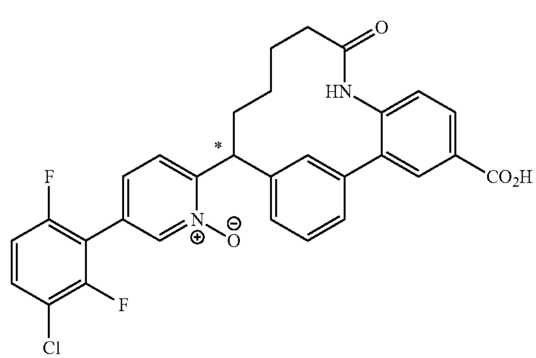 [SMILES: O=C1CCCCC(c2ccc(-c3c(F)ccc(Cl)c3F)c[n+]2[O-])c2cccc(c2)-c2cc(C(=O)O)ccc2N1] | 2-($2^5$-carboxy-4-oxo-3-aza-1(1,3),2(1,2)-dibenzenacyclononaphane-9-yl)-5-(3-chloro-2,6-difluorophenyl)pyridine 1-oxide | 565 |

Example 10 (racemate), 10a and 10b (Z)-9-(5-(5-chloro-2-(1H-tetrazol-1-yl)phenyl)pyridin-2-yl)-2$^5$-fluoro-1$^1$H -3-aza-1(4,2)-imidazola-2(1,2)-benzenacyclononaphan-4-one

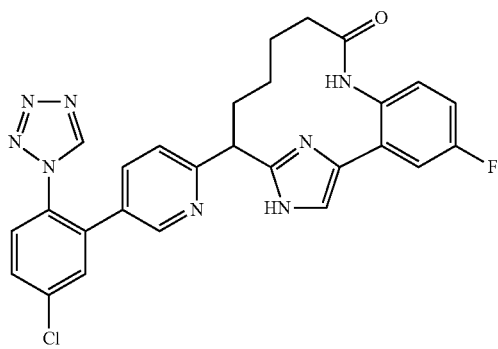 [SMILES: O=C1CCCCC(c2ccc(-c3cc(Cl)ccc3-n3cnnn3)cn2)c2nc(c[nH]2)-c2cc(F)ccc2N1]

10A: 5-((4-Methoxybenzyl)oxy)-2-methylpyridine

To a stirred mixture of 6-methylpyridin-3-ol (10 g, 92 mmol) in DMF (150 mL) at 0° C., NaH (5.50 g, 137 mmol, 60% wt) was added in small portions. After addition, the mixture was stirred under nitrogen at 0° C. for 30 min. PMB-Cl (14.86 mL, 110 mmol) was added dropwise to the reaction and it was allowed to warm to rt with stirring over 2 h. The reaction was quenched with saturated aqueous ammonium chloride (200 mL) and extracted with EtOAc (3×100 mL). The combined organic layers were washed with water, dried over sodium sulfate, and filtered. The filtrate was concentrated under reduced pressure and purified by flash column chromatography on silica gel (eluting with petroleum ether:EtOAc=4:1 v/v) to give the title compound. MS (ES$^+$) m/z: 230 (M+H).

10B: Ethyl 2-(5-((4-methoxybenzyl)oxy)pyridin-2-yl)acetate

To a stirred mixture of 10A (7 g, 30.5 mmol) in anhydrous THF (140 mL) at −78° C., a solution of LDA (30.5 mL, 61.1 mmol, 2M in THF) was added. It was stirred for 45 min and diethyl carbonate (5.52 mL, 45.8 mmol) was added dropwise to the reaction mixture. It was stirred for another 1 h. The reaction was quenched with saturated aqueous ammonium chloride (20 mL) and extracted with EtOAc (3×30 mL). The combined organic layers were washed with brine (20 mL), dried over sodium sulfate, filtered and concentrated under reduced pressure. The crude product was purified by flash column chromatography on silica gel (eluting with petroleum ether:EtOAc=10:1 to 3:1 v/v) to give the title compound. $^1$H NMR (CDCl$_3$, 400 MHz): δ 8.36-8.22 (m, 1H), 7.35 (d, J=8.6 Hz, 2H), 7.25-7.17 (m, 2H), 6.92 (d, J=8.6 Hz, 2H), 5.09-4.96 (m, 2H), 4.18 (q, J=7.1 Hz, 2H), 3.82 (s, 3H), 3.80-3.73 (m, 2H), 1.26 (t, J=7.1 Hz, 3H).

10C: Ethyl 2-(5-((4-methoxybenzyl)oxy)pyridin-2-yl)pent-4-enoate

To a stirred mixture of 10B (6 g, 19.91 mmol) in THF (100 mL) at −78° C. was added a solution of LDA (11.45 mL, 22.90 mmol, 2 M in THF). It was stirred at −78° C. for 30 min and allyl bromide (1.9 mL, 21.90 mmol) was added dropwise to the reaction mixture. The reaction was allowed to warm to 20° C. and stirred for another 1 h before it was quenched with aqueous saturated ammonium chloride (60 mL). The mixture was transferred to a separatory funnel and extracted with EtOAc (3×60 mL).

The combined organic layers were washed with brine (saturated, 60 mL), dried (sodium sulfate), filtered and concentrated. The crude product was purified by flash column chromatography on silica gel (eluting with petroleum ether:EtOAc=10:1 v/v) to give the title compound. MS (ES$^+$) m/z: 342.1 (M+H).

10D: 2-(5-((4-Methoxybenzyl)oxy)pyridin-2-yl)pent-4-enoic acid

A mixture of 10C (8.6 g, 25.2 mmol), lithium hydroxide monohydrate (5.29 g, 126 mmol) in a co-solvent of MeOH (25 mL)/THF (25 mL)/water (25 mL) was stirred at 20° C. for 1 h. The mixture was acidified with HCl (aqueous 1 M) to pH 5, and it was extracted with EtOAc (3×50 mL). The combined organic layers were washed with brine (saturated, 60 mL), dried (sodium sulfate), filtered and concentrated to give the title compound, which was used in the next step without further purification. MS (ES$^+$) m/z: 314 (M+H).

10E: 2-(2-Bromo-5-fluorophenyl)-2-oxoethyl 2-(5-((4-methoxybenzyl)oxy)pyridin-2-yl)pent-4-enoate A solution of 10D (2.0 g, 6.38 mmol), 2-bromo-1-(2-bromo-5-fluorophenyl)ethan-1-one (2.267 g, 7.66 mmol), and DIEA (2.2 mL, 12.5 mmol) in acetonitrile (20 mL) was stirred at 20° C. for 2 h. The mixture was concentrated under reduced pressure. The residue was purified by flash column chromatography on silica gel (eluting with petroleum ether:EtOAc=10:1 to 3:1 v/v) to give the title compound. MS (ES$^+$) m/z: 528, 530 (M+H);

10F: 2-(1-(4-(2-Bromo-5-fluorophenyl)-1H-imidazol-2-yl)but-3-en-1-yl)-5-((4-methoxybenz-yl)oxy)pyridine A mixture of 10E (2.2 g, 4.16 mmol), ammonium acetate (2.74 mL, 41.6 mmol) and a co-solvent of toluene (25 mL)/HOAc (5 mL) in a sealed microwave vial was heated in a microwave reactor at 140° C. for 30 min. The mixture was extracted with EtOAc (3×50 mL). The combined organic layers were washed with water (50 mL) and brine (saturated, 50 mL) and concentrated under reduced pressure. The residue was purified by flash column chromatography on silica gel (eluting with petroleum ether:EtOAc=20:1 to 5:1) to afford the title compound.

MS (ES$^+$) m/z: 508, 510 (M+H).

10G: 2-(1-(4-(2-Bromo-5-fluorophenyl)-1-((2-(trimethylsilyl)ethoxy)methyl)-1H-imidazol-2-yl)but-3-en-1-yl)-5-((4-methoxybenzyl)oxy)pyridine To a suspension of 10F (1.7 g, 3.34 mmol) in DMF (15 mL) a solution of DIEA (0.7 mL, 4.0 mmol) in DMF (3 mL) at 0° C. was added and the mixture was stirred for 30 min. A solution of SEM-Cl (0.65 mL, 3.68 mmol) in DMF (3 mL) was added to the reaction solution. It was stirred for another 2 h at 0° C. The mixture was diluted with EtOAc (200 mL) and washed with water (100 mL). The organic layer was separated, dried over sodium sulfate, and filtered. The filtrate was concentrated under reduced pressure and purified by flash column chromatography on silica gel (eluting with petroleum ether:EtOAc=30:1 to 5:1 v/v) to afford the title compound. MS (ES+) m/z: 638, 640 (M+H).

10H: 4-Fluoro-2-(2-(1-(5-((4-methoxybenzyl)oxy) pyridin-2-yl)but-3-en-1-yl)-1-((2-(trimethyl silyl) ethoxy)methyl)-1H-imidazol-4-yl)aniline 10G (1.7 g, 2.66 mmol), DMSO (17 mL), potassium carbonate (1.104 g, 7.99 mmol), copper(I) iodide (0.051 g, 0.266 mmol) and L-proline (0.092 g, 0.799 mmol) were added to a dry seal tube. A stream of nitrogen was bubbled through the mixture for 2 min and then ammonium hydroxide (0.414 g, 2.95 mmol) was added. The tube was sealed and stirred in an oil bath at 90° C. for 20 h. It was cooled to rt and the reaction was quenched with water (20 mL). The mixture was extracted with EtOAc (3×50 mL). The combined organic layers were washed with brine (2×30 mL), dried over sodium sulfate, filtered, and concentrated under reduced pressure. The residue was purified by flash column chromatography on silica gel (eluting with petroleum ether:EtOAc=10:1 to 3:1 v/v) to give the title compound. MS (ES+) m/z: 575 (M+H).

10I: N-(4-Fluoro-2-(2-(1-(5-((4-methoxybenzyl)oxy) pyridin-2-yl)but-3-en-1-yl)-1-((2-(tri methylsilyl) ethoxy)methyl)-1H-imidazol-4-yl)phenyl)but-3-enamide To a solution of 10H (600 mg, 1.044 mmol), but-3-enoic acid (108 mg, 1.253 mmol) in DMF (10 mL), DIEA (0.547 mL, 3.13 mmol) was added. The reaction mixture was cooled to 0° C., and 2,4,6-tripropyl-1,3,5,2,4,6-trioxatriphosphorinane-2,4,6-trioxide (1329 mg, 2.088 mmol) (50% Wt in ethyl acetate) was added dropwise. The reaction was stirred for 5 min and it was allowed to warm to 30° C. for 1.5 h. The mixture was cooled to 0° C. and a solution of aqueous sodium bicarbonate (saturated, 20 mL) was added. It was extracted with EtOAc (2×30 mL). The combined organic layers were washed with brine (saturated, 20 mL), dried over sodium sulfate, filtered and concentrated under reduced pressure. The crude residue was purified by flash column chromatography on silica gel (eluting with 0-30% ethyl acetate/petroleum ether gradient) to give the title compound. MS (ES+) m/z: 643 (M+H).

10J: ($1^2$Z,6E)-$2^5$-Fluoro-9-(5-((4-methoxybenzyl) oxy)pyridin-2-yl)-$1^1$-((2-(trimethylsilyl)ethoxy) methyl)-$1^1$H-3-aza-1(4,2)-imidazola-2(1,2)-benzenacyclononaphan-6-en-4-one

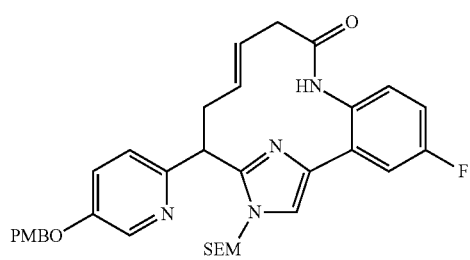

To a solution of 10I (825 mg, 1.283 mmol) in DCE (45 mL) (divided into 3 tubes) was added Grubbs II ((1,3-Bis (2,4,6-trimethylphenyl)-2-imidazolidinylidene)dichloro (phenylmethylene)(tricyclohexylphosphine)ruthenium) (3×109 mg, 0.385 mmol). The resulting mixture under nitrogen was stirred at 120° C. for 30 min in a microwave reactor. The combined crude products were purified by flash column chromatography on silica gel (eluting with petroleum ether:EtOAc=10:1 to 2:1 v/v) to give the title compound. MS (ES+) m/z: 615 (M+H).

10K: (Z)-$2^5$-Fluoro-9-(5-hydroxypyridin-2-yl)-$1^1$-((2-(trimethylsilyl)ethoxy)methyl)-$1^1$H-3-aza-1(4,2)-imidazola-2(1,2)-benzenacyclononaphan-4-one

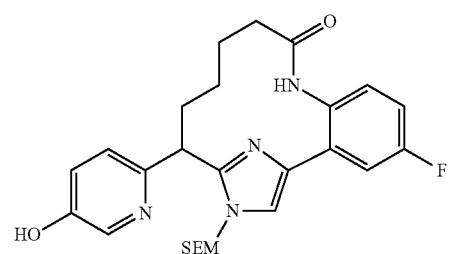 [SMILES: C[Si](C)(C)CCOCn1cc2nc1C(c1ccc(O)cn1)CCCCC(=O)Nc1ccc(F)cc1-2]

A mixture of 10J (500 mg, 0.813 mmol), 10% Pd/C (173 mg, 0.163 mmol) and MeOH (20 mL) was stirred at 30° C. under $H_2$ (1 atm) for 20 h. The mixture was filtered through a pad of Celite and the filtrate was concentrated under reduced pressure to give the title compound, which was used in the next step without further purification. MS (ES+) m/z: 497 (M+H)

10L: (Z)-6-($2^5$-Fluoro-4-oxo-$1^1$-((2-(trimethylsilyl) ethoxy)methyl)-$1^1$H-3-aza-1(4,2)-imidazola-2(1,2)-benzenacyclononaphane-9-yl)pyridin-3-yl trifluoromethanesulfonate

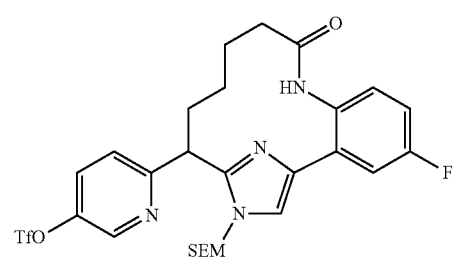 [SMILES: C[Si](C)(C)CCOCn1cc2nc1C(c1ccc(OS(=O)(=O)C(F)(F)F)cn1)CCCCC(=O)Nc1ccc(F)cc1-2]

To a solution of 10K (500 mg, 1.007 mmol) and $Et_3N$ (0.421 mL, 3.02 mmol) in DCM (8 mL) at 0° C., triflic anhydride (1.510 mL, 1.510 mmol) was added under nitrogen. The mixture was stirred for 20 min and was purified by flash column chromatography on silica gel (eluting with petroleum ether:EtOAc=5:1 to 1:1 v/v) to give the title compound. $^1$H NMR (CDCl$_3$, 400 MHz): δ 12.02 (m, 1H), 8.53 (d, J=2.8 Hz, 1H), 7.94 (dd, J=5.4, 8.9 Hz, 1H), 7.59 (dd, J=2.8, 8.5 Hz, 1H), 7.42 (d, J=8.8 Hz, 1H), 7.17 (dd, J=2.9, 9.2 Hz, 1H), 7.11 (s, 1H), 7.00 (dt, J=2.8, 8.5 Hz, 1H), 5.10 (q, J=11.0 Hz, 2H), 4.44 (dd, J=3.6, 11.7 Hz, 1H), 3.32 (dt, J=6.7, 10.0 Hz, 2H), 2.71-2.58 (m, 1H), 2.56-2.44 (m, 1H), 2.43-2.31 (m, 1H), 2.18 (dd, J=3.9, 8.2 Hz, 1H), 2.08-1.94 (m, 1H), 1.84-1.62 (m, 2H), 1.36-1.19 (m, 1H), 0.83-0.61 (m, 2H), −0.05 (s, 9H).

10M: (Z)-9-(5-(2-Amino-5-chlorophenyl)pyridin-2-yl)-2⁵-fluoro-1¹-((2-(trimethylsilyl)ethoxy)methyl)-1¹H-3-aza-1(4,2)-imidazola-2(1,2)-benzenacyclononaphan-4-one

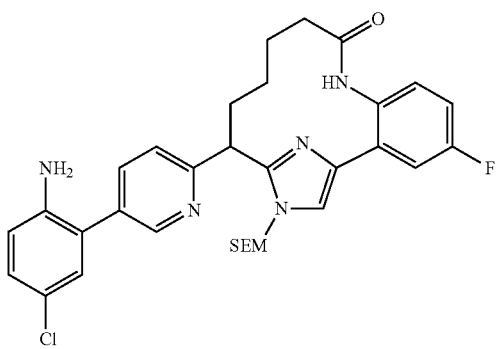 [SMILES: C[Si](C)(C)CCOCn1cc2nc1C(c1ccc(-c3cc(Cl)ccc3N)cn1)CCCCC(=O)Nc1ccc(F)cc1-2]

To a solution of 10L (400 mg, 0.636 mmol) in DMF (10 mL) in a sealed tube, 4-chloro-2-(4,4,5,5-tetramethyl-1,3,2-dioxaborolan-2-yl)aniline (323 mg, 1.272 mmol), $K_3PO_4$ (405 mg, 1.909 mmol) and $PdCl_2(dppf)$ (46.6 mg, 0.064 mmol) were added. The tube was capped and was purged with nitrogen three times. The mixture was stirred at 90° C. under nitrogen for 1 h. It was cooled to rt and diluted with $H_2O$ (30 mL). The mixture was extracted with EtOAc (3×30 mL). The combined organic layers were washed with brine (20 mL), dried over sodium sulfate, filtered and concentrated under reduced pressure. The residue was purified by flash column chromatography on silica gel (eluting with petroleum ether:EtOAc=5:1 to 1:1 v/v) to give the title compound. MS (ES⁺) m/z: 606 (M+H).

10N: (Z)-9-(5-(5-Chloro-2-(1H-tetrazol-1-yl)phenyl)pyridin-2-yl)-2⁵-fluoro-1¹-((2-(trimethylsilyl)ethoxy)methyl)-1¹H-3-aza-1(4,2)-imidazola-2(1,2)-benzenacyclononaphan-4-one

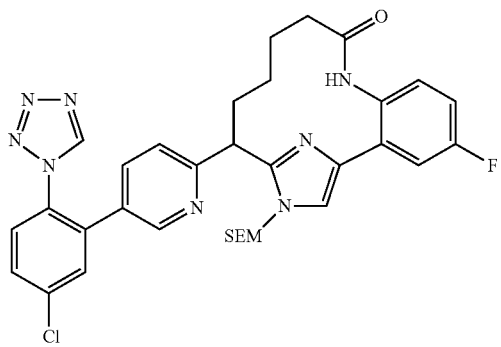 [SMILES: C[Si](C)(C)CCOCn1cc2nc1C(c1ccc(-c3cc(Cl)ccc3-n3cnnn3)cn1)CCCCC(=O)Nc1ccc(F)cc1-2]

To a solution of 10M (390 mg, 0.643 mmol) in HOAc (10 mL) trimethyl orthoformate (1365 mg, 12.87 mmol) and sodium azide (836 mg, 12.87 mmol) were added. The mixture was stirred at 30° C. for 13 h. The mixture was quenched with saturated $NaNO_2$ (30 mL), adjusted to pH to 7 with saturated aqueous sodium bicarbonate, and extracted with EtOAc (3×20 mL). The combined organic layers were dried over anhydrous sodium sulfate, filtered and concentrated. The residue was purified by flash column chromatography on silica gel (eluting with petroleum ether:EtOAc=3:1 to 1:1 v/v) to give the title compound. MS (ES⁺) m/z: 659 (M+H).

Example 10

To a solution of 10N (250 mg, 0.265 mmol) in DCM (8 mL) and TFA (4 mL, 51.9 mmol), (R)-2-amino-3-mercaptopropanoic acid (161 mg, 1.327 mmol) at 25° C. was added. The mixture was stirred for 2 h. It was concentrated under reduced pressure and the residue was purified by HPLC to give the racemic compound. MS (ES⁺) m/z: 529 (M+H).

A sample of racemic Example 10 was subjected to chiral separation by SFC (AS, 250 mm×30 mm, 5 um, 40% $MeOH/CO_2$, 60 mL/min) to give Example 10-a (slower eluting) and Example 10-b (faster eluting). MS (ES⁺) m/z: 529 (M+H); ¹H NMR (400 MHz, MeOH-$d_4$): δ 9.28 (s, 1H), 8.35 (s, 1H), 7.80-7.70 (m, 3H), 7.56 (m, 1H), 7.50-7.30 (m, 4H), 7.15 (m, 1H), 4.59 (m, 1H), 2.54 (m, 1H), 2.30-1.90 (m, 4H), 1.64 (m, 1H), 1.35 (m, 1H), 1.05 (m, 1H).

Example 11 (racemate), 11a and 11b (Z)-5-(5-Chloro-2-(1H-tetrazol-1-yl)phenyl)-2-(2⁵-fluoro-4-oxo-1¹h-3-aza-1(4,2)-imidazola-2(1,2)-benzenacyclononaphane-9-yl)pyridine 1-oxide

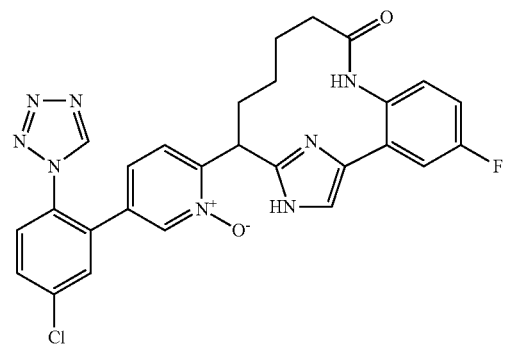 [SMILES: O=C1CCCCC(c2ccc(-c3cc(Cl)ccc3-n3cnnn3)c[n+]2[O-])c2nc(c[nH]2)-c2cc(F)ccc2N1]

11A: (Z)-5-(5-Chloro-2-(1H-tetrazol-1-yl)phenyl)-2-(2⁵-fluoro-4-oxo-1¹-((2-(trimethylsilyl)ethoxy)methyl)-1¹H-3-aza-1(4,2)-imidazola-2(1,2)-benzenacyclononaphane-9-yl)pyridine 1-oxide

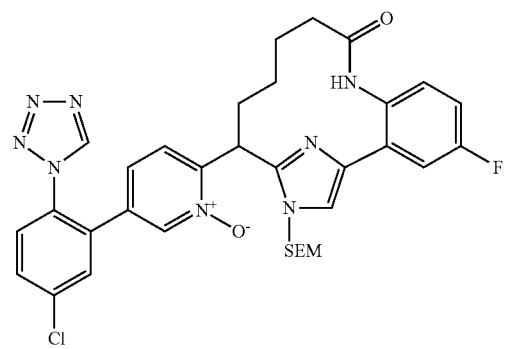 [SMILES: C[Si](C)(C)CCOCn1cc2nc1C(c1ccc(-c3cc(Cl)ccc3-n3cnnn3)c[n+]1[O-])CCCCC(=O)Nc1ccc(F)cc1-2]

A mixture of 10N (350 mg, 0.531 mmol) in peracetic acid (10% in acetic acid, 20 mL, 0.531 mmol) was stirred at 25°

C. for 13 h. The reaction was quenched with Na₂SO₃ (sat, 40 mL) and extracted with EtOAc (3×30 mL). The combined organic layers were washed with saturated sodium bicarbonate (30 mL) and brine (30 mL), dried over sodium sulfate, filtered and concentrated under reduced pressure to give the title compound, which was used for next step without further purification. MS (ES⁺) m/z: 675 (M+H)

Example 11

A solution of 11A (25 mg, 0.037 mmol) and (R)-2-amino-3-mercaptopropanoic acid (22.43 mg, 0.185 mmol) in DCM (0.5 mL) and TFA (0.5 mL, 6.49 mmol) was stirred at 25° C. for 3 h. The mixture was concentrated and purified by reverse phase HPLC to give the racemic product. MS (ES⁺) m/z: 545 (M+H).

A sample of Example 11 was subjected to chiral separation by SFC (OJ, 4.6×50 mm, 3 um. methanol (0.05% diethylamine)/CO₂, 4 mL/min, 40° C.) to give Example 11-a (slower eluting) and Example 11-b (faster eluting). MS (ES⁺) m/z: 545 (M+H); ¹H NMR (CD₃OD, 400 MHz): δ 9.42 (s, 1H), 8.31 (s, 1H), 7.84-7.77 (m, 2H), 7.73 (d, J=8.2 Hz, 2H), 7.52 (s, 1H), 7.44-7.38 (m, 1H), 7.36-7.24 (m, 3H), 2.55 (d, J=11.7 Hz, 1H), 2.38-2.10 (m, 3H), 1.85 (d, J=11.3 Hz, 1H), 1.64 (m, 1H), 1.46 (m, 1H), 1.30-1.20 (m, 1H), 1.09 (m, 1H).

Example 12 methyl (9-(5-(3-chloro-2,6-difluorophenyl)pyridin-2-yl)-4-oxo-3-aza -1(1,3),2(1,2)-dibenzenacyclononaphane-2⁴-yl)carbamate

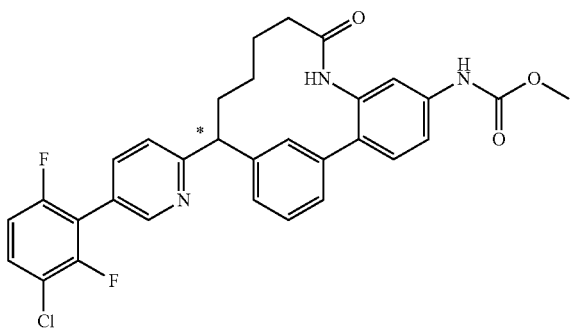

12A: Methyl (2-amino-3'-(5-chloropicolinoyl)-[1,1'-biphenyl]-4-yl)carbamate

A round bottom flask was charged with a magnetic stirring bar, Intermediate 19 (2.483 g, 8.50 mmol), Intermediate 2 (2.1 g, 7.08 mmol) and 1,1'-bis(diphenylphosphino)ferrocene-palladium(II)dichloride dichloromethane complex (0.578 g, 0.708 mmol). It was degassed and backfilled with nitrogen three times. Degassed THF (28.3 mL) and aqueous potassium phosphate tribasic (3 M, 7.08 mL) were added subsequently. The mixture was stirred to 70° C. for 3 h and cooled to rt. It was diluted with ethyl acetate (60 mL) and washed with water (30 mL). The organic layer was separated and dried over anhydrous magnesium sulfate. It was filtered and the filtrate was concentrated under reduced pressure. The residue was purified by flash column chromatography on silica gel (eluting with EtOAc/hexane=25% to 80%) to give the title compound. MS (ES⁺) m/z: 382 (M+H).

12B: (5-((3'-(5-Chloropicolinoyl)-4-((methoxycarbonyl)amino)-[1,1'-biphenyl]-2-yl)amino)-5-oxopentyl)triphenylphosphonium bromide To a stirred solution of (4-carboxybutyl)triphenylphosphonium bromide (6.94 g, 15.66 mmol), 12A (4.6 g, 12.05 mmol) and Hunig's Base (6.31 mL, 36.1 mmol) in DMF (58.9 mL) HATU (5.96 g, 15.66 mmol) was added. The mixture was stirred at rt overnight. Most solvent was removed under reduced pressure and the residue was purified by flash column chromatography on silica gel (eluting with MeOH/CH₂Cl₂=6%) to give the title compound. MS (ES⁺) m/z: 726 (M).

12C: Methyl (E)-(9-(5-chloropyridin-2-yl)-4-oxo-3-aza-1(1,3),2(1,2)-dibenzenacyclononaphan -8-en-2⁴-yl)carbamate

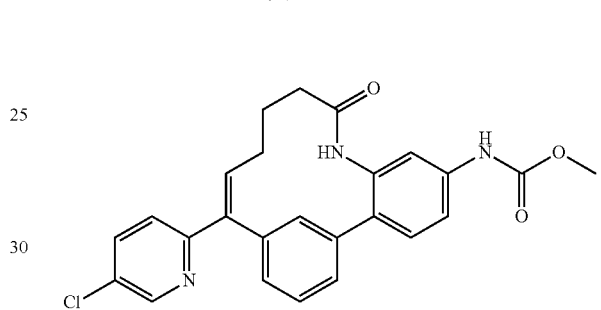

A solution of LiHMDS (1 M in THF, 68.1 mL, 68.1 mmol) was added to a stirred mixture of 12B (11 g, 13.63 mmol) in anhydrous THF (681 mL) at 0° C. over a period of 1 h by a syringe pump. The resulting mixture was stirred at rt overnight and it was quenched with aqueous ammonium chloride (saturated, 100 mL) and water (100 mL). The mixture was extracted with ethyl acetate (2×200 mL). The combined organic layer washed with brine (150 mL), dried over anhydrous magnesium sulfate, filtered and the filtrate was concentrated under reduced pressure. The residue was slurred in a mixture of dichloromethane (20 mL) and methanol (5 mL) and the solids were collected by filtration to give the title compound. The filtrate was concentrated, and the residue was purified by flash column chromatography on silica gel (eluting with MeOH/CH₂Cl₂=5%) to another batch of the title compound. MS (ES⁺) m/z: 448 (M+H).

12D: Methyl (9-(5-chloropyridin-2-yl)-4-oxo-3-aza-1(1,3),2(1,2)-dibenzenacyclononaphane-2⁴-yl)carbamate

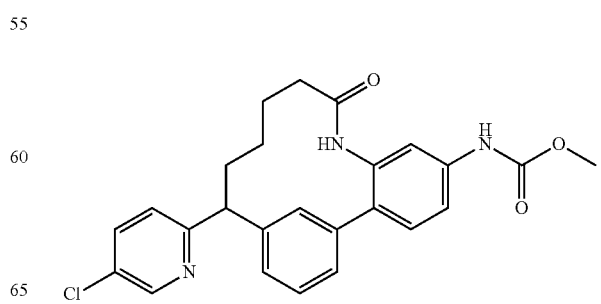

A mixture of 12C (3.0 g, 6.70 mmol), a homogenous Rh catalyst (0.2 g) and 2,2,2-trifluoroethanol (80 mL) were stirred in an autoclave at 50° C. under hydrogen (200 psi) for 4 h. It was cooled to rt and concentrated under reduced pressure. The crude product was purified by flash column chromatography on silica gel (eluting with MeOH/CH$_2$Cl$_2$=7%) to give the title compound. MS (ES$^+$) m/z: 450 (M+H).

Example 12

To a vial charged with a magnetic stirring bar, bis(pinacolato)diboron (183 mg, 0.720 mmol), 12D (270 mg, 0.600 mmol), potassium acetate (177 mg, 1.800 mmol) and 2nd generation Xphos precatalyst (47.2 mg, 0.060 mmol) were added. It was degassed and backfilled with nitrogen three times. To the vial degassed dioxane (6 mL) was added, and the mixture was stirred at 85° C. for 1 h. It was allowed to cool to rt. To the mixture was added a solution of 1-bromo-3-chloro-2,6-difluorobenzene and 1,1'-bis(diphenylphosphino)ferrocene-palladium(II)dichloride dichloromethane complex (49.1 mg, 0.060 mmol) in dioxane (6 mL) followed by the addition of aqueous potassium phosphate tribasic (3 M, 0.600 mL, 1.80 mmol). The resulting mixture was degassed and backfilled with nitrogen three times and it was stirred at 85° C. for 1 h. It was cooled to rt and most solvent was removed under reduced pressure. The residue was purified by flash column chromatography (eluting with EtOAc-EtOH (3:1)/Hexane=45%) to give the title compound. MS (ES$^+$) m/z: 562 (M+H).

Example 13 (racemate), 13-a and 13-b 5-(3-Chloro-2,6-difluorophenyl)-2-(2$^4$-((methoxycarbonyl)amino)-4-oxo-3-aza-1(1,3),2(1,2)-dibenzenacyclononaphane-9-yl)pyridine 1-oxide

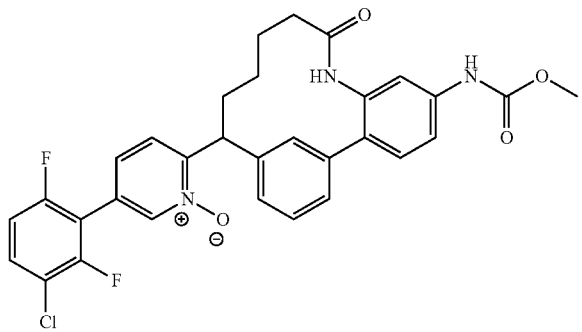

To a stirred mixture of Example 12 (198 mg, 0.352 mmol) in dichloromethane (4 mL), m-CPBA (237 mg, 1.057 mmol) was added. It was stirred at rt for 3 h. The mixture was purified by flash column chromatography on silica gel (eluting with EtOAc-EtOH (3:1)/Hexane=55%) to give the racemic product. MS (ES$^+$) m/z: 578 (M+H).

A sample of racemic Example 13 was subjected to chiral separation by SFC (IC, 21×250 mm, 70% methanol-MeCN (2:1)/CO$_2$, 100 bar, 70 mL/min, 35° C.) to afford the Example 13-a (faster eluting) and Example 13-b (slower eluting). MS (ES$^+$) m/z: 597 (M+H); $^1$H NMR (500 MHz, CH$_3$OH-d$_4$): δ 8.50 (s, 1H), 7.81 (d, 1H), 7.66-7.73 (m, 2H), 7.62-7.65 (m, 1H), 7.43-7.49 (m, 3H), 7.38 (t, 1H), 7.30 (d, 1H), 7.20 (t, 1H), 6.97 (d, 1H), 3.74 (s, 3H), 2.42 (t, 1H), 2.07-2.15 (m, 3H), 1.98 (d, 1H), 1.60-1.64 (m, 1H), 1.40-1.45 (m, 1H), 1.28-1.30 (m, 1H).

By using the procedures described in Example 12, and appropriate starting materials, the following compounds were synthesized and characterized by LC/MS.

| Ex | Structure | Name | MS (M + H) |
|---|---|---|---|
| 14 | 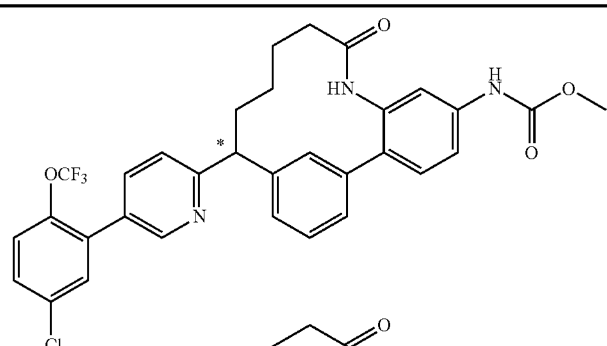 | methyl (9-(5-(5-chloro-2-(trifluoromethoxy)phenyl)pyridin-2-yl)-4-oxo-3-aza-1(1,3),2(1,2)-dibenzenacyclononaphane-2$^4$-yl)carbamate | 609 |
| 15 | 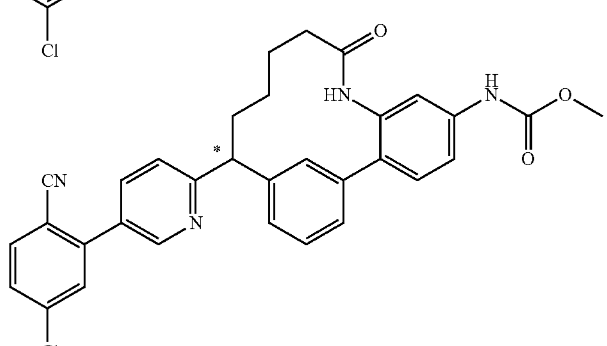 | methyl (9-(5-(5-chloro-2-cyanophenyl)pyridin-2-yl)-4-oxo-3-aza-1(1,3),2(1,2)-dibenzenacyclononaphane-2$^4$-yl)carbamate | 550 |

| Ex | Structure | Name | MS (M + H) |
|---|---|---|---|
| 16 | 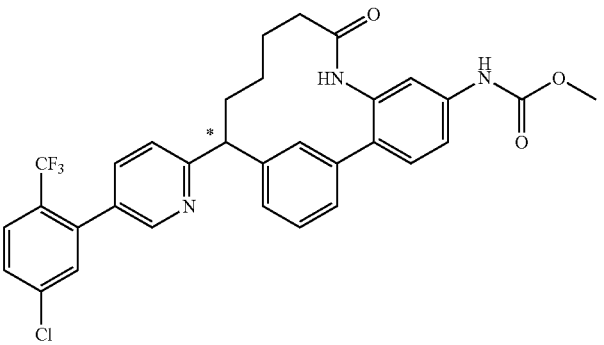 [SMILES: COC(=O)Nc1ccc2c(c1)NC(=O)CCCCC(c1ccc(-c3cc(Cl)ccc3C#N)cn1)c1cccc-2c1] | methyl (9-(5-(5-chloro-2-(trifluoromethyl)phenyl)pyridin-2-yl)-4-oxo-3-aza-1(1,3),2(1,2)-dibenzenacyclononaphane-2⁴-yl)carbamate | 593 |
| 17 | 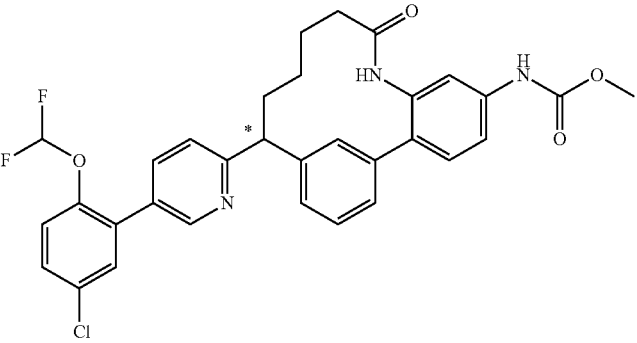 [SMILES: COC(=O)Nc1ccc2c(c1)NC(=O)CCCCC(c1ccc(-c3cc(Cl)ccc3OC(F)F)cn1)c1cccc-2c1] | methyl (9-(5-(5-chloro-2-(difluoromethoxy)phenyl)pyridin-2-yl)-4-oxo-3-aza-1(1,3),2(1,2)-dibenzenacyclononaphane-2⁴-yl)carbamate | 591 |
| 18 | 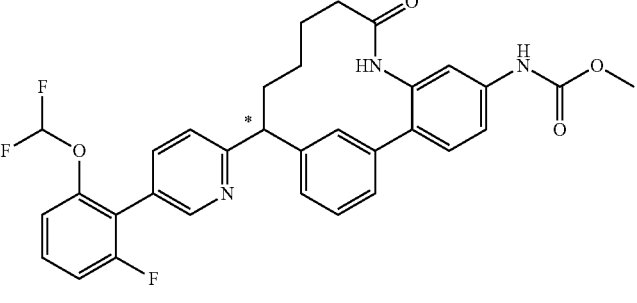 | methyl (9-(5-(2-(difluoromethoxy)-6-fluorophenyl)pyridin-2-yl)-4-oxo-3-aza-1(1,3),2(1,2)-dibenzenacyclononaphane-2⁴-yl)carbamate | 575 |
| 19 | 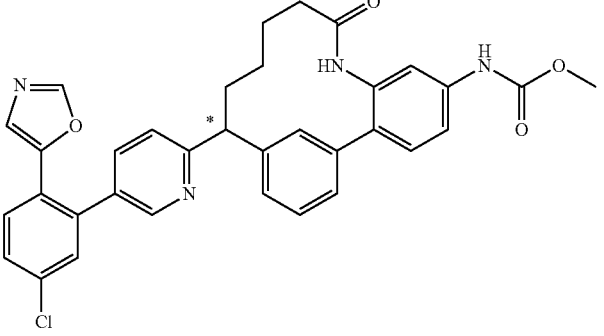 | methyl (9-(5-(5-chloro-2-(oxazol-5-yl)phenyl)pyridin-2-yl)-4-oxo-3-aza-1(1,3),2(1,2)-dibenzenacyclononaphane-2⁴-yl)carbamate | 592 |

-continued

| Ex | Structure | Name | MS (M + H) |
|---|---|---|---|
| 20 | 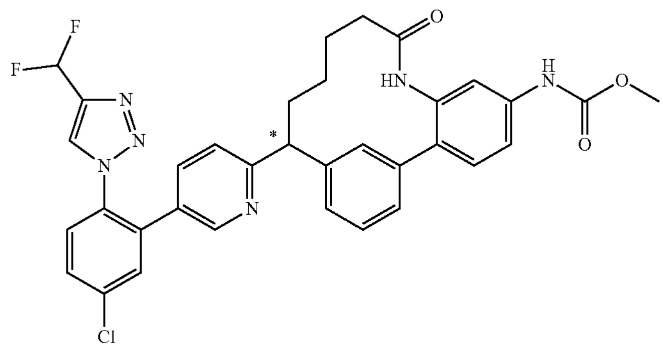 [SMILES: COC(=O)Nc1ccc2c(c1)NC(=O)CCCCC(c1ccc(-c3cc(Cl)ccc3-n3cc(C(F)F)nn3)cn1)c1cccc-2c1] | methyl (9-(5-(5-chloro-2-(4-(difluoromethyl)-1h-1,2,3-triazol-1-yl)phenyl)pyridin-2-yl)-4-oxo-3-aza-1(1,3),2(1,2)-dibenzenacyclononaphane-2⁴-yl)carbamate | 642 |
| 21 | 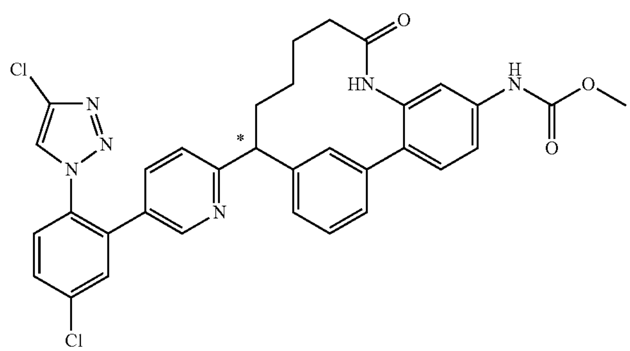 [SMILES: COC(=O)Nc1ccc2c(c1)NC(=O)CCCCC(c1ccc(-c3cc(Cl)ccc3-n3cc(Cl)nn3)cn1)c1cccc-2c1] | methyl (9-(5-(5-chloro-2-(4-chloro-1h-1,2,3-triazol-1-yl)phenyl)pyridin-2-yl)-4-oxo-3-aza-1(1,3),2(1,2)-dibenzenacyclononaphane-2⁴-yl)carbamate | 626 |
| 22 | 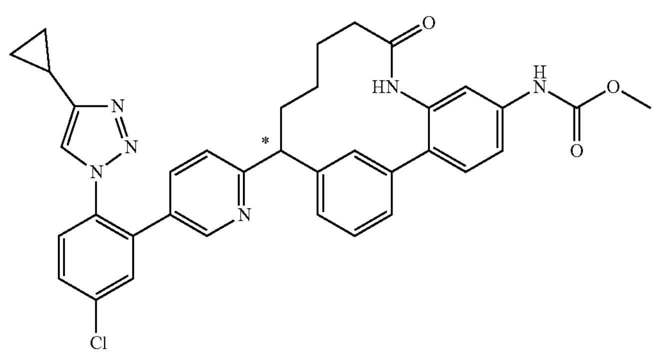 [SMILES: COC(=O)Nc1ccc2c(c1)NC(=O)CCCCC(c1ccc(-c3cc(Cl)ccc3-n3cc(C4CC4)nn3)cn1)c1cccc-2c1] | methyl (9-(5-(5-chloro-2-(4-cyclopropyl-1h-1,2,3-triazol-1-yl)phenyl)pyridin-2-yl)-4-oxo-3-aza-1(1,3),2(1,2)-dibenzenacyclononaphane-2⁴-yl)carbamate | 632 |
| 23 | 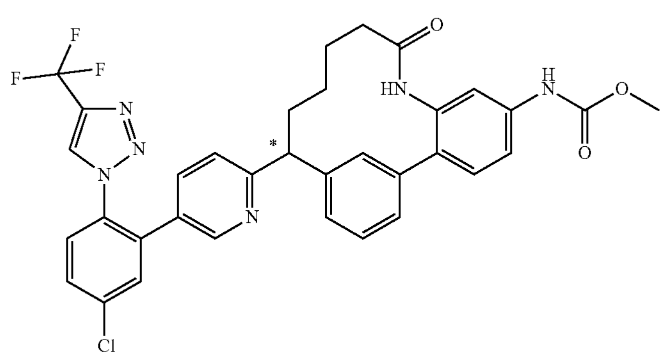 [SMILES: COC(=O)Nc1ccc2c(c1)NC(=O)CCCCC(c1ccc(-c3cc(Cl)ccc3-n3cc(C(F)(F)F)nn3)cn1)c1cccc-2c1] | methyl (9-(5-(5-chloro-2-(4-(trifluoromethyl)-1h-1,2,3-triazol-1-yl)phenyl)pyridin-2-yl)-4-oxo-3-aza-1(1,3),2(1,2)-dibenzenacyclononaphane-2⁴-yl)carbamate | 660 |

| Ex | Structure | Name | MS (M + H) |
|---|---|---|---|
| 24 | 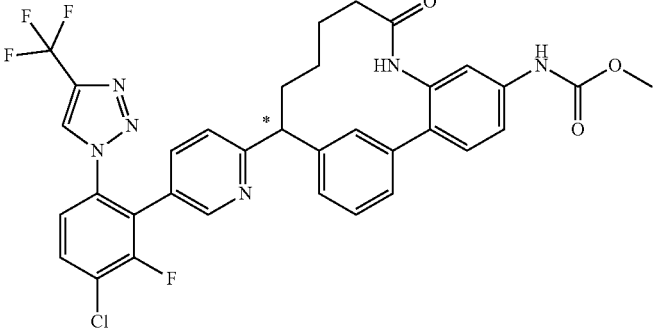 | methyl (9-(5-(3-chloro-2-fluoro-6-(4-(trifluoromethyl)-1h-1,2,3-triazol-1-yl)phenyl)pyridin-2-yl)-4-oxo-3-aza-1(1,3),2(1,2)-dibenzenacyclononaphane-2⁴-yl)carbamate | 678 |
| 25 | 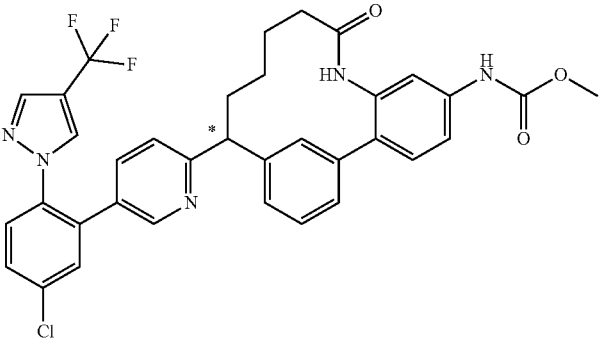 [SMILES: COC(=O)Nc1ccc2c(c1)NC(=O)CCCCC(c1ccc(-c3cc(Cl)ccc3-n3cc(C(F)(F)F)cn3)cn1)c1cccc-2c1] | methyl (9-(5-(5-chloro-2-(4-(trifluoromethyl)-1h-pyrazol-1-yl)phenyl)pyridin-2-yl)-4-oxo-3-aza-1(1,3),2(1,2)-dibenzenacyclononaphane-24-yl)carbamate | 659 |
| 26 | 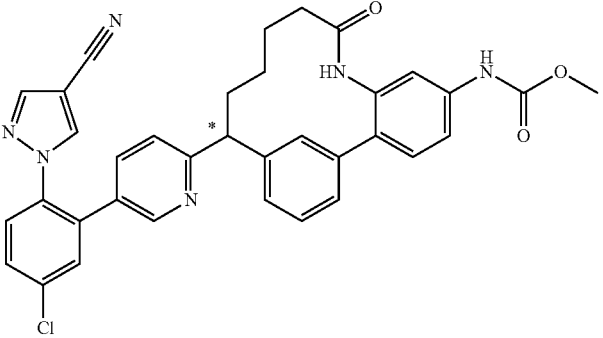 [SMILES: COC(=O)Nc1ccc2c(c1)NC(=O)CCCCC(c1ccc(-c3cc(Cl)ccc3-n3cc(C#N)cn3)cn1)c1cccc-2c1] | methyl (9-(5-(5-chloro-2-(4-cyano-1h-pyrazol-1-yl)phenyl)pyridin-2-yl)-4-oxo-3-aza-1(1,3),2(1,2)-dibenzenacyclononaphane-24-yl)carbamate | 616 |
| 27 | 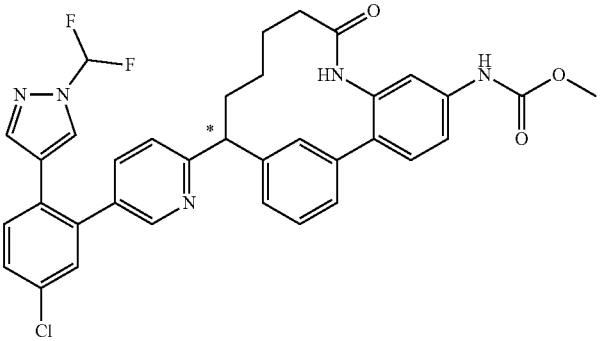 [SMILES: COC(=O)Nc1ccc2c(c1)NC(=O)CCCCC(c1ccc(-c3cc(Cl)ccc3-c3cnn(C(F)F)c3)cn1)c1cccc-2c1] | methyl (9-(5-(5-chloro-2-(1-(difluoromethyl)-1h-pyrazol-4-yl)phenyl)pyridin-2-yl)-4-oxo-3-aza-1(1,3),2(1,2)-dibenzenacyclononaphane-24-yl)carbamate | 641 |

| Ex | Structure | Name | MS (M + H) |
|---|---|---|---|
| 28 | 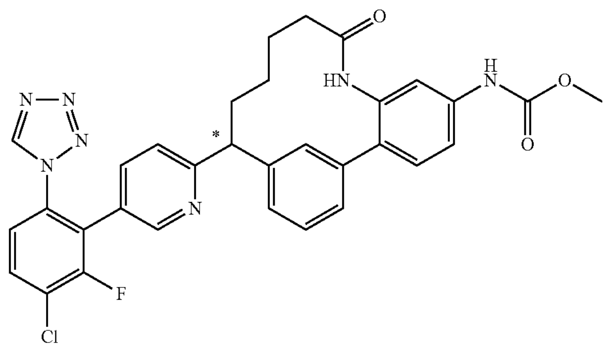 [SMILES: COC(=O)Nc1ccc2c(c1)NC(=O)CCCCC(c1ccc(-c3c(-n4cnnn4)ccc(Cl)c3F)cn1)c1cccc-2c1] | methyl (9-(5-(3-chloro-2-fluoro-6-(1h-tetrazol-1-yl)phenyl)pyridin-2-yl)-4-oxo-3-aza-1(1,3),2(1,2)-dibenzenacyclononaphane-24-yl)carbamate | 611 |
| 29 | 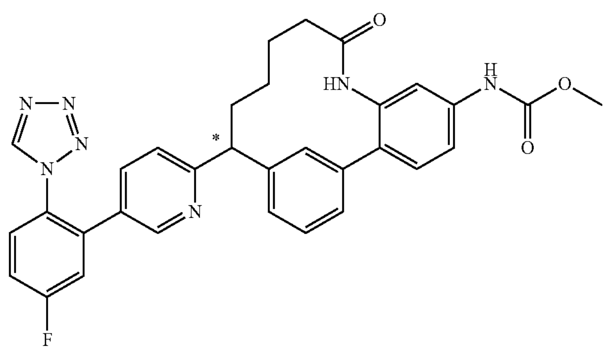 [SMILES: COC(=O)Nc1ccc2c(c1)NC(=O)CCCCC(c1ccc(-c3cc(F)ccc3-n3cnnn3)cn1)c1cccc-2c1] | methyl (9-(5-(5-fluoro-2-(1h-tetrazol-1-yl)phenyl)pyridin-2-yl)-4-oxo-3-aza-1(1,3),2(1,2)-dibenzenacyclononaphane-24-yl)carbamate | 577 |

By using the procedures described in Example 13, and appropriate starting materials, the following compounds were synthesized and characterized by LC/MS.

| Ex | Structure and Names | Chiral Separation SFC Condition | V |
|---|---|---|---|
| 30 | (S)-5-(5-chloro-2-(trifluoromethoxy)phenyl)-2-(2⁴-((methoxycarbonyl)amino)-4-oxo-3-aza-1(1,3),2(1,2)-dibenzenacyclononaphane-9-yl)pyridine 1-oxide | IC, 30 × 200 mm, 55% IPA (0.2% diethylamine)/CO$_2$, 100 bar, 70 mL/min, 35° C. Faster eluting | 626.3 |

-continued

| Ex | Structure and Names | Chiral Separation SFC Condition | V |
|---|---|---|---|
| 31 | (S)-5-(5-chloro-2-cyanophenyl)-2-(2⁴-((methoxycarbonyl)amino)-4-oxo-3-aza-1(1,3),2(1,2)-dibenzenacyclononaphane-9-yl)pyridine 1-oxide | OJ, 21 × 250 mm, 18% MeOH (0.2% diethylamine)/ $CO_2$, 100 bar, 55 mL/min, 35° C. Slower eluting | 567.1 |
| 32 | (S)-5-(5-chloro-2-(trifluoromethyl)phenyl)-2-(2⁴-((methoxycarbonyl) amino)-4-oxo-3-aza-1(1,3),2(1,2)-dibenzenacyclononaphane-9-yl)pyridine 1-oxide | IC, 30 × 200 mm, 55% MeOH (0.2% diethylamine)/ $CO_2$, 100 bar, 70 mL/min, 35° C. Faster eluting | 610.3 |
| 33 | (S)-5-(5-chloro-2-(difluoromethoxy)phenyl)-2-(2⁴-((methoxycarbonyl) amino)-4-oxo-3-aza-1(1,3),2(1,2)-dibenzenacyclononaphane-9-yl)pyridine 1-oxide | IC, 20 × 200 mm, 55% MeOH/$CO_2$, 100 bar, 65 mL/min, 35° C. Faster eluting | 608.2 |
| 34 | (S)-5-(2-(difluoromethoxy)-6-fluorophenyl)-2-(2⁴-((methoxycarbonyl)amino)-4-oxo-3-aza-1(1,3),2(1,2)-dibenzenacyclononaphane-9-yl)pyridine 1-oxide | AS-H, 20 × 250 mm, 20% ethanol (DEA)/$CO_2$, 100 bar, 70 mL/min, 35° C. Slower eluting | 592.2 |

| Ex | Structure and Names | Chiral Separation SFC Condition | V |
|---|---|---|---|
| 35 | (S)-5-(5-chloro-2-(oxazol-5-yl)phenyl)-2-(2⁴-((methoxycarbonyl)amino)-4-oxo-3-aza-1(1,3),2(1,2)-dibenzenacyclononaphane-9-yl)pyridine 1-oxide | OD, 21 × 200 mm, 40% MeOH/CO$_2$, 100 bar, 55 mL/min, 35° C. Slower eluting | 609.3 |

Example 36 (racemate), 36-a, 36-b 5-(5-chloro-2-(4-(difluoromethyl)-1H-1,2,3-triazol-1-yl)phenyl)-2-(2⁴-((methoxycarbonyl)amino)-4-oxo-3-aza-1(1,3),2(1,2)-dibenzenacy clononaphane-9-yl)pyridine 1-oxide

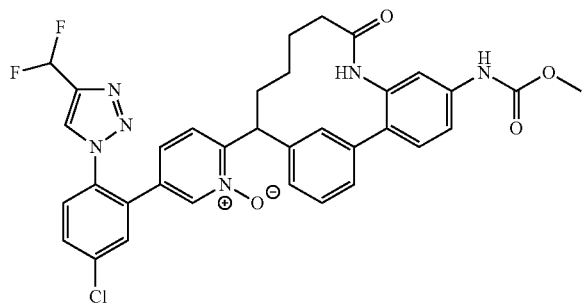 [SMILES: COC(=O)Nc1ccc2c(c1)NC(=O)CCCCC(c1ccc(-c3cc(Cl)ccc3-n3cc(C(F)F)nn3)c[n+]1[O-])c1cccc-2c1]

36: 5-Chloro-2-(2⁴-((methoxycarbonyl)amino)-4-oxo-3-aza-1(1,3),2(1,2)-dibenzen acyclononaphane-9-yl)pyridine 1-oxide

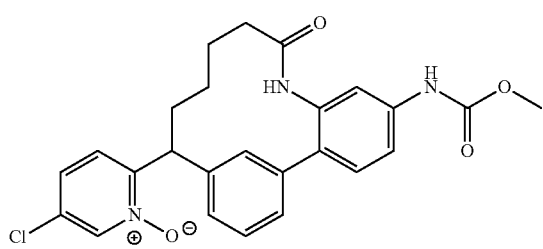 [SMILES: COC(=O)Nc1ccc2c(c1)NC(=O)CCCCC(c1ccc(Cl)c[n+]1[O-])c1cccc-2c1]

m-CPBA (345 mg, 2.000 mmol) was added to a stirred mixture of 12D (300 mg, 0.667 mmol) in dichloromethane (6.668 mL) and the mixture was stirred at rt for 4 h. The reaction mixture was purified by flash column chromatography on silica gel (eluting with MeOH/DCM=7%) to afford the title compound. MS (ES⁺) m/z: 466 (M+H).

36B: 5-(5-Chloro-2-(4-(difluoromethyl)-1H-1,2,3-triazol-1-yl)phenyl)-2-(2⁴-((methoxycarbonyl)amino)-4-oxo-3-aza-1(1,3),2(1,2)-dibenzenacy-clononaphane-9-yl)pyridine 1-oxide Bis(pinacolato)diboron (65.4 mg, 0.258 mmol), 36A (100 mg, 0.215 mmol), potassium acetate (63.2 mg, 0.644 mmol) and 2$^{nd}$ generation XPHOS precatalyst (16.89 mg, 0.021 mmol) and dioxane (1.1 mL) were mixed in a pressure release vial, degassed and backfilled with nitrogen (3×). The mixture was stirred at 80° C. for 30 min. It was cooled to rt. 1-(4-Chloro-2-iodophenyl)-4-(difluoromethyl)-1H-1,2,3-triazole (99 mg, 0.279 mmol) and 1,1'-bis(diphenylphosphino)-ferrocene-palladium(II)dichloride dichloromethane complex (17.57 mg, 0.021 mmol) were quickly added to the reaction mixture, followed by the addition of potassium phosphate tribasic (3 M aqueous) (6.67 mL, 20.01 mmol). The mixture was degassed and backfilled with N$_2$ (3×) and stirred at 80° C. for 1 h. It was cooled to rt and purified by flash column chromatography on silica gel (eluting with MeOH/DCM=7%) to give the title compound. MS (ES⁺) m/z: 659 (M+H).

A sample of racemic Example 36 was subjected to chiral separation by SFC (OD, 21×200 mm, 45% MeOH/CO$_2$, 100 bar, 60 mL/min, 35° C.) to afford the Example 36-a (faster eluting) and Example 36-b (slower eluting). MS (ES⁺) m/z: 659 (M+H).

By using the procedures described in Example 36, and appropriate starting materials, the following compounds were synthesized and characterized by LC/MS.

| Ex | Structure and Name | Chiral Separation SFC Condition | MS (M + H) |
|---|---|---|---|
| 37 | (S)-5-(5-chloro-2-(4-chloro-1h-1,2,3-triazol-1-yl)phenyl)-2-(2$^4$-((methoxycarbonyl)amino)-4-oxo-3-aza-1(1,3),2(1,2)-dibenzenacyclononaphane-9-yl)pyridine 1-oxide | OJ, 30 × 250 mm, 57% MeOH/CO$_2$, 100 bar, 55 mL/min, 35° C. Faster eluting | 643.1 |
| 38 | (S)-5-(5-chloro-2-(4-cyclopropyl-1H-1,2,3-triazol-1-yl)phenyl)-2-(2$^4$-((methoxycarbonyl)amino)-4-oxo-3-aza-1(1,3),2(1,2)-dibenzenacyclononaphane-9-yl)pyridine 1-oxide | OD, 21 × 200 mm, 45% MeOH/CO$_2$, 100 bar, 55 mL/min, 35° C. Slower eluting | 649.1 |
| 39 | (S)-5-(5-chloro-2-(4-(trifluoromethyl)-1H-1,2,3-triazol-1-yl)phenyl)-2-(2$^4$-((methoxycarbonyl)amino)-4-oxo-3-aza-1(1,3),2(1,2)-dibenzenacyclononaphane-9-yl)pyridine 1-oxide | (R,R) Whelk, 30 × 250 mm, 60% 2:1 MeOH: MeCN/CO$_2$, 100 bar, 70 mL/min, 35° C. | 677.0 |

| Ex | Structure and Name | Chiral Separation SFC Condition | MS (M + H) |
|---|---|---|---|
| 40 | (S)-5-(5-chloro-2-(4-(trifluoromethyl)-1H-pyrazol-1-yl)phenyl)-2-(2$^4$-((methoxycarbonyl)amino)-4-oxo-3-aza-1(1,3),2(1,2)-dibenzenacyclononaphane-9-yl)pyridine 1-oxide | IC, 21 × 200 mm, 50% MeOH/CO$_2$, 100 bar, 55 mL/min, 35° C. Faster eluting | 676.1 |
| 41 | (S)-5-(5-chloro-2-(4-cyano-1H-pyrazol-1-yl)phenyl)-2-(2$^4$-((methoxycarbonyl)amino)-4-oxo-3-aza-1(1,3),2(1,2)-dibenzenacyclononaphane-9-yl)pyridine 1-oxide | OD, 30 × 250 mm, 55% MeOH/CO$_2$, 100 bar, 70 mL/min, 35° C. Slower eluting | 633.2 |
| 42 | (S)-5-(5-chloro-2-(1-(difluoromethyl)-1H-pyrazol-4-yl)phenyl)-2-(2$^4$-((methoxycarbonyl)amino)-4-oxo-3-aza-1(1,3),2(1,2)-dibenzenacyclononaphane-9-yl)pyridine 1-oxide | (R,R) Whelk, 30 × 250 mm, 60% 2:1 MeOH: MeCN/CO$_2$, 100 bar, 70 mL/min, 35° C. Faster eluting | 658.2 |

Example 43 (racemate), 43-a, 43-b 2-(2⁴-amino-4-oxo-3-aza-1(1,3),2(1,2)-dinenzenacyclononaphane-9-yl)-5-(3-chloro-2,6-difluorophenyl)pyridine 1-oxide

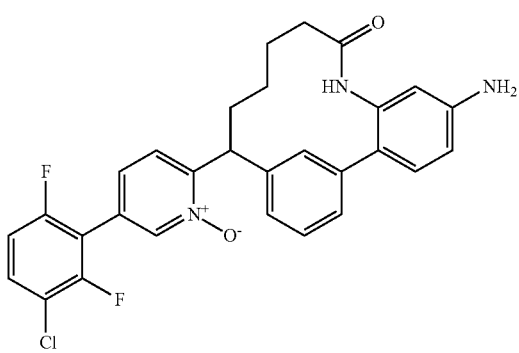 [SMILES: Nc1ccc2c(c1)NC(=O)CCCCC(c1ccc(-c3c(F)ccc(Cl)c3F)c[n+]1[O-])c1cccc-2c1]

43A: tert-Butyl (E)-(9-(5-chloropyridin-2-yl)-4-oxo-3-aza-1(1,3),2(1,2)-dibenzenacyclononaphan-8-en-2⁴-yl)carbamate

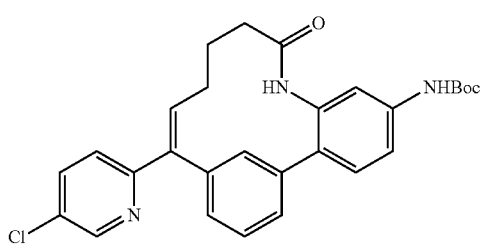 [SMILES: CC(C)(C)OC(=O)Nc1ccc2c(c1)NC(=O)CCC/C=C(/c1ccc(Cl)cn1)c1cccc-2c1]

The title compound was prepared from Intermediate 2 and Intermediate 21 by the procedure described in the synthesis of 12C. It was purified by flash column chromatography on silica gel (eluting with petroleum ether:EtOAc=3:1 v/v). MS (ES⁺) m/z: 490 (M+H).

43B: tert-Butyl (E)-(9-(5-(3-chloro-2,6-difluorophenyl)pyridin-2-yl)-4-oxo-3-aza-1(1,3),2(1,2)-dibenzenacyclononaphan-8-en-2⁴-yl)carbamate

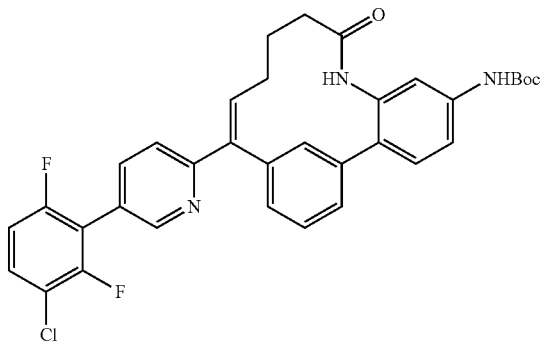 [SMILES: CC(C)(C)OC(=O)Nc1ccc2c(c1)NC(=O)CCC/C=C(/c1ccc(-c3c(F)ccc(Cl)c3F)cn1)c1cccc-2c1]

A mixture of 43A (266 mg, 0.543 mmol), second generation Xphos precatalyst (42.7 mg, 0.054 mmol), potassium acetate (107 mg, 1.086 mmol) and bis(pinacolato)diboron (207 mg, 0.814 mmol) in dioxane (15 mL) was stirred at 100° C. under nitrogen for 30 min, heated in a microwave reactor. It was cooled to rt and a solution of second generation Xphos precatalyst (42.7 mg, 0.054 mmol), 2-bromo-4-chloro-1,3-difluorobenzene (185 mg, 0.814 mmol) in dioxane (1 mL) was added followed by the addition of aqueous potassium phosphate tribasic (1 M, 1.086 mL, 1.086 mmol). The reaction mixture was stirred at 80° C. for 16 h. The mixture was diluted with EtOAc (200 mL) and washed with brine (2×100 mL). The organic layer was separated, dried over sodium sulfate, filtered and concentrated under reduced pressure. The residue was purified by flash column chromatography on silica gel (eluting with petroleum ether:EtOAc=3:1 v/v) to give the title compound. MS (ES⁺) m/z: 602 (M+H).

43C: tert-Butyl (9-(5-(3-chloro-2,6-difluorophenyl)pyridin-2-yl)-4-oxo-3-aza-1(1,3),2(1,2)-dinenzenacyclononaphane-2⁴-yl)carbamate

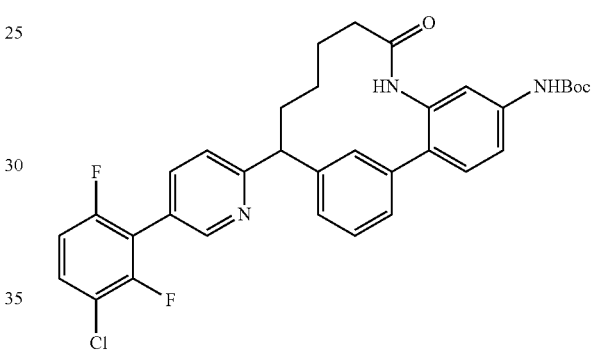

A mixture of 43B (20 mg, 0.033 mmol) and Raney-nickel (7.80 mg, 0.133 mmol) in THF (2 mL) was stirred at 25° C. under H₂ (1 atm) for 10 min. The mixture was filtered through a pad of Celite and the filter cake washed with MeOH (20 mL). The filtrate was concentrated under reduced pressure to give the title compound. MS (ES⁺) m/z: 604 (M+H).

43D: 2-(2⁴-((tert-Butoxycarbonyl)amino)-4-oxo-3-aza-1(1,3),2(1,2)-dinenzenacyclononaphane-9-yl)-5-(3-chloro-2,6-difluorophenyl)pyridine 1-oxide

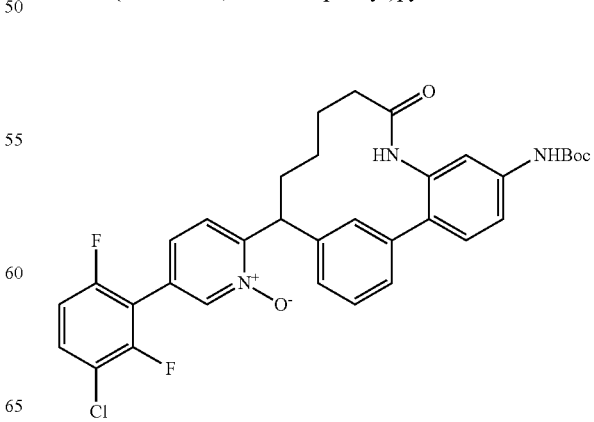

To a mixture of 43C (100 mg, 0.166 mmol) in CHCl₃ (5 mL), m-CPBA (55.6 mg, 0.248 mmol) was added and the mixture was stirred at 25° C. for 2 h. It was quenched with aqueous Na₂SO₃ (saturated, 5 mL) and the mixture was extracted with dichloromethane (2×50 mL). The combined organic fractions were washed with aqueous sodium carbonate (saturated, 2×20 mL), dried over sodium sulfate, filtered and concentrated under reduced pressure to give the title compound. MS (ES⁺) m/z: 620 (M+H). The crude material was used for next step without further purification.

Example 43

To a mixture of 43D (100 mg, 0.161 mmol) in DCM (5 mL) at 25° C. was added TFA (0.5 mL, 6.49 mmol) and the mixture was stirred at 25° C. for 1 h. Most solvent was removed and the residue was purified by reverse phase HPLC to give the title compound. MS (ES⁺) m/z: 520 (M+H).

A sample of the racemic product was subjected to chiral separation by SFC (OJ, 250×30 mm I.D, 5 um; ethanol (0.05% diethylamine)/CO₂, gradient, 60 mL/min, 40° C.) to give Example 43-a (slower isomer) and Example 43-b (faster isomer). MS (ES⁺) m/z: 520 (M+H); ¹H NMR (CDCl₃, 400 MHz): δ 8.49 (s, 1H), 7.83 (m, 1H), 7.73 (d, J=8.2 Hz, 1H), 7.57-7.69 (m, 3H), 7.46 (m, 1H), 7.31 (d, J=7.7 Hz, 1H), 7.26 (dd, J=2.0, 8.2 Hz, 1H), 7.11-7.23 (m, 2H), 7.00 (d, J=7.5 Hz, 1H), 4.80 (m, 1H), 2.40 (m, 1H), 2.05-2.19 (m, 3H), 1.95 (d, J=7.3 Hz, 1H), 1.43-1.62 (m, 2H), 1.30 (d, J=9.5 Hz, 1H).

Example 44

(s)-5-(3-chloro-2,6-difluorophenyl)-2-(2⁴-((ethoxycarbonyl)amino)-4-oxo-3-aza-1(1,3),2(1,2)-dinenzenacyclononaphane-9-yl)pyridine 1-oxide

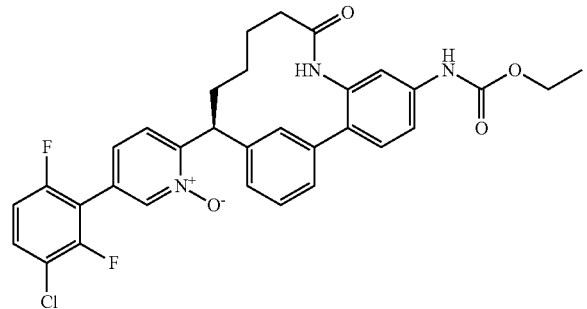 [SMILES: CCOC(=O)Nc1ccc2c(c1)NC(=O)CCCC[C@H](c1ccc(-c3c(F)ccc(Cl)c3F)c[n+]1[O-])c1cccc-2c1]

44A: tert-Butyl (S)-(9-(5-(3-chloro-2,6-difluorophenyl)pyridin-2-yl)-4-oxo-3-aza-1(1,3),2(1,2) -dinenzenacyclononaphane-2⁴-yl)carbamate

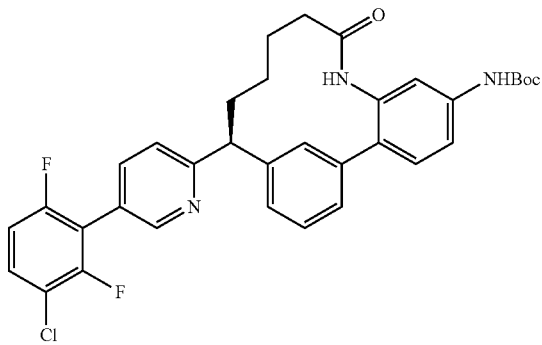 [SMILES: CC(C)(C)OC(=O)Nc1ccc2c(c1)NC(=O)CCCC[C@H](c1ccc(-c3c(F)ccc(Cl)c3F)cn1)c1cccc-2c1]

A sample of 43C was subjected for chiral separation by SFC (Column: Chiralpak AD 250 ×30 mm I.D, 10 um; Mobile phase: A: CO₂, B: ethanol (0.05% DEA); Gradient: hold 5% for 0.5 min, then from 5% to 50% of B in 3.5 min and hold 50%, Flow rate: 80 mL/min. Column temp: 40° C.) to give the desired enantiomer (faster eluting). MS (ESI) m/z 604.1 (M+H).

44B: (S)-2⁴-amino-9-(5-(3-chloro-2,6-difluorophenyl)pyridin-2-yl)-3-aza-1(1,3),2(1,2) -dibenzenacyclononaphan-4-one

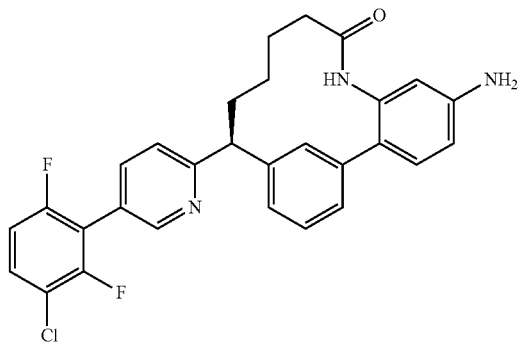 [SMILES: Nc1ccc2c(c1)NC(=O)CCCC[C@H](c1ccc(-c3c(F)ccc(Cl)c3F)cn1)c1cccc-2c1]

To a stirred solution of 44A (100 mg, 0.166 mmol) in DCM (0.5 mL) was added TFA (0.5 mL, 6.49 mmol) at 25° C. The mixture was stirred for 2 h and concentrated under reduced pressure to yield the title compound. MS (ESI) m/z 504.1 (M+H).

44C: Ethyl (S)-(9-(5-(3-chloro-2,6-difluorophenyl)pyridin-2-yl)-4-oxo-3-aza-1(1,3),2(1,2) -dinenzenacyclononaphane-2⁴-yl)carbamate

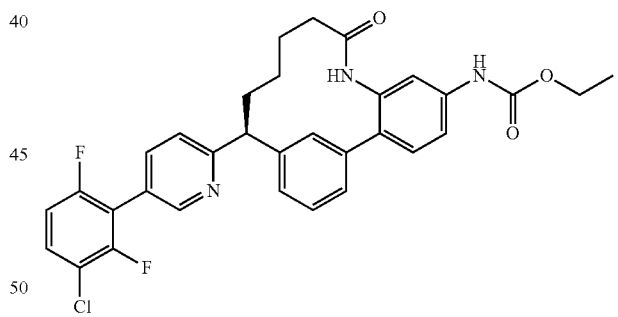

To a stirred solution of 44B (85 mg, 0.169 mmol) and DIEA (0.236 mL, 1.349 mmol) in DCM (3 mL) was added ethyl chloroformate (27.5 mg, 0.253 mmol) at 25° C. The mixture was stirred for 16 h. Aqueous HCl (1 M, 20 mL) was added and the mixture was extracted with dichloromethane (2×50 mL). The combined organic layers were washed with saturated aqueous NaHCO₃ (2×50 mL), dried over sodium sulfate, filtered. The filtrate was evaporated under reduced pressure to yield the title compound. MS (ESI) m/z 576.1 (M+H).

Example 44

To a stirred solution of 44C (85 mg, 0.125 mmol) in CHCl₃ (3 mL) was added m-CPBA (42.2 mg, 0.188 mmol, 77% purity) at 25° C. The mixture was stirred at 25° C. for 1 h and was concentrated under reduced pressure. The residue was purified by reverse-phase prep-HPLC to give the title compound. $^1$H NMR (400 MHz, CD$_3$OD): δ 8.50 (s, 1H), 7.84-7.78 (m, 1H), 7.72-7.58 (m, 3H), 7.50-7.45 (m, 3H), 7.43-7.29 (m, 2H), 7.19 (t, J=9.0 Hz, 1H), 6.96 (d, J=7.3 Hz, 1H), 4.82-4.78 (m, 1H), 4.21-4.12 (m, 2H), 2.49-2.35 (m, 1H), 2.19-2.04 (m, 3H), 2.01-1.98 (m, 1H), 1.69-1.37 (m, 3H), 1.29 (t, J=6.9 Hz, 3H).

Example 45

(S)-2-(2$^4$-(((2-(tert-butoxy)ethoxy)carbonyl)amino)-4-oxo-3-aza -1(1,3),2(1,2)-dinenzenacyclononaphane-9-yl)-5-(3-chloro-2,6-difluorophenyl)pyridine 1-oxide

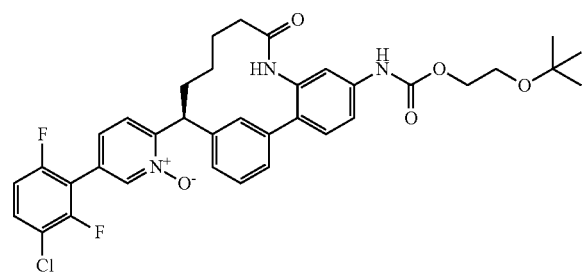 [SMILES: CC(C)(C)OCCOC(=O)Nc1ccc2c(c1)NC(=O)CCCC[C@H](c1ccc(-c3c(F)ccc(Cl)c3F)c[n+]1[O-])c1cccc-2c1]

The title compound was prepared from 44B by the procedure described in the synthesis of Example 44. It was purified by reverse-phase HPCL. $^1$H NMR (400 MHz, CD$_3$OD): δ 8.50 (s, 1H), 7.82-7.59 (m, 4H), 7.51-7.33 (m, 4H), 7.31-7.25 (m, 1H), 7.19 (t, J=8.6 Hz, 1H), 6.96 (d, J=7.4 Hz, 1H), 4.83-4.76 (m, 1H), 4.19 (t, J=4.5 Hz, 2H), 3.62 (t, J=4.9 Hz, 2H), 2.45-2.32 (m, 1H), 2.18-1.95 (m, 4H), 1.59-1.29 (m, 3H), 1.28 (s, 9H).

Example 46

(S)-5-(3-chloro-2,6-difluorophenyl)-2-(2$^4$-(((2-hydroxyethoxy)carbonyl)amino)-4-oxo-3-aza-1(1,3),2 (1,2) -dinenzenacyclononaphane-9-yl)pyridine 1-oxide

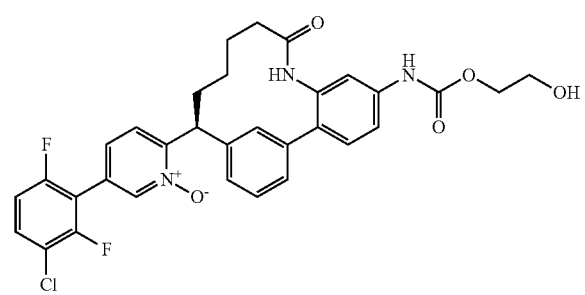 [SMILES: O=C1CCCC[C@H](c2ccc(-c3c(F)ccc(Cl)c3F)c[n+]2[O-])c2cccc(c2)-c2ccc(NC(=O)OCCO)cc2N1]

To a solution of Example 45 (20 mg, 0.030 mmol) in CH$_2$Cl$_2$ (5 mL) was added TFA (1 mL, 12.97 mmol). The mixture was stirred at 26° C. for 2 h. The solvent was removed under reduced pressure and the residue was purified by reverse-phase HPLC to give the title compound.

$^1$H NMR (400 MHz, CD$_3$OD): δ 8.47 (s, 1H), 7.80-7.75 (m, 1H), 7.72-7.65 (m, 2H), 7.63-7.57 (m, 1H), 7.47-7.41 (m, 3H), 7.38-7.33 (m, 1H), 7.28 (d, J=7.4 Hz, 1H), 7.17 (t, J=8.6 Hz, 1H), 6.95 (d, J=7.4 Hz, 1H), 4.79-4.77 (m, 1H), 4.19 (t, J=4.5 Hz, 2H), 3.76 (t, J=4.7 Hz, 2H), 2.45-2.32 (m, 1H), 2.18-1.78 (m, 4H), 1.59-1.49 (m, 1H), 1.47-1.29 (m, 1H), 1.27-1.13 (m, 1H).

Example 47

5-(3-chloro-2,6-difluorophenyl)-2-(4-oxo-2$^4$-(pyridin-3-ylamino)-3-aza -1(1,3),2(1,2)-dinenzenacyclononaphane-9-yl)pyridine 1-oxide

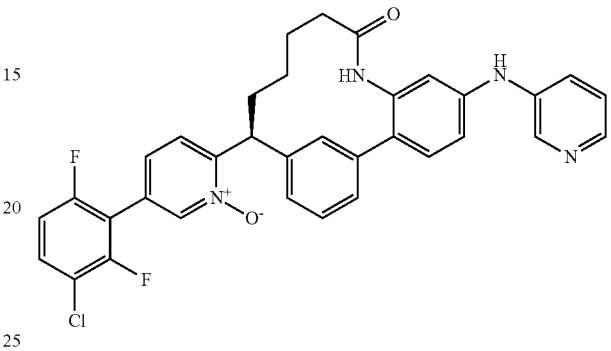

A mixture of Example 43 (50 mg, 0.096 mmol), Pd$_2$(dba)$_3$ (1.761 mg, 1.923 µmol), Xantphos (2.226 mg, 3.85 µmol), 3-bromopyridine (22.79 mg, 0.144 mmol) and sodium 2-methylpropan-2-olate (9.24 mg, 0.096 mmol) in dioxane (5 mL) was stirred at 80° C. for 16 h in a sealed tube under nitrogen. The mixture was filtered and the filter cake washed with dichloromethane (50 mL). The combined organic layers were concentrated and the residue was purified by reverse-phase HPLC and further separated with SFC (Chiralpak AS 250×30 mm, Mobile phase: A: CO$_2$; B: ethanol (0.05% DEA); Gradient: hold 5% for 0.5 min, then from 5% to 40% of B in 3.5 min and hold 40%, Flow rate: 45 mL/min. Column temp: 40° C.) to give the title compound (slower eluting). $^1$H NMR (400 MHz, CD$_3$OD): δ 8.48 (s, 1H), 8.40 (s., 1H), 8.18-8.03 (m, 2H), 7.80 (d, J=8.2 Hz, 2H), 7.74-7.69 (m, 1H), 7.67-7.59 (m, 2H), 7.57 (d, J=8.2 Hz, 1H), 7.42-7.38 (m, 1H), 7.37-7.25 (m, 2H), 7.21-7.15 (m, 2H), 6.97 (d, J=7.4 Hz, 1H), 4.78-4.71 (m, 1H), 2.45-2.33 (m, 1H), 2.19-2.04 (m, 3H), 1.99-1.90 (m, 1H), 1.68-1.40 (m, 2H), 1.35-1.27 (m, 1H).

Example 48

(S)-5-(3-chloro-2,6-difluorophenyl)-2-(4-oxo-2$^4$-(pyrimidin-2-YLAMINO)-3-AZA-1 (1,3),2(1,2)-dinenzenacyclononaphane-9-yl)pyridine 1-oxide

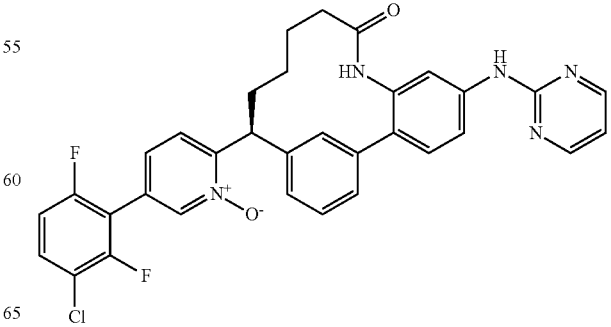

To a seal tube was charged with Example 43-a (100 mg, 0.135 mmol), t-BuOH (1 mL), 2-chloropyrimidine (77 mg, 0.673 mmol) and HCl/dioxane (0.4 mL, 1.600 mmol, 4 M). The mixture was heated at 85° C. for 16 h under nitrogen. It was cooled to rt and concentrated under reduced pressure. The residue was purified by reverse-phase HPLC to yield the title compound.

$^1$H NMR (400 MHz, CD$_3$OD): δ 8.50 (s, 1H), 8.46 (d, J=5.1 Hz, 2H), 7.83-7.78 (m, 1H), 7.74-7.58 (m, 5H), 7.48 (d, J=8.2 Hz, 1H), 7.40-7.34 (m, 1H), 7.33-7.28 (m, 1H), 7.18 (t, J=8.8 Hz, 1H), 6.95 (d, J=7.4 Hz, 1H), 6.85 (t, J=4.9 Hz, 1H), 4.81-4.77 (m, 1H), 2.49-2.37 (m, 1H), 2.21-2.05 (m, 3H), 2.02-1.89 (m, 1H), 1.67-1.54 (m, 1H), 1.52-1.39 (m, 1H), 1.32-1.21 (m, 1H).

Example 49

3-(5-(3-chloro-2,6-difluorophenyl)pyridin-2-yl)-1$^4$-hydroxy-1$^1$,1$^2$-dihydro-9-aza-1 (6,7)-quinolina-2(1,3)-benzenacyclononaphane-1$^2$,8-dione

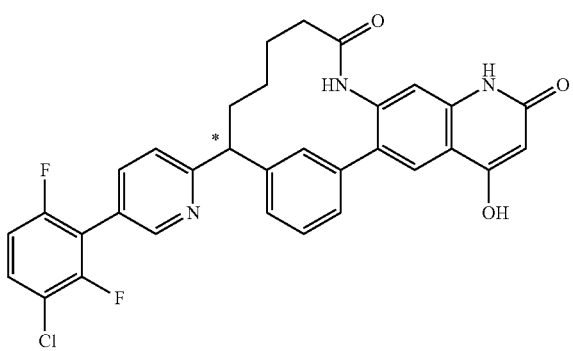 [SMILES: O=C1CCCCC(c2ccc(-c3c(F)ccc(Cl)c3F)cn2)c2cccc(c2)-c2cc3c(O)cc(=O)[nH]c3cc2N1]

49A: Ethyl 3-((9-(5-(3-chloro-2,6-difluorophenyl)pyridin-2-yl)-4-oxo-3-aza-1(1,3),2(1,2)-dinenzenacyclononaphane-2$^4$-yl)amino)-3-oxopropanoate

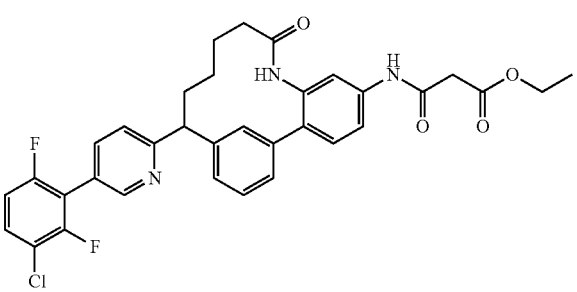 [SMILES: CCOC(=O)CC(=O)Nc1ccc2c(c1)NC(=O)CCCCC(c1ccc(-c3c(F)ccc(Cl)c3F)cn1)c1cccc-2c1]

To a stirred mixture of 44B (40 mg, 0.079 mmol), N-ethyl-N-isopropylpropan-2-amine (41.0 mg, 0.317 mmol) in DCM (2 mL) was added ethyl 3-chloro-3-oxopropanoate (23.90 mg, 0.159 mmol). The mixture was stirred at 25° C. for 16 h. It was diluted with DCM (50 mL), washed with HCl (1M, 20 mL) and aqueous NaHCO$_3$ (20 mL), dried over sodium sulfate, filtered and the solvent was evaporated under reduced pressure. The residue was purified by prep-TLC (petroleum ether:EtOAc=1:2) to give the title compound. MS (ESI) m/z 618.2 (M+H).

49B: 3-((9-(5-(3-chloro-2,6-difluorophenyl)pyridin-2-yl)-4-oxo-3-aza-1(1,3),2(1,2)-dinenzenacyclononaphane-2$^4$-yl)amino)-3-oxopropanoic acid

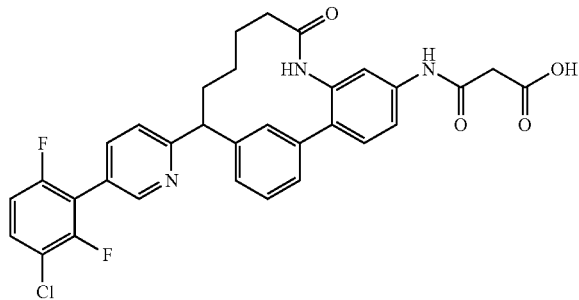 [SMILES: O=C(O)CC(=O)Nc1ccc2c(c1)NC(=O)CCCCC(c1ccc(-c3c(F)ccc(Cl)c3F)cn1)c1cccc-2c1]

To a stirred mixture of 49A (30 mg, 0.049 mmol) in THF (2 mL) and MeOH (0.5 mL) was added aqueous lithium hydrOXIDE (0.097 mL, 0.194 mmol, 2 M); the mixture was stirred at 25° C. for 1 h. HCl (1 M) was added to adjust pH=3 and the mixture was extracted with EtOAc (20 mL×2). The combined organic layers were dried over sodium sulfate, filtered and the solvent was evaporated under reduced pressure to give the title compound. MS (ESI) m/z 590.2 (M+H).

Example 49

A mixture of 49B (200 mg, 0.339 mmol) in Eaton's Reagent (1 mL, 0.339 mmol) was stirred at 90° C. for 16 h in a sealed tube. LCMS showed the reaction was completed. The mixture was poured into water (10 mL). Aqueous NaHCO$_3$ (20 mL) was added and the mixture was extracted with EtOAc (30 mL×2). The combined organic fractions were dried over sodium sulfate, filtered and the solvent was evaporated under reduced pressure. The residue was purified by reverse-phase HPLC (TFA) to give the title compound. MS (ESI) m/z 572.2 (M+H); $^1$H NMR (400 MHz, DMSO-d$_6$): δ 11.41 (s, 1H), 9.72 (s, 1H), 8.64 (s, 1H), 7.88 (d, J=7.9 Hz, 1H), 7.83 (s, 1H), 7.77-7.68 (m, 1H), 7.58-7.53 (m, 2H), 7.42-7.30 (m, 3H), 7.28 (d, J=7.5 Hz, 1H), 7.18 (d, J=7.5 Hz, 1H), 7.11 (s, 1H), 5.76 (s, 1H), 4.22 (d, J=9.5 Hz, 1H), 2.39-2.17 (m, 2H), 2.13-1.90 (m, 2H), 1.88-1.73 (m, 1H), 1.54-1.49 (m, 1H), 1.31-1.08 (m, 2H).

Example 50 (racemate), 50-a, 50-b, 50-c, 50-d 5-(3-chloro-2,6-difluorophenyl)-2-(2$^4$-((methoxycarbonyl)amino)-5-methyl-4-oxo-3-aza-1(1,3),2(1,2)-dinenzenacyclononaphane-9-yl)pyridine 1-oxide

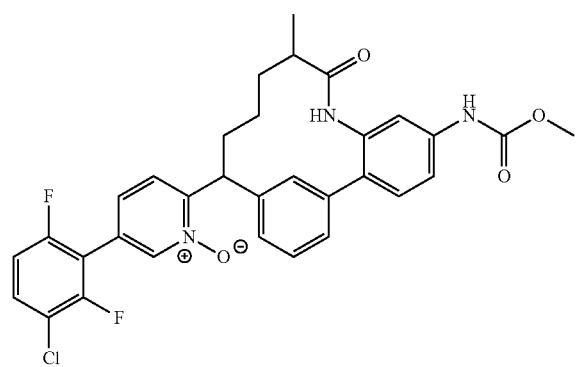 [SMILES: COC(=O)Nc1ccc2c(c1)NC(=O)C(C)CCCC(c1ccc(-c3c(F)ccc(Cl)c3F)c[n+]1[O-])c1cccc-2c1]

50A: (5-((3'-(5-chloropicolinoyl)-4-((methoxycarbonyl)amino)-[1,1'-biphenyl]-2-yl)amino)-4-methyl-5-oxopentyl)triphenylphosphonium bromide To a stirred mixture of 12A (6.9 g, 18.07 mmol), (4-carboxypentyl) triphenylphosphonium bromide (10.74 g, 23.49 mmol) and Hunig's Base (31.6 mL, 181 mmol) in CH$_2$Cl$_2$ (90 mL) at rt was added 2,4,6-tripropyl-1,3,5,2,4,6-trioxatriphosphorinane-2,4,6-triOXIDE (50% in EtOAc) (23.00 g, 36.1 mmol). The mixture was stirred at rt overnight. It was concentrated; the residue was purified by flash column chromatography on silica (eluting with MeOH/CH$_2$Cl$_2$=5%) to give the title compound. MS (ES$^+$) m/z: 741 (M).

50B: Methyl (E)-(9-(5-chloropyridin-2-yl)-5-methyl-4-oxo-3-aza-1(1,3),2(1,2)-dibenzenacyclono-naphan-8-en-24-yl)carbamate

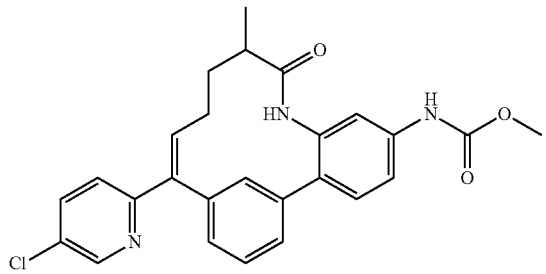 [SMILES: COC(=O)Nc1ccc2c(c1)NC(=O)C(C)CC/C=C(/c1ccc(Cl)cn1)c1cccc-2c1]

A solution of LiHMDS (1 M in THF) (67.0 mL, 67.0 mmol) was added to a stirred solution of 50A (10.0 g, 12.2 mmol) in tetrahydrofuran (609 mL) at 0° C. The mixture was stirred at rt overnight. It was diluted with ethyl acetate (500 mL), washed with aqueous ammonium chloride (saturated, 150 mL), water (150 mL), dried (MgSO$_4$), filtered. The filtrate was concentrated under reduced pressure; the residue was triturated in dichloromethane (10 mL)-methanol (5 mL). The precipitate was filtered and dried to give the title compound. MS (ES$^+$) m/z: 462 (M+H).

50C: Methyl (E)-(9-(5-(3-chloro-2,6-difluorophenyl)pyridin-2-yl)-5-methyl-4-OXO-3-AZA-1(1,3),2(1,2)-dibenzenacyclononaphan-8-en-2$^4$-yl)carbamate

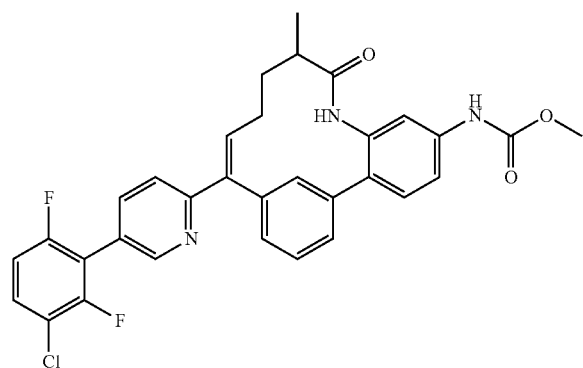 [SMILES: COC(=O)Nc1ccc2c(c1)NC(=O)C(C)CC/C=C(/c1ccc(-c3c(F)ccc(Cl)c3F)cn1)c1cccc-2c1]

A mixture of bis(pinacolato)diboron (198 mg, 0.779 mmol), 50B (300 mg, 0.649 mmol), potassium acetate (191 mg, 1.948 mmol), 2$^{nd}$ generation XPHOS precatalyst (51.1 mg, 0.065 mmol) and dioxane (3.2 mL) in a pressure release vial was degassed and backfilled with nitrogen (3×). The mixture was heated at 80° C. for 30 min. It was cooled to rt and subsequently added 1-bromo-3-chloro-2,6-difluorobenzene (192 mg, 0.844 mmol), 1,1'-bis(diphenylphosphino)-ferrocene-palladium(II)dichloride dichloromethane complex (53.2 mg, 0.065 mmol) and aqueous potassium phosphate tribasic (3 M, 0.649 mL, 1.948 mmol). The mixture was degassed and backfilled with nitrogen (3×). It was stirred at 80° C. for 1 h, cooled to rt and purified by flash column chromatography on silica gel (eluting with MeOH/CH$_2$Cl$_2$=5 to 8%) to give the title compound. MS (ES$^+$) m/z: 574 (M+H).

50D: Methyl (9-(5-(3-chloro-2,6-difluorophenyl)pyridin-2-yl)-5-methyl-4-oxo-3-aza -1(1,3),2(1,2)-dinenzenacyclononaphane-2$^4$-yl)carbamate

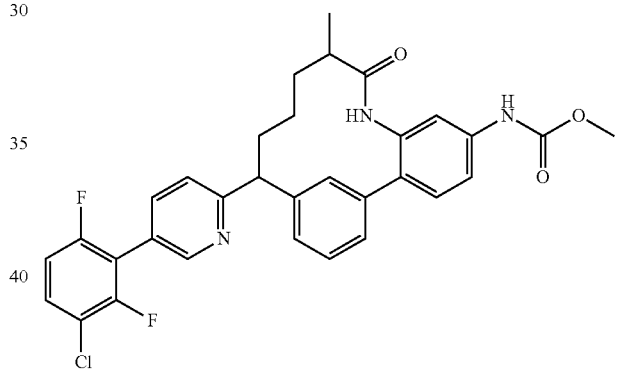

A mixture of Raney-Nickel (552 mg, 9.41 mmol) and 50C (270 mg, 0.470 mmol) in tetrahydrofuran (20 mL) was shaken on a Parr shaker under hydrogen (P=40 Psi) for 15 min. The catalyst was removed by filtration through Celite (with caution), The filtrate was concentrated under reduced pressure to give the title compound. MS (ES$^+$) m/z: 576 (M+H).

Example 50, 50-a, 50-b, 50-c, 50-d 50D (165 mg, 0.286 mmol) in dichloromethane (2.9 mL) was stirred with m-CPBA (128 mg, 0.573 mmol) at rt for 2 h. The reaction mixture was purified by flash column chromatography (eluting with MeOH/CH$_2$Cl$_2$=4%) to give the title compound. MS (ES$^+$) m/z: 592 (M+H).

A sample of racemic Example 50 was subjected to chiral separation by SFC (IC, 21×200 mm, 48% MeOH/CO$_2$, 100 bar, 58 mL/min, 35° C.) to afford Example 50-a (peak 1), Example 50-b (peak 2), Example 50-c (peak 3) and Example 50-d (peak 4). MS (ES$^+$) m/z: 592 (M+H).

Example 51

Methyl (9-(5-(5-chloro-2-(1H-tetrazol-1-yl)phenyl)pyridin-2-yl)-1⁵-fluoro-4-oxo-3-aza-1(1,3),2(1,2)-dinenzenacyclononaphane-2⁴-yl)carbamate

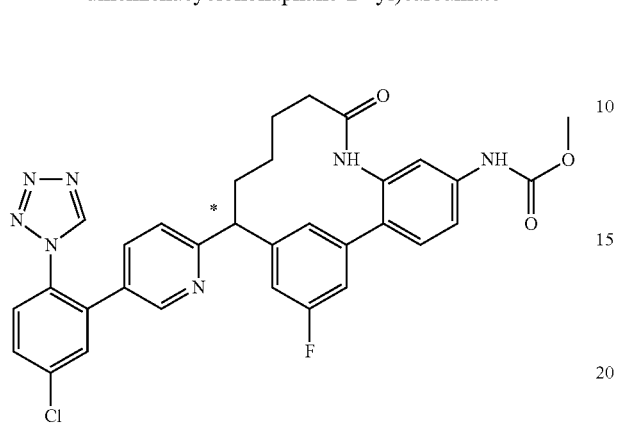

51A: Methyl (2-amino-3'-(5-chloropicolinoyl)-5'-fluoro-[1,1'-biphenyl]-4-yl)carbamate

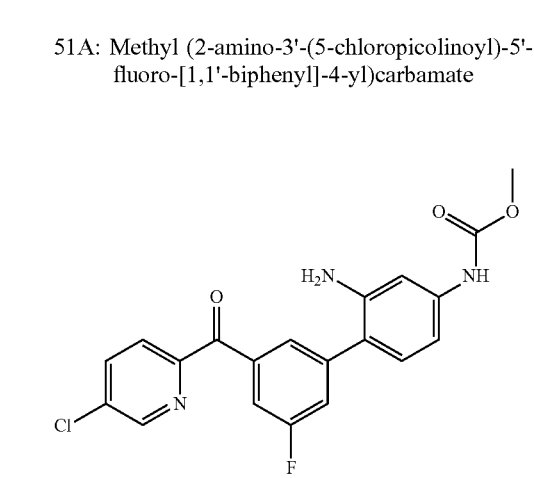

51A was prepared from the Suzuki coupling of Intermediate 19 and Intermediate 4 by the procedure described in 12A. MS (ES⁺) m/z: 400 (M+H).

51B: (5-((3'-(5-Chloropicolinoyl)-5'-fluoro-4-((methoxycarbonyl)amino)-[1,1'-biphenyl]-2-yl)amino)-5-oxopentyl)triphenylphosphonium bromide to a solution of 51a (6.0 g, 15.01 mmol) in DMF (50 mL), (4-carboxybutyl)triphenylphosphonium bromide (7.98 g, 18.01 mmol), 2,4,6-tripropyl-1,3,5,2,4,6-trioxatriphosphinane 2,4,6-triOXIDE (50% wt in ethyl acetate, 19.10 g, 30.0 mmol) and DIEA (7.86 mL, 45.0 mmol) were added at 20° C. The mixture was stirred at 20° C. for 2 h and it was quenched with saturated aqueous ammonium chloride (500 mL). The mixture was extracted with EtOAc (300 mL×3). The combined organic layers were washed with brine (300 mL×5), dried over sodium sulfate, filtered and concentrated in vacuo. The residue was purified by flash column chromatography on silica gel (eluting with DCM:MeOH=30:1 v/v) to give the title compound. MS (ES⁺) m/z: 744 (M).

51C: Methyl (E)-(9-(5-chloropyridin-2-yl)-1⁵-fluoro-4-oxo-3-aza-1(1,3),2(1,2)-dibenzenacyclononaphan-8-en-2⁴-yl)carbamate

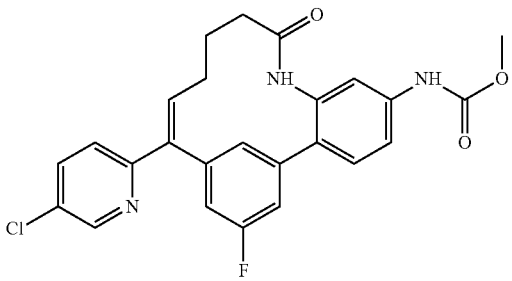 [SMILES: COC(=O)Nc1ccc2c(c1)NC(=O)CCC/C=C(/c1ccc(Cl)cn1)c1cc(F)cc-2c1]

51C was prepared from 51B by the procedure described in the synthesis of 12C. MS (ES⁺) m/z: 466 (M+H).

51D: Methyl (E)-(9-(5-(2-amino-5-chlorophenyl)pyridin-2-yl)-1⁵-fluoro-4-oxo-3-aza-1(1,3),2(1,2)-dibenzenacyclononaphan-8-en-2⁴-yl)carbamate

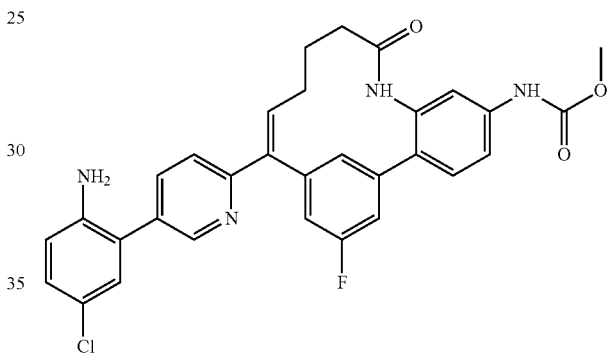

A mixture of 51C (230 mg, 0.494 mmol), Intermediate 33 (250 mg, 0.987 mmol), K₂CO₃ (205 mg, 1.481 mmol), 1,1'-bis(di-tert-butylphosphino)ferrocene palladium dichloride (32.2 mg, 0.049 mmol), THF (3 mL) and water (1 mL) was stirred at 120° C. under nitrogen for 40 min in a microwave reactor. It was cooled to rt and the reaction was quenched with water (20 mL). The mixture was extracted with EtOAc (10 mL×3). The combined organic layers were washed with brine (10 mL), dried over sodium sulfate, filtered and concentrated under reduced pressure to give the title compound. MS (ES⁺) m/z: 557 (M+H).

51E: Methyl (9-(5-(2-AMINO-5-chlorophenyl)pyridin-2-yl)-1⁵-fluoro-4-oxo-3-aza-1(1,3),2(1,2)-dinenzenacyclononaphane-2⁴-yl)carbamate

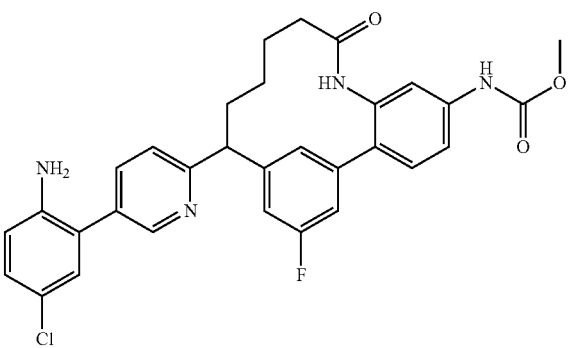 [SMILES: COC(=O)Nc1ccc2c(c1)NC(=O)CCCCC(c1ccc(-c3cc(Cl)ccc3N)cn1)c1cc(F)cc-2c1]

A mixture of 51D (200 mg, 0.359 mmol) and Raney-nickel (42.1 mg, 0.718 mmol) in THF (100 mL) was stirred at 25° C. under a hydrogen balloon for 10 min. The reaction mixture was filtered and the filtrate was concentrated to give the title compound, which was used in the next step without further purification. MS (ES+) m/z: 559 (M+H).

Example 51

To a mixture of 51E (66 mg, 0.118 mmol) in HOAc (5.0 mL) trimethyl orthoformate (251 mg, 2.361 mmol) and NaN$_3$ (46.1 mg, 0.708 mmol) were added. The mixture was stirred at 30° C. for 18 h. The reaction was quenched with saturated NaNO$_2$ (7 mL) and the pH was adjusted to 8 with sodium bicarbonate (saturated). The mixture was extracted with EtOAc (20 mL×3). The combined organic layers were washed with brine (20 mL), dried over sodium sulfate, filtered and concentrated under reduced pressure. The residue was purified by reverse phase HPLC to give the title compound. MS (ES+) m/z: 612 (M+H); $^1$H NMR (CD$_3$OD, 400 MHz): δ 9.29 (s, 1H), 8.36 (d, J=1.8 Hz, 1H), 7.64-7.82 (m, 4H), 7.53 (d, J=8.2 Hz, 1H), 7.39-7.50 (m, 3H), 7.35 (s, 1H), 7.02 (d, J=9.3 Hz, 1H), 6.77 (d, J=9.5 Hz, 1H), 4.21-4.33 (m, 1H), 3.75 (s, 3H), 2.35-2.47 (m, 1H), 1.96-2.23 (m, 3H), 1.81-1.95 (m, 1H), 1.60 (m, 1H), 1.39 (m, 1H), 1.08-1.25 (m, 1H).

Example 52

5-(5-chloro-2-(1h-tetrazol-1-yl)phenyl)-2-(1$^5$-fluoro-2$^4$-((methoxycarbonyl)amino)-4-oxo-3-aza-1(1,3),2(1,2)-dinenzenacyclononaphane-9-yl)pyridine 1-oxide

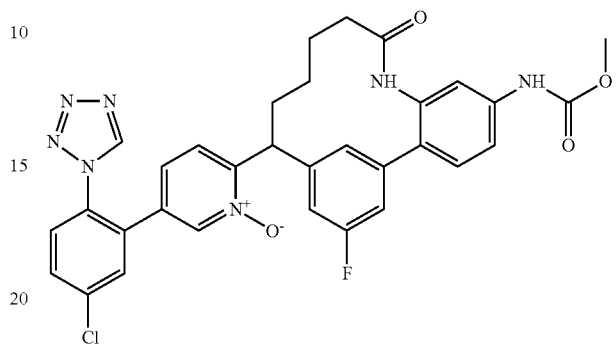

Example 52 was prepared from Example 51 by the procedure described in Example 13. MS (ES+) m/z: 628 (M+H); $^1$H NMR (DMSO d$_6$, 400 MHz): δ 9.86 (m, 1H), 9.65-9.71 (m, 1H), 9.63 (s, 1H), 8.20 (s, 1H), 7.90 (s, 1H), 7.83 (s, 2H), 7.56 (d, J=8.2 Hz, 1H), 7.27-7.51 (m, 4H), 7.03 (d, J=9.4 Hz, 1H), 6.97 (d, J=9.0 Hz, 1H), 6.60 (d, J=9.8 Hz, 1H), 4.56 (d, J=10.6 Hz, 1H), 3.69 (s, 3H), 2.33 (m, 1H), 1.67-2.06 (m, 4H), 1.32-1.56 (m, 1H), 1.11-1.30 (m, 1H), 0.97 (m, 1H).

The following compounds were synthesized by the procedures described in Example 51 with the appropriate starting materials. They are characterized by LC/MS.

| Ex | Structure | Name | MS (M + H) |
|---|---|---|---|
| 53 | 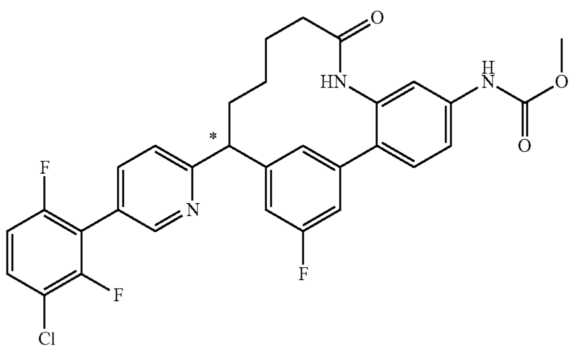 [SMILES: COC(=O)Nc1ccc2c(c1)NC(=O)CCCCC(c1ccc(-c3c(F)ccc(Cl)c3F)cn1)c1cc(F)cc-2c1] | methyl (9-(5-(3-chloro-2,6-difluorophenyl)pyridin-2-yl)-1$^5$-fluoro-4-oxo-3-aza-1(1,3),2(1,2)-dibenzenacyclononaphane-2$^4$-yl)carbamate | 580 |
| 54 | 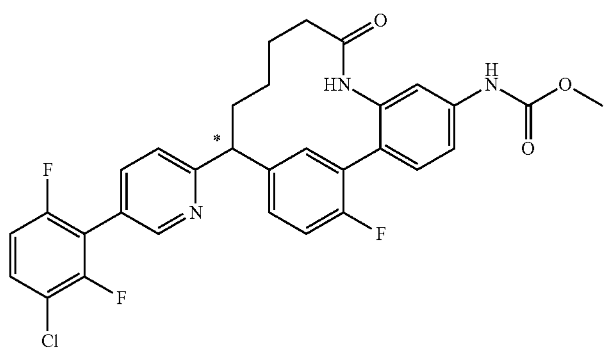 [SMILES: COC(=O)Nc1ccc2c(c1)NC(=O)CCCCC(c1ccc(-c3c(F)ccc(Cl)c3F)cn1)c1ccc(F)c-2c1] | methyl (9-(5-(3-chloro-2,6-difluorophenyl)pyridin-2-yl)-1$^6$-fluoro-4-oxo-3-aza-1(1,3),2(1,2)-dibenzenacyclononaphane-2$^4$-yl)carbamate | 580 |

| Ex | Structure | Name | MS (M + H) |
|---|---|---|---|
| 55 | 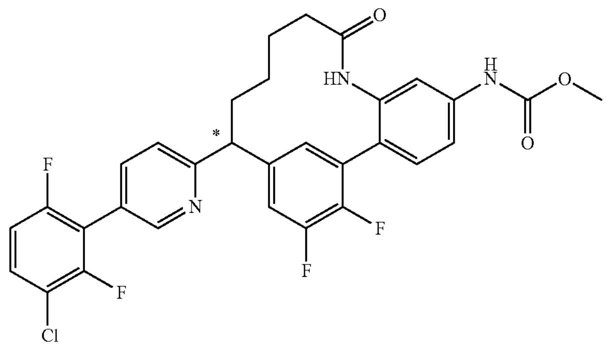 [SMILES: COC(=O)Nc1ccc2c(c1)NC(=O)CCCCC(c1ccc(-c3c(F)ccc(Cl)c3F)cn1)c1cc(F)c(F)c-2c1] | methyl (9-(5-(3-chloro-2,6-difluorophenyl)pyridin-2-yl)-1$^5$,1$^6$-difluoro-4-oxo-3-aza-1(1,3),2(1,2)-dibenzenacyclononaphane-2$^4$-yl)carbamate | 598 |
| 56 | 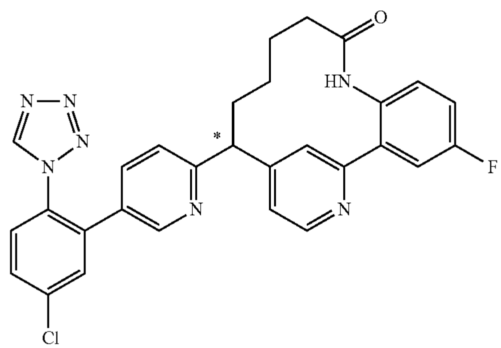 [SMILES: O=C1CCCCC(c2ccc(-c3cc(Cl)ccc3-n3cnnn3)cn2)c2ccnc(c2)-c2cc(F)ccc2N1] | 9-(5-(5-chloro-2-(1h-tetrazol-1-yl)phenyl)pyridin-2-yl)-25-fluoro-3-aza-1(2,4)-pyridina-2(1,2)-benzenacyclononaphan-4-one | 540 |
| 57 | 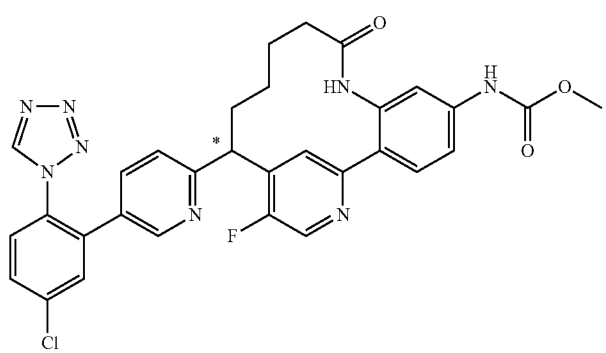 [SMILES: COC(=O)Nc1ccc2c(c1)NC(=O)CCCCC(c1ccc(-c3cc(Cl)ccc3-n3cnnn3)cn1)c1cc-2ncc1F] | methyl (9-(5-(5-chloro-2-(1h-tetrazol-1-yl)phenyl)pyridin-2-yl)-1$^5$-fluoro-4-oxo-3-aza-1(2,4)-pyridina-2(1,2)-benzenacyclononaphane-2$^4$-yl)carbamate | 613 |
| 58 | 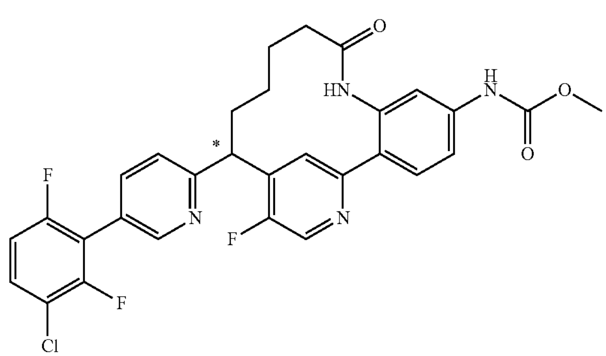 [SMILES: COC(=O)Nc1ccc2c(c1)NC(=O)CCCCC(c1ccc(-c3c(F)ccc(Cl)c3F)cn1)c1cc-2ncc1F] | methyl (9-(5-(3-chloro-2,6-difluorophenyl)pyridin-2-yl)-1$^5$-fluoro-4-oxo-3-aza-1(2,4)-pyridina-2(1,2)-benzenacyclononaphane-2$^4$-yl)carbamate | 581 |

-continued

| Ex | Structure | Name | MS (M + H) |
|---|---|---|---|
| 59 | 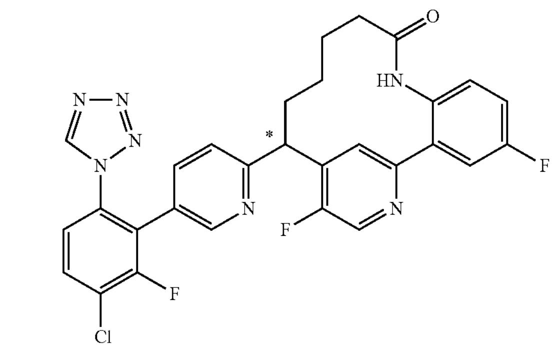 [SMILES: O=C1CCCCC(c2ccc(-c3c(-n4cnnn4)ccc(Cl)c3F)cn2)c2cc(ncc2F)-c2cc(F)ccc2N1] | 9-(5-(3-chloro-2-fluoro-6-(1h-tetrazol-1-yl)phenyl)pyridin-2-yl)-1⁵,2⁵-difluoro-3-aza-1(2,4)-pyridina-2(1,2)-benzenacyclononaphan-4-one | 576 |
| 60 | 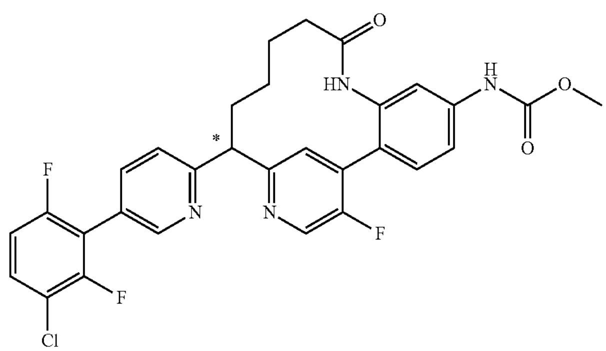 [SMILES: COC(=O)Nc1ccc2c(c1)NC(=O)CCCCC(c1ccc(-c3c(F)ccc(Cl)c3F)cn1)c1cc-2c(F)cn1] | methyl (9-(5-(3-chloro-2,6-difluorophenyl)pyridin-2-yl)-1⁵-fluoro-4-oxo-3-aza-1(4,2)-pyridina-2(1,2)-benzenacyclononaphane-2⁴-yl)carbamate | 581 |
| 61 | 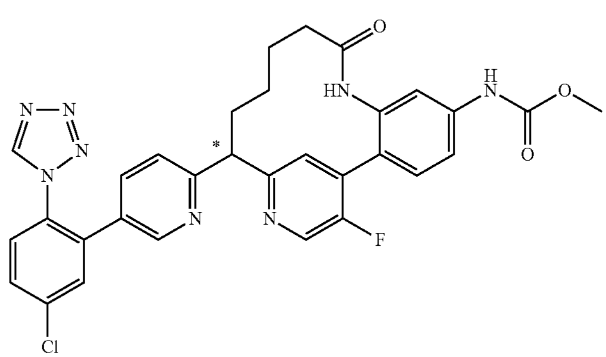 [SMILES: COC(=O)Nc1ccc2c(c1)NC(=O)CCCCC(c1ccc(-c3cc(Cl)ccc3-n3cnnn3)cn1)c1cc-2c(F)cn1] | methyl (9-(5-(5-chloro-2-(1h-tetrazol-1-yl)phenyl)pyridin-2-yl)-1⁵-fluoro-4-oxo-3-aza-1(4,2)-pyridina-2(1,2)-benzenacyclononaphane-2⁴-yl)carbamate | 613 |
| 62 | 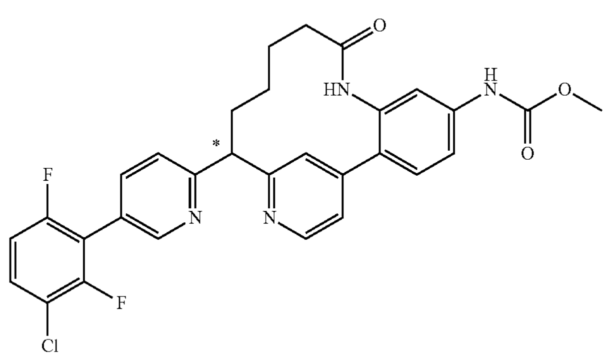 [SMILES: COC(=O)Nc1ccc2c(c1)NC(=O)CCCCC(c1ccc(-c3c(F)ccc(Cl)c3F)cn1)c1cc-2ccn1] | methyl (9-(5-(3-chloro-2,6-difluorophenyl)pyridin-2-yl)-4-oxo-3-aza-1(4,2)-pyridina-2(1,2)-benzenacyclononaphane-2⁴-yl)carbamate | 563 |

-continued

| Ex | Structure | Name | MS (M + H) |
|---|---|---|---|
| 63 | 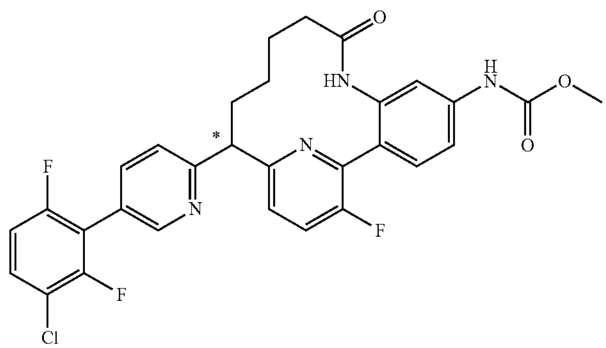 [SMILES: COC(=O)Nc1ccc2c(c1)NC(=O)CCCCC(c1ccc(-c3c(F)ccc(Cl)c3F)cn1)c1ccc(F)c-2n1] | methyl (9-(5-(3-chloro-2,6-difluorophenyl)pyridin-2-yl)-1³-fluoro-4-oxo-3-aza-1(2,6)-pyridina-2(1,2)-benzenacyclononaphane-2⁴-yl)carbamate | 581 |
| 64 | 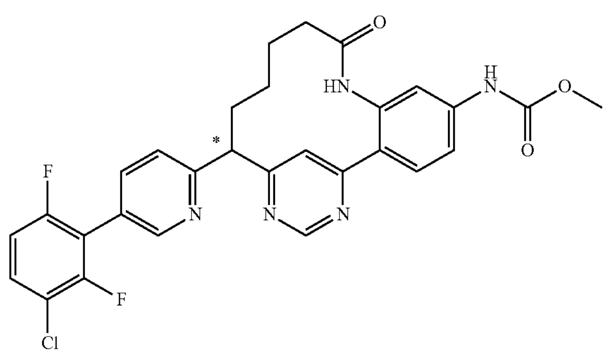 [SMILES: COC(=O)Nc1ccc2c(c1)NC(=O)CCCCC(c1ccc(-c3c(F)ccc(Cl)c3F)cn1)c1cc-2ncn1] | methyl (9-(5-(3-chloro-2,6-difluorophenyl)pyridin-2-yl)-4-oxo-3-aza-1(4,6)-pyrimidina-2(1,2)-benzenacyclononaphane-2⁴-yl)carbamate | 564 |
| 65 | 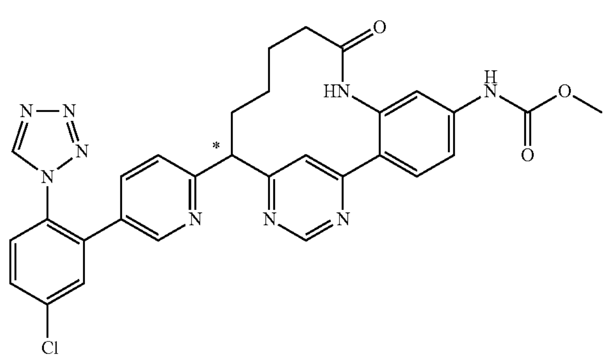 [SMILES: COC(=O)Nc1ccc2c(c1)NC(=O)CCCCC(c1ccc(-c3cc(Cl)ccc3-n3cnnn3)cn1)c1cc-2ncn1] | methyl (9-(5-(5-chloro-2-(1h-tetrazol-1-yl)phenyl)pyridin-2-yl)-4-oxo-3-aza-1(4,6)-pyrimidina-2(1,2)-benzenacyclononaphane-2⁴-yl)carbamate | 596 |

By using the procedures described in Example 13, and appropriate starting materials, the following compounds were synthesized and characterized by LC/MS.

| Ex | Structure and Name | Chiral Separation SFC Condition | MS (M + H) |
|----|--------------------|----------------------------------|------------|
| 66 | 5-(3-chloro-2,6-difluorophenyl)-2-(($5^1$R,$5^2$R,3S)-$1^4$-((methoxycarbonyl)amino)-7-oxo-8-aza-1(1,2),2(1,3)-dibenzena-5(1,2)-cyclopropanacyclooctaphane-3-yl)pyridine 1-oxide 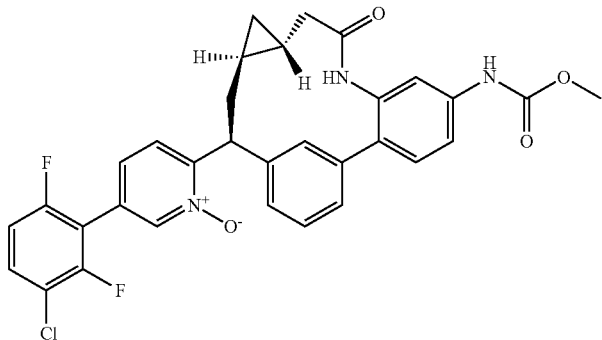 [SMILES: COC(=O)Nc1ccc2c(c1)NC(=O)C[C@H]1C[C@@H]1C[C@H](c1ccc(-c3c(F)ccc(Cl)c3F)c[n+]1[O-])c1cccc-2c1] | IC, 250 × 21 mm, 55% MeOH/$CO_2$, 55 ml/min Slower eluting | 590.0 |
| 67 | (S)-5-(3-chloro-2,6-difluorophenyl)-2-($1^5$-fluoro-$2^4$-((methoxycarbonyl)amino)-4-oxo-3-aza-1(1,3),2(1,2)-dibenzenacyclononaphane-9-yl)pyridine 1-oxide 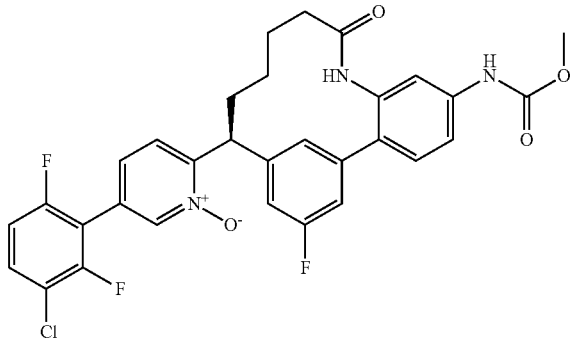 [SMILES: COC(=O)Nc1ccc2c(c1)NC(=O)CCCC[C@H](c1ccc(-c3c(F)ccc(Cl)c3F)c[n+]1[O-])c1cc(F)cc-2c1] | AD, 250 × 30 mm; 40% iso-propanol (0.05% diethylamine) in $CO_2$; 60 mL/min; Slower eluting | 596.1 |
| 68 | (S)-5-(3-chloro-2,6-difluorophenyl)-2-($1^6$-fluoro-$2^4$-((methoxycarbonyl)amino)-4-oxo-3-aza-1(1,3),2(1,2)-dibenzenacyclononaphane-9-yl)pyridine 1-oxide 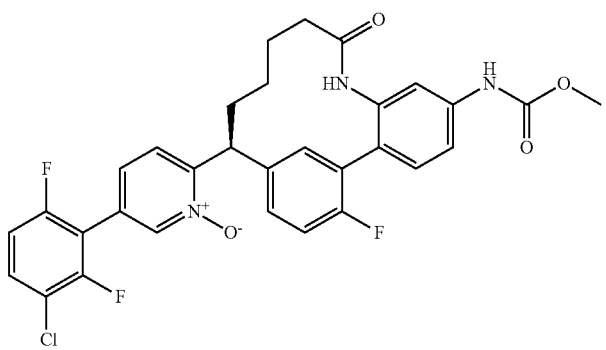 [SMILES: COC(=O)Nc1ccc2c(c1)NC(=O)CCCC[C@H](c1ccc(-c3c(F)ccc(Cl)c3F)c[n+]1[O-])c1ccc(F)c-2c1] | Column AD; 250 × 30 mm, EtOH (0.1% $NH_3H_2O$)/ $CO_2$, 80 mL/min Faster eluting | 596.2 |

| Ex | Structure and Name | Chiral Separation SFC Condition | MS (M + H) |
|---|---|---|---|
| 69 | (S)-5-(3-chloro-2,6-difluorophenyl)-2-(1⁵,1⁶-difluoro-2⁴-((methoxycarbonyl)amino)-4-oxo-3-aza-1(1,3),2(1,2)-dibenzenacyclononaphane-9-yl)pyridine 1-oxide | AD; 250 × 30 mm, 50% IPA (NH$_4$OH)/ CO$_2$; 55 mL/min Faster eluting | 614.0 |

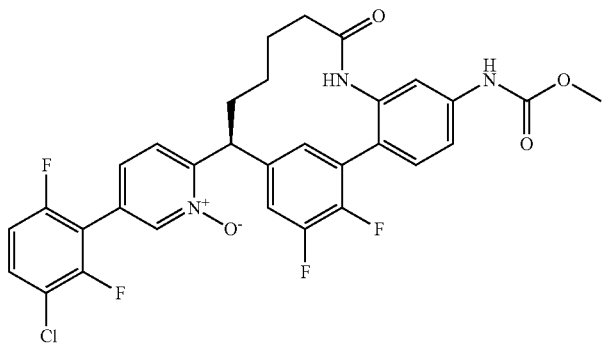 [SMILES: COC(=O)Nc1ccc2c(c1)NC(=O)CCCC[C@H](c1ccc(-c3c(F)ccc(Cl)c3F)c[n+]1[O-])c1cc(F)c(F)c-2c1]

| | | | |
|---|---|---|---|
| 70 | 5-(5-chloro-2-(1H-tetrazol-1-yl)phenyl)-2-(2⁵-fluoro-4-oxo-3-aza-1(2,4)-pyridina-2(1,2)-benzenacyclononaphane-9-yl)pyridine 1-oxide | | 556.1 |

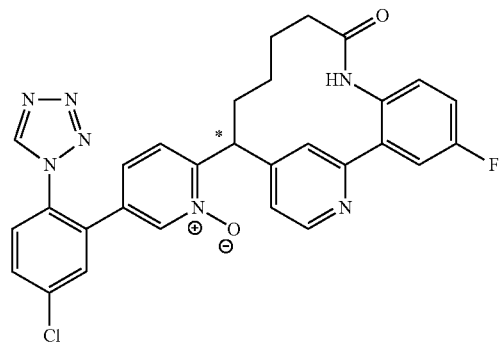 [SMILES: O=C1CCCCC(c2ccc(-c3cc(Cl)ccc3-n3cnnn3)c[n+]2[O-])c2ccnc(c2)-c2cc(F)ccc2N1]

| | | | |
|---|---|---|---|
| 71 | (S)-5-(5-chloro-2-(1H-tetrazol-1-yl)phenyl)-2-(1⁵-fluoro-2⁴-((methoxycarbonyl)amino)-4-oxo-3-aza-1(2,4)-pyridina-2(1,2)-benzenacyclononaphane-9-yl)pyridine 1-oxide | OJ-H, 2 × 25 cm, 18% methanol (0.1% DEA)/ CO$_2$, 65 mL/min Slower eluting | 629.1 |

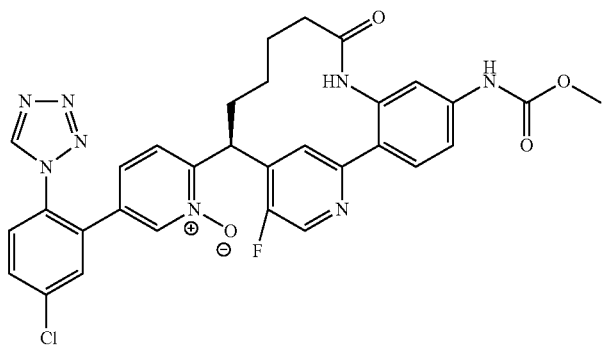 [SMILES: COC(=O)Nc1ccc2c(c1)NC(=O)CCCC[C@H](c1ccc(-c3cc(Cl)ccc3-n3cnnn3)c[n+]1[O-])c1cc-2ncc1F]

| Ex | Structure and Name | Chiral Separation SFC Condition | MS (M + H) |
|---|---|---|---|
| 72 | (S)-5-(3-chloro-2,6-difluorophenyl)-2-(1⁵-fluoro-2⁴-((methoxycarbonyl)amino)-4-oxo-3-aza-1(2,4)-pyridina-2(1,2)-benzenacyclononaphane-9-yl)pyridine 1-oxide | IA, 30 × 250 mm, 70% methanol (0.2% ammonia)/ CO$_2$, 70 mL/min Faster eluting | 597.1 |// 
| | 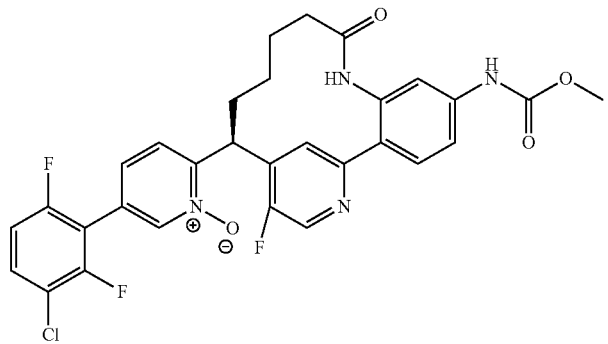 [SMILES: COC(=O)Nc1ccc2c(c1)NC(=O)CCCC[C@H](c1ccc(-c3c(F)ccc(Cl)c3F)c[n+]1[O-])c1cc-2ncc1F] | | |
| 73 | (S)-5-(3-chloro-2,6-difluorophenyl)-2-(2⁴-((methoxycarbonyl)amino)-4-oxo-3-aza-1(4,2)-pyridina-2(1,2)-benzenacyclononaphane-9-yl)pyridine 1-oxide | AS, 250 × 30 mm, 45% MeOH/CO$_2$, 80 mL/min Faster Eluting | 579.2 |
| | 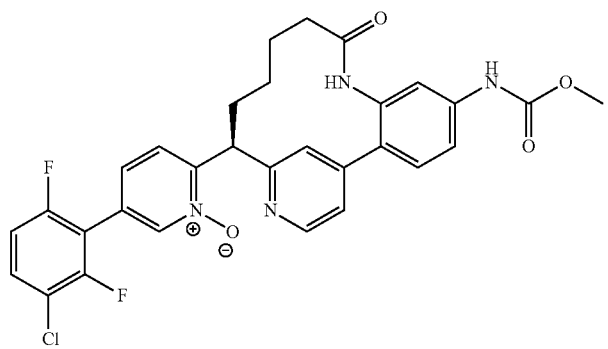 [SMILES: COC(=O)Nc1ccc2c(c1)NC(=O)CCCC[C@H](c1ccc(-c3c(F)ccc(Cl)c3F)c[n+]1[O-])c1cc-2ccn1] | | |
| 74 | 5-(3-chloro-2,6-difluorophenyl)-2-(1³-fluoro-2⁴-((methoxycarbonyl)amino)-4-oxo-3-aza-1(2,6)-pyridina-2(1,2)-benzenacyclononaphane-9-yl)pyridine 1-oxide | | 597.1 |
| | 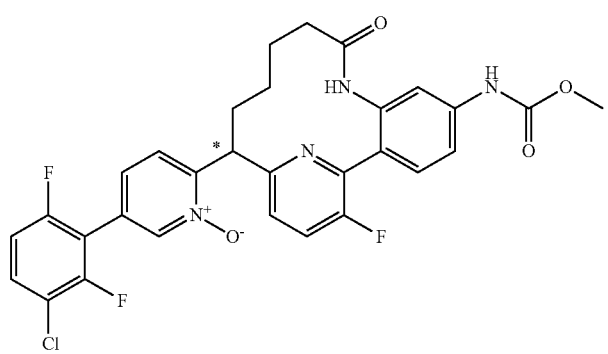 [SMILES: COC(=O)Nc1ccc2c(c1)NC(=O)CCCCC(c1ccc(-c3c(F)ccc(Cl)c3F)c[n+]1[O-])c1ccc(F)c-2n1] | | |

-continued

| Ex | Structure and Name | Chiral Separation SFC Condition | MS (M + H) |
|---|---|---|---|
| 75 | (S)-5-(3-chloro-2,6-difluorophenyl)-2-(2⁴-((methoxycarbonyl)amino)-4-oxo-3-aza-1(4,6)-pyrimidina-2(1,2)-benzenacyclononaphane-9-yl)pyridine 1-oxide | AD, 250 mm × 30 mm, 55% IPA/CO$_2$, 80 mL/min Faster eluting | 580.2 |

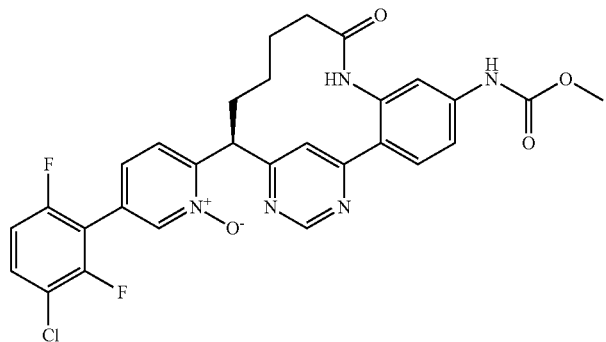 [SMILES: COC(=O)Nc1ccc2c(c1)NC(=O)CCCC[C@H](c1ccc(-c3c(F)ccc(Cl)c3F)c[n+]1[O-])c1cc-2ncn1]

| 76-a | 5-(3-chloro-2,6-difluorophenyl)-2-((5R,9S)-1⁵-fluoro-2⁴-((methoxycarbonyl)amino)-5-methyl-4-oxo-3-aza-1(2,4)-pyridina-2(1,2)-benzenacyclononaphane-9-yl)pyridine 1-oxide | AD, 250 mm × 30 mm, 40% EtOH/CO$_2$, 80 mL/min First eluting | 611.1 |

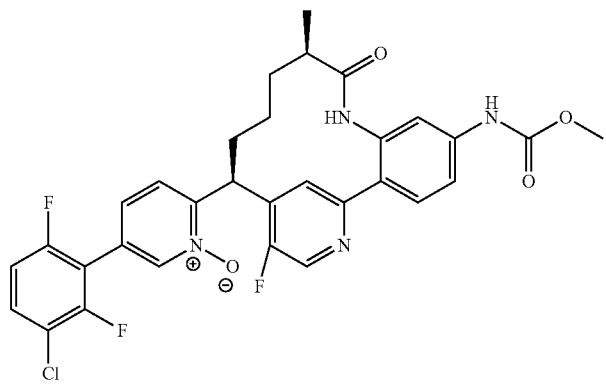 [SMILES: COC(=O)Nc1ccc2c(c1)NC(=O)[C@H](C)CCC[C@H](c1ccc(-c3c(F)ccc(Cl)c3F)c[n+]1[O-])c1cc-2ncc1F]

| 76-b | 5-(3-chloro-2,6-difluorophenyl)-2-((5S,9S)-1⁵-fluoro-2⁴-((methoxycarbonyl)amino)-5-methyl-4-oxo-3-aza-1(2,4)-pyridina-2(1,2)-benzenacyclononaphane-9-yl)pyridine 1-oxide | AD, 250 mm × 30 mm, 40% EtOH/CO$_2$, 80 mL/min Second eluting | 611.1 |

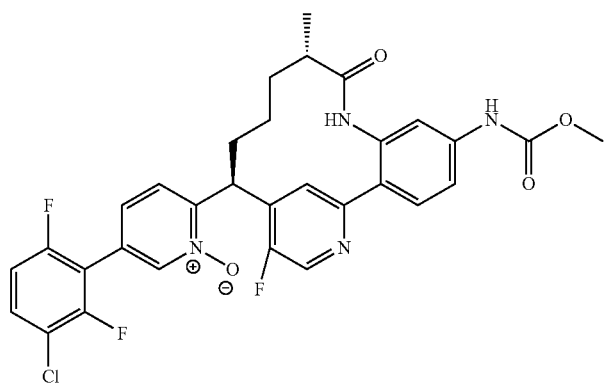 [SMILES: COC(=O)Nc1ccc2c(c1)NC(=O)[C@@H](C)CCC[C@H](c1ccc(-c3c(F)ccc(Cl)c3F)c[n+]1[O-])c1cc-2ncc1F]

| Ex | Structure and Name | Chiral Separation SFC Condition | MS (M + H) |
|---|---|---|---|
| 76-c | 5-(3-chloro-2,6-difluorophenyl)-2-((5S,9R)-1$^5$-fluoro-2$^4$-((methoxycarbonyl)amino)-5-methyl-4-oxo-3-aza-1(2,4)-pyridina-2(1,2)-benzenacyclononaphane-9-yl)pyridine 1-oxide | AD, 250 mm × 30 mm, 40% EtOH/CO$_2$, 80 mL/min Third eluting | 611.1 |
| 76-d | 5-(3-chloro-2,6-difluorophenyl)-2-((5R,9R)-1$^5$-fluoro-2$^4$-((methoxycarbonyl)amino)-5-methyl-4-oxo-3-aza-1(2,4)-pyridina-2(1,2)-benzenacyclononaphane-9-yl)pyridine 1-oxide | AD, 250 mm × 30 mm, 40% EtOH/CO$_2$, 80 mL/min Fourth eluting | 611.1 |
| 77-a | 5-(5-chloro-2-(trifluoromethoxy)phenyl)-2-((5R,9S)-2$^4$-((methoxycarbonyl)amino)-5-methyl-4-oxo-3-aza-1(1,3),2(1,2)-dibenzenacyclononaphane-9-yl)pyridine 1-oxide | IC, 200 × 21 mm, 45% MeOH/CO$_2$, 55 mL/min First eluting | 640.4 |

| Ex | Structure and Name | Chiral Separation SFC Condition | MS (M + H) |
|---|---|---|---|
| 77-b | 5-(5-chloro-2-(trifluoromethoxy)phenyl)-2-((5S,9S)-2⁴-((methoxycarbonyl)amino)-5-methyl-4-oxo-3-aza-1(1,3),2(1,2)-dibenzenacyclononaphane-9-yl)pyridine 1-oxide | IC, 200 × 21 mm, 45% MeOH/CO₂, 55 mL/min Second eluting | 640.4 |

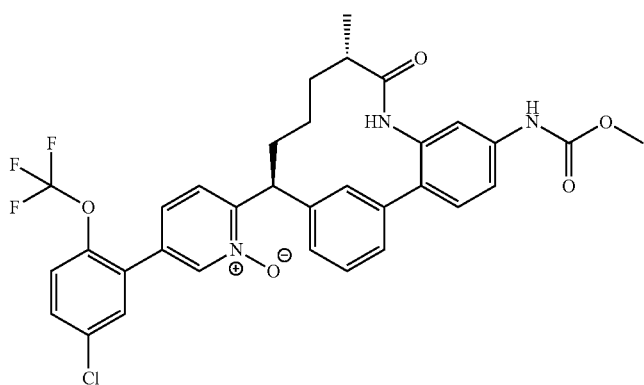 [SMILES: COC(=O)Nc1ccc2c(c1)NC(=O)[C@@H](C)CCC[C@H](c1ccc(-c3cc(Cl)ccc3OC(F)(F)F)c[n+]1[O-])c1cccc-2c1]

Example 78

2-((3S,8S)-8-carboxy-1⁵-fluoro-1(1,2),2(1,3)-dinenzenacyclononaphane-3-yl)-5-(5-chloro-2-(1H-tetrazol-1-yl)phenyl)pyridine 1-oxide

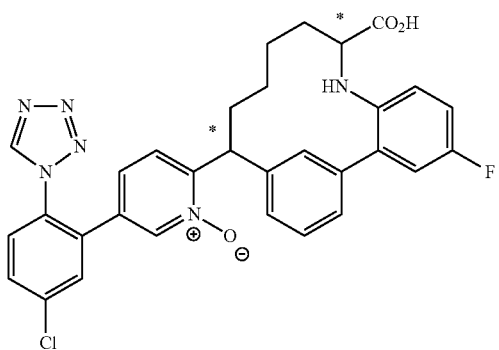 [SMILES: O=C(O)C1CCCCC(c2ccc(-c3cc(Cl)ccc3-n3cnnn3)c[n+]2[O-])c2cccc(c2)-c2cc(F)ccc2N1]

78A: Ethyl 2-((5-fluoro-3'-(1-(5-hydroxypyridin-2-yl)but-3-en-1-yl)-[1,1'-biphenyl]-2-yl)amino)pent-4-enoate To a solution of 1A (5.92 g, 17.70 mmol) and fumaric acid (2.3 g, 19.83 mmol) in acetonitrile (89 mL), ethyl 2-OXOacetate (5.42 g, 26.6 mmol) and allyltributylstannane (9.88 mL, 31.9 mmol) were added. The mixture was stirred at rt for 2 h. It was diluted with ethyl acetate (200 mL) and washed with NaOH (0.1 M, 2×50 mL), then brine. The organic layer was dried over sodium sulfate, filtered and concentrated under reduced pressure. The residue was purified by flash column chromatography on silica gel (eluting with 0-70% ethyl acetate in hexane) to give the title compound. MS (ES⁺) m/z: 461 (M+H).

78B: Ethyl 2-((3'-(1-(5-((tert-butyldiphenylsilyl)oxy)PYRIDIN-2-yl)but-3-en-1-yl)-5-fluoro-[1,1'-biphenyl]-2-yl)AMINO)pent-4-enoate To a solution of 78A (6.17 g, 13.40 mmol) and TEA (3.73 mL, 26.8 mmol) in DCM (67.0 mL), TBDPS-Cl (4.13 mL, 16.08 mmol) was added. The mixture was stirred at rt overnight. It was concentrated and purified by flash column chromatography on silica gel (eluting with 0-30% ethyl acetate in hexane) to give the title compound. MS (ES⁺) m/z: 700 (M+H).

78C: Ethyl (E)-2⁵-fluoro-9-(5-hydroxypyridin-2-yl)-3-aza-1(1,3),2(1,2)-dibenzenacyclononaphan-6-ene-4-carboxylate

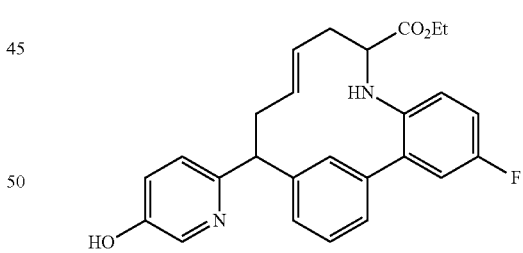

A mixture of 78B (9.36 g, 13.39 mmol), Zhan catalyst-1B (2.95 g, 4.02 mmol) and p-toluenesulfonic acid monohydrate (2.1 g, 10.71 mmol) in toluene (700 mL) was degassed by bubbling nitrogen through for 15 min. It was at 50° C. for 16 h. Most solvent was removed under reduced pressure. The residue was dissolved in DCM and washed with saturated aqueous sodium bicarbonate (30 mL) and brine. The aqueous layer was extracted with DCM (2×200 mL). The combined organic layers were dried over sodium sulfate, filtered and concentrated under reduced pressure. The residue was purified by flash column chromatography on silica gel (eluting with 0-6% MeOH in DCM) to give the title compound. MS (ES⁺) m/z: 433 (M+H).

78D: Ethyl 2⁵-fluoro-9-(5-hydroxypyridin-2-yl)-3-aza-1(1,3),2(1,2)-dinenzenacyclononaphane-4-carboxylate

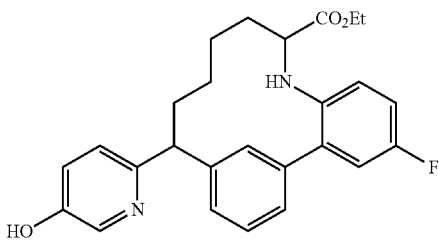 [SMILES: CCOC(=O)C1CCCCC(c2ccc(O)cn2)c2cccc(c2)-c2cc(F)ccc2N1]

A mixture of 78C (1.25 g, 2.89 mmol) and Pd-C (10% wt, 0.615 g, 0.578 mmol) in MeOH (15 mL) was shaken at rt under hydrogen (45 psi) for 16 h. The catalyst was removed by filtration through a pad of Celite. The filtrate was concentrated to give the title compound. MS (ES$^+$) m/z: 435 (M+H).

78E: Ethyl 2⁵-fluoro-9-(5-(((trifluoromethyl)sulfonyl)oxy)pyridin-2-yl)-3-aza-1(1,3),2(1,2)-dibenzenacyclononaphane-4-carboxylate

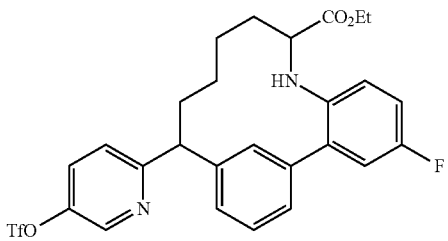 [SMILES: CCOC(=O)C1CCCCC(c2ccc(OS(=O)(=O)C(F)(F)F)cn2)c2cccc(c2)-c2cc(F)ccc2N1]

To a solution of 78D (1.16 g, 2.67 mmol) in DCM (12 mL) TEA (1.2 mL, 8.01 mmol) and Tf$_2$O (3.2 mL, 3.20 mmol) were added at 0° C. The mixture was stirred for 0.5 h. It was purified by flash column chromatography on silica gel (eluting with 0-40% ethyl acetate in hexane) to give the title compound. MS (ES$^+$) m/z: 567 (M+H).

78F: Ethyl 9-(5-(2-amino-5-chlorophenyl)pyridin-2-yl)-2⁵-fluoro-3-aza-1(1,3),2(1,2)-dibenzenacyclononaphane-4-carboxylate

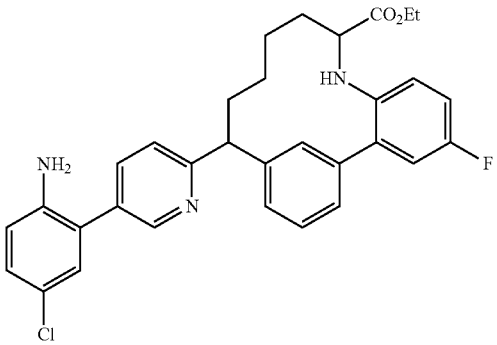 [SMILES: CCOC(=O)C1CCCCC(c2ccc(-c3cc(Cl)ccc3N)cn2)c2cccc(c2)-c2cc(F)ccc2N1]

78E (1.92 g, 3.39 mmol), Intermediate 33 (1.117 g, 4.41 mmol), Pd-Xphos-precatalyst (0.280 g, 0.339 mmol) and degassed dioxane (13.6 mL) were added to a flask with a magnetic stirring bar. A degassed aqueous solution of potassium phosphate (3 M, 3.4 mL, 10.2 mmol) was added to the mixture. The flask was stirred at 80° C. under nitrogen for 3 h. It was purified by flash column chromatography on silica gel (eluting with 0-3% MeOH in DCM) to give the title compound. MS (ES$^+$) m/z: 544 (M+H).

78G: Ethyl 9-(5-(5-chloro-2-(2,2,2-trifluoroacetamido)phenyl)pyridin-2-yl)-2⁵-fluoro-3-(2,2,2-trifluoroacetyl)-3-aza-1(1,3),2(1,2)-dibenzenacyclononaphane-4-carboxylate

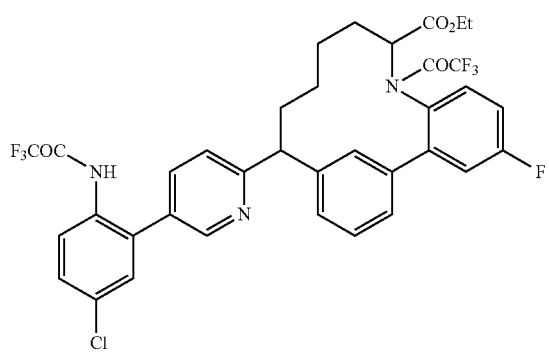

To a solution of 78F (1.79 g, 3.29 mmol) in DCM (16.45 mL) and PYRIDINE (1.8 g, 23.03 mmol), 2,2,2-trifluoroacetic anhydride (2.3 mL, 16.45 mmol) was added at 0° C. It was allowed to warm to rt and stirred overnight. The reaction mixture washed with saturated aqueous sodium bicarbonate and brine. The organic layer was dried over sodium sulfate, filtered and concentrated under reduced pressure. The residue was purified by flash column chromatography on silica gel (eluting with 0-70% ethyl acetate in hexane) to give the title compound. MS (ES$^+$) m/z: 736 (M+H).

78H: 5-(5-Chloro-2-(2,2,2-trifluoroacetamido)phenyl)-2-(4-(ethoxycarbonyl)-2⁵-fluoro-3-(2,2,2-trifluoroacetyl)-3-aza-1(1,3),2(1,2)-dibenzenacyclononaphane-9-yl)pyridine 1-oxide

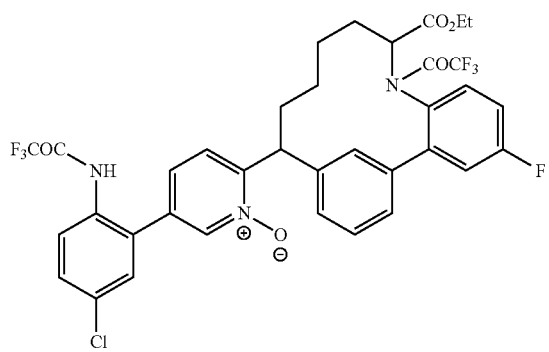

To a solution of 78G (1.69 g, 2.296 mmol) in DCM (20 mL) m-CPBA (1.03 g, 4.59 mmol) was added. The mixture was stirred at rt for 2 h. It was purified by flash column chromatography on silica gel (eluting with 0-7% methanol in DCM) to give the title compound. MS (ES$^+$) m/z: 752 (M+H).

145

78I: 5-(2-amino-5-chlorophenyl)-2-(4-carboxy-2⁵-fluoro-3-aza-1(1,3),2(1,2)-dibenzenacyclononaphane-9-yl)pyridine 1-oxide

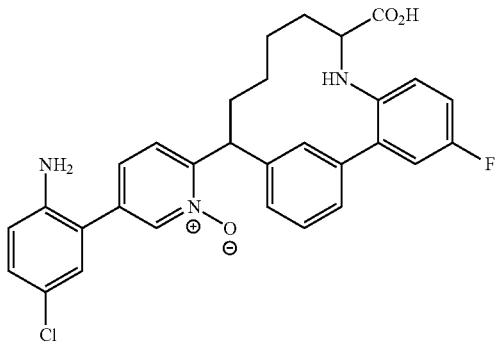 [SMILES: Nc1ccc(Cl)cc1-c1ccc(C2CCCCC(C(=O)O)Nc3ccc(F)cc3-c3cccc2c3)[n+]([O-])c1]

To a solution of 78H (1.7 g, 2.260 mmol) in MeOH (7.5 mL) and THF (7.5 mL), an aqueous solution of LiOH (1 M, 7.5 mL, 37.5 mmol) was added. The resulting mixture was heated at 80° C. in a seal tube for 3 h. It was acidified with 4 M HCl to pH=5. The mixture was extracted with CHCl₃/IPA (4:1) twice. The combined organic layers were washed with water, dried over sodium sulfate, filtered and the filtrate was concentrated under reduced pressure. The residue was triturated in 10% MeOH in DCM (5 mL) and filtered to give the title compound as a solid (9:1 ratio of two diastereomers). MS (ES⁺) m/z: 532 (M+H).

Example 78

To a solution of 78I (70 mg, 0.132 mmol) and sodium azide (51.3 mg, 0.789 mmol) in acetic acid (1.3 mL), trimethyl orthoformate (54 µl, 0.49 mmol) was added. The mixture was stirred at 80° C. for 5 h and was allowed to cool to rt overnight. It was diluted with 3 mL of MeCN and subjected to purification by reverse phase HPLC (Shimadzu, Sunfire 30×100 mm, 40-50% MeCN in water with 0.05% TFA, 50 mL/min, 10 min gradient). The fraction of desired product was collected and purified by flash column chromatography on silica gel (eluting with 0-10% methanol in DCM) to give the title compound. MS (ES⁺) m/z: 585 (M+H).

Example 79

5-(5-Chloro-2-(1H-tetrazol-1-yl)phenyl)-2-(2⁵-fluoro-4-(pyrrolidine-1-carbonyl)-3-aza-1(1,3),2(1,2)-dibenzenacyclononaphane-9-yl)pyridine 1-oxide

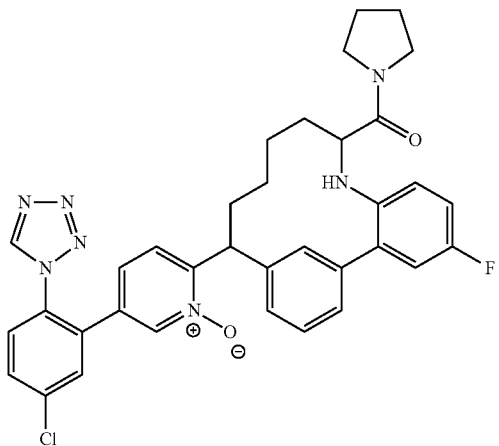 [SMILES: O=C(C1CCCCC(c2ccc(-c3cc(Cl)ccc3-n3cnnn3)c[n+]2[O-])c2cccc(c2)-c2cc(F)ccc2N1)N1CCCC1]

146

79A: 5-(2-Amino-5-chlorophenyl)-2-(2⁵-fluoro-4-(pyrrolidine-1-carbonyl)-3-aza-1(1,3),2(1,2)-dinenzenacyclononaphane-9-yl)pyridine 1-oxide

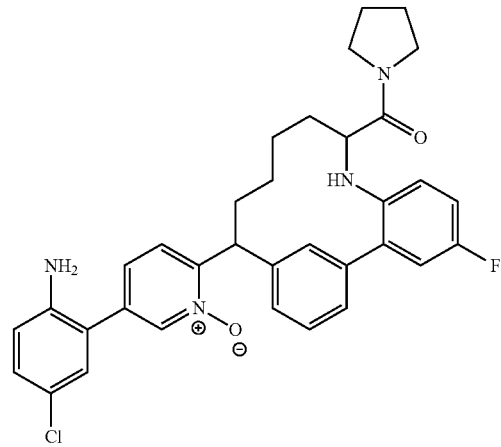 [SMILES: Nc1ccc(Cl)cc1-c1ccc(C2CCCCC(C(=O)N3CCCC3)Nc3ccc(F)cc3-c3cccc2c3)[n+]([O-])c1]

To a solution of 78I (250 mg, 0.470 mmol) and pyrrolidine (0.12 mL, 1.451 mmol) and DIEA (0.16 mL, 0.916 mmol) in DMF (4 mL), HATU (214 mg, 0.564 mmol) was added. It was stirred at rt for 4 h. Most DMF was removed under reduced pressure. The residue was purified by flash column chromatography on silica gel (eluting with 0-5% MeOH in DCM) to give the title compound. MS (ES⁺) m/z: 585 (M+H).

Example 79/79-a/79-b/79-c/79-d

To a mixture of 79A (208 mg, 0.355 mmol), sodium azide (116 mg, 1.777 mmol) in acetic acid (3.5 mL) TFA (83 µL, 1.077 mmol) and trimethyl orthoformate (0.23 mL, 2.102 mmol) were added. It was stirred at rt overnight. LC-MS showed a clean reaction. TEA (1 mL) was added and loaded on a silica gel sampler, dried under vacuum and purified by flash column chromatography on silica gel (eluting with 0-5% methanol in DCM) to give the desired product. MS (ES⁺) m/z: 638 (M+H).

A sample of the racemic product was subjected to chiral separation by SFC (OJ, 30×250 mm, 35% MeOH (0.2 NH₄OH)/CO₂, 70 mL/min, 100 bar, 35° C.) to give Example 79-a (Peak 1), Example 79-b (Peak 2), Example 79-c (Peak 3) and Example 79-d (Peak 4).

Example 80

9-(5-(5-chloro-2-(1h-tetrazol-1-yl)phenyl)-1-oxidopyridin-2-yl)-2⁵-fluoro-4-oxo-3-aza-1(2,4)-pyridin-1-iuma-2(1,2)-benzenacyclononaphane 1¹-oxide

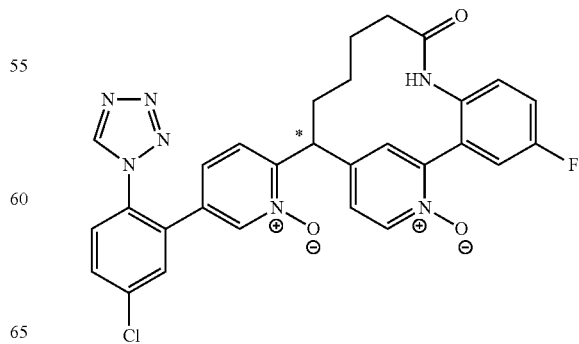

Example 80 was isolated from Example 70 by reverse phase HPLC. The fractions containing the title compound were concentrated and the residue was re-purified by flash column chromatography on silica gel (eluting with 0-10% 7 N ammonia in methanol/DCM) to give the title compound. MS (ES+) m/z: 572 (M+H); $^1$H NMR (500 MHz, DMSO-$d_6$): δ 9.67 (s, 1H), 9.66 (s, 1H), 8.24 (d, 1H), 8.21 (d, 1H), 7.87 (d, 1H), 7.83 (m, 2H), 7.68 (dd, 1H), 7.52 (d, 1H), 7.28-7.35 (m, 3H), 6.96 (m, 2H), 4.42 (m, 1H), 3.15 (d, 1H), 2.20 (m, 1H), 1.79-2.00 (m, 3H), 1.65 (m, 1H), 1.43 (m, 1H), 1.25 (m, 1H).

Example 81 (racemate), 81-a and 81-b 9-(5-(5-chloro-2-(1h-tetrazol-1-yl)phenyl)-1-oxi-dopyridin-2-yl)-1$^5$-fluoro-2$^4$-((methoxycarbonyl)amino)-4-oxo-3-aza-1(2,4)-pyridin-1-iuma -2(1,2)-benzenacyclononaphane 1$^1$-oxide

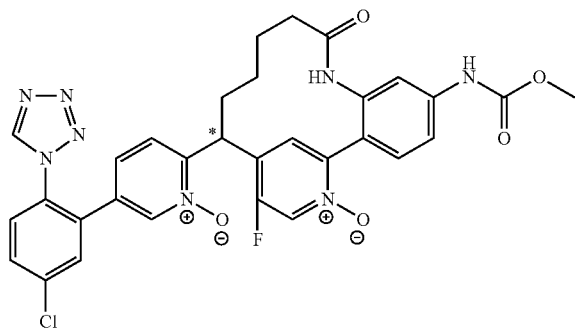 [SMILES: COC(=O)Nc1ccc2c(c1)NC(=O)CCCCC(c1ccc(-c3cc(Cl)ccc3-n3cnnn3)c[n+]1[O-])c1cc-2[n+]([O-])cc1F]

Example 81 was isolated as a from Example 71 by reverse phase HPLC (Sunfire 30×100 mm, 20-50% MeCN in water with 0.05% TFA, 50 mL/min, 10 min). MS (ES+) m/z: 645 (M+H).

A sample of racemic Example 81 was subjected to chiral separation by SFC (AD-H, 2×25 cm, 35% ethanol/CO$_2$, 100 bar, 60 mL/min, 35° C.) to afford Example 81-a (slower eluting) and Example 81-b (faster eluting). MS (ES+) m/z: 645 (M+H); $^1$H NMR (500 MHz, DMSO-$d_6$): δ 9.94 (s, 1H), 9.74 (s, 1H), 9.66 (s, 1H), 8.54 (d, 1H), 8.24 (s, 1H), 7.90 (s, 1H), 7.83 (t, 2H), 7.75 (d, 1H), 7.35-7.43 (m, 4H), 6.91 (d, 1H), 4.50 (d, 1H), 3.69 (s, 3H), 2.27 (s, 1H), 1.96 (m, 3H), 1.67 (m, 1H), 1.51 (m, 1H), 1.31 (m, 2H).

Example 82

9-(5-(3-chloro-2,6-difluorophenyl)-1-oxidopyridin-2-yl)-1$^5$-fluoro-2$^4$-((methoxycarbonyl)amino)-4-oxo-3-aza-1(2,4)-pyridin-1-iuma-2(1,2)-benzenacy-clononaphane 1$^1$-oxide

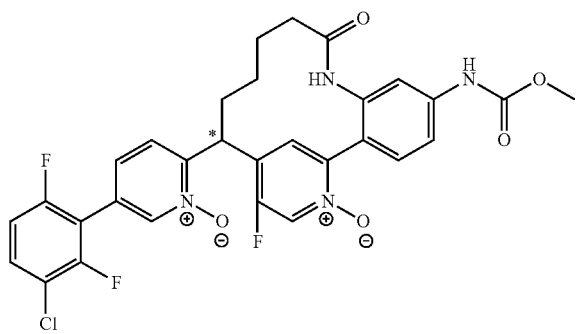 [SMILES: COC(=O)Nc1ccc2c(c1)NC(=O)CCCCC(c1ccc(-c3c(F)ccc(Cl)c3F)c[n+]1[O-])c1cc-2[n+]([O-])cc1F]

Example 82 was isolated from Example 72 by reverse phase HPLC (Sunfire 30×100 mm, 20-50% MeCN in water with 0.05% TFA, 50 mL/min, 10 min). MS (ES+) m/z: 613 (M+H).

Example 83

9-(5-(3-chloro-2, 6-difluorophenyl)-1-oxidopyridin-2-yl)-2$^4$-((methoxycarbonyl)amino)-4-oxo-3-aza-1(4,2)-pyridin-1-iuma-2(1,2)-benzenacyclononaphane 1$^1$-oxide

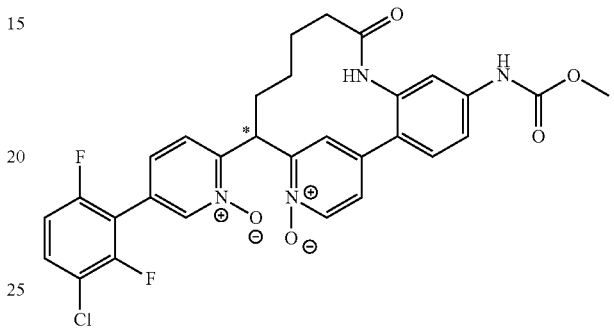

Example 83 was isolated from Example 73 by reverse phase HPLC (YMC-Actus Pro C18, 150×30 mm, 20-50% MeCN in water with 0.5% TFA, 40 mL/min). MS (ESI) m/z 595.2 (M+H); $^1$H NMR (400 MHz, DMSO-$d_6$): δ 9.94 (s, 1H), 9.80 (s, 1H), 8.48 (s, 1H), 8.19 (d, J=6.5 Hz, 1H), 7.82-7.70 (m, 2H), 7.60-7.48 (m, 2H), 7.47-7.22 (m, 5H), 4.84 (d, J=9.6 Hz, 1H), 3.67 (s, 3H), 2.35-2.06 (m, 4H), 1.93-1.78 (m, 1H), 1.59-1.45 (m, 1H), 1.28-1.19 (m, 2H).

Example 84

5-(5-chloro-2-(1H-tetrazol-1-yl)phenyl)-2-(2$^4$-cyano-5-Methyl-4-OXO-3-aza-1(1,3), 2(1,2)-dinen-zenacyclononaphane-9-yl)pyridine 1-oxide

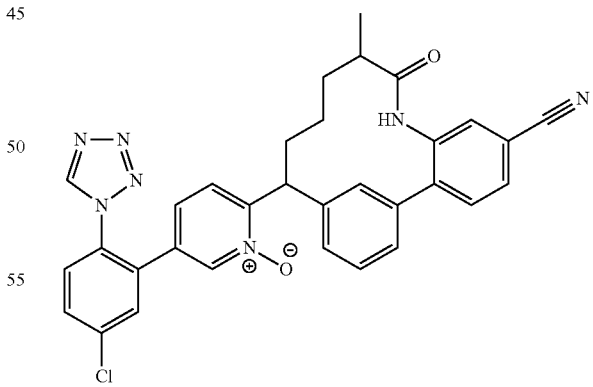

84A: 3'-(5-Chloropicolinoyl)-2-nitro-[1,1'-biphenyl]-4-carbonitrile

A mixture of (5-chloropyridin-2-yl)(3-(4,4,5,5-tetramethyl-1,3,2-dioxaborolan-2-yl)phenyl)methanone (Intermediate 3) (5.00 g, 14.55 mmol), 4-bromo-3-nitrobenzonitrile (3.63 g, 16.01 mmol), Pd(dtbpf)Cl$_2$ (0.95 g, 1.46 mmol), aqueous K$_3$PO$_4$ solution (29.10 mL, 29.10 mmol, 1 M) and toluene (100 mL) under nitrogen was stirred at 80° C. for 12 h. The mixture was cooled to rt and diluted with water (80 mL). It was extracted with EtOAc (150 mL×3). The combined organic layers were dried over sodium sulfate, filtered and concentrated under reduced pressure. The residue was purified by flash column chromatography (petroleum ether: EtOAc=10:1 to 2:1) to give the title compound. MS (ESI) m/z 364.0 (M+H); $^1$H NMR (400 MHz, CDCl$_3$): δ 8.69 (d, J=1.8 Hz, 1H), 8.18-8.25 (m, 2H), 8.08-8.12 (m, 2H), 7.88-7.97 (m, 2H), 7.67 (d, J=7.9 Hz, 1H), 7.62 (d, J=7.7 Hz, 1H), 7.54-7.59 (m, 1H).

84B: 2-Amino-3'-(5-chloropicolinoyl)-[1,1'-biphenyl]-4-carbonitrile

A mixture of 84A (1.00 g, 2.75 mmol), iron (1.54 g, 27.50 mmol) and ammonium chloride (1.47 g, 27.50 mmol) in EtOH:H$_2$O=3:1 (20 mL) was stirred at 80° C. under nitrogen for 1 h. It was cooled to rt and concentrated under reduced pressure. The residue was diluted with water (20 mL) and extracted with a mixture of DCM/MeOH (10/1, 30 mL×4). The combined organic layers were dried over sodium sulfate, filtered and concentrated under reduced pressure. The residue was purified by flash column chromatography on silica gel (petroleum ether:ethyl acetate=3:1) to give the title compound. MS (ESI) m/z 334.1 (M+H); $^1$H NMR (400 MHz, CDCl$_3$): δ 8.66 (d, J=2.0 Hz, 1H), 8.06-8.18 (m, 3H), 7.92 (dd, J=8.2, 2.4 Hz, 1H), 7.58-7.72 (m, 2H), 7.22 (d, J=7.8 Hz, 1H), 7.10 (dd, J=7.8, 0.8 Hz, 1H), 7.02 (s, 1H), 4.04 (brs, 2H).

Example 84

Example 84 was prepared from 84B by the procedure described in the synthesis of Example 51 and Example 52. The residue was purified by reversed phase prep-HPLC to give the title compound. MS (ESI) m/z 576.2 (M+H); $^1$H NMR (400 MHz, CD$_3$OD): δ 9.35-9.41 (m, 1H), 8.22 (s, 1H), 7.58-7.83 (m, 7H), 7.27-7.47 (m, 3H), 7.12-7.25 (m, 1H), 7.05 (d, J=7.5 Hz, 1H), 4.62-4.75 (m, 1H), 2.55 (brs., 1H), 1.77-2.10 (m, 3H), 1.27-1.53 (m, 3H), 1.05-1.22 (m, 2H).

Example 85-a, 85-b, 85-c, 85-d 5-(3-Chloro-2,6-difluorophenyl)-2-(2$^6$-fluoro-2$^4$-((methoxycarbonyl)amino)-5-methyl-4-oxo-3-aza-1 (1,3),2(1,2)-dibenzenacyclononaphane-9-yl)pyridine 1-oxide

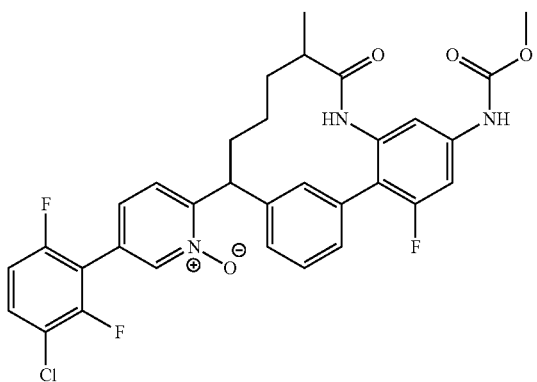 [SMILES: COC(=O)Nc1cc(F)c2c(c1)NC(=O)C(C)CCCC(c1ccc(-c3c(F)ccc(Cl)c3F)c[n+]1[O-])c1cccc-2c1]

85A: Methyl (E)-(9-(5-(3-chloro-2,6-difluorophenyl)pyridin-2-yl)-2$^6$-fluoro-5-methyl-4-oxo-3-aza-1 (1,3),2(1,2)-dibenzenacyclononaphan-8-en-2$^4$-yl) carbamate

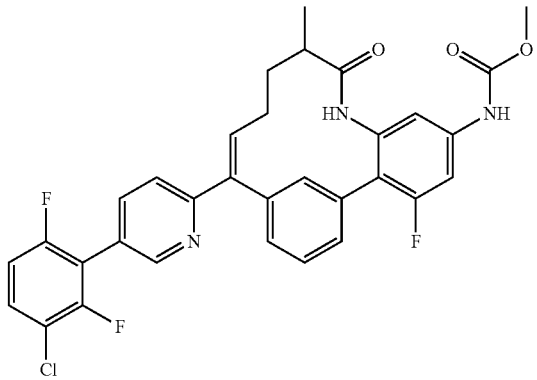 [SMILES: COC(=O)Nc1cc(F)c2c(c1)NC(=O)C(C)CC/C=C(/c1ccc(-c3c(F)ccc(Cl)c3F)cn1)c1cccc-2c1]

85A was prepared from Intermediate 3 and Intermediate 53 by the procedure similar to that described in the synthesis of Example 50C. MS (ESI) m/z 592.2 (M+H).

A sample of racemic 85A was subjected to chiral separation by SFC (OD, 30×250 mm, 50% EtOH/CO$_2$, 100 bar, 80 mL/min, 35° C.) to afford the 85A-a (faster eluting), and 85A-b (slower eluting). MS (ES$^+$) m/z: 592.2 (M+H).

85B-a/85B-b: Methyl (9-(5-(3-chloro-2,6-difluorophenyl)pyridin-2-yl)-2$^6$-fluoro-5-methyl-4-oxo-3-aza-1(1,3),2(1,2)-dibenzenacyclononaphane-2$^4$-yl) carbamate A mixture of 85A-a (710 mg, 1.20 mmol) and Raney nickel (352 mg, 6.00 mmol) in THF (30 mL) was added and the mixture was stirred at 40° C. under H$_2$ (1 atm) for 4 h. The reaction mixture was filtered and washed with THF (10 mL×3) (Caution! Never expose catalyst in air). The filtrate was concentrated to give a mixture of two diastereomers. MS (ESI) m/z 594.2 (M+H).

The mixture of two diastereomers were separated by SFC (Column C2 250 mm×30 mm, 35% MeOH/CO$_2$, Flow rate: 80 mL/min) to give 85B-a (faster eluting) and 85B-b (slower eluting). MS (ESI) m/z 594.2 (M+H).

85B-c/85B-d: Methyl (9-(5-(3-chloro-2,6-difluorophenyl)pyridin-2-yl)-2$^6$-fluoro-5-methyl-4-oxo-3-aza-1(1,3),2(1,2)-dinenzenacyclononaphane-2$^4$-yl) carbamate A mixture of 85A-b (340 mg, 0.554 mmol) and Raney nickel (169 mg, 2.87 mmol) in THF (30 mL) was added and the mixture was stirred at 30° C. under H$_2$ (1 atm) for 4 h. The reaction mixture was filtered and washed with EtOAc (10 mL×3). The filtrate was concentrated and the residue was purified by HPLC (YMC-Actus Pro C18, 150 mm×30 mm, 50-70% MeCN in water (0.1% TFA), gradient, 25 mL/min) to give a mixture of two diastereomers. MS (ESI) m/z 594.2 (M+H).

The mixture of two diastereomers were separated by SFC (AD, 30×250 mm, 40% MeOH (0.05% DEA)/CO$_2$, 100 bar, 80 mL/min, 40° C.) to give 85B-c (faster eluting) and 85B-d (slower eluting). MS (ESI) m/z 594.2 (M+H).

Example 85-a/85-b/85-c/85-d

Example 85-a/85-b/85-c/85-d was prepared from 85B-a/85B-b/85B-c/85B-d respectively by the procedure described in the synthesis of Example 50.

Example 85-a: MS (ESI) m/z 610.1 (M+H); $^1$H NMR (400 MHz, DMSO_$d_6$): δ 10.01 (s, 1H), 9.58 (s, 1H), 8.50 (s, 1H), 7.71-7.82 (m, 1H), 7.40-7.58 (m, 4H), 7.31-7.39 (m, 2H), 7.27 (d, J=6.4 Hz, 1H), 7.03-7.18 (m, 2H), 4.58-4.70 (m, 1H), 3.70 (s, 3H), 2.40-2.48 (m, 1H), 2.01-1.91 (m, 2H), 1.81-1.66 (m, 1H), 1.26-1.43 (m, 1H), 0.97-1.25 (m, 2H), 0.92 (d, J=6.6 Hz, 3H).

Example 85-b: MS (ESI) m/z 610.1 (M+H); $^1$H NMR (400 MHz, DMSO_$d_6$): δ 10.01 (s, 1H), 9.44 (s, 1H), 8.49 (s, 1H), 7.91 (d, J=8.2 Hz, 1H), 7.72-7.84 (m, 1H), 7.59 (d, J=7.8 Hz, 1H), 7.46 (d, J=12.1 Hz, 1H), 7.27-7.40 (m, 3H), 7.08-7.24 (m, 2H), 6.86 (d, J=7.4 Hz, 1H), 4.52 (d, J=10.6 Hz, 1H), 3.70 (s, 3H), 2.31-2.19 (m, 1H), 2.01-1.89 (m, 1H), 1.61-1.86 (m, 2H), 1.47-1.29 (m, 1H), 1.13-1.26 (m, 1H), 1.07 (d, J=7.0 Hz, 3H), 1.02-0.91 (m, 1H).

Example 85-c: MS (ESI) m/z 610.1 (M+H); $^1$H NMR (400 MHz, DMSO_$d_6$): δ 10.01 (s, 1H), 9.44 (s, 1H), 8.49 (s, 1H), 7.91 (d, J=8.2 Hz, 1H), 7.72-7.84 (m, 1H), 7.59 (d, J=7.8 Hz, 1H), 7.46 (d, J=12.1 Hz, 1H), 7.27-7.40 (m, 3H), 7.08-7.24 (m, 2H), 6.86 (d, J=7.4 Hz, 1H), 4.52 (d, J=10.6 Hz, 1H), 3.70 (s, 3H), 2.31-2.19 (m, 1H), 2.01-1.89 (m, 1H), 1.61-1.86 (m, 2H), 1.47-1.29 (m, 1H), 1.13-1.26 (m, 1H), 1.07 (d, J=7.0 Hz, 3H), 1.02-0.91 (m, 1H).

Example 85-d: MS (ESI) m/z 610.1 (M+H); $^1$H NMR (400 MHz, DMSO_$d_6$): δ 10.01 (s, 1H), 9.58 (s, 1H), 8.50 (s, 1H), 7.71-7.82 (m, 1H), 7.40-7.58 (m, 4H), 7.31-7.39 (m, 2H), 7.27 (d, J=6.4 Hz, 1H), 7.03-7.18 (m, 2H), 4.58-4.70 (m, 1H), 3.70 (s, 3H), 2.40-2.48 (m, 1H), 2.01-1.91 (m, 2H), 1.81-1.66 (m, 1H), 1.26-1.43 (m, 1H), 0.97-1.25 (m, 2H), 0.92 (d, J=6.6 Hz, 3H).

Example 86 (racemate), 86-a, 86-b, 86-c, 86-d 5-(3-Chloro-2,6-difluorophenyl)-2-($1^6$-fluoro-$2^4$-((methoxycarbonyl)amino)-5-methyl-4-oxo-3-aza-1(1,3),2(1,2)-dibenzenacyclononaphane-9-yl)pyridine 1-oxide

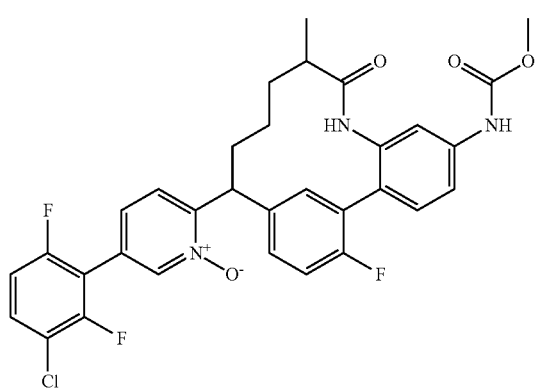 [SMILES: COC(=O)Nc1ccc2c(c1)NC(=O)C(C)CCCC(c1ccc(-c3c(F)ccc(Cl)c3F)c[n+]1[O-])c1ccc(F)c-2c1]

86A: Methyl (E)-(9-(5-(3-chloro-2,6-difluorophenyl)pyridin-2-yl)-$1^6$-fluoro-5-methyl-4-oxo-3-aza-1(1,3),2(1,2)-dibenzenacyclononaphan-8-en-$2^4$-yl)carbamate

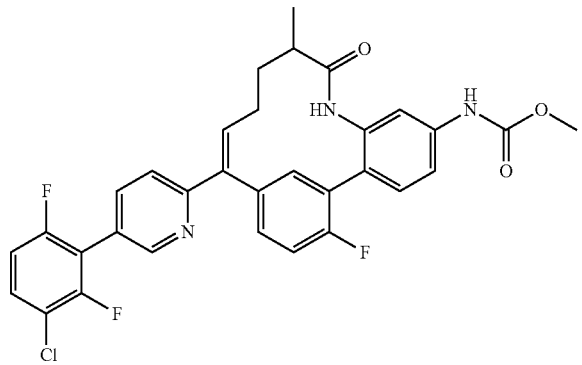 [SMILES: COC(=O)Nc1ccc2c(c1)NC(=O)C(C)CC/C=C(/c1ccc(-c3c(F)ccc(Cl)c3F)cn1)c1ccc(F)c-2c1]

86A was prepared from Intermediate 6 and Intermediate 19 by the procedure similar to that described in the synthesis of Example 50C. MS (ESI) m/z 592.1 (M+H).

A sample of racemic 86A was subjected to chiral separation by SFC (Column AD, 250 mm×30 mm, 55% isopropanol/$CO_2$, 70 mL/min) to give 86A-a (faster eluting) MS (ESI) m/z 665.3 (M+71) and 86A-b (slower eluting).

86B: Methyl (9-(5-(3-chloro-2,6-difluorophenyl)pyridin-2-yl)-$1^6$-fluoro-5-methyl-4-oxo-3-aza -1(1,3),2(1,2)-dinenzenacyclononaphane-$2^4$-yl)carbamate

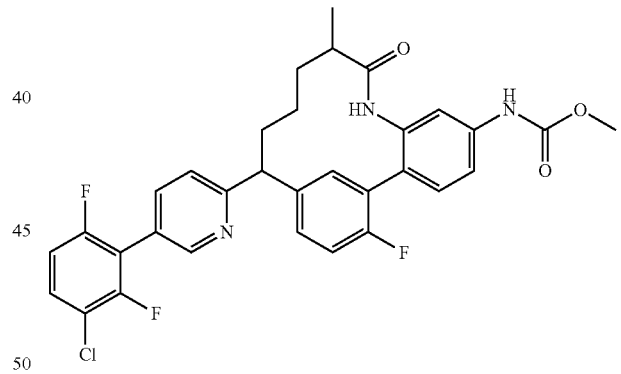

A mixture of 86A-a (210 mg, 0.355 mmol) and nickel (100 mg, 1.704 mmol) in THF (100 mL) was stirred at 30° C. under $H_2$ balloon for 2 h. The reaction mixture was filtered through a pad of Celite and the filtrate was concentrated to give the title compound as a mixture of two diastereomers. MS (ESI) m/z 616.1 (M+Na).

Example 86-a/86-b

To a solution of 86B (100 mg, 0.168 mmol) in DCM (4 mL) was added m-CPBA (83 mg, 0.337 mmol, 70% purity) at 25° C. in a round bottom flask. The mixture was stirred at 25° C. for 4 h. It was concentrated and purified by reverse-phase HPLC (YMC-Actus Pro C18, 150×30 mm, 40-70% MeCN in water (0.1% TFA), gradient) to give a mixture of two diastereomers. MS (ESI) m/z 610.2 (M+H).

A sample of the mixture of diastereomers was separated by SFC (Column AD, 250 mm×30 mm, 50% IPA/CO$_2$, 70 mL/min) to give Example 86-a (faster eluting) as a solid and Example 86-b (slower eluting).

Example 86-a: MS (ESI) m/z 610.1 (M+H); $^1$H NMR (400 MHz, CD$_3$OD): δ 8.49 (s, 1H), 7.51-7.65 (m, 4H), 7.39-7.50 (m, 3H), 7.07-7.20 (m, 3H), 4.75 (d, J=9.5 Hz, 1H), 3.73 (s, 3H), 2.44 (brs, 1H), 2.12-2.25 (m, 1H), 2.02 (brs, 1H), 1.76 (brs, 1H), 1.44 (brs, 2H), 1.19-1.26 (m, 1H), 1.08 (d, J=6.8 Hz, 3H).

Example 86-b: MS (ESI) m/z 610.1 (M+H); $^1$H NMR (400 MHz, CD$_3$OD): δ 8.48 (brs, 1H), 7.94 (d, J=8.4 Hz, 1H), 7.77 (d, J=8.2 Hz, 1H), 7.62-7.66 (m, 2H), 7.44-7.52 (m, 3H), 7.17-7.23 (m, 1H), 7.07-7.13 (m, 1H), 6.89 (brs, 1H), 4.70 (d, J=8.4 Hz, 1H), 3.75 (s, 3H), 2.36 (brs, 1H), 1.98-2.03 (m, 3H), 1.78-1.82 (m, 2H), 1.52 (brs, 1H), 1.20 (d, J=7.1 Hz, 3H).

Example 86-c/58-d

Example 86-c/86-d (a mixture of two diastereomers) was prepared from 86A-b by the procedure as the synthesis of Example 86-a/86-b. It was purified by reverse-phase HPLC (YMC-Actus Pro C18, 150×30 mm, 40-70% MeCN in water (0.1% TFA), gradient). MS (ESI) m/z 610.2 (M+H).

A sample of the mixture of diastereomers was separated by SFC (Column AD, 250 mm×30 mm, 50% IPA/CO$_2$, 70 mL/min) to give Example 86-c (faster eluting) as a solid and Example 86-d (slower eluting).

Example 86-c: MS (ESI) m/z 610.1 (M+H); $^1$H NMR (400 MHz, CD$_3$OD): δ 8.48 (brs, 1H), 7.94 (d, J=8.4 Hz, 1H), 7.77 (d, J=8.2 Hz, 1H), 7.62-7.66 (m, 2H), 7.44-7.52 (m, 3H), 7.17-7.23 (m, 1H), 7.07-7.13 (m, 1H), 6.89 (brs, 1H), 4.70 (d, J=8.4 Hz, 1H), 3.75 (s, 3H), 2.36 (brs, 1H), 1.98-2.03 (m, 3H), 1.78-1.82 (m, 2H), 1.52 (brs, 1H), 1.20 (d, J=7.1 Hz, 3H).

Example 86-b: MS (ESI) m/z 610.1 (M+H); $^1$H NMR (400 MHz, CD$_3$OD): δ 8.49 (s, 1H), 7.51-7.65 (m, 4H), 7.39-7.50 (m, 3H), 7.07-7.20 (m, 3H), 4.75 (d, J=9.5 Hz, 1H), 3.73 (s, 3H), 2.44 (brs, 1H), 2.12-2.25 (m, 1H), 2.02 (brs, 1H), 1.76 (brs, 1H), 1.44 (brs, 2H), 1.19-1.26 (m, 1H), 1.08 (d, J=6.8 Hz, 3H).

Example 87 (racemate), 87-a, 87-b 5-(3-Chloro-2,6-difluorophenyl)-4-methoxy-2-(2$^4$-((methoxycarbonyl)amino)-4-oxo-3-aza-1(1,3),2(1,2) -dibenzenacyclononaphane-9-yl)pyridine 1-oxide

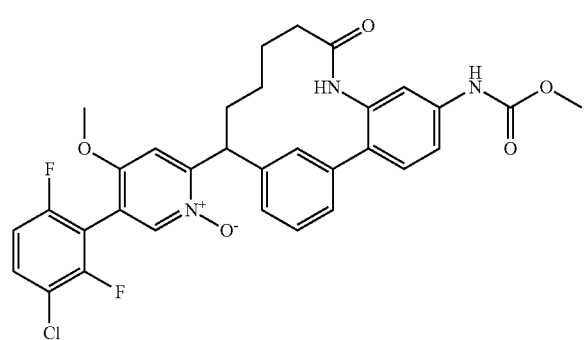 [SMILES: COC(=O)Nc1ccc2c(c1)NC(=O)CCCCC(c1cc(OC)c(-c3c(F)ccc(Cl)c3F)c[n+]1[O-])c1cccc-2c1]

87A: Methyl (2-amino-3'-(5-chloro-4-methoxypicolinoyl)-[1,1'-biphenyl]-4-yl)carbamate 87A was prepared from Intermediate 19 and Intermediate 12 by the procedure as described in the synthesis of 12A. The product was purified by flash column chromatography (SiO$_2$, DCM:EtOAc=50:1 to 1:1). MS (ESI) m/z 412.1 (M+H).

87B: Methyl (2-(5-(benzo[d]thiazol-2-ylsulfonyl) pentanamido)-3'-(5-chloro-4-methoxypicolinoyl)-[1, 1'-biphenyl]-4-yl)carbamate To a solution of 87A (100 mg, 0.24 mmol) and Intermediate 26 (104 mg, 0.24 mmol, 70% purity) in PYRIDINE (2 mL) was added POCl$_3$ (0.045 mL, 0.49 mmol) at 0° C. The reaction was stirred at 0° C. for 30 min and then quenched with water (10 mL). The mixture was extracted with DCM (10 mL×3). The combined organic layers were washed with brine (20 mL), dried over anhydrous sodium sulfate, filtered, and concentrated under reduced pressure. The residue was purified by prep-TLC (SiO$_2$, petroleum ether:EtOAc=1:1) to give the title compound. MS (ESI) m/z 693.1 (M+H).

87C: Methyl (E)-(9-(5-chloro-4-methoxypyridin-2-yl)-4-oxo-3-aza-1(1,3),2(1,2) -dibenzenacyclononaphan-8-en-2$^4$-yl)carbamate

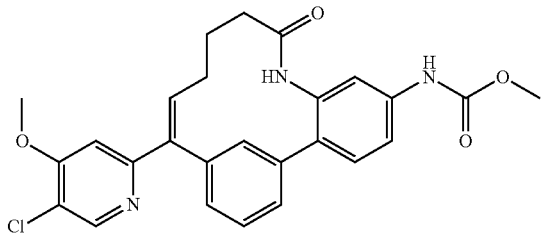 [SMILES: COC(=O)Nc1ccc2c(c1)NC(=O)CCC/C=C(/c1cc(OC)c(Cl)cn1)c1cccc-2c1]

To a solution of 87B (1.00 g, 1.44 mmol) in THF (50 mL) at −78° C. was added a solution of LiHMDS (8.66 mL, 8.66 mmol, 1M in THF). The reaction was stirred at −78° C. for 2 h and was allowed to warm to 25° C. It was quenched with saturated aqueous ammonium chloride (20 mL) and extracted with EtOAc (30 mL×3). The combined organic layers were dried over anhydrous sodium sulfate, filtered, and concentrated under reduced pressure. The residue was triturated in EtOAc (100 mL) for 0.5 h. The solids were collected by filtration to give the title compound. MS (ESI) m/z 478.0 (M+H).

Example 87/87-a/87-b

Example 87 was prepared from 87C by the procedure described in the synthesis of Example 50. The product was purified by reverse-phase HPLC (YMC-Actus Pro C18, 150×30 mm, 29-59% MeCN in water (0.1% MeCN), 40 mL/min). MS (ESI) m/z 608.2 (M+H); $^1$H NMR (400 MHz, CD$_3$OD): δ 8.52 (s, 1H), 8.29 (s, 1H), 7.67-7.68 (m, 1H), 7.57-7.63 (m, 1H), 7.44-7.46 (m, 2H), 7.36-7.41 (m, 1H), 7.26-7.33 (m, 2H), 7.11-7.14 (m, 1H), 7.06-7.08 (m, 1H), 4.78-4.82 (m, 1H), 3.94 (s, 3H), 3.73 (s, 3H), 2.35-2.47 (m, 2H), 2.08-2.15 (m, 2H), 1.55-1.65 (m, 2H), 0.86-0.88 (m, 2H).

A racemic sample of Example 87 was subjected to chiral separation by SFC (Column: OD, 250 mm×30 mm, 50%

EtOH/CO$_2$, 70 mL/min) to give Example 87-a (slower eluting) and Example 87-b (faster eluting).

Example 88 (racemate), 88-a, 88-b, 88-c, 88-d 5-(3-Chloro-2,6-difluorophenyl)-4-methoxy-2-(2$^4$-((methoxycarbonyl)amino)-5-methyl-4-oxo-3-aza-1(1,3),2(1,2)-dibenzenacyclononaphane-9-yl)pyridine 1-oxide

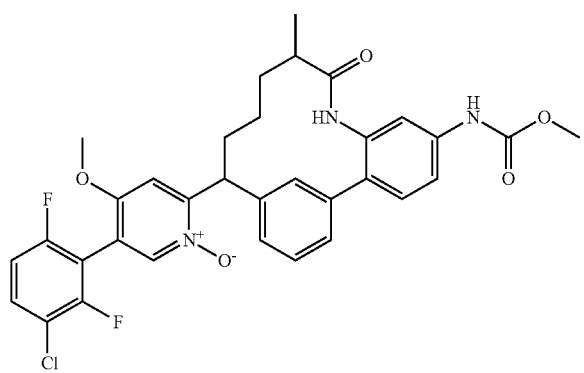 [SMILES: COC(=O)Nc1ccc2c(c1)NC(=O)C(C)CCCC(c1cc(OC)c(-c3c(F)ccc(Cl)c3F)c[n+]1[O-])c1cccc-2c1]

88A: Methyl (E)-(9-(5-(3-chloro-2,6-difluorophenyl)-4-methoxypyridin-2-yl)-5-methyl-4-oxo-3-aza-1(1,3),2(1,2)-dibenzenacyclononaphan-8-en-2$^4$-yl)carbamate

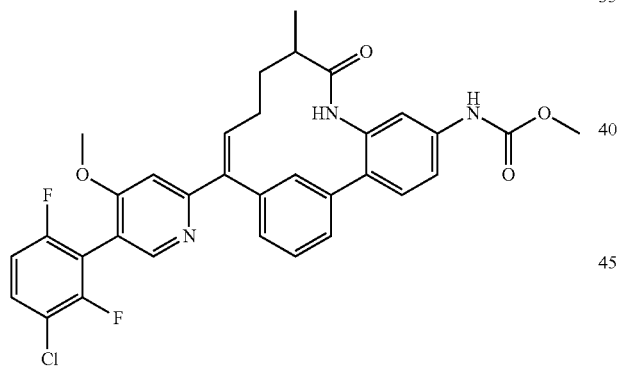

88A was prepared from 59A by the procedure described in the synthesis of 50C. MS (ESI) m/z 604.2 (M+H).

A racemic sample of 88A was subjected to chiral separation by SFC (Column AD, 250 mm×30 mm, 50% isopropanol/CO$_2$, 80 mL/min) to give 88A-a (faster eluting) as a solid and 88A-b (slower eluting).

Example 88-a/88-b

A mixture of diastereomers Example 88-a and 88-b was prepared from 88A-a by the procedure described in the synthesis of Example 50. The product was purified by reverse-phase HPLC (YMC-Actus Pro C18, 150×30 mm, 30-60% MeCN in water (0.1% TFA), 40 mL/min). MS (ESI) m/z 622.3 (M+H).

A sample of the two diastereomers was subjected for chiral separation by SFC (Column AS, 250 mm×30 mm, 50% MeOH/CO$_2$, 80 mL/min) to give Example 88-a (faster eluting) as a solid and Example 88-b (slower eluting).

Example 88-a: MS (ESI) m/z 622.1 (M+H); $^1$H NMR (400 MHz, CD$_3$OD): δ 8.33 (s, 1H), 7.72 (s, 1H), 7.59-7.64 (m, 1H), 7.38-7.47 (m, 4H), 7.33-7.35 (m, 1H), 7.07-7.19 (m, 3H), 4.78-4.83 (m, 1H), 3.85 (s, 3H), 3.75 (s, 3H), 2.54 (brs, 1H), 2.13-2.15 (m, 2H), 1.85-1.91 (m, 1H), 1.47-1.50 (m, 1H), 1.34-1.37 (m, 2H), 1.10 (d, J=6.6 Hz, 3H).

Example 88-b: MS (ESI) m/z 622.1 (M+H); $^1$H NMR (400 MHz, CD$_3$OD): δ 8.30 (s, 1H), 7.69 (s, 1H), 7.62-7.64 (m, 1H), 7.36-7.47 (m, 5H), 7.28-7.30 (m, 1H), 7.14-7.17 (m, 1H), 6.96-6.99 (m, 1H), 4.77-4.79 (m, 1H), 4.03 (s, 3H), 3.74 (s, 3H), 2.37-2.39 (m, 1H), 1.88-2.05 (m, 3H), 1.39-1.51 (m, 2H), 1.24 (d, J=6.8 Hz, 3H), 1.16-1.18 (m, 1H).

Example 88-c/88-d

A mixture of diastereomers Example 88-c and 88-d was prepared from 88A-b by the procedure described in the synthesis of Example 50. The product was purified by reverse-phase HPLC (YMC-Actus Pro C18, 150×30 mm, 30-60% MeCN in water (0.1% TFA), 40 mL/min). MS (ESI) m/z 622.3 (M+H).

A sample of the two diastereomers was subjected for chiral separation by SFC (Column AS, 250 mm×30 mm, 50% MeOH/CO$_2$, 80 mL/min) to give Example 88-c (faster eluting) as a solid and Example 88-d (slower eluting).

Example 88-c: MS (ESI) m/z 622.3 (M+H); $^1$H NMR (400 MHz, CD$_3$OD): δ 8.30 (s, 1H), 7.68 (s, 1H), 7.60-7.64 (m, 1H), 7.36-7.48 (m, 5H), 7.27-7.29 (m, 1H), 7.13-7.16 (m, 1H), 6.96-6.99 (m, 1H), 4.79-4.82 (m, 1H), 4.03 (s, 3H), 3.71 (s, 3H), 2.35-2.38 (m, 1H), 1.95-2.11 (m, 3H), 1.39-1.41 (m, 2H), 1.26 (d, J=6.8 Hz, 3H), 1.18-1.21 (m, 1H).

Example 88-d: MS (ESI) m/z 622.2 (M+H), $^1$H NMR (400 MHz, CD$_3$OD): δ 8.41 (s, 1H), 7.72 (s, 1H), 7.58-7.66 (m, 1H), 7.39-7.49 (m, 4H), 7.31-7.37 (m, 1H), 7.08-7.20 (m, 3H), 4.81-4.87 (m, 1H), 3.88 (s, 3H), 3.75 (s, 3H), 2.49-2.58 (m, 1H), 2.13-2.17 (m, 2H), 1.84-1.94 (m, 1H), 1.51-1.54 (m, 1H), 1.36 (brs, 2H), 1.10 (d, J=6.8 Hz, 3H).

Example 89, 89-a, 89-b 5-(5-fluoro-2-(1H-tetrazol-1-yl)phenyl)-2-(2$^5$-fluoro-4-oxo-3-aza-1(1,3),2(1,2)-dibenzenacyclononaphane-9-yl)pyridine 1-oxide

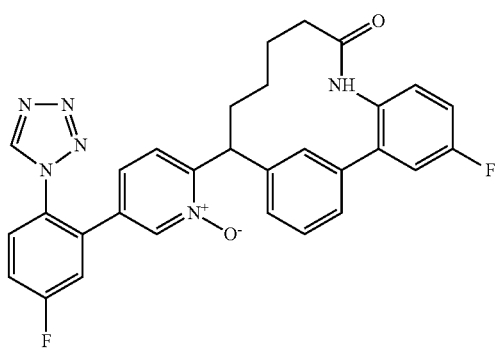 [SMILES: O=C1CCCCC(c2ccc(-c3cc(F)ccc3-n3cnnn3)c[n+]2[O-])c2cccc(c2)-c2cc(F)ccc2N1]

89A: (2'-amino-5'-fluoro-[1,1'-biphenyl]-3-yl)(5-chloropyridin-2-yl)methanone

To a solution of Intermediate 2 (9.00 g, 30.30 mmol) in DMF (150 mL) and water (20 mL) was added Intermediate 18 (7.91 g, 33.40 mmol), K$_3$PO$_4$ (19.33 g, 91.00 mmol) and Pd(Ph$_3$P)$_4$ (3.51 g, 3.03 mmol). The mixture was stirred at 60° C. under nitrogen for 3 h. It was cooled to rt and filtered through a pad of Celite. The solid cake washed with EtOAc (30 mL×2). The filtrate was diluted with water (100 mL) and extracted with EtOAc (100 mL×3). The combined organic layers were washed with brine, dried over sodium sulfate, filtered and concentrated. The residue was purified by flash column chromatography on silica gel (petroleum ether: EtOAc=20:1 to 5:1) to give the title compound. MS (ESI) m/z 326.8 (M+H).

89B: N-(3'-(5-Chloropicolinoyl)-5-fluoro-[1,1'-biphenyl]-2-yl)-5-((1-phenyl-1H-tetrazol-5-yl)sulfonyl)pentanamide A solution of 89A (11.40 g, 34.90 mmol), Intermediate 25 (11.91 g, 38.40 mmol) and EDC (13.38 g, 69.80 mmol) in PYRIDINE (150 mL) was stirred at 20° C. for 16 h. It was diluted with EtOAc (200 mL), washed with brine, dried over sodium sulfate, filtered and concentrated. The residue was triturated with EtOAc (30 mL). The solid was collected by filtration and rinsed with ethyl acetate to give the title compound. MS (ESI) m/z 619.0 (M+H).

89C: (E)-9-(5-Chloropyridin-2-yl)-2$^5$-fluoro-3-AZA-1(1,3),2(1,2)-dibenzenacyclononaphan-8-en-4-one

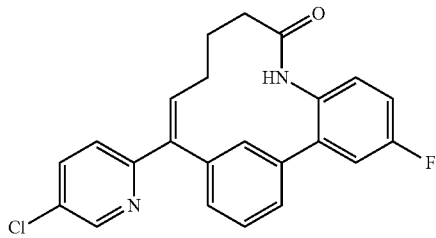 [SMILES: O=C1CCC/C=C(/c2ccc(Cl)cn2)c2cccc(c2)-c2cc(F)ccc2N1]

To a solution of 89B (5.00 g, 8.08 mmol) in THF (100 mL) at −78° C. was added a solution of LiHMDS (40.40 mL, 40.40 mmol, 1 M in THF) and stirred for 2 h. It was warmed to 20° C. and stirred for 16 h. The reaction was quenched with aqueous ammonium chloride (sat, 30 mL) and extracted with EtOAc (100 mL×3). The combined organic layers were washed with brine, dried over sodium sulfate, filtered and concentrated. The residue was triturated with (petroleum ether:EtOAc=3:1) to give the title compound. MS (ESI) m/z 393.1 (M+H).

89D: (E)-9-(5-(2-Amino-5-fluorophenyl)pyridin-2-yl)-2$^5$-fluoro-3-aza-1(1,3),2(1,2)-dibenzenacyclononaphan-8-en-4-one

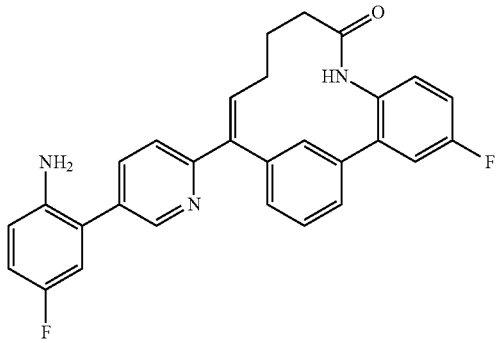 [SMILES: Nc1ccc(F)cc1-c1ccc(/C2=C/CCCC(=O)Nc3ccc(F)cc3-c3cccc2c3)nc1]

To s solution of 89C (2.10 g, 4.28 mmol) in THF (40 mL) was added Intermediate 18 (1.83 g, 7.70 mmol), 2nd generation Xphos precatalyst (0.34 g, 0.43 mmol) and potassium phosphate (12.83 mL, 12.83 mmol, 1 M in water) at 25° C. The mixture was stirred at 90° C. under N$_2$ for 16 h. It was cooled to rt and quenched with H$_2$O (30 mL). The mixture was extracted with EtOAc (50 mL×3), washed with brine, dried over sodium sulfate, filtered and concentrated. The residue was purified by flash column chromatography on silica gel (petroleum ether:EtOAc=5:1 to 1:1) to give the title compound. MS (ESI) m/z 468.2 (M+H).

89E: 9-(5-(2-Amino-5-fluorophenyl)pyridin-2-yl)-2$^5$-fluoro-3-aza-1(1,3),2(1,2)-dibenzenacyclononaphan-4-one

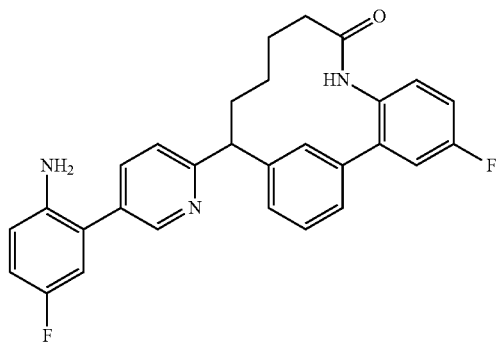 [SMILES: Nc1ccc(F)cc1-c1ccc(C2CCCCC(=O)Nc3ccc(F)cc3-c3cccc2c3)nc1]

A mixture of 89D (1.40 g, 2.99 mmol) and Raney nickel (3.00 g, 51.10 mmol) in THF (30 mL) was stirred at 25° C. for 4 h under H$_2$ (1 atm). The catalyst was removed by filtration through a pad of Celite. (Caution! Never expose catalyst in air.) The filtrate was concentrated to give the title compound. MS (ESI) m/z 470.2 (M+H).

Example 89 was prepared from 89E by the procedure described in the synthesis of Example 51. The product was purified by reverse phase HPLC (YMC-Actus Pro C18, 150×30 mm, 27-57% MeCN in water (0.1% TFA), 40 mL/min) to give the title compound. MS (ESI) m/z 539.2 (M+H).

A racemic sample of Example 89 was subjected for chiral separation by SFC (Column: AS, 250 mm×30 mm, Condition: 40% MeOH (0.1% NH$_3$)/CO$_2$) to give Example 89-a (slower eluting) and Example 89-b (faster eluting).

Example 90 (racemate), 90-a, 90-b

5-(2-(4-Chloro-1H-1,2,3-triazol-1-yl)-5-fluorophenyl)-2-(2$^5$-fluoro-4-oxo-3-aza-1(1,3),2(1,2)-dinenzenacyclononaphane-9-yl)pyridine 1-oxide

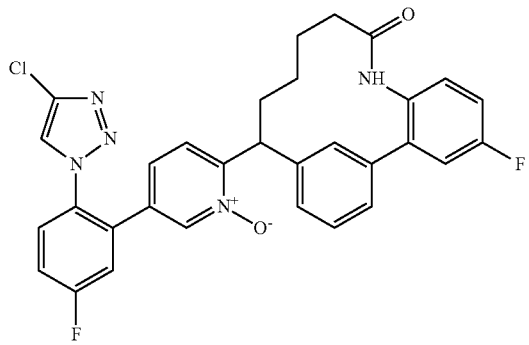 [SMILES: O=C1CCCCC(c2ccc(-c3cc(F)ccc3-n3cc(Cl)nn3)c[n+]2[O-])c2cccc(c2)-c2cc(F)ccc2N1]

90A: 9-(5-(2-Azido-5-fluorophenyl)pyridin-2-yl)-2⁵-fluoro-3-aza-1(1,3),2(1,2)-dibenzenacyclononaphan-4-one

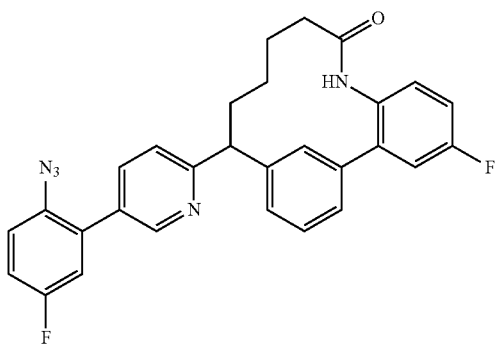 [SMILES: [N-]=[N+]=Nc1ccc(F)cc1-c1ccc(C2CCCCC(=O)Nc3ccc(F)cc3-c3cccc2c3)nc1]

To a solution of 60D (350 mg, 0.75 mmol) in hydrogen chloride (5 mL) at −5° C. was added a solution of sodium nitrite (103 mg, 1.49 mmol) in H₂O (15 mL). It was stirred at −5° C. for 1 h, and then a solution of sodium azide (97 mg, 1.49 mmol) in H₂O (15 mL) was added. The mixture was stirred at 25° C. for 16 h. Aqueous NaHCO₃ (saturated) was added to adjust pH to 8. The mixture was extracted with EtOAc (50 mL×3). The combined organic layers were washed with brine, dried over sodium sulfate, filtered and concentrated to give the title compound. MS (ESI) m/z 496.2 (M+H).

90B: 2⁵-Fluoro-9-(5-(5-fluoro-2-(4-(tributylstannyl)-1H-1,2,3-triazol-1-yl)phenyl)PYRIDIN-2-yl)-3-AZA-1(1,3),2(1,2)-dibenzenacyclononaphan-4-one

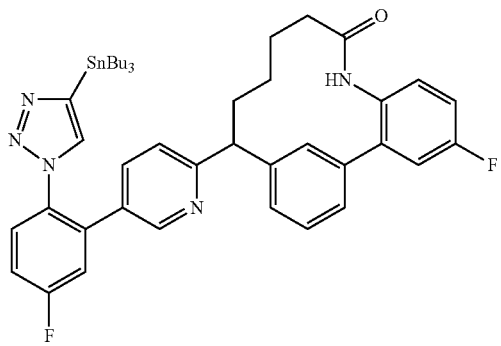

To s solution of 90A (200 mg, 0.40 mmol) in toluene (5 mL) was added tributyl(ethynyl)stannane (254 mg, 0.81 mmol) and the mixture was stirred at 110° C. under N₂ for 48 h. It was cooled to rt and quenched with aqueous KF (sat, 20 mL). The mixture was stirred for 1 h and then extracted with EtOAc (20 mL×3). The combined organic layers were washed with brine, dried over sodium sulfate, filtered and concentrated. The residue was purified by flash column chromatography on silica (petroleum ether:EtOAc=10:1 to 1:1) to give the title compound. MS (ESI) m/z 812.4 (M+H).

90C: 9-(5-(2-(4-Chloro-1H-1,2,3-triazol-1-yl)-5-fluorophenyl)pyridin-2-yl)-2⁵-fluoro-3-aza-1(1,3),2(1,2)-dibenzenacyclononaphan-4-one

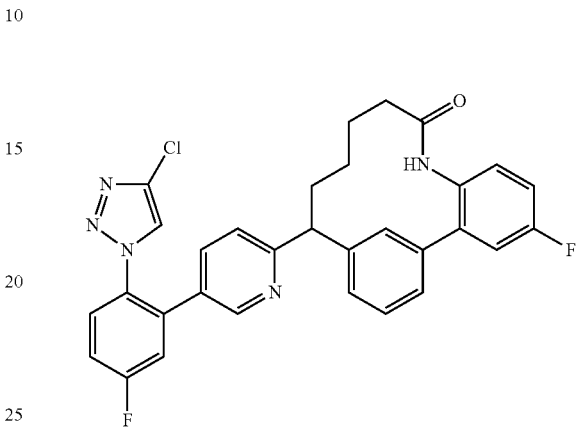

To s solution of 90B (200 mg, 0.247 mmol) in acetonitrile (5 mL) was added NCS (65.90 mg, 0.493 mmol) and the mixture was stirred at 90° C. under N₂ for 48 h. It was cooled to rt and most solvent was removed under reduced pressure. To the residue was added water (10 mL) and it was extracted with EtOAc (10 mL×3). The combined organic layers were washed with brine, dried over sodium sulfate, filtered and concentrated to give the title compound. MS (ESI) m/z 556.2 (M+H).

Example 90/90-a/90-b

To a solution of 90C (160 mg, 0.288 mmol) in AcOH (2 mL) was added m-CPBA (93 mg, 0.432 mmol, 85%) and the mixture was stirred at 25° C. for 16 h. It was quenched with aqueous Na₂SO₃ (sat, 15 mL). Aqueous sodium carbonate (saturated) was added to adjust pH to 8. The mixture was extracted with EtOAc (20 mL×3). The combined organic layers were washed with brine, dried over sodium sulfate, filtered and concentrated under reduced pressure. The residue was purified by reverse phase HPLC (YMC-Actus Pro C18, 150×30 mm, 33-63% MeCN in water (0.1% TFA), gradient, 40 mL/min) to give the title compound. MS (ESI) m/z 572.2 (M+H).

¹H NMR (400 MHz, CD₃OD) δ 9.53 (s, 1H), 8.65 (s, 1H), 8.15 (s, 1H), 7.83-7.75 (m, 1H), 7.67 (dd, J=2.8, 9.1 Hz, 1H), 7.61-7.50 (m, 3H), 7.39-7.31 (m, 2H), 7.29-7.19 (m, 3H), 6.96-6.85 (m, 2H), 4.61-4.52 (m, 1H), 2.31-2.22 (m, 1H), 2.04-1.74 (m, 4H), 1.51-1.39 (m, 1H), 1.28-1.15 (m, 1H), 1.10-0.95 (m, 1H).

A racemic sample of Example 90 was subjected for chiral separation by SFC (Column: OD, 250 mm×30 mm, 40% EtOH (0.1% NH₃), 40 mL/min) to give Example 90-a (fast eluting) and Example 90-b (slower eluting).

Example 91 (racemate), 91-a, 91-b 1-(4-chloro-2-(6-(2$^4$-((methoxycarbonyl)amino)-4-oxo-3-aza-1(1,3),2(1,2)-dibenzenacyclononaphane-9-yl)pyridin-3-yl)phenyl)-1H-1,2,3-triazole-4-carboxylic acid

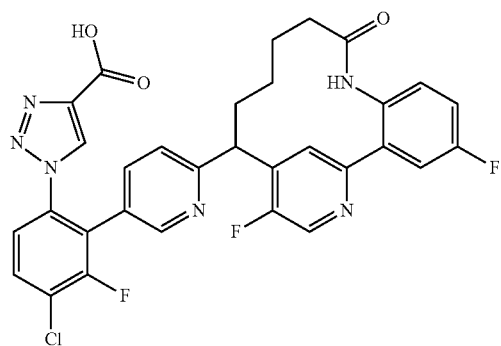 [SMILES: O=C1CCCCC(c2ccc(-c3c(-n4cc(C(=O)O)nn4)ccc(Cl)c3F)cn2)c2cc(ncc2F)-c2cc(F)ccc2N1]

91A. (2-(2-Amino-5-fluorophenyl)-5-fluoropyridin-4-yl)(5-chloropyridin-2-yl)methanone To a flask was charged with Intermediate 9 (2.5 g, 7.92 mmol), Intermediate 18 (2.104 g, 8.87 mmol), 1,1'-bis(diphenylphosphino)ferrocene-palladium(II)dichloride dichloromethane complex (0.582 g, 0.713 mmol) and degassed THF (39.6 mL). The resulting mixture was degassed and backfilled with N$_2$ three times. Degassed potassium phosphate tribasic (7.92 mL, 23.77 mmol) was added. The reaction mixture was heated at 60° C. under N$_2$ for 1 h. It was cooled to rt and filtered through a pad of Celite. The solids were washed with ethyl acetate (50 mL). The filtrate was concentrated under reduced pressure. The residue was purified by flash column chromatography on silica gel (eluting with 0 to 40% ethyl acetate in hexane) to give the title compound. MS (ES$^+$) m/z: 346.0 (M+H).

91B. 5-(Benzo[d]thiazol-2-ylsulfonyl)-N-(2-(4-(5-chloropicolinoyl)-5-fluoropyridin-2-yl)-4-fluorophenyl)pentanamide To a mixture of 91A and Intermediate 26 (2.390 g, 7.98 mmol) in DMF (66.5 mL), was added HATU (3.04 g, 7.98 mmol) and N,N-diisopropylethylamine (3.48 mL, 19.96 mmol). The reaction mixture was stirred at rt under N$_2$ for 8 h. It was diluted with water (50 mL) and extracted with ethyl acetate (3×75 mL). The combined organic layers were washed with brine, dried over sodium sulfate, filtered. The filtrate was concentrated under reduced pressure and the residue was purified by flash column chromatography on silica gel (eluting with 0-40% ethyl acetate in hexane) to give the compound. MS (ES$^+$) m/z: 626.7 (M).

91C. (E)-9-(5-Chloropyridin-2-yl)-1$^5$,2$^5$-difluoro-3-aza-1(2,4)-pyridina-2(1,2)-benzenacyclononaphan-8-en-4-one

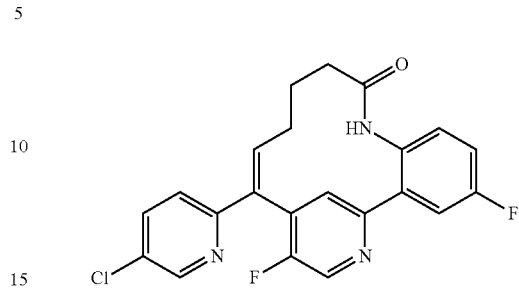

To a solution of 91B (780 mg, 1.244 mmol) in THF (25 mL) at −78° C. was added a solution of LHMDS (1.0 M in THF, 8.7 mL, 8.71 mmol) under N$_2$ atmosphere. The reaction was stirred at −78° C. for 1 h. It was quenched with saturated aqueous ammonium chloride (15 mL) and water (30 mL) at 0° C., The aqueous layer was extracted with ethyl acetate (3×30 mL). The combined organic layers were washed with brine (30 mL) and dried over sodium sulfate, filtered and concentrated under reduced pressure. The residue was purified by flash column chromatography on silica gel (eluting with 0-100% ethyl acetate in hexane) to give the title compound. MS (ES$^+$) m/z: 412.2 (M+H).

91D. (E)-9-(5-(6-Amino-3-chloro-2-fluorophenyl)pyridin-2-yl)-1$^5$,2$^5$-difluoro-3-aza-1(2,4)-pyridina-2(1,2)-benzenacyclononaphan-8-en-4-one

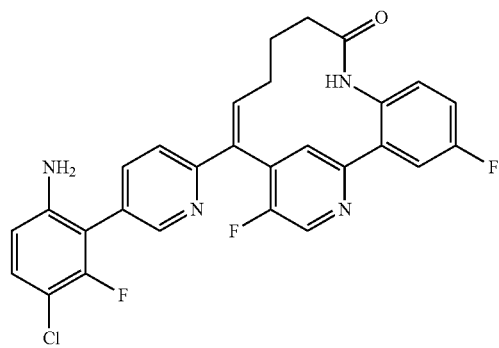 [SMILES: Nc1ccc(Cl)c(F)c1-c1ccc(/C2=C/CCCC(=O)Nc3ccc(F)cc3-c3cc2c(F)cn3)nc1]

A mixture of 91C (230 mg, 0.560 mmol), bis(pinacolato)diboron (171 mg, 0.672 mmol), Xphos palladium(II) complex (41.4 mg, 0.056 mmol) and potassium acetate (165 mg, 1.679 mmol) and dioxane (5.6 mL) was stirred at 80° C. under nitrogen for 1.5 h. It was cooled to rt, 4-chloro-3-fluoro-2-iodoaniline (152 mg, 0.560 mmol), 1,1'-bis(diphenylphosphino) ferrocene-palladium(II)dichloride dichloromethane complex (45.7 mg, 0.056 mmol) and potassium phosphate tribasic (3 M aqueous solution, 0.56 mL, 1.679 mmol) were added. The resulting mixture wad degassed and backfilled with N$_2$ three times. It was stirred at 80° C. for 2 h, cooled to rt and filtered through a pad of Celite. The solids were washed with ethyl acetate (50 mL). The filtrate was concentrated under reduced pressure. The residue was purified by prep-TLC (developed with 80% ethyl acetate in hexane) to get title product. MS (ES$^+$) m/z: 520.9 (M+H).

91E. tert-Butyl (E)-1-(4-chloro-2-(6-($1^5$,$2^5$-difluoro-4-oxo-3-aza-1(2,4)-pyridina-2(1,2)-benzenacyclononaphan-8-en-9-yl)pyridin-3-yl)-3-fluorophenyl)-1H-1,2,3-triazole-4-carboxylate

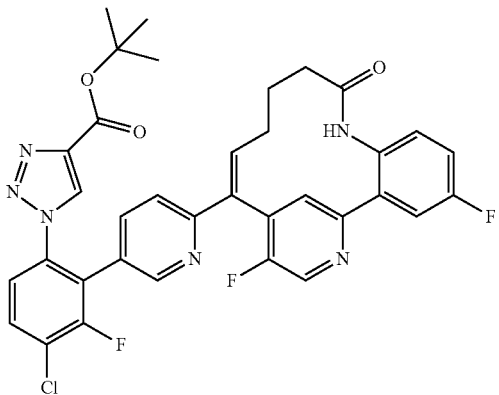 [SMILES: CC(C)(C)OC(=O)c1cn(-c2ccc(Cl)c(F)c2-c2ccc(/C3=C/CCCC(=O)Nc4ccc(F)cc4-c4cc3c(F)cn4)nc2)nn1]

To a stirred solution of 91D (30 mg, 0.058 mmol) in acetonitrile (0.83 mL) at 0° C. was added a solution of isopropyl nitrite (24.47 µl, 0.239 mmol) in acetonitrile (0.2 mL) followed by addition of azidotrimethylsilane (31.7 µl, 0.239 mmol) in acetonitrile (0.2 mL). The mixture was stirred for 10 min at 0° C. and it was allowed to warm to rt, stirring for 1 h. A solution of tert-butyl propiolate (36.3 mg, 0.288 mmol) in acetonitrile (0.2 mL) and copper(I) OXIDE (0.412 mg, 2.88 µmol) were added. The mixture was stirred for 3 h before it was diluted with DCM and washed with saturated ammonium chloride and brine. The organic layer was dried over sodium sulfate, filtered and concentrated under reduced pressure. The residue was purified by flash column chromatography on silica gel (eluting with 0 to 100% ethyl acetate in hexane) to give the title compound. MS (ES$^+$) m/z: 673.1 (M+H).

91F. tert-Butyl 1-(4-chloro-2-(6-($1^5$,$2^5$-difluoro-4-oxo-3-aza-1(2,4)-pyridina-2(1,2)-benzenacyclononaphane-9-yl)pyridin-3-yl)-3-fluorophenyl)-1H-1,2,3-triazole-4-carboxylate

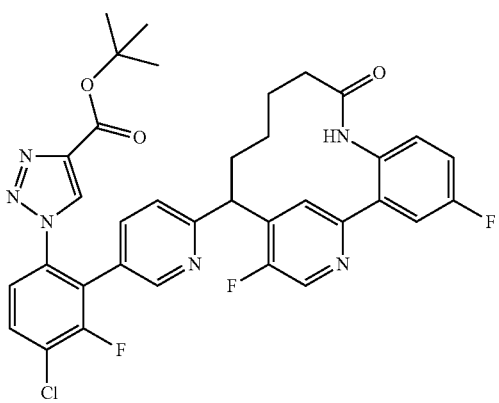 [SMILES: CC(C)(C)OC(=O)c1cn(-c2ccc(Cl)c(F)c2-c2ccc(C3CCCCC(=O)Nc4ccc(F)cc4-c4cc3c(F)cn4)nc2)nn1]

A mixture of 91E (23 mg, 0.034 mmol) and catalyst Platinum (1%)/Vanadium (2%) on activity carbon (219 mg, 0.034 mmol) in ethyl acetate:ethanol (3:1 v/v with 1% AcOH, 7.7 mL) was shaken under hydrogen (45 psi) for 22 h. It was diluted with 10% MeOH in DCM (20 mL) and filtered through a pad of Celite. The solids were added MeOH in DCM (30% v/v, 30 mL) and ammonia in MeOH (7 N, 1 mL) and sonicated for a few minutes. It was filtered through a pad of Celite. The filtrate was concentrated under reduced pressure to give the title compound.
MS (ES$^+$) m/z: 675.4 (M+H).

Example 91

91F (88 mg, 0.130 mmol) was stirred in DCM (10 mL) and TFA (5 mL) at rt for 1 h. Most solvent was concentrated under reduced pressure. The crude material was purified by prep TLC (developed with 15% MeOH/DCM with 1% AcOH) to give titled compound. MS (ES$^+$) m/z: 618.9 (M+H).

A racemic sample of Example 91 was subjected to chiral separation by SFC (AS, 21×250 mm, 18% MeOH/CO$_2$, 60 mL/min, 35° C.) to afford Example 91-a (slower eluting) and Example 91-b (faster eluting).

Example 92, 92-a, 92-b 1-(4-chloro-2-(6-($2^4$-((methoxycarbonyl)amino)-4-oxo-3-aza-1(1,3),2(1,2)-dinenzenacyclononaphane-9-yl)pyridin-3-yl)phenyl)-1H-1,2,3-triazole-4-carboxylic acid

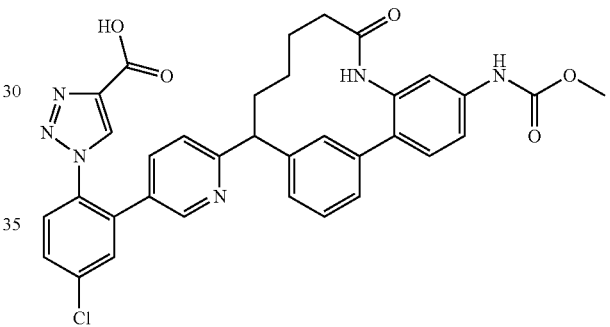

Example 92 was prepared from 12C following a similar procedure as described in the synthesis of Example 91. MS (ES$^+$) m/z: 637 (M+H).

A racemic sample of Example 92 was subjected to chiral separation by SFC (IC, 21×200 mm, 50% MeOH/CO$_2$, 60 mL/min, 35° C.) to afford Example 92-a (slower eluting) and Example 92-b (faster eluting).

Example 93, 93-a, 93-b 5-(3-Chloro-2,6-difluorophenyl)-2-($2^4$-((methoxycarbonyl)amino)-4-oxo-3-aza-1(2,4)-pyridina-2(1,2)-benzenacyclononaphane-9-yl)pyridine 1-oxide

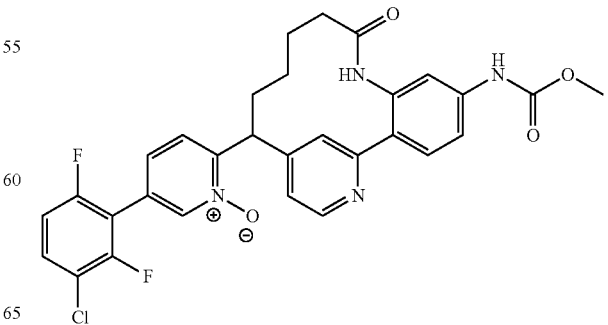

93A: Methyl (3-amino-4-(4-(5-chloropicolinoyl) pyridin-2-yl)phenyl)carbamate The title compound was prepared from Intermediate 8 following a similar procedure as described in the synthesis of 12A. The product was purified by flash column chromatography (SiO$_2$, DCM:EtOAc=100:1 to 5:1). MS (ESI) m/z 383.0 (M+H).

93B: Methyl (3-(5-bromopentanamido)-4-(4-(5-chloropicolinoyl)pyridin-2-yl)phenyl)carbamate To a mixture of 93A (4.00 g, 10.45 mmol) and 5-bromopentanoyl chloride (2.29 g, 11.49 mmol) in DCM (100 mL) at 0° C. was added Et$_3$N (4.37 mL, 31.30 mmol). The mixture was stirred at 25° C. for 1 h. It was diluted with water (50 mL) and extracted with DCM (50 mL×3). The combined organic layers were dried over magnesium sulfate, filtered, and concentrated under reduced pressure. The residue was purified by flash column chromatography (SiO$_2$, petroleum ether:EtOAc=5:1-1:1) to give the title compound. MS (ESI) m/z 545.7, 546.7 (M+H).

93C: Methyl (3-(5-bromopentanamido)-4-(4-((5-chloropyridin-2-yl)(hydroxy)methyl)pyridin-2-yl) phenyl)carbamate To a solution of 93B (4.00 g, 7.33 mmol) in DCM/MeOH (3:1, 100 mL) at 0° C. was added NaBH$_4$ (1.39 g, 36.60 mmol). The resulting mixture was stirred at 25° C. for 1 h before quenched with saturated aqueous ammonium chloride solution (50 mL). It was extracted with DCM (50 mL×3). The combined organic layers were washed with water (50 mL) and brine (50 mL), dried over anhydrous sodium sulfate, filtered and concentrated to give the title compound. MS (ESI) m/z 547.1.7, 549.1 (M+H).

93D: S-(5-((2-(4-((5-Chloropyridin-2-yl)(hydroxy) methyl)pyridin-2-yl)-5-((methoxycarbonyl)amino) phenyl)amino)-5-oxopentyl)ethanethioate To a solution of 93 C (5.00 g, 9.13 mmol) and DIEA (4.78 mL, 27.40 mmol) in DMF (100 mL) at 0° C. was added thioacetic acid (1.957 mL, 27.40 mmol). The resulting mixture was stirred at 25° C. for 1 h. It was diluted with water (300 mL) and extracted with DCM (200 mL×3). The combined organic layers were washed with water (200 mL) and brine (200 mL), dried over anhydrous sodium sulfate, filtered and concentrated. The crude product was purified by flash column chromatography (SiO$_2$, petroleum ether: EtOAc=5:1-1:1) to give the title compound. MS (ESI) m/z 543.2 (M+H).

93E: S-(5-((2-(4-((5-Chloropyridin-2-yl)((methyl sulfonyl)oxy)methyl)pyridin-2-yl)-5-((methoxycarbonyl)amino)phenyl)amino)-5-oxopentyl) ethanethioate To a solution of 93D (4.70 g, 8.66 mmol) and TEA (3.62 mL, 26.00 mmol) in DCM (120 mL) at 0° C. was added methanesulfonyl chloride (1.38 mL, 17.31 mmol). The resulting mixture was stirred at 25° C. for 3 h. It was diluted with water (100 mL) and extracted with DCM (100 mL×3). The combined organic layers were washed with water (100 mL) and brine (100 mL), dried over anhydrous sodium sulfate, filtered and concentrated under reduced pressure to give the title compound. MS (ESI) m/z 621.1 (M+H).

93F: Methyl (10-(5-chloropyridin-2-yl)-4-oxo-9-thia-3-aza-1(2,4)-pyridina-2(1,2) -benzenacyclodecaphane-2$^4$-yl)carbamate

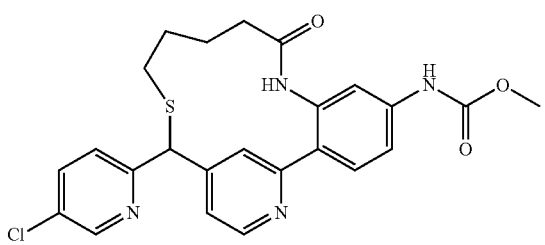 [SMILES: COC(=O)Nc1ccc2c(c1)NC(=O)CCCCSC(c1ccc(Cl)cn1)c1ccnc-2c1]

To a mixture of KOH (0.542 g, 9.66 mmol) in EtOH (300 mL) at 0° C. was added a solution of 93E (4.00 g, 6.44 mmol) in DCM (10 mL). The resulting mixture was stirred at 25° C. for 3 h. It was diluted with water (50 mL) and extracted with DCM (100 mL×3). The combined organic layers washed with brine (100 mL), dried over anhydrous sodium sulfate, filtered and concentrated under reduced pressure to give the title compound. MS (ESI) m/z 483.1 (M+H).

93G: Methyl (10-(5-chloropyridin-2-yl)-9,9-dioxido-4-oxo-9-thia-3-aza-1(2,4)-pyridina-2(1,2) -benzenacyclodecaphane-2$^4$-yl)carbamate

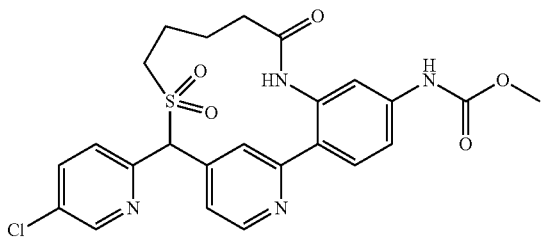 [SMILES: COC(=O)Nc1ccc2c(c1)NC(=O)CCCCS(=O)(=O)C(c1ccc(Cl)cn1)c1ccnc-2c1]

To a solution of potassium peroxymonosulfate (4.84 g, 7.87 mmol) in water (75 mL) at 0° C. was added a solution of 93F (3.80 g, 7.87 mmol) in MeOH (75 mL). The mixture was stirred at 20° C. for 13 h. It was diluted with saturated aqueous NaHCO$_3$ solution (200 mL) and extracted with DCM (200 mL×3). The combined organic layers were washed with water (200 mL) and brine (200 mL), dried over anhydrous sodium sulfate, filtered and concentrated to give the title compound. MS (ESI) m/z 515.1 (M+H).

93H: Methyl (E)-(9-(5-chloropyridin-2-yl)-4-oxo-3-aza-1(2,4)-pyridina-2(1,2)-benzenacyclononaphan-8-en-2⁴-yl)carbamate

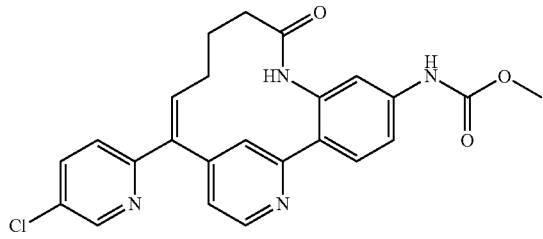 [SMILES: COC(=O)Nc1ccc2c(c1)NC(=O)CCC/C=C(/c1ccc(Cl)cn1)c1ccnc-2c1]

To a suspension of KOH (5.88 g, 105 mmol) and 93G (2.70 g, 5.24 mmol) in DCM (10 mL) and t-BuOH (30 mL) was added CCl₄ (2.024 mL, 20.97 mmol) at 40° C. The mixture was stirred for 4 h at 40° C. It was diluted with water (100 mL) and extracted with DCM (100 mL×3). The organic layers were dried over magnesium sulfate, filtered, and concentrated under reduced pressure. The residue was purified by flash column chromatography (SiO₂, petroleum ether:EtOAc=3:1-1:3) to give the title compound as a solid. MS (ESI) m/z 449.1 (M+H).

Example 93

Example 93 was prepared from 93H following a similar procedure as described as the synthesis of Example 50. The product was purified by reverse-phase HPLC (YMC-Actus Pro C18, 150×30 mm, MeCN/water (0.1% TFA), 40 mL/min) to give the title compound as a solid. MS (ESI) m/z 579.2 (M+H). ¹H NMR (400 MHz, CD₃OD): δ 8.51 (s, 1H), 8.47 (d, J=5.1 Hz, 1H), 7.92 (d, J=8.4 Hz, 1H), 7.82 (s, 1H), 7.77 (d, J=8.2 Hz, 1H), 7.60-7.69 (m, 2H), 7.43-7.51 (m, 2H), 7.18-7.22 (m, 1H), 6.93 (d, J=4.4 Hz, 1H), 4.80 (dd, J=12.1, 4.2 Hz, 1H), 3.72 (s, 3H), 2.46-2.56 (m, 1H), 1.98-2.19 (m, 4H), 1.68-1.72 (m, 1H), 1.50 (brs, 1H), 1.10-1.18 (m, 1H).

A racemic sample of Example 93 was subjected for chiral separation by SFC (Column AD, 250 mm×30 mm, 55% EtOH 80 mL/min) to give Example 93-a (fast eluting) and Example 93-b (slower eluting).

Example 94

9-(5-(3-Chloro-2,6-difluorophenyl)-1-oxidopyridin-2-yl)-2⁴-((methoxycarbonyl)amino)-4-oxo-3-aza-1 (2,4)-pyridin-1-iuma-2(1,2)-benzenacyclononaphane 1-oxide

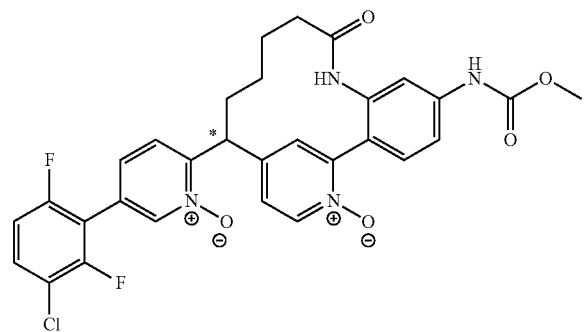 [SMILES: COC(=O)Nc1ccc2c(c1)NC(=O)CCCCC(c1ccc(-c3c(F)ccc(Cl)c3F)c[n+]1[O-])c1cc[n+]([O-])c-2c1]

Example 94 was isolated from Example 93 by reverse phase HPLC (YMC-Actus Pro C18, 150×30 mm, 20-50% MeCN in water with 0.5% TFA, 40 mL/min). MS (ES⁺) m/z: 595 (M+H); ¹H NMR: (CD₃OD, 400 MHz): δ 9.60 (br. s., 1H), 8.59-8.71 (m, 1H), 8.49 (br. s., 1H), 8.36 (d, J=6.7 Hz, 1H), 7.89 (d, J=7.8 Hz, 1H), 7.69-7.83 (m, 2H), 7.58-7.67 (m, 2H), 7.43 (d, J=8.6 Hz, 1H), 7.16-7.23 (m, 1H), 4.67-4.75 (m, 1H), 3.69-3.81 (m, 3H), 2.31-2.43 (m, 1H), 2.03-2.24 (m, 3H), 1.80 (br. s., 1H), 1.53 (br. s., 2H), 1.35 (br. s., 1H).

Example 95-a, 95-b, 95-c, 95-d

Methyl (9-(5-(3-chloro-2,6-difluorophenyl)pyridin-2-yl)-5-methyl-4-oxo-3-aza-1(4,2)-pyridina-2(1,2)-benzenacyclononaphane-2⁴-yl)carbamate

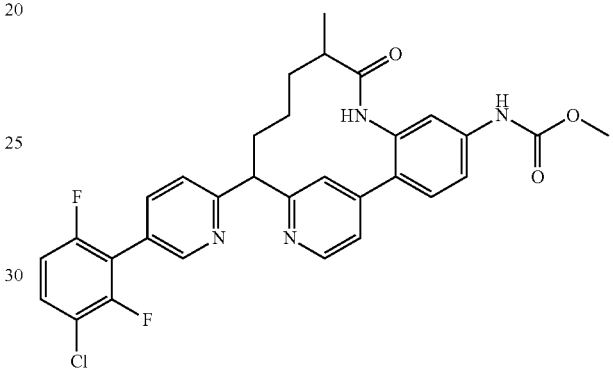

95A: Methyl (Z)-(9-(5-(3-chloro-2,6-difluorophenyl)pyridin-2-yl)-5-methyl-4-oxo-3-aza-1(4,2)-pyridina-2(1,2)-benzenacyclononaphan-8-en-2⁴-yl)carbamate

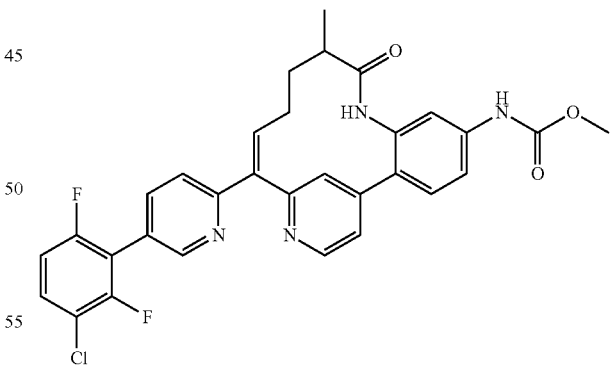

The title compound was prepared from Intermediate 10 following a similar procedure described in the synthesis of 50C. The product was purified by flash column chromatography on silica gel (eluting with petroleum ether:EtOAc=1:1). MS (ESI) m/z 575.1 (M+H).

A racemic sample of 95A was subjected to chiral separation by SFC (Chiralpak AD, 250×30 mm, 50% EtOH (0.05% DEA)/CO₂, 80 mL/min) to give 95A-a (faster eluting) and 95A-b (slower eluting).

95B-a/95B-b: Methyl (9-(5-(3-chloro-2,6-difluorophenyl)pyridin-2-yl)-5-methyl-4-oxo-3-aza-1 (4,2)-pyridina-2(1,2)-benzenacyclononaphane-2⁴-yl)carbamate

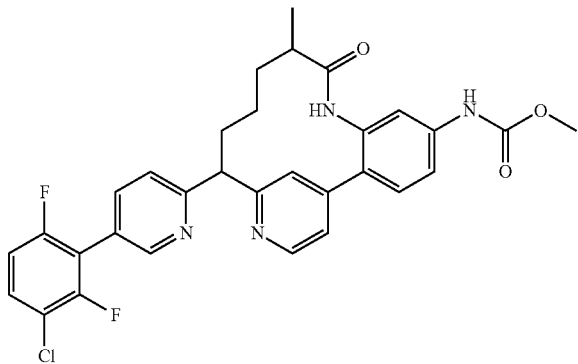

A mixture of 95A-a (120 mg, 0.209 mmol) and Raney-nickel (12.25 mg, 0.209 mmol) in THF (2 mL) was stirred at 25° C. under hydrogen (1 atm) for 10 min. The mixture was filtered through a pad of Celite (caution, flammable) and the filter cake washed with methanol (50 mL). The filtrate was concentrated under reduced pressure. The residue was purified by reverse phase HPLC (YMC-Actus Pro C18, 150×30 mm, MeCN/water (0.1% TFA), 40 mL/min) to give 95B-a, MS (ESI) m/z 577.2 (M+H) and 95B-b, MS (ESI) m/z 577.2 (M+H).

95B-c/95B-d: Methyl (9-(5-(3-chloro-2,6-difluorophenyl)pyridin-2-yl)-5-methyl-4-oxo-3-aza -1(4,2)-pyridina-2(1,2)-benzenacyclononaphane-2⁴-yl)carbamate

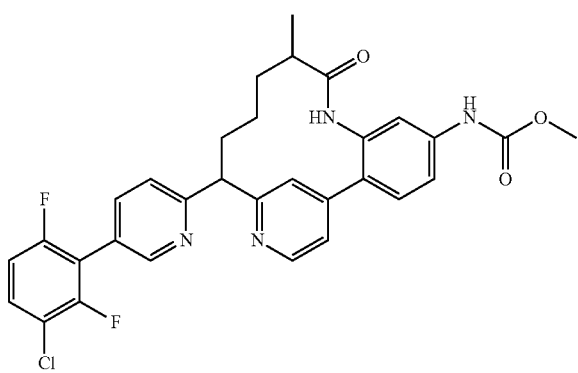 [SMILES: COC(=O)Nc1ccc2c(c1)NC(=O)C(C)CCCC(c1ccc(-c3c(F)ccc(Cl)c3F)cn1)c1cc-2ccn1]

A mixture of two diastereomers 95B-c/95B-d was prepared from 95A-b by the procedure described in the synthesis of 95B-a/95B-d. The product was purified by reverse phase HPLC (YMC-Actus Pro C18, 150×30 mm, MeCN/water (0.1% TFA), 40 mL/min) to give 95B-c (faster eluting), MS (ESI) m/z 577.2 (M+H) and 95B-d (slower eluting), MS (ESI) m/z 577.2 (M+H).

Example 95-a/95-b/95-c/95-d

Example 95-a/95-b/95-c/95-d was prepared from 95B-a/95B-b/95B-c/95B-d respectively by the procedure described in the synthesis of Example 13. The products were purified by reverse phase HPLC (YMC-Actus Pro C18, 100×21 mm, MeCN/water (0.1% TFA), 25 mL/min).

Example 95-a: MS (ESI) m/z 593.2 (M+H); ¹H NMR (400 MHz, CD₃OD): δ 8.61 (d, J=5.9 Hz, 1H), 8.54 (s, 1H), 8.01 (d, J=8.2 Hz, 1H), 7.97 (s, 1H), 7.81 (d, J=8.2 Hz, 1H), 7.71 (d, J 5.5 Hz, 1H), 7.69-7.60 (m, 2H), 7.56 (d, J=2.7 Hz, 2H), 7.21 (t, J=9.2 Hz, 1H), 5.12-5.02 (m, 1H), 3.76 (s, 3H), 2.55-2.47 (m, 1H), 2.40-2.27 (m, 1H), 2.25-2.13 (m, 1H), 1.82 (q, J=10.7 Hz, 1H), 1.65-1.51 (m, 1H), 1.27 (d, J=6.7 Hz, 4H), 1.15-1.03 (m, 1H).

Example 95-b: MS (ESI) m/z 593.2 (M+H); ¹H NMR (400 MHz, CD₃OD): δ 8.61-8.54 (m, 2H), 8.11 (s, 1H), 7.98 (d, J=8.2 Hz, 1H), 7.82 (d, J=8.2 Hz, 1H), 7.71-7.64 (m, 2H), 7.60-7.56 (m, 2H), 7.52-7.47 (m, 1H), 7.22 (t, J=8.6 Hz, 1H), 4.99-4.95 (m, 1H), 3.77 (s, 3H), 2.91-2.75 (m, 1H), 2.44 (t, J=12.7 Hz, 1H), 2.11 (t, J=11.2 Hz, 2H), 1.71-1.54 (m, 2H), 0.99 (d, J=7.0 Hz, 3H), 0.63-0.47 (m, 1H).

Example 95-c: MS (ESI) m/z 593.2 (M+H); ¹H NMR (400 MHz, CD₃OD): δ 8.61 (d, J=5.9 Hz, 1H), 8.54 (s, 1H), 8.01 (d, J=8.2 Hz, 1H), 7.97 (s, 1H), 7.81 (d, J=8.2 Hz, 1H), 7.71 (d, J=5.5 Hz, 1H), 7.69-7.60 (m, 2H), 7.56 (d, J=2.7 Hz, 2H), 7.21 (t, J=9.2 Hz, 1H), 5.12-5.02 (m, 1H), 3.76 (s, 3H), 2.55-2.47 (m, 1H), 2.40-2.27 (m, 1H), 2.25-2.13 (m, 1H), 1.82 (q, J=10.7 Hz, 1H), 1.65-1.51 (m, 1H), 1.27 (d, J=6.7 Hz, 4H), 1.15-1.03 (m, 1H).

Example 95-d: MS (ESI) m/z 593.2 (M+H); ¹H NMR (400 MHz, CD₃OD): δ 8.61-8.54 (m, 2H), 8.11 (s, 1H), 7.98 (d, J=8.2 Hz, 1H), 7.82 (d, J=8.2 Hz, 1H), 7.71-7.64 (m, 2H), 7.60-7.56 (m, 2H), 7.52-7.47 (m, 1H), 7.22 (t, J=8.6 Hz, 1H), 4.99-4.95 (m, 1H), 3.77 (s, 3H), 2.91-2.75 (m, 1H), 2.44 (t, J=12.7 Hz, 1H), 2.11 (t, J=11.2 Hz, 2H), 1.71-1.54 (m, 2H), 0.99 (d, J=7.0 Hz, 3H), 0.63-0.47 (m, 1H).

Example 96 (racemate), 96-a and 96-b (Z)-5-(3-chloro-2,6-difluorophenyl)-2-(2⁴-((methoxycarbonyl)amino)-4-oxo-1¹H-3-aza-1(4,2)-imidazola-2(1,2)-benzenacyclononaphane-9-yl)pyridine 1-oxide

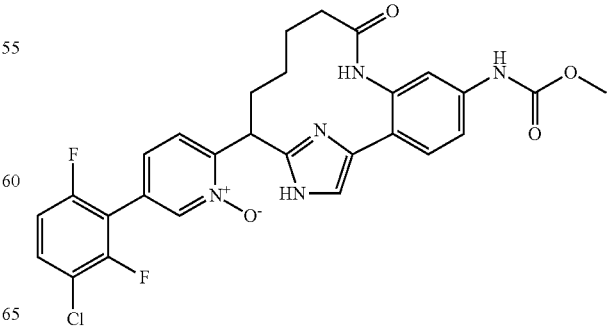

96A: Methyl ((1²Z,8Z)-9-(5-(3-chloro-2,6-difluoro-phenyl)pyridin-2-yl)-4-oxo-1¹-((2-(trimethylsilyl)ethoxy)methyl)-1¹H-3-aza-1(4,2)-imidazola-2(1,2)-benzenacyclononaphan-8-en -2⁴-yl)carbamate 96C: (Z)-5-(3-Chloro-2,6-difluorophenyl)-2-(2⁴-((methoxycarbonyl)amino)-4-oxo-1¹-((2-(trimethyl-silyl)ethoxy)methyl)-1¹H-3-aza-1(4,2)-imidazola-2(1,2)-benzenacyclononaphane-9-yl)pyridine 1-oxide

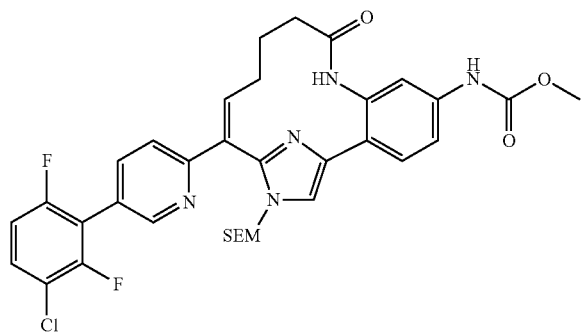 [SMILES: COC(=O)Nc1ccc2c(c1)NC(=O)CCC/C=C(/c1ccc(-c3c(F)ccc(Cl)c3F)cn1)c1nc-2cn1COCC[Si](C)(C)C]

The title compound was prepared from Intermediate 56 by the procedure described in 50C. The product was purified by flash column chromatography on silica gel (eluting with petroleum ether:EtOAc=1:1 v/v). MS (ES⁺) m/z: 680 (M+H.

96B: Methyl (Z)-(9-(5-(3-chloro-2,6-difluorophe-nyl)pyridin-2-yl)-4-oxo-1¹-((2-(trimethylsilyl)ethoxy)methyl)-1¹H-3-aza-1(4,2)-imidazola-2(1,2)-NENZENACYCLONONAPHANE-2⁴-yl)carbamate

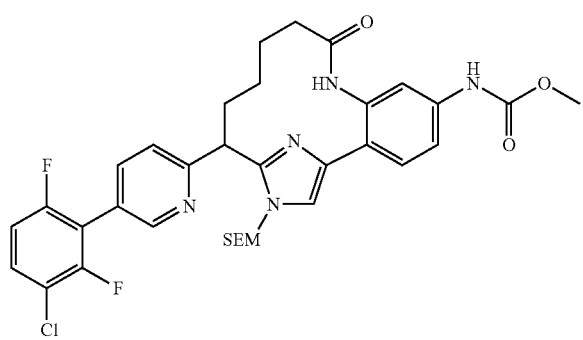 [SMILES: COC(=O)Nc1ccc2c(c1)NC(=O)CCCCC(c1ccc(-c3c(F)ccc(Cl)c3F)cn1)c1nc-2cn1COCC[Si](C)(C)C]

A cloudy solution of 96A (1.1 g, 1.455 mmol) in THF (40 ml) was added large excess amount of Raney nickel. The mixtures were shaken under hydrogen (40 psi) at rt for 1 h. To the bottle was added 200 mL of 10% methanol in DCM and it was sonicated for 10 min. The catalysts were removed by filtration through a pad of Celite and washed with 200 mL of 10% MeOH in DCM followed by 50 mL of methanol (Caution! Never expose catalyst in air). The catalyst was covered with water (10 mL) and disposed in a container covered with water. The filtrate was concentrated under reduced pressure. The residue was suspended in methanol (50 mL) and filtered. The solids were rinsed with methanol, then diethyl ether. It was air-dried overnight to give the title compound. MS (ES⁺) m/z: 683 (M+H).

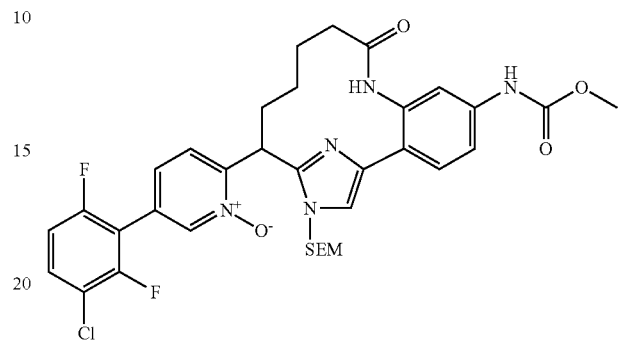

A 100 ml of round bottom flask was charged with a magnetic stirring bar, 96B (7 g, 10.26 mmol) and acetic acid (35.0 ml). It was placed in a water bath at rt and to the stirred slurry mixture was added cooled peracetic acid (39% wt in acetic acid, 51.1 ml, 308 mmol. It was stirred for 5 h. The reaction mixture transferred into a separatory funnel and was slowly dropped into a stirring mixture of ice (1000 g), sodium thiosulfate (81 g, 513 mmol) and sodium carbonate (98 g, 923 mmol) in a large beaker. After dropping, the mixture was stirred for 30 min until all ice melted. The precipitate was collected by filtration. The solid cake was rinsed with water and air-dried. The crude product was re-dissolved in DCM/MeOH (5:1) and purified by column chromatography on silica gel (eluting with 0-85% EtOAc/DCM and 0-6% MeOH/DCM, respectively) to give the title compound. MS (ES⁺) m/z: 698 (M+H).

Example 96

To a flask charged with 96C (2.4 g, 3.44 mmol) and DCM (12.00 ml) was added TFA (13.24 ml, 172 mmol). The mixture was stirred at rt for 6 h. It was transferred into a separatory funnel and slowly dropped to a stirred mixture of ice (200 g) and sodium carbonate (25.5 g, 241 mmol). The mixture was extracted with DCM (150 ml×3). The combined organic layers were washed with brine, dried over MgSO₄, filtered and concentrated under reduced pressure. he The residue was purified by flash column chromatography on silica gel (eluting with 0-6% MeOH/DCM) to give the title compound. MS (ES⁺) m/z: 568 (M+H).

A sample of racemic Example 96 was subjected to chiral separation by SFC (AS-H, 250×30 mm; 50% methanol (0.05% diethylamine)/CO₂, 80 mL/min) to afford Example 96-a (slower eluting) and Example 96-b (faster eluting). MS (ES⁺) m/z: 568 (M+H); ¹H NMR (CD₃OD, 400 MHz): δ 8.57 (s, 1H), 7.96 (d, J=8.4 Hz, 1H), 7.81 (d, J=8.4 Hz, 1H), 7.68 (dt, J=5.7, 8.6 Hz, 1H), 7.61 (s, 1H), 7.54-7.48 (m, 1H), 7.44-7.40 (m, 2H), 7.27-7.18 (m, 1H), 4.97 (dd, J=6.9, 10.7 Hz, 1H), 3.77 (s, 3H), 2.57 (d, J=12.8 Hz, 1H), 2.44-2.28 (m, 2H), 2.11 (m, 1H), 1.95-1.80 (m, 1H), 1.76-1.51 (m, 2H), 1.12 (m, 1H).

Example 97 methyl (Z)-(9-(5-(5-chloro-2-(1H-tetrazol-1-yl)phenyl)pyridin-2-yl)-4-oxo-1¹H-3-AZA-1(4,2)-imidazola-2(1,2)-benzenacyclononaphane-2⁴-yl)carbamate

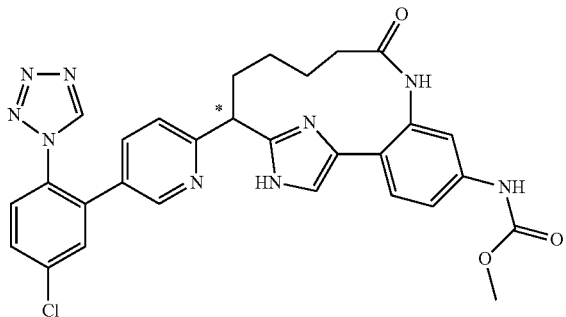 [SMILES: COC(=O)Nc1ccc2c(c1)NC(=O)CCCCC(c1ccc(-c3cc(Cl)ccc3-n3cnnn3)cn1)c1nc-2c[nH]1]

97A: Methyl ((1²Z,8Z)-9-(5-(2-amino-5-chlorophenyl)pyridin-2-yl)-4-oxo-1¹-((2-(trimethylsilyl)ethoxy)methyl)-1¹H-3-aza-1(4,2)-imidazola-2(1,2)-benzenacyclononaphane-8-en -2⁴-yl)carbamate

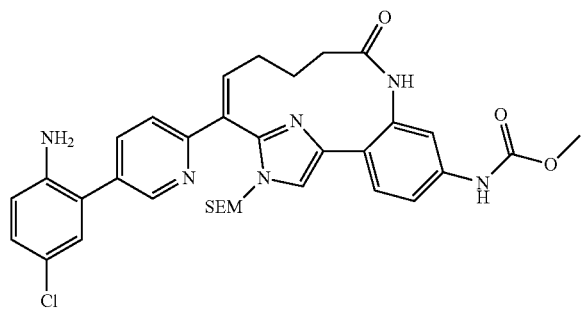 [SMILES: COC(=O)Nc1ccc2c(c1)NC(=O)CCC/C=C(/c1ccc(-c3cc(Cl)ccc3N)cn1)c1nc-2cn1COCC[Si](C)(C)C]

A microwave reactor vial was charged with a magnetic stirring bar, Intermediate 56 (200 mg, 0.326 mmol), Intermediate 33 (166 mg, 0.653 mmol), 1,1'-bis(di-tert-butylphosphino)ferrocene palladium dichloride (21.28 mg, 0.033 mmol), K₂CO₃ (135 mg, 0.979 mmol), THF (9 mL) and water (3 mL). The mixture was heated at 120° C. in a microwave reactor for 0.5 h. It was cooled to rt and was diluted with H₂O (10 mL). The mixture was extracted with DCM (3×20 mL). The combined organic layers were dried over sodium sulfate, filtered and concentrated in vacuo. The residue was purified by TLC (1000 μm, petroleum ether: EtOAc=1:2) to give the title compound. MS (ES⁺) m/z: 659 (M+H).

97B: Methyl (Z)-(9-(5-(2-amino-5-chlorophenyl)pyridin-2-yl)-4-oxo-1¹-((2-(trimethylsilyl)ethoxy)methyl)-1¹H-3-aza-1(4,2)-imidazola-2(1,2)-benzenacyclononaphane-2⁴-yl)carbamate

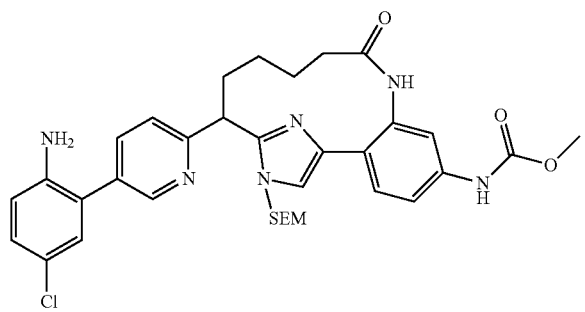 [SMILES: COC(=O)Nc1ccc2c(c1)NC(=O)CCCCC(c1ccc(-c3cc(Cl)ccc3N)cn1)c1nc-2cn1COCC[Si](C)(C)C]

The title compound was prepared from 97A by the procedure described in 102B. It was used without purification. MS (ES⁺) m/z: 661 (M+H).

97C: Methyl (Z)-(9-(5-(5-chloro-2-(1H-tetrazol-1-yl)phenyl)pyridin-2-yl)-4-oxo-1¹-((2-(trimethylsilyl)ethoxy)methyl)-1¹H-3-aza-1(4,2)-imidazola-2(1,2)-benzenacyclononaphane-2⁴-yl)carbamate

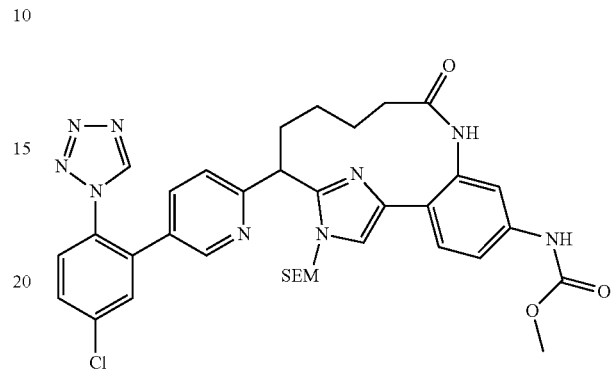

To a solution of 97B (120 mg, 0.127 mmol) in HOAc (5 mL), trimethyl orthoformate (135 mg, 1.270 mmol) and sodium azide (49.5 mg, 0.762 mmol) were added. The mixture was stirred at 30° C. for 15 h. The mixture was quenched with saturated NaNO₂ (30 mL) and saturated aqueous sodium bicarbonate. It was extracted with EtOAc (3×20 mL). The combined organic layers were dried over anhydrous sodium sulfate, filtered and concentrated under reduced pressure to give the title compound, which was used in the next step without further purification.
MS (ES⁺) m/z: 714 (M+H).

Example 97

Example 97 was prepared from 97C by the procedure described in Example 11. The residue was purified by reverse phase HPLC (YMC-Actus Pro C18, 150×30 mm, MeCN/water (0.1% TFA), 40 mL/min) to give the title compound. MS (ES⁺) m/z: 584 (M+H).

Example 98 (racemate), 98-a and 98-b (Z)-5-(5-chloro-2-(1H-tetrazol-1-yl)phenyl)-2-(2⁴-((methoxycarbonyl)amino)-4-oxo-1¹H-3-aza-1(4,2)-imidazola-2(1,2) -benzenacyclononaphane-9-yl) pyridine 1-oxide

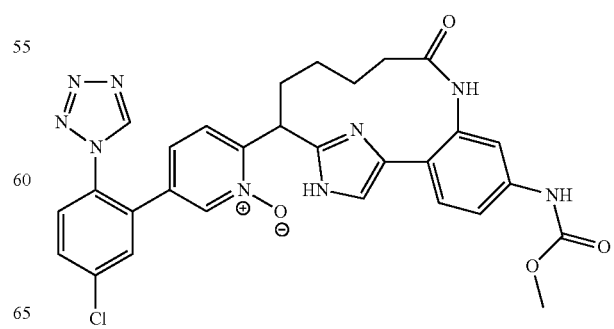

Example 98 was prepared from 97C by the procedures described in Example 96. It was purified by reverse phase HPLC to give the racemic product. MS (ES+) m/z: 600 (M+H).

A sample of Example 98 was subjected to chiral separation by SFC (OD-3, 4.6×50 mm, 40% methanol (0.05% diethylamine) in $CO_2$; 4 mL/min; 40° C.) to give Example 98-a (faster eluting) and Example 98-b (slower eluting). MS (ES+) m/z: 600 (M+H); $^1$H NMR: (CD$_3$OD, 400 MHz): δ 9.42 (s, 1H), 8.31 (s, 1H), 7.78-7.83 (m, 2H), 7.67-7.76 (m, 2H), 7.61 (s, 1H), 7.49 (d, J=8.6 Hz, 1H), 7.41 (m, 1H), 7.35 (s, 1H), 7.30 (d, J=7.8 Hz, 1H), 3.76 (s, 3H), 2.53 (d, J=11.7 Hz, 1H), 2.11-2.35 (m, 3H), 1.87 (d, J=11.0 Hz, 1H), 1.63 (m, 1H), 1.45 (m, 1H), 1.29 (q, J=6.9 Hz, 1H), 1.13 (m, 1H).

Example 99, 99-a, 99-b (Z)-5-(5-chloro-2-(trifluoromethoxy)phenyl)-2-(2$^4$-((methoxycarbonyl)amino)-4-oxo-1$^1$H-3-aza-1(4,2)-imidazola-2(1,2)-benzenacyclononaphane-9-yl) pyridine 1-oxide

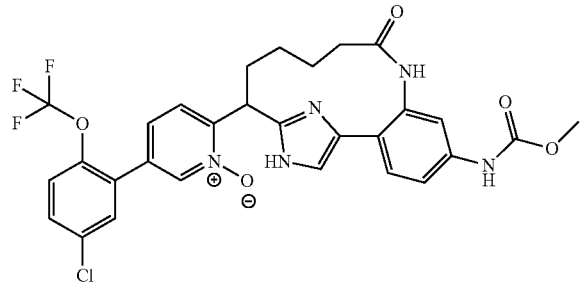 [SMILES: COC(=O)Nc1ccc2c(c1)NC(=O)CCCCC(c1ccc(-c3cc(Cl)ccc3OC(F)(F)F)c[n+]1[O-])c1nc-2c[nH]1]

Example 99 was prepared by the procedure described in the synthesis of Example 96. The product was purified by reverse phase HPLC (YMC-Actus Pro C18, 150×30 mm, MeCN/water (0.1% TFA), 40 mL/min) to give the title compound. MS (ESI) m/z 616.2 (M+H).

A racemic sample of Example 99 was subjected to chiral separation by SFC (AS-H, 250×21 mm, 40% ethanol (0.05% DEA)/$CO_2$, 60 mL/min) to give Example 99-a (faster eluting) and Example 99-b (second eluting). MS (ESI) m/z 616.1 (M+H); $^1$H NMR (400 MHz, CD$_3$OD): δ 8.53 (s, 1H), 7.74-7.54 (m, 5H), 7.53-7.43 (m, 2H), 7.38 (d, J=7.9 Hz, 1H), 7.14 (s, 1H), 4.95 (d, J=5.1 Hz, 1H), 3.74 (s, 3H), 2.56-2.24 (m, 3H), 2.23-2.09 (m, 1H), 2.08-1.93 (m, 1H), 1.73-1.57 (m, 1H), 1.31-1.14 (m, 2H).

Example 100, 100-a, 100-b (Z)-5-(3-Chloro-6-(difluoromethoxy)-2-fluorophenyl)-2-(2$^4$-((methoxycarbonyl)amino)-4-oxo-1$^1$H-3-aza-1(4,2)-imidazola-2(1,2)-benzenacyclononaphane-9-yl)pyridine 1-oxide

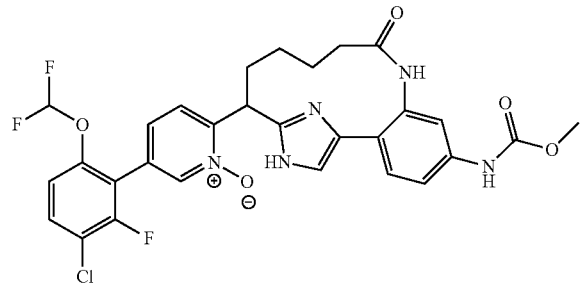 [SMILES: COC(=O)Nc1ccc2c(c1)NC(=O)CCCCC(c1ccc(-c3c(OC(F)F)ccc(Cl)c3F)c[n+]1[O-])c1nc-2c[nH]1]

100A: (Z)-5-(3-Chloro-6-(difluoromethoxy)-2-fluorophenyl)-2-(2$^4$-((methoxycarbonyl)amino)-4-oxo-1-((2-(trimethylsilyl)ethoxy)methyl)-1$^1$H-3-aza-1(4,2)-imidazola-2(1,2)-benzenacyclononaphane-9-yl) pyridine 1-oxide

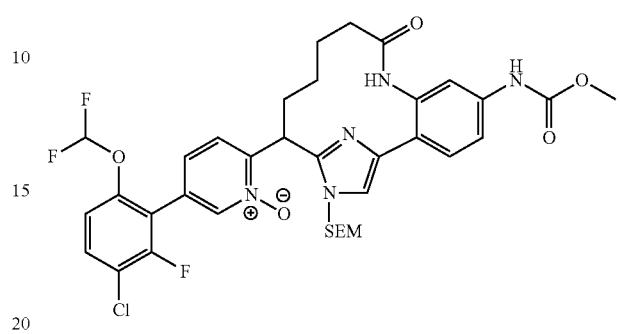

The title compound was prepared by the procedure described in the synthesis of 96C. The product was purified by flash column chromatography (eluting with MeOH/$CH_2Cl_2$=5%). MS (ES+) m/z: 746 (M+H).

Example 100, 100-a and 100-b

A mixture of 100A (89 mg, 0.119 mmol), HCl (4 N in dioxane) (1.2 mL, 4.77 mmol) and water (0.298 mL) was stirred at 50° C. for 2 h. It was cooled to rt and most solvent was removed under reduced pressure. The residue was purified by flash column chromatography (eluting with MeOH/$CH_2Cl_2$=7%) to give the title compound. MS (ES+) m/z: 616 (M+H).

A racemic sample of Example 100 was subjected to chiral separation by SFC (IC, 21×250 mm, 48% MeOH/$CO_2$, 100 bar, 60 mL/min, 35° C.) to afford Example 100-a (faster eluting) and Example 100-b (slower eluting). MS (ES+) m/z: 616(M+H).

Example 101, 101-a, 101-b (Z)-5-(2-(Difluoromethoxy)-6-fluorophenyl)-2-(2$^4$-((methoxycarbonyl)amino)-4-oxo-1$^1$H-3-aza-1(4,2)-imidazola-2(1,2)-benzenacyclononaphane-9-yl) pyridine 1-oxide

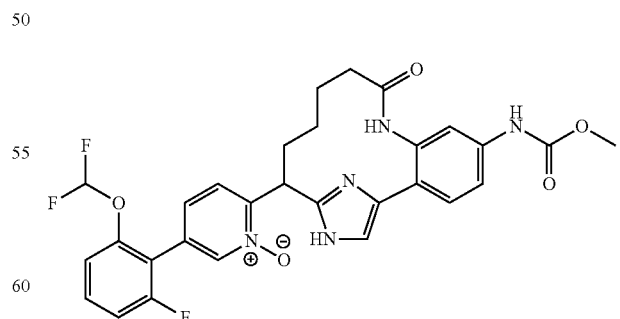

Example 101 was prepared by the procedure described in the synthesis of Example 100. MS (ES+) m/z: 582(M+H).

A racemic sample of Example 101 was subjected to chiral separation by SFC (OJ, 30×250 mm, 45% MeOH+0.2%

DEA/CO₂, 100 bar, 70 mL/min, 35° C.) to afford Example 101-a (faster eluting) and Example 101-b (slower eluting). MS (ES⁺) m/z: 582 (M+H).

Example 102, 102-a, 102-b (Z)-5-(5-Chloro-2-(difluoromethoxy)phenyl)-2-(2⁴-((methoxycarbonyl)amino)-4-oxo-1¹H-3-aza-1(4,2)-imidazola-2(1,2)-benzenacyclononaphane-9-yl)pyridine 1-oxide

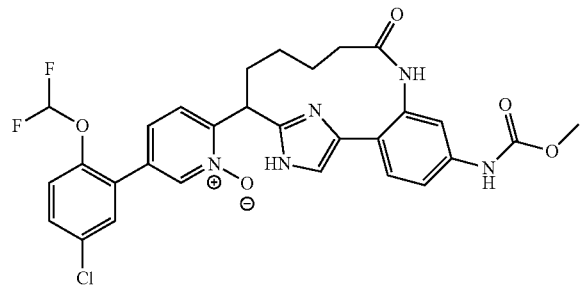 [SMILES: COC(=O)Nc1ccc2c(c1)NC(=O)CCCCC(c1ccc(-c3cc(Cl)ccc3OC(F)F)c[n+]1[O-])c1nc-2c[nH]1]

102A: Methyl (Z)-(9-(5-(5-chloro-2-(difluoromethoxy)phenyl)pyridin-2-yl)-4-oxo-1-((2-(trimethylsilyl)ethoxy)methyl)-1¹H-3-aza-1(4,2)-imidazola-2(1,2)-benzenacyclononaphane-2⁴-yl)carbamate

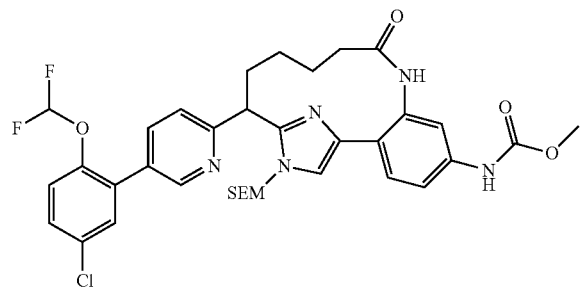 [SMILES: COC(=O)Nc1ccc2c(c1)NC(=O)CCCCC(c1ccc(-c3cc(Cl)ccc3OC(F)F)cn1)c1nc-2cn1COCC[Si](C)(C)C]

The title compound was prepared by the procedure described in the synthesis of 96B. MS (ESI) m/z 712 (M+H).

102B: Methyl (Z)-(9-(5-(5-chloro-2-(difluoromethoxy)phenyl)pyridin-2-yl)-4-oxo-1H-3-aza -1(4,2)-imidazola-2(1,2)-benzenacyclononaphane-2⁴-yl)carbamate

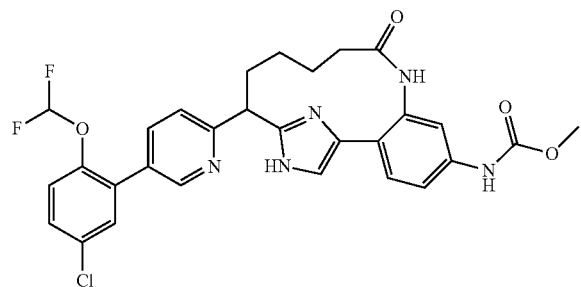 [SMILES: COC(=O)Nc1ccc2c(c1)NC(=O)CCCCC(c1ccc(-c3cc(Cl)ccc3OC(F)F)cn1)c1nc-2c[nH]1]

102A (2.82 g, 3.96 mmol) were dissolved in HCl (4 M in dioxane) (36 ml, 144 mmol) and water (3.60 ml). The solution was stirred at 50° C. for 3 h. It was cooled to rt and most solvent was removed under reduced pressure. The residue was slowly added to a stirring mixture of ice (30 g) and saturated aqueous sodium carbonate (30 mL). Solids precipitated out and the mixture was aged overnight. The solid was collected by filtration and rinsed with water (2×20 mL) and diethyl ether (20 mL). It was air-dried to give the title compound. MS (ESI) m/z 581.9 (M+H).

Example 102

To a solution of 102B (1.85 g, 3.18 mmol) in 16 mL of acetic acid was added peracetic acid (39% solution in acetic acid) (16 mL, 96 mmol). The solution was stirred at rt for 6 h. It was slowly added to a stirred mixture of ice (500 g), saturated sodium carbonate (100 mL) and saturated sodium thiosulfate (100 mL). Precipitates were formed and aged for 1 h before filtration. The gray solids were collected and purified by flash column chromatography (0-10% methanol in DCM) to give the title compound. MS (ES⁺) m/z: 598.0 (M+H).

A racemic sample of Example 102 was subjected to chiral separation by SFC (Kromasil-5, 30×250 mm, 60% MeOH-MeCN (2:1)/CO₂, 100 bar, 70 mL/min, 35° C.) to afford Example 102-a (slower eluting) and Example 102-b (faster eluting). MS (ES+) m/z: 582 (M+H). ¹H NMR (500 MHz, DMSO-d₆): δ 12.13 (s, 1H), 11.85 (s, 1H), 9.66 (s, 1H), 8.51 (s, 1H), 7.77 (s, 1H), 7.63 (m, 1H), 7.57 (m, 1H), 7.50-7.40 (m, 2H), 7.38-7.25 (m, 4H), 7.22 (t, J=73.5 Hz, 1 H), 4.82 (t, J=8.0 Hz, 1 H), 3.64 (s, 3 H), 2.47 (m, 1H), 2.25 (m, 2H), 2.01 (m, 1H), 1.87 (m, 1H), 1.57 (m, 1H), 1.46 (m, 1H), 1.14 (m, 1H).

Example 103, 103-a, 103-b (Z)-5-(3-Chloro-2,6-difluoro-4-iodophenyl)-2-(2⁴-((methoxycarbonyl)amino)-4-oxo-1¹H-3-aza-1(4,2)-imidazola-2(1,2)-benzenacyclononaphane-9-yl)pyridine 1-oxide

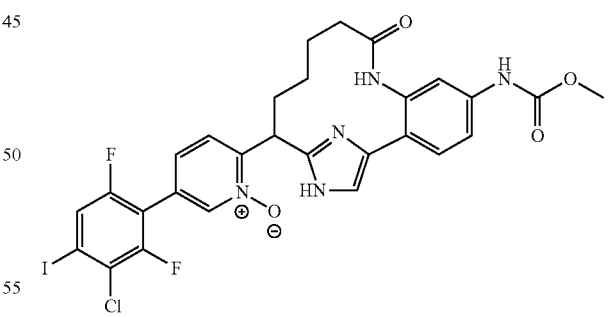

103A: 4-Bromo-2-chloro-3,5-difluoroaniline

A mixture of 4-bromo-3,5-difluroaniline (400 mg, 1.923 mmol) and NCS (257 mg, 1.923 mmol) in DMF (3.8 mL) was stirred at 60° C. for 90 min. It was diluted with diethyl ether (40 mL), washed with water (20 mL), and brine (20 mL). The organic layer was dried over magnesium sulfate, filtered and the solvent was evaporated under reduced pressure. The residue was purified by flash column chromatography (eluting with EtOAc/hexane=50%) to give the title compound. MS (ES+) m/z: 242, 244 (M+H).

103B: Methyl (Z)-(9-(5-(4-amino-3-chloro-2,6-difluorophenyl)pyridin-2-yl)-4-oxo-1¹-((2-(trimethylsilyl)ethoxy)methyl)-1¹H-3-aza-1(4,2)-imidazola-2(1,2)-benzenacyclononaphane-2⁴-yl)carbamate

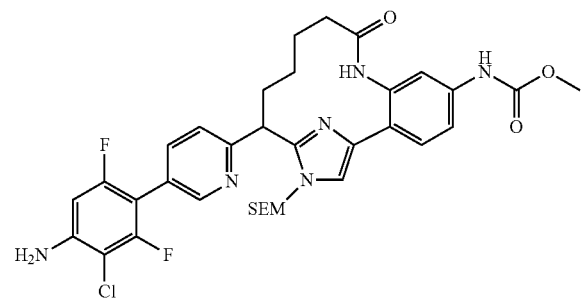 [SMILES: COC(=O)Nc1ccc2c(c1)NC(=O)CCCCC(c1ccc(-c3c(F)cc(N)c(Cl)c3F)cn1)c1nc-2cn1COCC[Si](C)(C)C]

The title compound was prepared from Intermediate 55 and 109A by the procedure described in the synthesis of 102B. MS (ES+) m/z: 698 (M+H).

103C: Methyl (Z)-(9-(5-(3-chloro-2,6-difluoro-4-iodophenyl)pyridin-2-yl)-4-oxo-1¹-((2-(trimethylsilyl)ethoxy)methyl)-1¹H-3-aza-1(4,2)-imidazola-2(1,2)-benzenacyclononaphane-2⁴-yl)carbamate

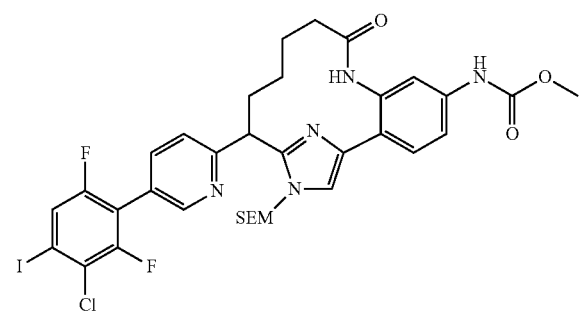 [SMILES: COC(=O)Nc1ccc2c(c1)NC(=O)CCCCC(c1ccc(-c3c(F)cc(I)c(Cl)c3F)cn1)c1nc-2cn1COCC[Si](C)(C)C]

A mixture of sodium nitrite (0.252 mL, 0.252 mmol), 103B (160 mg, 0.229 mmol), hydrochloric acid (37% wt, 1.5 mL), water (3.00 mL) and acetonitrile (3 mL) was stirred at 0° C. for 10 min. Aqueous KI (1 M, 0.241 mL, 0.241 mmol) was added to the mixture and stirred at rt for 1 h. Aqueous potassium carbonate (10% wt, 1 mL) and aqueous sodium thiosulfate (saturated, 1 mL) were added. The pH of the solution was adjusted to 8 by addition of aqueous sodium carbonate (10%). Yellow precipitate was formed and aged for 1 h. Solids were collected by filtration and air-dried. The crude product was purified by flash column chromatography (eluting with MeOH/CH₂Cl₂=7%) to give the title compound. MS (ES+) m/z: 808 (M+H).

Example 103, 103-a and 103-b

Example 103 was prepared from 103C by the procedures in the synthesis of Example 102. The product was purified by flash column chromatography (eluting with MeOH/CH₂Cl₂=5%) to give the title compound. MS (ES+) m/z: 694 (M+H).

A sample of racemic Example 103 was subjected to chiral separation by SFC (OJ, 21×250 mm, 25% MeOH (0.2% NH₄OH)/CO₂, 100 bar, 60 mL/min, 35° C.) to afford the Example 103-a (faster eluting) and Example 103-b (slower eluting). MS (ES+) m/z: 694 (M+H).

Example 104, 104-a and 104-b ((Z)-9-(5-(3-chloro-2,6-difluorophenyl)pyridin-2-yl)-2⁵-fluoro-¹H-3-aza -1(4,2)-imidazola-2(1,2)-benzenacyclononaphan-4-one

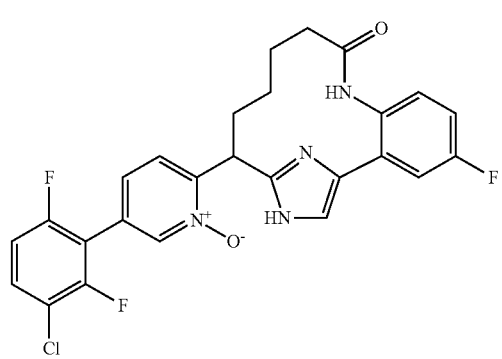 [SMILES: O=C1CCCCC(c2ccc(-c3c(F)ccc(Cl)c3F)c[n+]2[O-])c2nc(c[nH]2)-c2cc(F)ccc2N1]

104A: (1²Z,8Z)-9-(5-bromopyridin-2-yl)-2⁵-fluoro-1¹-((2-(trimethylsilyl)ethoxy)methyl)-1H-3-aza-1(4,2)-imidazola-2(1,2)-benzenacyclononaphan-8-en-4-one

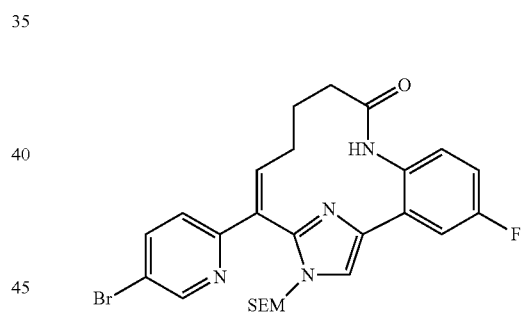

The title compound was prepared from Intermediate 15 and Intermediate 18 by the procedure described in the synthesis of 12C. It was purified by flash column chromatography on silica gel (eluting with petroleum ether:EtOAc=5:1 v/v). MS (ES+) m/z: 557, 559 (M+H).

Example 104

Example 104 was prepared from 104A by the procedure described in the synthesis of Example 96. The product was purified by reverse phase HPLC. MS (ES+) m/z: 513 (M+H).

A sample of the racemic product was subjected to chiral separation with SFC (AS-H, 4.6×150 mm, 5 um; ethanol (0.05% diethylamine)/CO₂ gradient; 3 mL/min, 40° C.) to afford Example 104-a (faster eluting) and Example 104-b (slower eluting). MS (ES+) m/z: 513 (M+H); ¹H NMR (CD₃OD, 400 MHz): δ 8.57 (s, 1H), 7.97 (d, J=8.4 Hz, 1H), 7.81 (d, J=8.4 Hz, 1H), 7.68 (dt, J=6.0, 8.6 Hz, 1H), 7.54 (s, 1H), 7.43 (dd, J=2.3, 8.5 Hz, 1H), 7.38-7.27 (m, 2H), 7.23 (t, J=8.5 Hz, 1H), 5.00-4.96 (m, 1H), 2.57 (d, J=12.8 Hz, 1H), 2.36 (d, J=3.7 Hz, 2H), 2.16 (t, J=12.1 Hz, 1H), 1.88 (q, J=12.1 Hz, 1H), 1.75-1.50 (m, 2H), 1.12 (m, 1H).

Example 105, 105-a, 105-b (Z)-5-(5-Chloro-2-(4-(difluoromethyl)-1H-1,2,3-triazol-1-yl)phenyl)-2-(2⁵-fluoro-4-oxo-1¹H-3-aza-1(4,2)-imidazola-2(1,2)-benzenacyclononaphane-9-yl)pyridine 1-oxide

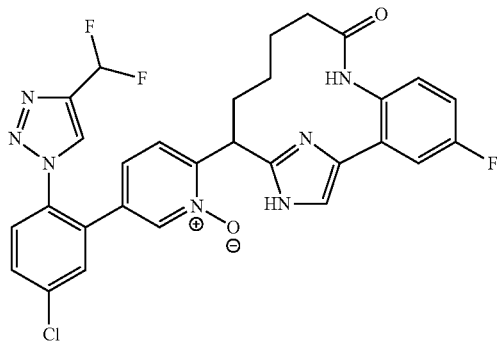 [SMILES: O=C1CCCCC(c2ccc(-c3cc(Cl)ccc3-n3cc(C(F)F)nn3)c[n+]2[O-])c2nc(c[nH]2)-c2cc(F)ccc2N1]

105A: (1²Z,8Z)-9-(5-(5-Chloro-2-(4-(difluoromethyl)-1h-1,2,3-triazol-1-yl)phenyl)pyridin-2-yl)-2⁵-fluoro-1¹-((2-(trimethylsilyl)ethoxy)methyl)-1H-3-aza-1(4,2)-imidazola-2(1,2)-benzenacyclononaphan-8-en-4-one

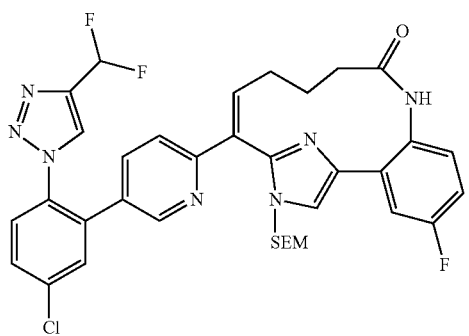 [SMILES: C[Si](C)(C)CCOCn1cc2nc1/C(c1ccc(-c3cc(Cl)ccc3-n3cc(C(F)F)nn3)cn1)=C\CCCC(=O)Nc1ccc(F)cc1-2]

To a solution of 104A (230 mg, 0.413 mmol) and Intermediate 46 (194 mg, 0.495 mmol) in toluene (10 mL), K₃PO₄ (175 mg, 0.835 mmol) and Ad₂nBuP Biphenyl Precatalyst (55.2 mg, 0.083 mmol) were added in a glove box under nitrogen. The resulting mixture was stirred at 80° C. under nitrogen for 18 h. It was allowed to cool to rt and the mixture was extracted with EtOAc (3×10 mL). The combined organic layers were washed with brine (10 mL), dried over sodium sulfate, filtered and concentrated under reduced pressure. The residue was purified by TLC (petroleum ether:EtOAc=2:1) to give the title compound. MS (ES⁺) m/z: 706 (M+H).

Example 105

Example 105 was prepared from 105A by the procedures described in the synthesis of Example 96. The product was purified by reverse phase HPLC to give the title compound. MS (ES⁺) m/z: 594 (M+H).

A sample of Example 105 was subjected to chiral separation by SFC (Lux Cellulose-2, 30×250 mm, 45% EtOH/CO₂; 80 mL/min) to give Example 105-a (faster eluting) and Example 105-b (slower eluting). MS (ES⁺) m/z: 594 (M+H); ¹H NMR: (CD₃OD, 400 MHz): δ 8.54 (s, 1H), 8.26 (m, 1H), 7.72-7.81 (m, 2H), 7.65-7.72(m, 1H), 7.50 (m, 2H), 7.27-7.38 (m, 2H), 7.20 (d, J=7.0 Hz, 1H), 6.81-7.13 (m, 2H), 2.58 (m, 1H), 2.24-2.50 (m, 2H), 1.87-2.15 (m, 2H), 1.45-1.69 (m, 2H), 1.12 (m, 1H), 0.79-1.01 (m, 1H).

Example 106, 106-a, 106-b (Z)-2-(2⁵-carboxy-4-oxo-1¹H-3-aza-1(4,2)-imidazola-2(1,2)-benzenacyclononaphane-9-yl)-5-(3-chloro-2,6-difluorophenyl)pyridine 1-oxide

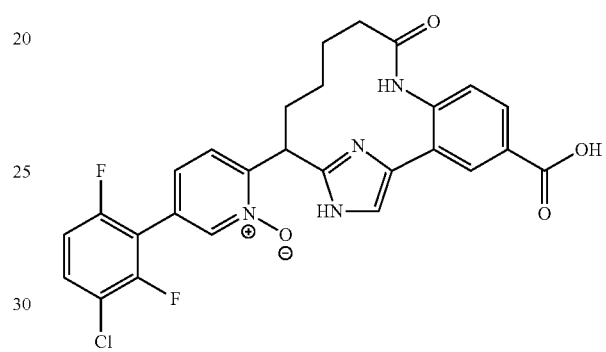

106A: (Z)-5-(3-Chloro-2,6-difluorophenyl)-2-(2⁵-(methoxycarbonyl)-4-oxo-1¹H-3-aza-1(4,2)-imidazola-2(1,2)-benzenacyclononaphane-9-yl)pyridine 1-oxide

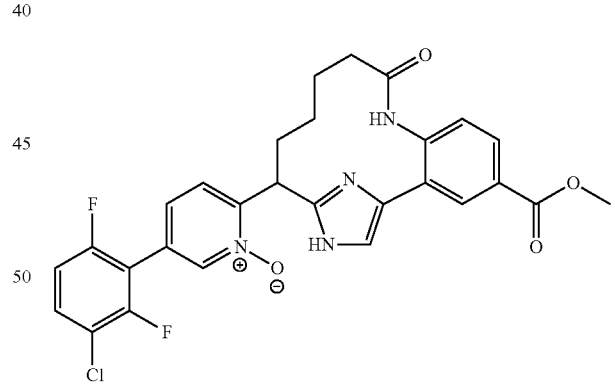

The title compound was prepared from Intermediate 15 and Intermediate 20 by the procedure described in the synthesis of Example 96. MS (ES⁺) m/z: 553 (M+H).

Example 106

To a solution of 106A (100 mg, 0.181 mmol) in THF/H₂O (5:1, 5 mL) was added LiOH (13 mg, 0.543 mmol) at 25° C. The mixture was stirred at 25° C. for 12 h and it was concentrated under reduced pressure. The residue was purified by reverse phase HPLC to give the title compound. MS (ES⁺) m/z: 539 (M+H).

A sample of Example 106 was subjected to chiral separation by SFC (AD, 30 mm×250 mm, 10 um; 45% IPA/CO₂, 100 bar, 40° C.) to give Example 106-a (slower eluting) and Example 106-b (faster eluting). MS (ES⁺) m/z: 539 (M+H); ¹H NMR: (CD₃OD, 400 MHz): δ 8.57 (s, 1H), 8.22 (s, 1H), 7.83-7.96 (m, 2H), 7.57-7.70 (m, 3H), 7.35 (s, 1H), 7.18 (t, J=8.6 Hz, 1H), 5.02 (dd, J=3.7, 11.2 Hz, 1H), 3.90 (td, J=6.2, 12.2 Hz, 1H), 2.33-2.61 (m, 3H), 2.06-2.28 (m, 2H), 1.76 (m, 1H), 1.57 (m, 1H), 1.38 (m, 1H), 1.26 (m, 2H), 1.13 (d, J=6.3 Hz, 3H).

Example 107 (racemate), 107-a and 107-b (Z)-5-(5-Chloro-2-(1H-tetrazol-1-yl)phenyl)-2-(2⁵-fluoro-9-hydroxy-4-oxo-1¹H-3-aza-1(4,2)-imidazola-2(1,2)-benzenacyclononaphane-9-yl)pyridine 1-oxide

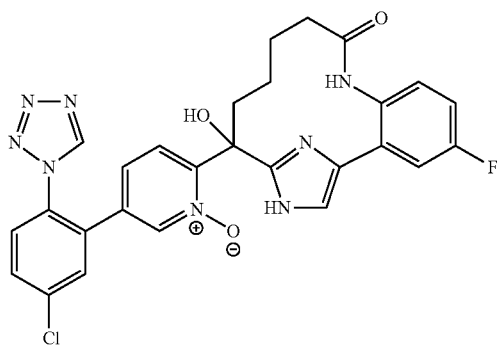 [SMILES: O=C1CCCCC(O)(c2ccc(-c3cc(Cl)ccc3-n3cnnn3)c[n+]2[O-])c2nc(c[nH]2)-c2cc(F)ccc2N1]

107A: 1-(5-Bromopyridin-2-yl)-1-(4-iodo-1-((2-(trimethylsilyl)ethoxy)methyl)-1H-imidazol-2-yl)but-3-en-1-ol To a solution of Intermediate 15 (3.2 g, 6.30 mmol) in THF (40 mL) at −40° C., a solution of allylmagnesium bromide (1 M in THF, 12.59 mL, 12.59 mmol) was added dropwise. The mixture was stirred for 10 min and it was warmed to 0° C. with stirring for 30 min. It was quenched with saturated aqueous ammonium chloride (20 mL) and extracted with EtOAc (100 mL). The organic layer washed with brine, dried over sodium sulfate and filtered. The filtrate was concentrated and the residue was purified by flash column chromatography on silica gel (eluting with petroleum ether/ethyl acetate=20:1 v/v) to afford the title compound. MS (ES⁺) m/z: 550, 552 [M+H].

107B: 1-(4-(2-Amino-5-fluorophenyl)-1-((2-(trimethylsilyl)ethoxy)methyl)-1H-imidazol-2-yl)-1-(5-bromopyridin-2-yl)but-3-en-1-ol The title compound was prepared from 107A by the procedure described in the synthesis of 12A. It was purified by flash column chromatography on silica gel (eluting with petroleum ether:EtOAc=30:1 to 5:1 v/v). MS (ES⁺) m/z: 533, 535 [M+H].

107C: N-(2-(2-(1-(5-Bromopyridin-2-yl)-1-hydroxybut-3-en-1-yl)-1-((2-(trimethylsilyl)ethoxy)methyl)-1H-imidazol-4-yl)-4-fluorophenyl)but-3-enamide The title compound was prepared from 107B by the procedure described in the synthesis of 1C. The crude product was purified by flash column chromatography on silica gel (eluting with 0-30% ethyl acetate in petroleum ether, gradient). MS (ES⁺) m/z: 601, 603 [M+H].

107D: (12Z,6E)-9-(5-Bromopyridin-2-yl)-2⁵-fluoro-9-hydroxy-1₁-((2-(trimethylsilyl)ethoxy)methyl)-1¹H-3-aza-1(4,2)-imidazola-2(1,2)-benzenacyclononaphan-6-en-4-one

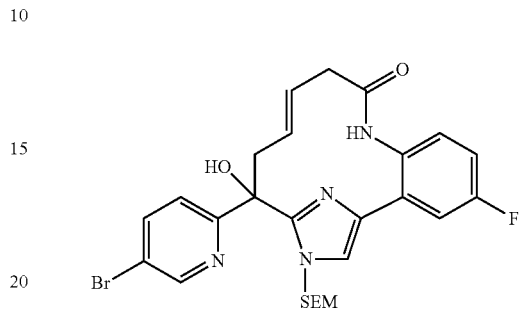

A solution of 107C (280 mg, 0.465 mmol) and Grubbs II catalyst ((1,3-Bis(2,4,6-trimethylphenyl)-2-imidazolidinylidene)dichloro(phenylmethylene)(tricyclohexylphosphine) ruthenium) (158 mg, 0.186 mmol) in DCE (degassed, 15 mL) was stirred at 120° C. under nitrogen for 30 min in a microwave reactor. Most solvent was removed under reduced pressure and the residue was purified by flash column chromatography on silica gel (eluting with petroleum ether:ethyl acetate=10:1 to 2:1 v/v) to give the title compound. MS (ES⁺) m/z: 573, 575 [M+H].

107E: tert-Butyl (4-Chloro-2-(6-((1²Z,6E)-2⁵-fluoro-9-hydroxy-4-oxo-1¹-((2-(trimethylsilyl)ethoxy)methyl)-1¹H-3-aza-1(4,2)-imidazola-2(1,2)-benzenacyclononaphan-6-en-9-yl)pyridin-3-yl)phenyl)carbamate

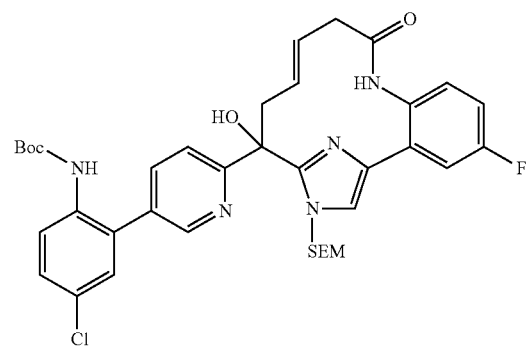 [SMILES: CC(C)(C)OC(=O)Nc1ccc(Cl)cc1-c1ccc(C2(O)C/C=C/CC(=O)Nc3ccc(F)cc3-c3cn(COCC[Si](C)(C)C)c2n3)nc1]

A mixture of 107D (120 mg, 0.209 mmol), Intermediate 40 (89 mg, 0.251 mmol), PdCl₂(dppf) (15.3 mg, 0.021 mmol), K₂CO₃ (72.3 mg, 0.523 mmol) in THF (8 mL) and water (2 mL) was stirred at 65° C. under nitrogen for 2 h. It was cooled to rt and diluted with water (10 mL). The mixture was extracted with EtOAc (30 mL×3). The combined organic layers were washed with water (20 mL) and brine (20 mL), dried over anhydrous sodium sulfate, filtered and concentrated. The residue was purified by prep-TLC (silica gel, petroleum:EtOAc=2:1 v/v) to give the title compound. MS (ES⁺) m/z: 720 [M+H].

107F: tert-Butyl (Z)-(4-chloro-2-(6-(2⁵-fluoro-9-hydroxy-4-oxo-1¹-((2-(trimethylsilyl)ethoxy)methyl)-1¹H-3-aza-1(4,2)-imidazola-2(1,2)-benzenacyclononaphane-9-yl)pyridin-3-yl)phenyl)carbamate

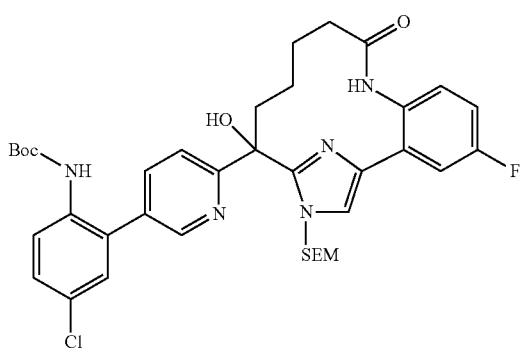 [SMILES: CC(C)(C)OC(=O)Nc1ccc(Cl)cc1-c1ccc(C2(O)CCCCC(=O)Nc3ccc(F)cc3-c3cn(COCC[Si](C)(C)C)c2n3)nc1]

A mixture of 107E (450 mg, 0.625 mmol) and Raney-nickel (3.67 mg, 0.062 mmol) in THF (5 mL) was stirred under hydrogen (1 atm) for 18 h. It was filtered through a pad of Celite and the solids were rinsed with DCM. The filtrate was concentrated to afford the title compound. It was used in the next step without further purification. MS (ES⁺) m/z: 722 [M+H].

107G: (Z)-9-(5-(2-Amino-5-chlorophenyl)pyridin-2-yl)-2⁵-fluoro-9-hydroxy-1¹-((2-(trimethylsilyl)ethoxy)methyl)-1¹H-3-AZA-1(4,2)-imidazola-2(1,2)-benzenacyclononaphan-4-one

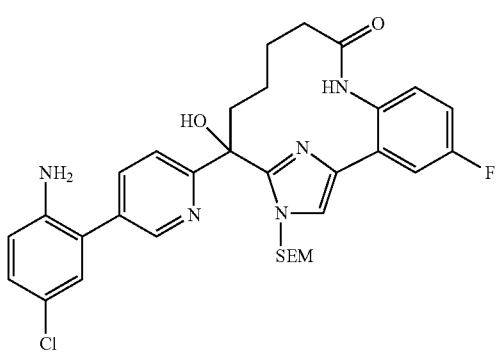 [SMILES: C[Si](C)(C)CCOCn1cc2nc1C(O)(c1ccc(-c3cc(Cl)ccc3N)cn1)CCCCC(=O)Nc1ccc(F)cc1-2]

Compound 107F (400 mg, 0.554 mmol) was treated with trifluoroacetic acid (1 mL, 12.98 mmol) in DCM (5 mL) at 20° C. for 3 h. Most solvent was removed under reduced pressure and the residue was diluted with DCM. The solution was carefully quenched with saturated aqueous sodium carbonate (20 mL). The mixture was extracted with DCM (20 mL×3). The combined organic layers were washed with brine, dried over sodium sulfate, and filtered. The filtrate was concentrated to afford the title compound. It was used in next step without further purification. MS (ES⁺) m/z: 622 [M+H].

107H: (Z)-9-(5-(5-Chloro-2-(1H-tetrazol-1-yl)phenyl)pyridin-2-yl)-2⁵-fluoro-9-hydroxy-1¹-((2-(trimethylsilyl)ethoxy)methyl)-1¹H-3-aza-1(4,2)-imidazola-2(1,2)-benzenacyclononaphan-4-one

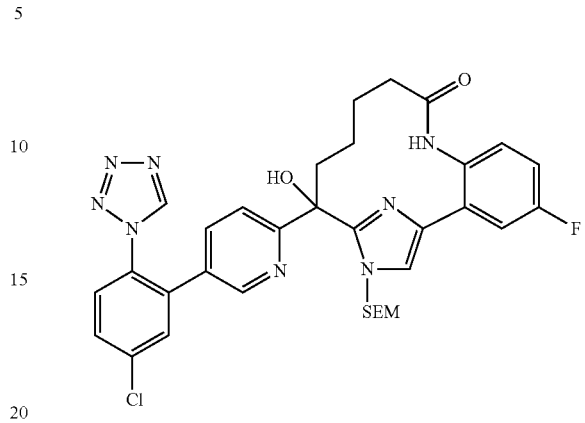

To a solution of 107G (345 mg, 0.554 mmol) in AcOH (3 mL) was added trimethyl orthoformate (1.23 mL, 11.09 mmol) and sodium azide (721 mg, 11.09 mmol) at rt. The mixture was stirred for 12 h. It was quenched with saturated aqueous sodium carbonate (30 mL), and extracted with EtOAc (40 mL×3). The combined organic layers were washed with brine, dried over sodium sulfate and filtered. The filtrate was concentrated under reduced pressure and the residue was purified by prep-TLC (silica gel, petroleum ether:ethyl acetate=1:2 v/v) to afford the title compound. MS (ES⁺) m/z: 675 [M+H].

107I: (Z)-5-(5-Chloro-2-(1H-tetrazol-1-yl)phenyl)-2-(2⁵-fluoro-9-hydroxy-4-oxo-1¹-((2-(trimethylsilyl)ethoxy)methyl)-1¹H-3-aza-1(4,2)-imidazola-2(1,2)-benzenacyclononaphane-9-yl)pyridine 1-oxide

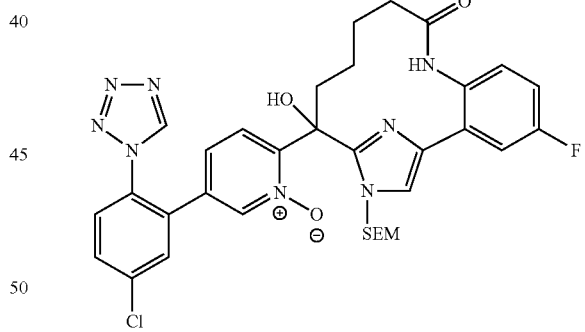

A mixture of 107H (90 mg, 0.133 mmol) in peracetic acid (10% in acetic acid, 2 mL, 0.133 mmol) was stirred at 25° C. for 16 h. The mixture was quenched with saturated aqueous Na₂SO₃ and pH of the mixture was adjusted to about 7 by saturated aqueous Na₂CO₃. The mixture was extracted with EtOAc (10 mL×3). The combined organic phase was dried over sodium sulfate, filtered, and concentrated under reduced pressure to give the title compound. It was used in the next step without further purification. MS (ES⁺) m/z: 691 [M+H].

Example 107

To a solution of 107I (110 mg, 0.064 mmol) in DCM (2 mL), (R)-2-amino-3-mercaptopropanoic acid (38.6 mg, 0.318 mmol) and TFA (2 mL, 26.0 mmol) was added at 20° C. The mixture was stirred for 4 h. It was neutralized with 30% aqueous ammonia (5 mL) and stirred for another 30 min at 0° C. The mixture was extracted with EtOAc (20 mL×3). The combined organic layers were dried over sodium sulfate, filtered and concentrated. The residue was purified by HPLC to give the racemic compound. MS (ES+) m/z: 561 [M+H].

A sample of the racemic Example 107 was subjected to chiral separation by SFC (OD, 50×4.6 mm, 40% of methanol (0.05% diethylamine) in $CO_2$, 4 mL/min, 40° C.) to afford Example 107-a (faster eluting) and Example 107-b (slower eluting). LCMS (ESI) m/z: 561.2 [M+H+]; $^1$H NMR: ($CD_3OD$, 400 MHz): δ 9.43 (s, 1H), 8.35 (s, 1H), 7.91 (d, J=5.2 Hz, 1H), 7.80-7.70 (m, 3H), 7.54 (s, 1H), 7.45-7.30 (m, 4H), 2.66 (m, 1H), 2.47 (m, 1H), 2.33 (m, 2H), 1.95 (m, 1H), 1.50-1.11 (m, 3H).

Example 108, 108-a, 108-b (Z)-2-($2^4$-Amino-4-OXO-$1^1$H-3-aza-1(4,2)-imidazola-2(1,2)-benzenacyclononaphane-9-yl)-5-(3-chloro-2,6-difluorophenyl)pyridine 1-oxide

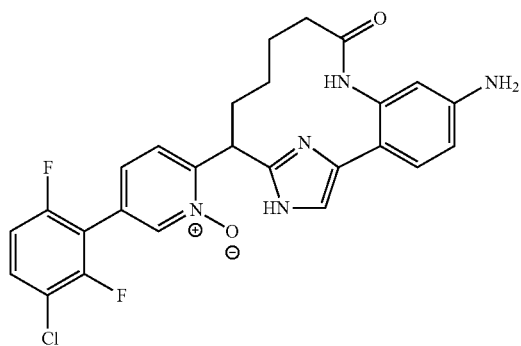 [SMILES: Nc1ccc2c(c1)NC(=O)CCCCC(c1ccc(-c3c(F)ccc(Cl)c3F)c[n+]1[O-])c1nc-2c[nH]1]

108A: tert-Butyl (Z)-(9-(5-(3-chloro-2,6-difluorophenyl)pyridin-2-yl)-4-oxo-$1^1$-((2-(trimethylsilyl)ethoxy)methyl)-$1^1$H-3-aza-1(4,2)-imidazola-2(1,2)-benzenacyclononaphane-$2^4$-yl)carbamate

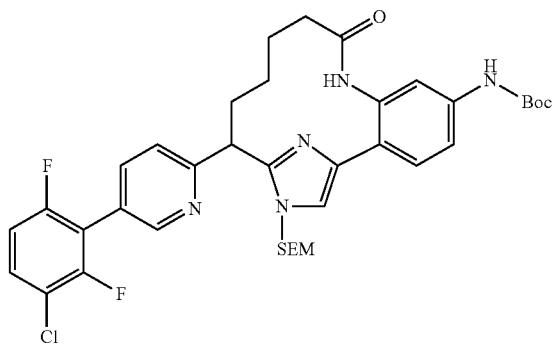 [SMILES: CC(C)(C)OC(=O)Nc1ccc2c(c1)NC(=O)CCCCC(c1ccc(-c3c(F)ccc(Cl)c3F)cn1)c1nc-2cn1COCC[Si](C)(C)C]

The title compound was prepared from Intermediate 15 and Intermediate 40 by the procedure described in the synthesis of 102B. MS (ESI) m/z 724.3 (M+H).

108B: (Z)-2-($2^4$-((tert-Butoxycarbonyl)amino)-4-oxo-$1^1$-((2-(trimethylsilyl)ethoxy)methyl)-$1^1$H-3-aza-1(4,2)-imidazola-2(1,2)-benzenacyclononaphane-9-yl)-5-(3-chloro-2,6-difluorophenyl)pyridine 1-oxide

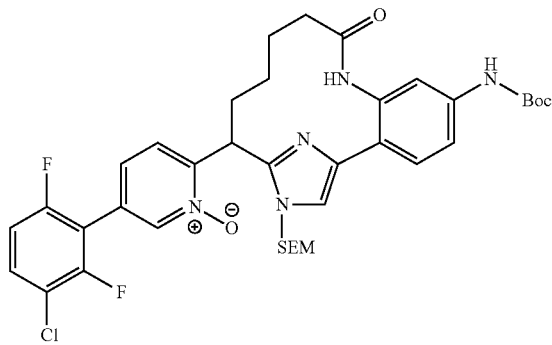 [SMILES: CC(C)(C)OC(=O)Nc1ccc2c(c1)NC(=O)CCCCC(c1ccc(-c3c(F)ccc(Cl)c3F)c[n+]1[O-])c1nc-2cn1COCC[Si](C)(C)C]

To a solution of 108A (4 g, 5.52 mmol), $NaHCO_3$ (1.39 g, 16.57 mmol) and urea-hydrogen perOXIDE complex (1:1) (1.56 g, 16.57 mmol) in DCM (50 mL) was added 2,2,2-trifluoroacetic anhydride (3.48 g, 16.57 mmol). The mixture was stirred at 25° C. for 1 h. The reaction mixture was poured into a mixture of aqueous sodium bicarbonate (saturated, 100 mL) and aqueous $Na_2SO_3$ (saturated, 100 mL) and was extracted with EtOAc (100 mL×3). The combined organic layers were washed with brine, dried over sodium sulfate, filtered and concentrated under reduced pressure. The residue was purified by reverse-phase HPLC to give the title compound. MS (ESI) m/z 740.2 (M+H).

A racemic sample of 108B was subjected to chiral separation by SFC (Column AD, 250 mm×50 mm, 45% EtOH/$CO_2$, 200 ml/min) to give 108B-a (faster eluting) and 108B-b (slower eluting).

Example 108-a: (R,Z)-2-($2^4$-Amino-4-oxo-$1^1$H-3-aza-1(4,2)-imidazola-2(1,2)-benzenacyclononaphane-9-yl)-5-(3-chloro-2,6-difluorophenyl)pyridine 1-oxide To a stirred mixture of 108B-a (1.5 g, 2.026 mmol) and (R)-2-AMINO-3-mercaptopropanoic acid (1.23 g, 10.13 mmol) in DCM (15 mL) was added TFA (10 mL, 130 mmol). The mixture was stirred at 40° C. for 2 h. Solvent was removed under reduced pressure and the residue was purified by reverse-phase HPLC to give the title compound. MS (ESI) m/z 509.9 (M+H).

Example 108-b: (S,Z)-2-($2^4$-Amino-4-OXO-$1^1$H-3-aza-1(4,2)-imidazola-2(1,2)-benzenacyclononaphane-9-yl)-5-(3-chloro-2,6-difluorophenyl)pyridine 1-oxide Example 108-b was prepared from 108B-b by the procedure described in the synthesis of Example 108-a. The product was purified by reverse-phase HPLC to give the title compound. MS (ESI) m/z 509.9 (M+H); $^1$H NMR (400 MHz, $CDCl_3$): δ 12.71 (brs, 1H), 11.42 (brs, 1H), 8.49 (s, 1H), 7.59-7.46 (m, 4H), 7.28 (s, 1H), 7.06 (dt, J=1.5, 9.0 Hz, 1H), 6.95 (s, 1H), 6.45 (dd, J=2.4, 8.2 Hz, 1H), 4.89 (dd, J=3.4, 12.7 Hz, 1H), 3.78 (s, 2H), 2.83-2.62 (m, 1H), 2.66-2.44 (m, 2H), 2.26 (d, J=8.2 Hz, 1H), 2.15-1.97 (m, 1H), 1.93-1.75 (m, 1H), 1.52-1.42 (m, 2H).

Example 109, 109-a, 109-b (Z)-5-(3-chloro-2,6-difluorophenyl)-2-(2⁴-((ethoxycarbonyl)amino)-4-oxo-1¹H-3-aza-1(4,2)-imidazola-2(1,2)-benzenacyclononaphane-9-yl)pyridine 1-oxide

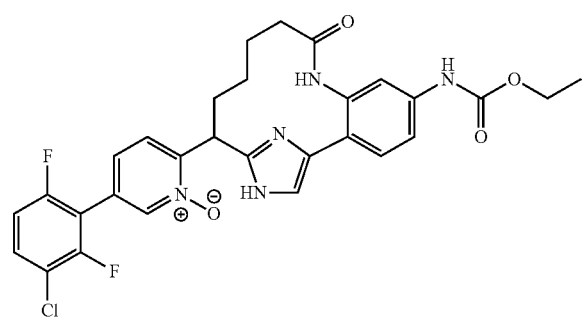 [SMILES: CCOC(=O)Nc1ccc2c(c1)NC(=O)CCCCC(c1ccc(-c3c(F)ccc(Cl)c3F)c[n+]1[O-])c1nc-2c[nH]1]

109A: (Z)-5-(3-Chloro-2,6-difluorophenyl)-2-(2⁴-nitro-4-oxo-1¹-((2-(trimethylsilyl)ethoxy)methyl)-1¹H-3-aza-1(4,2)-imidazola-2(1,2)-benzenacyclononaphane-9-yl)pyridine 1-oxide

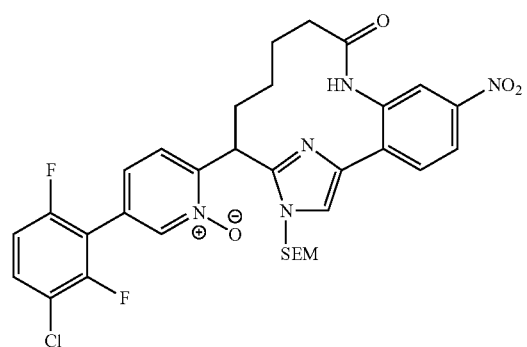 [SMILES: C[Si](C)(C)CCOCn1cc2nc1C(c1ccc(-c3c(F)ccc(Cl)c3F)c[n+]1[O-])CCCCC(=O)Nc1cc([N+](=O)[O-])ccc1-2]

A mixture of 118A (400 mg, 0.55 mmol, 50%) and peracetic acid (15 mL, 8% wt in acetic acid) was stirred at 30° C. for 16 h. The reaction was poured into ice water (200 mL) and saturated aqueous NaHCO₃ was added to adjust pH to 8. Aqueous Na₂SO₃ (sat, 400 mL) was added and the mixture was extracted with EtOAc (800 mL×2). The combined organic layers were washed with brine, dried over sodium sulfate, filtered and the solvent was removed under reduced pressure to give the title compound. MS (ESI) m/z 670.3 (M+H).

109B: (Z)-2-(2⁴-Amino-4-oxo-11-((2-(trimethylsilyl)ethoxy)methyl)-1¹H-3-aza-1(4,2)-imidazola-2(1,2)-benzenacyclononaphane-9-yl)-5-(3-chloro-2,6-difluorophenyl)pyridine 1-oxide)

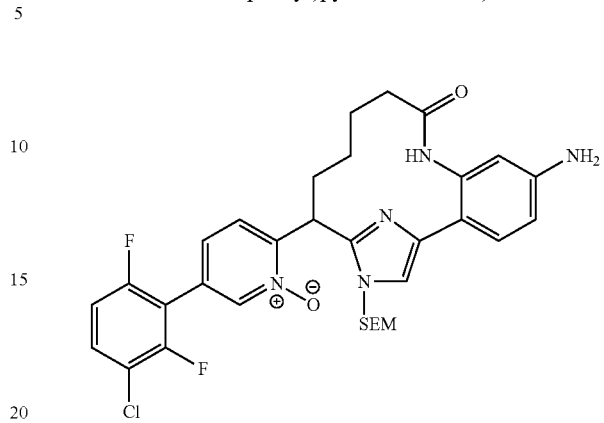

A mixture of 109A (400 mg, 0.30 mmol, 40%), Adam's catalyst (100 mg, 0.44 mmol), EtOAc (10 mL) and MeOH (2 mL) was stirred at 30° C. under H₂ balloon for 1 h. The catalyst was removed by filtration through a pad of Celite. The filtrate was concentrated to give the title compound. MS (ESI) m/z 640.3 (M+H).

109C: (Z)-5-(3-Chloro-2,6-difluorophenyl)-2-(2⁴-((ethoxycarbonyl)amino)-4-oxo-1¹-((2-(trimethylsilyl)ethoxy)methyl)-1¹H-3-aza-1(4,2)-imidazola-2(1,2)-benzenacyclononaphane-9-yl)pyridine 1-oxide

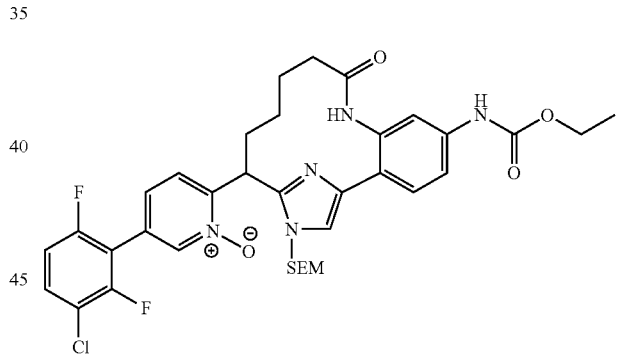

To a stirred mixture of 109B (350 mg, crude), and DIEA (0.12 mL, 0.66 mmol) in DCM (10 mL) at 0° C. was added ethyl chloroformate (47.50 mg, 0.44 mmol) dropwise. The mixture was stirred at 25° C. for 1 h. It was added H₂O (20 mL) and extracted with EtOAc (30 mL×3). The organic layers were dried over sodium sulfate, filtered and concentrated to give the title compound. MS (ESI) m/z 712.2 (M+H).

Example 109

To a stirred mixture of 109C (140 mg, crude) and (R)-2-amino-3-mercaptopropanoic acid (71.60 mg, 0.59 mmol) in DCM (3 mL) was added TFA (3 mL). The mixture was stirred at 40° C. for 2 h. Most solvent was removed under reduced pressure and the residue was purified by reverse-phase HPLC to give the title compound as a solid. MS (ESI) m/z 582.3 (M+H).

A racemic sample of Example 109 was subjected to chiral separation by SFC (Column: AS, 250×30 mm, 50% EtOH/CO$_2$, 70 mL/min) and further purified by reverse-phase HPLC to give Example 109-a (faster eluting) and Example 109-b (slower eluting). MS (ESI) m/z 581.9 (M+H); $^1$HNMR (400 MHz, CD$_3$OD): δ 8.58 (s, 1H), 7.96 (d, J=8.4 Hz, 1H), 7.81 (d, J=8.8 Hz, 1H), 7.68 (dt, J=5.9, 8.7 Hz, 1H), 7.60-7.55 (m, 1H), 7.53-7.48 (m, 1H), 7.46-7.39 (m, 2H), 7.27-7.20 (m, 1H), 4.97 (dd, J=6.4, 11.2 Hz, 1H), 4.22 (q, J=7.0 Hz, 2H), 2.57 (d, J=13.7 Hz, 1H), 2.34 (brs, 2H), 2.26-2.09 (m, 1H), 1.90-1.74 (m, 1H), 1.71-1.49 (m, 2H), 1.32 (t, J=7.1 Hz, 3H), 1.22-0.97 (m, 1H).

Example 110, 110-a, 110-b (Z)-5-(3-Chloro-2,6-difluorophenyl)-2-(1$^5$-chloro-2$^4$-((Methoxycarbonyl)amino)-4-oxo-1$^1$H-3-aza-1(4,2)-imidazola-2(1,2)-benzenacyclononaphane-9-yl)pyridine 1-oxide

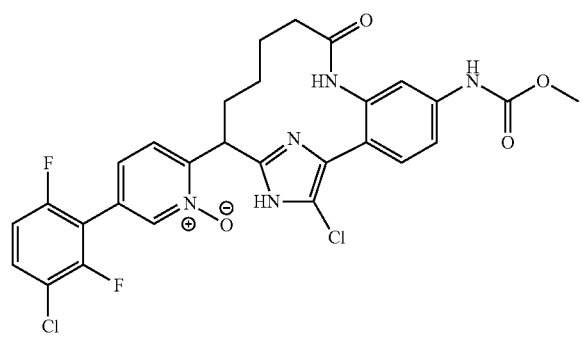 [SMILES: COC(=O)Nc1ccc2c(c1)NC(=O)CCCCC(c1ccc(-c3c(F)ccc(Cl)c3F)c[n+]1[O-])c1nc-2c(Cl)[nH]1]

110A: Methyl (Z)-(1$^5$-chloro-9-(5-(3-chloro-2,6-difluorophenyl)pyridin-2-yl)-4-oxo-1$^1$-((2-(trimethylsilyl)ethoxy)methyl)-1$^1$H-3-aza-1(4,2)-imidazola-2(1,2)-benzenacyclononaphane-2$^4$-yl)carbamate

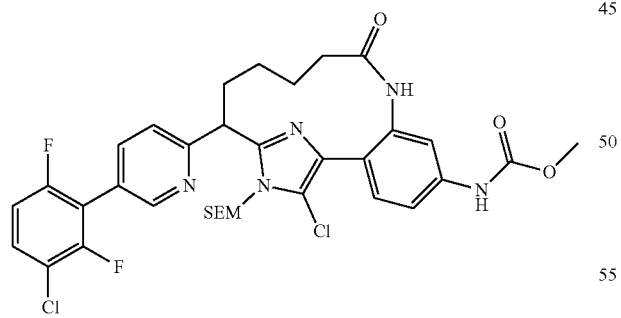

A solution of 96B (100 mg, 0.15 mmol) and 2-chloro-1,3-bis(methoxycarbonyl)guanidine (33.8 mg, 0.16 mmol) in CHCl$_3$ (4 mL) was stirred at 20° C. for 0.5 h. The mixture was added water (10 mL) and extracted with DCM (10 mL×3). The combined organic layers were washed with brine, dried over sodium sulfate, filtered and the solvent was evaporated under reduced pressure. The residue was purified by reverse phase HPLC to give the title compound. MS (ESI) m/z 716.1 (M+H).

Example 110

Example 110 was prepared from 110A by the procedure described in the synthesis of Example 96. MS (ESI) m/z 602.1 (M+H).

A racemic sample of Example 110 (55 mg, 0.091 mmol) was subjected to chiral separation by SFC (Column AS (250×30 mm), 45% EtOH/CO$_2$, 80 mL/min) to give Example 110-a (faster eluting) and Example 110-b (slower eluting). MS (ESI) m/z 602.1 (M+H); $^1$H NMR (400 MHz, CD$_3$OD): δ 8.49 (s, 1H), 8.05 (d, J=8.2 Hz, 1H), 7.75 (d, J=8.2 Hz, 1H), 7.59-7.69 (m, 1H), 7.45-7.56 (m, 2H), 7.39 (dd, J=1.7, 8.3 Hz, 1H), 7.20 (t, J=9.0 Hz, 1H), 3.75 (s, 3H), 2.39-2.48 (m, 1H), 2.18-2.03 (m, 3H), 1.98-1.86 (m, 1H), 1.61-1.42 (m, 2H), 1.26-1.08 (m, 1H).

Example 111, 111-a, 111-b (Z)-5-(3-chloro-2,6-difluorophenyl)-2-(2$^4$-((methoxycarbonyl)amino)-1$^5$-methyl-4-oxo-1$^1$H-3-aza-1(4,2)-imidazola-2(1,2)-benzenacyclononaphane-9-yl)pyridine 1-oxide

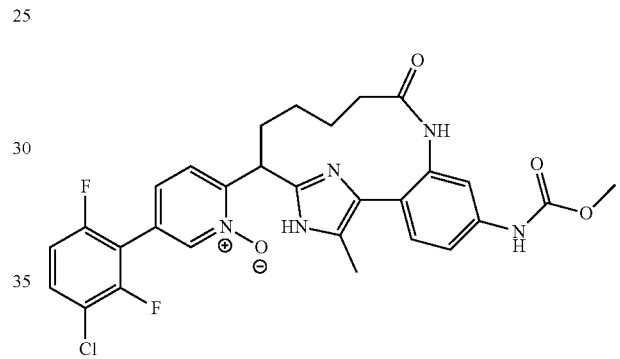

111A: Methyl (Z)-(1$^5$-bromo-9-(5-(3-chloro-2,6-difluorophenyl)pyridin-2-yl)-4-oxo-1$^1$-((2-(trimethylsilyl)ethoxy)methyl)-1$^1$H-3-aza-1(4,2)-imidazola-2(1,2)-benzenacyclononaphane-2$^4$-yl)carbamate

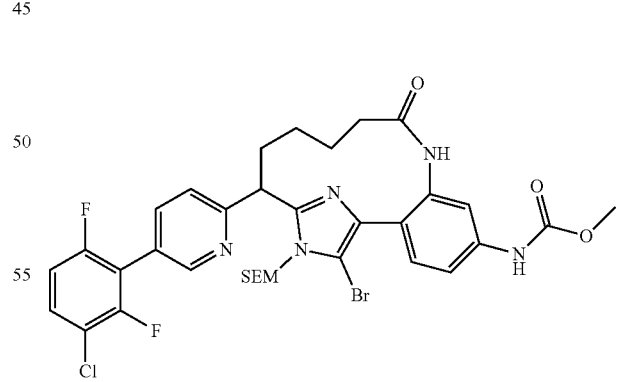

To a stirred mixture of 102B (650 mg, 0.857 mmol) in CHCl$_3$ (10 ml) was added PYRIDINium tribromide (233 mg, 0.729 mmol) and the mixture was stirred at 20° C. for 1 h. It was added aqueous sodium bicarbonate (saturated, 10 mL) and the mixture was extracted with dichloromethane (3×20 mL). The combined organic layers were washed with brine (2×15 mL), dried over sodium sulfate, filtered and the solvent was evaporated under reduced pressure to yield the title compound. MS (ES⁺) m/z: 760, 762 (M+H).

111B: Methyl (Z)-(9-(5-(3-chloro-2,6-difluorophenyl)pyridin-2-yl)-1⁵-methyl-4-oxo-1¹-((2-(trimethylsilyl)ethoxy)methyl)-1¹H-3-aza-1(4,2)-imidazola-2(1,2)-benzenacyclononaphane-2⁴-yl)carbamate

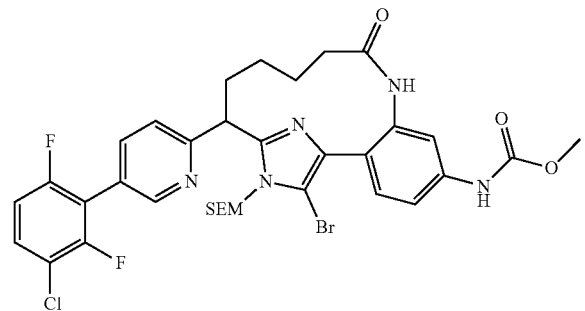 [SMILES: COC(=O)Nc1ccc2c(c1)NC(=O)CCCCC(c1ccc(-c3c(F)ccc(Cl)c3F)cn1)c1nc-2c(Br)n1COCC[Si](C)(C)C]

A mixture of 111A (570 mg, 0.599 mmol), 2,4,6-trimethyl-1,3,5,2,4,6-trioxatriborinane (226 mg, 1.797 mmol), potassium carbonate (331 mg, 2.396 mmol) and Pd(Ph₃P)₄ (208 mg, 0.180 mmol) in dioxane (10 ml) was stirred at 90° C. under nitrogen for 15 h. Aqueous ammonium chloride (saturated, 10 mL) was added and the mixture was extracted with ethyl acetate (3×20 mL). The combined organic layers were washed with brine (20 mL), dried over sodium sulfate, filtered and the solvent was evaporated under reduced pressure. The residue was purified by preparative HPLC (YMC-Actus Pro C18, 150×30 mm, 34-64% MeCN in water (0.1% TFA), 40 mL/min) to give the title compound. MS (ES⁺) m/z: 696.3 (M+H).

Example 111

Example 111 was prepared from 111B by the procedure in the synthesis of Example 96. The product was purified by reverse phase HPLC (YMC-Actus Pro C18, 150×30 mm, 17-47% MeCN in water (0.1% TFA), 40 mL/min) to give the title compound. MS (ES⁺) m/z: 582.2 (M+H).

A racemic sample of Example 111 was subjected to chiral separation by SFC (Column AS, 250×30 mm, 50% MeOH/CO₂, 80 ml/min) to give Example 111-a (slower eluting) and Example 111-b (faster eluting). MS (ES⁺) m/z: 582.2 (M+H).

Example 112, 112-a, 112-b (Z)-5-(3-Chloro-2,6-difluorophenyl)-2-(1⁵-ethyl-2⁴-((Methoxycarbonyl)amino)-4-oxo-1¹H-3-AZA-1(4,2)-imidazola-2(1,2)-benzenacyclononaphane-9-yl)pyridine 1-oxide

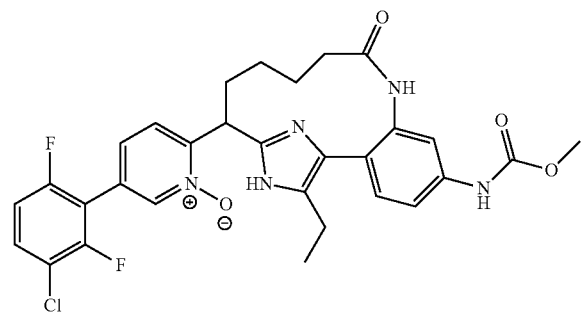 [SMILES: CCc1[nH]c2nc1-c1ccc(NC(=O)OC)cc1NC(=O)CCCCC2c1ccc(-c2c(F)ccc(Cl)c2F)c[n+]1[O-]]

112A: Methyl (Z)-(9-(5-(3-chloro-2,6-difluorophenyl)pyridin-2-yl)-4-oxo-1¹-((2-(trimethylsilyl)ethoxy)methyl)-1⁵-vinyl-1¹H-3-AZA-1(4,2)-imidazola-2(1,2)-benzenacyclononaphane-2⁴-yl)carbamate

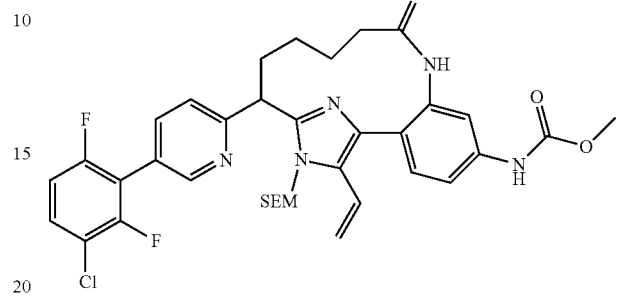

To a microwave seal tube with a stirring bar was added 102B (150 mg, 0.197 mmol), 1,1'-bis(diphenylphosphino)ferrocene-palladium(II)dichloride dichloromethane complex (32.2 mg, 0.039 mmol), potassium vinyltrifluoroborate (52.8 mg, 0.394 mmol). It was sealed and purged with nitrogen three times. To the mixture was added degassed ethanol (1 mL) and TEA (0.082 mL, 0.591 mmol). The mixture was stirred at 80° C. for 2 h. It was cooled to rt and purified by flash column chromatography on silica gel (eluting with 0-5% methanol in DCM) to give the title compound. MS (ES⁺) m/z: 708.3 (M+H).

112B: Methyl (Z)-(9-(5-(3-chloro-2,6-difluorophenyl)pyridin-2-yl)-1⁵-ethyl-4-oxo-1-((2-(trimethylsilyl)ethoxy)methyl)-1¹H-3-aza-1(4,2)-imidazola-2(1,2)-benzenacyclononaphane-2⁴-yl)carbamate

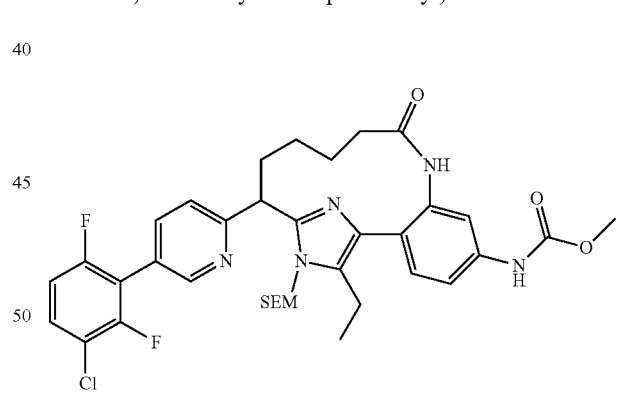

A mixture of 112A (210 mg, 0.296 mmol) and Raney nickel (348 mg, 5.93 mmol) in THF (5 ml) were shaken under hydrogen (40 psi) for 30 min. It was filtered through a pad of Celite, rinsed with 10% methanol in DCM (2×10 mL). The filtrate was concentrated and the residue was purified by flash column chromatography on silica gel (eluting with 0-5% methanol in DCM) to give the title compound. MS (ES⁺) m/z: 710.3 (M+H).

Example 112

Example 112 was prepared from 112B by the procedure in the synthesis of Example 108. The product was purified by flash column chromatography on silica gel (eluting with 0-7% methanol in DCM). MS (ES+) m/z: 596.2 (M+H).

A racemic sample of Example 112 was subjected to chiral separation by SFC (RR Whelk, 30×250 mm, 65% MeOH (0.2% NH4OH)/CO2, 70 mL/min, 100 bar, 35° C.) to give Example 112-a (faster eluting) and Example 112-b (slower eluting). The two enantiomers were re-purified by flash column chromatography on silica gel (0-7% methanol in DCM). MS (ES+) m/z: 596.2 (M+H). $^1$H NMR (500 MHz, DMSO-$d_6$): δ 12.00 (s, 1H), 11.75 (s, 1H), 9.66 (s, 1H), 8.59 (s, 1H), 7.84 (s, 1H), 7.71 (m, 1H), 7.62 (d, J=8.5 Hz, 1H), 7.49 (d, J=8.5 Hz, 1H), 7.40-7.20 (m, 3H), 4.84 (d, J=4.0 Hz, 1H), 3.64 (s, 3H), 2.62 (q, J=7.5 Hz, 2H), 2.40 (m, 1 H), 2.26 (m, 1 H), 2.18 (brs, 1 H), 2.04 (brs, 1H), 1.85 (brs, 1H), 1.57 (brs, 1H). 1.33 (brs, 1H), 1.15 (t, J=7.5 Hz, 3H), 1.04 (brs, 1H).

Example 113, 113-a, 113-b (Z)-2-(1$^5$-cyclopropyl-2$^4$-((methoxycarbonyl)amino)-4-oxo-1$^1$H-3-aza -1(4,2)-imidazola-2(1,2)-benzenacyclononaphane-9-yl)-5-(2-(difluoromethoxy)-6-fluorophenyl)pyridine 1-oxide

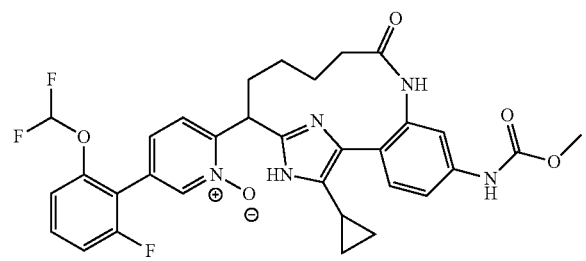 [SMILES: COC(=O)Nc1ccc2c(c1)NC(=O)CCCCC(c1ccc(-c3c(F)cccc3OC(F)F)c[n+]1[O-])c1nc-2c(C2CC2)[nH]1]

113A: Methyl (Z)-(1$^5$-bromo-9-(5-(2-(difluoromethoxy)-6-fluorophenyl)pyridin-2-yl)-4-oxo-1$^1$-((2-(trimethylsilyl)ethoxy)methyl)-1$^1$H-3-aza-1(4,2)-imidazola-2(1,2)-benzenacyclononaphane -2$^4$-yl) carbamate The title compound was prepared from Intermediate 56 and Intermediate 36 by the procedure described in the synthesis of 111A. The product was purified by flash column chromatography on silica gel (eluting with 0-4.5% methanol in DCM). MS (ES+) m/z: 774.1, 776.1 (M+H).

113B: Methyl (Z)-(1$^5$-cyclopropyl-9-(5-(2-(difluoromethoxy)-6-fluorophenyl)pyridin-2-yl)-4-oxo-1$^1$-((2-(trimethylsilyl)ethoxy)methyl)-1$^1$H-3-aza-1(4,2)-imidazola-2(1,2) -benzenacyclononaphane-2$^4$-yl) carbamate

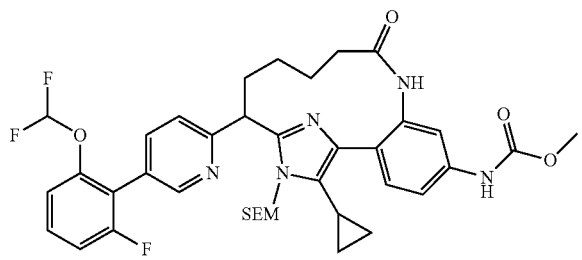 [SMILES: COC(=O)Nc1ccc2c(c1)NC(=O)CCCCC(c1ccc(-c3c(F)cccc3OC(F)F)cn1)c1nc-2c(C2CC2)n1COCC[Si](C)(C)C]

A vial charged with 113A (420 mg, 0.542 mmol), cyclopropylboronic acid (69.9 mg, 0.813 mmol), Tetrakis (188 mg, 0.163 mmol) and potassium carbonate (300 mg, 2.169 mmol) was degassed and backfilled with nitrogen (3×). Dioxane (5.4 mL) was added subsequently; the resultant mixture was heated at 80° C. overnight. It was cooled to rt and purified by flash column chromatography (eluting with MeOH/CH2Cl2=4.5%) to give the title compound. MS (ES+) m/z: 736 (M+H).

Example 113

Example 113 was prepared from 113B by the procedure described in the synthesis of Example 102. The product was purified by flash column chromatography on silica gel (eluting with MeOH/CH2Cl2=7%). MS (ES+) m/z: 622.3 (M+H).

A racemic sample of Example 113 was subjected to chiral separation by SFC (RR Whelk, 30×250 mm, 45% MeOH (0.2% NH4OH)/CO2, 70 mL/min, 100 bar, 35° C.) to give Example 113-a (faster eluting) and Example 113-b (slower eluting). MS (ES+) m/z: 622.3 (M+H).

Example 114, 114-a, 114-b, 114-c, 114-d (Z)-5-(3-chloro-2,6-difluorophenyl)-2-(2$^4$-((methoxycarbonyl)amino)-5-methyl-4-oxo-1$^1$H-3-aza-1(4,2)-imidazola-2(1,2) -benzenacyclononaphane-9-yl)pyridine 1-oxide

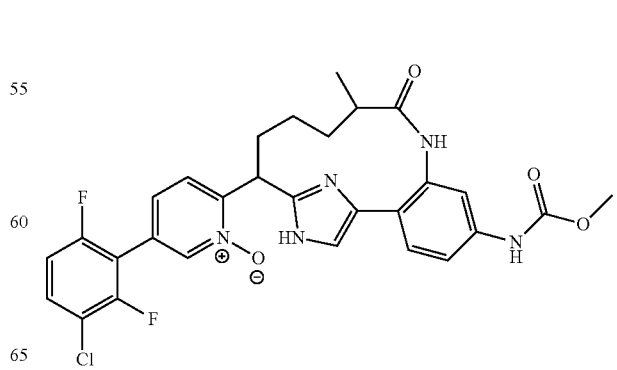

114A: Methyl (Z)-(9-(5-(3-chloro-2,6-difluorophenyl)pyridin-2-yl)-5-methyl-4-oxo-1¹-((2-(trimethylsilyl)ethoxy)methyl)-1¹H-3-aza-1(4,2)-imidazola-2(1,2)-benzenacyclononaphane-2⁴-yl)carbamate

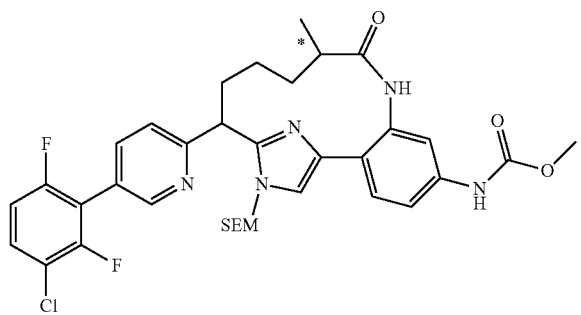

A mixture of Intermediate 57 (1.50 g, 2.39 mmol), 2-(3-chloro-2,6-difluorophenyl)-4,4,5,5-tetramethyl-1,3,2-dioxaborolane (1.31 g, 4.79 mmol), Pd(dtbpf)Cl$_2$ (0.16 g, 0.24 mmol), K$_2$CO$_3$ (0.99 g, 7.18 mmol), THF (24 mL) and water (8 mL) in a sealed vial was stirred at 120° C. for 16 h. It was cooled to rt and diluted with water (10 mL). The mixture was extracted with EtOAc (100 mL×2). The combined organic layers were washed with brine, dried over sodium sulfate, filtered and the solvent was evaporated under reduced pressure. The residue was purified by flash column chromatography on silica gel (0-6% methanol in DCM, gradient) to give the title compound. MS (ESI) m/z 694.3 (M+H).

A racemic sample of the above product was subjected to chiral separation by SFC (Chiralpak AD 250×50 mm, 45% EtOH (0.05% DEA)/CO$_2$, 200 mL/min) to give 114A-a (faster eluting) and 114A-b (slower eluting). MS (ESI) m/z 694.3 (M+H).

Example 114-a/114-b

A mixture of Example 114-a/114-b was prepared from 114A-a by the procedure described in the synthesis of Example 102.

A sample of the two diastereomers was subjected to chiral separation by SFC (Chiralpak AS-H 250×30 mm, 40% of ethanol (0.05% DEA)/CO$_2$, 70 mL/min) to give Example 114-a (faster eluting) and Example 114-b (slower eluting).

Example 114-a: MS (ESI) m/z 582.2 (M+H); ¹H NMR (400 MHz, CD$_3$OD): δ 8.56 (s, 1H), 7.96 (d, J=8.4 Hz, 1H), 7.81 (d, J=8.4 Hz, 1H), 7.67 (dt, J=5.8, 8.5 Hz, 1H), 7.58 (s, 1H), 7.50-7.46 (m, 1H), 7.43-7.38 (m, 2H), 7.22 (t, J=8.6 Hz, 1H), 4.98 (dd, J=6.0, 11.9 Hz, 1H), 3.76 (s, 3H), 2.83-2.75 (m, 1H), 2.42 (t, J=12.6 Hz, 1H), 2.25-2.21 (m, 1H), 2.00-1.91 (m, 1H), 1.78-1.59 (m, 2H), 1.05 (d, J=6.8 Hz, 3H), 0.78-0.65 (m, 1H).

Example 114-b: MS (ESI) m/z 582.1 (M+H); ¹H NMR (400 MHz, CD$_3$OD): δ 8.56 (s, 1H), 7.85 (d, J=8.4 Hz, 1H), 7.72 (d, J=8.4 Hz, 1H), 7.65 (dt, J=5.7, 8.5 Hz, 1H), 7.56 (s, 1H), 7.51-7.47 (m, 1H), 7.43-7.38 (m, 1H), 7.25 (s, 1H), 7.20 (t, J=8.6 Hz, 1H), 4.88-4.85 (m, 1H), 3.74 (s, 3H), 2.66-2.57 (m, 1H), 2.34-2.18 (m, 2H), 1.76 (d, J=7.7 Hz, 1H), 1.44-1.32 (m, 2H), 1.22 (brd, J=7.1 Hz, 3H), 1.16-1.04 (m, 1H).

Example 114-c/114-d

A mixture of Example 114-c/114-d was prepared from 114A-b by the procedure described in the synthesis of Example 102.

A sample of the two diastereomers was subjected to chiral separation by SFC (Chiralpak AS-H 250×30 mm, 40% of ethanol (0.05% DEA)/CO$_2$, 70 mL/min) to give Example 114-c (faster eluting) and Example 114-d (slower eluting).

Example 114-c: MS (ESI) m/z 582.1 (M+H); ¹H NMR (400 MHz, CD$_3$OD): δ 8.56 (s, 1H), 7.85 (d, J=8.4 Hz, 1H), 7.72 (d, J=8.4 Hz, 1H), 7.65 (dt, J=5.7, 8.5 Hz, 1H), 7.56 (s, 1H), 7.51-7.47 (m, 1H), 7.43-7.38 (m, 1H), 7.25 (s, 1H), 7.20 (t, J=8.6 Hz, 1H), 4.88-4.85 (m, 1H), 3.74 (s, 3H), 2.66-2.57 (m, 1H), 2.34-2.18 (m, 2H), 1.76 (d, J=7.7 Hz, 1H), 1.44-1.32 (m, 2H), 1.22 (brd, J=7.1 Hz, 3H), 1.16-1.04 (m, 1H).

Example 114-d: MS (ESI) m/z 582.2 (M+H); ¹H NMR (400 MHz, CD$_3$OD): δ 8.56 (s, 1H), 7.96 (d, J=8.4 Hz, 1H), 7.81 (d, J=8.4 Hz, 1H), 7.67 (dt, J=5.8, 8.5 Hz, 1H), 7.58 (s, 1H), 7.50-7.46 (m, 1H), 7.43-7.38 (m, 2H), 7.22 (t, J=8.6 Hz, 1H), 4.98 (dd, J=6.0, 11.9 Hz, 1H), 3.76 (s, 3H), 2.83-2.75 (m, 1H), 2.42 (t, J=12.6 Hz, 1H), 2.25-2.21 (m, 1H), 2.00-1.91 (m, 1H), 1.78-1.59 (m, 2H), 1.05 (d, J=6.8 Hz, 3H), 0.78-0.65 (m, 1H).

The following compounds were synthesized by the procedures described in Example 96 or Example 102 with the appropriate starting materials. They are characterized by LC/MS.

| Ex | Structure and Name | Chiral Separation SFC Condition | MS (M + H) |
|---|---|---|---|
| 115 | (R,Z)-5-(2-fluoro-6-(4-(trifluoromethyl)-1H-pyrazol-1-yl)phenyl)-2-(2⁴-((methoxycarbonyl)amino)-4-oxo-1¹H-3-aza-1(4,2)-imidazola-2(1,2)-benzenacyclononaphane-9-yl)pyridine 1-oxide 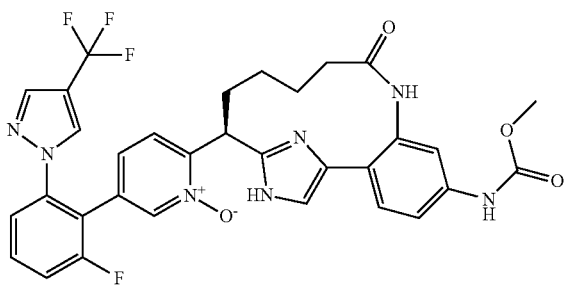 | OJ (250 x 30 mm), 45% MeOH/CO$_2$, 100 bar, 60 mL/min, 35° C. Faster eluting | 650.2 |

-continued

| Ex | Structure and Name | Chiral Separation SFC Condition | MS (M + H) |
|---|---|---|---|
| 116 | (Z)-5-(3-chloro-2-fluoro-6-(4-(trifluoromethyl)-1H-pyrazol-1-yl)phenyl)-2-(2$^4$-((methoxycarbonyl)amino)-4-oxo-1$^1$H-3-aza-1(4,2)-imidazola-2(1,2)-benzenacyclononaphane-9-yl)pyridine 1-oxide | | 684.1 |
| 117 | (R,Z)-5-(5-fluoro-2-(1H-tetrazol-1-yl)phenyl)-2-(2$^4$-((methoxycarbonyl)amino)-4-oxo-1$^1$H-3-aza-1(4,2)-imidazola-2(1,2)-benzenacyclononaphane-9-yl)pyridine 1-oxide | Kromasil 5 (250 x 30 mm), 50% MeOH:MeCN (2:1)/CO$_2$, 100 bar, 70 mL/min, 35° C. Faster eluting | 650.2 |
| 118 | (Z)-5-(5-chloro-2-(oxazol-5-yl)phenyl)-2-(25-fluoro-4-oxo-1$^1$H-3-aza-1(4,2)-imidazola-2(1,2)-benzenacyclononaphane-9-yl)pyridine 1-oxide | OJ (250 x 21 mm), ethanol (0.05% diethylamine)/ CO$_2$, gradient; 60 mL/min, 40° C. Slower eluting | |

| Ex | Structure and Name | Chiral Separation SFC Condition | MS (M + H) |
|---|---|---|---|
| 119 | (R,Z)-5-(2,6-difluorophenyl)-2-(2$^4$-((methoxycarbonyl)amino)-1$^5$-methyl-4-oxo-1$^1$H-3-aza-1(4,2)-imidazola-2(1,2)-benzenacyclononaphane-9-yl)pyridine 1-oxide 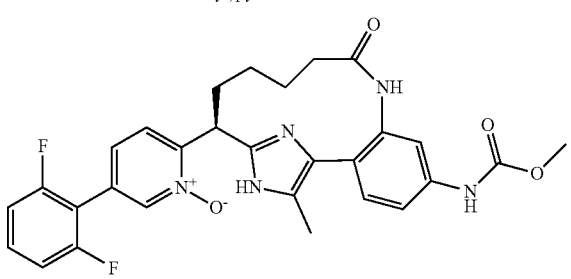 | AD (250 x 30 mm), 55% EtOH (0.1% NH$_3$H$_2$O)/ CO$_2$, 70 mL/min Faster eluting | 548.0 |
| 120 | (R,Z)-2-(2$^4$-((methoxycarbonyl)amino)-1$^5$-methyl-4-oxo-1$^1$H-3-aza-1(4,2)-imidazola-2(1,2)-benzenacyclononaphane-9-yl)-5-(2,3,6-trifluorophenyl)pyridine 1-oxide 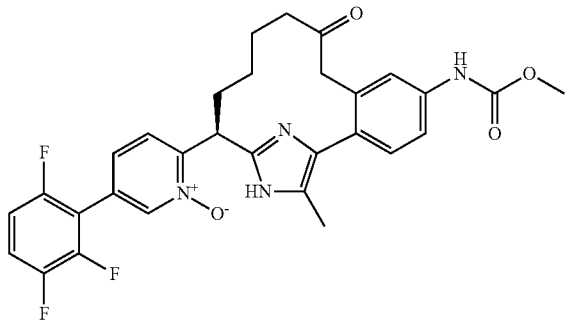 | AS-H (250 x 20 mm), 35% MeOH (0.1% DEA)/ CO$_2$, 60 mL/min Slower eluting | 566.1 |
| 121 | (R,Z)-2-(2$^4$-((methoxycarbonyl)amino)-1$^5$-methyl-4-oxo-1$^1$H-3-aza-1(4,2)-imidazola-2(1,2)-benzenacyclononaphane-9-yl)-5-(2-(trifluoromethyl)phenyl)pyridine 1-oxide 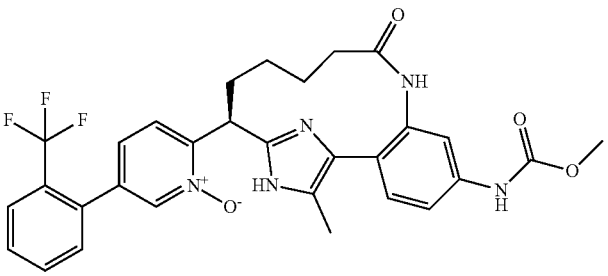 | OD (250 x 30 mm), 50% MeOH (0.1% NH$_3$H$_2$O)/ CO$_2$, 70 ml/min Faster eluting | 580.0 |

| Ex | Structure and Name | Chiral Separation SFC Condition | MS (M + H) |
|---|---|---|---|
| 122 | (R,Z)-5-(2-fluoro-6-(trifluoromethyl)phenyl)-2-(2⁴-((methoxycarbonyl)amino)-1⁵-methyl-4-oxo-1¹H-3-aza-1(4,2)-imidazola-2(1,2)-benzenacyclononaphane-9-yl)pyridine 1-oxide | (S,S) WHELK-O 1 (250 x 30 mm) 40% MeOH (0.1% NH$_3$H$_2$O)/ CO$_2$, 60 ml/min Slower eluting | 598.0 |
| 123 | (R,Z)-5-(3-chloro-2-fluoro-6-(trifluoromethyl)phenyl)-2-(2⁴-((methoxycarbonyl)amino)-1⁵-methyl-4-oxo-1¹H-3-aza-1(4,2)-imidazola-2(1,2)-benzenacyclononaphane-9-yl)pyridine 1-oxide | OD (250 x 30 mm), 40% (0.1% NH$_3$H$_2$O)/ CO$_2$, 60 ml/min Faster eluting | 632.2 |
| 124 | (R,Z)-5-(3-chloro-6-(difluoromethyl)-2-fluorophenyl)-2-(2⁴-((methoxycarbonyl)amino)-1⁵-methyl-4-oxo-1¹H-3-aza-1(4,2)-imidazola-2(1,2)-benzenacyclononaphane-9-yl)pyridine 1-oxide | (S,S) WHELK-O 1 (250 x 30 mm) 50% MeOH (0.1% NH$_3$H$_2$O)/ CO$_2$, 60 ml/min Slower eluting | 613.9 |

| Ex | Structure and Name | Chiral Separation SFC Condition | MS (M + H) |
|---|---|---|---|
| 125 | (R,Z)-5-(2-(difluoromethyl)-6-fluorophenyl)-2-($2^4$-((methoxycarbonyl)amino)-$1^5$-methyl-4-oxo-$1^1$H-3-aza-1(4,2)-imidazola-2(1,2)-benzenacyclononaphane-9-yl)pyridine 1-oxide | (S,S) WHELK-O 1 (250 x 30 mm) 50% MeOH (0.1% $NH_3H_2O$)/ $CO_2$, 60 ml/min Slower eluting | 580.0 |
| 126 | (R,Z)-5-(2-(difluoromethoxy)-6-fluorophenyl)-2-($2^4$-((methoxycarbonyl)amino)-$1^5$-methyl-4-oxo-$1^1$H-3-aza-1(4,2)-imidazola-2(1,2)-benzenacyclononaphane-9-yl)pyridine 1-oxide | (R,R) WHELK-O 1 (250 x 30 mm) 65% MeOH (0.2% $NH_3H_2O$)/ $CO_2$, 70 ml/min Faster eluting | 596.2 |
| 127 | (R,Z)-5-(2-(difluoromethoxy)-6-fluorophenyl)-2-($1^5$-ethyl-$2^4$-((methoxycarbonyl)amino)-4-oxo-$1^1$H-3-aza-1(4,2)-imidazola-2(1,2)-benzenacyclononaphane-9-yl)pyridine 1-oxide | OD (250 x 21 mm), 45% MeOH (0.2% DEA)/ $CO_2$, 60 ml/min Slower eluting | 610.3 |

| Ex | Structure and Name | Chiral Separation SFC Condition | MS (M + H) |
|---|---|---|---|
| 128 | (R,Z)-2-($2^4$-amino-$1^5$-methyl-4-oxo-$1^1$H-3-aza-1(4,2)-imidazola-2(1,2)-benzenacyclononaphane-9-yl)-5-(3-chloro-2,6-difluorophenyl)pyridine 1-oxide | AS-H (250 x 30 mm), 40% EtOH (0.05% DEA)/ $CO_2$, 60 mL/min Slower eluting | 524.1 |
| 129 | (R,Z)-5-(2-(difluoromethoxy)-5-fluorophenyl)-2-($2^4$-((methoxycarbonyl)amino)-$1^5$-methyl-4-oxo-$1^1$H-3-aza-1(4,2)-imidazola-2(1,2)-benzenacyclononaphane-9-yl)pyridine 1-oxide | AS-H (250 x 30 mm), 40% MeOH (0.1% $NH_3H_2O$)/ $CO_2$, 80 mL/min Slower eluting | 596.0 |
| 130 | (R,Z)-5-(6-(difluoromethoxy)-2,6-difluorophenyl)-2-($2^4$-((methoxycarbonyl)amino)-$1^5$-methyl-4-oxo-$1^1$H-3-aza-1(4,2)-imidazola-2(1,2)-benzenacyclononaphane-9-yl)pyridine 1-oxide | OD (250 x 21 mm), 40% MeOH (0.05% DEA)/ $CO_2$, 60 ml/min Slower eluting | 614.0 |

| Ex | Structure and Name | Chiral Separation SFC Condition | MS (M + H) |
|---|---|---|---|
| 131 | (R,Z)-5-(2-fluoro-6-(trifluoromethoxy)phenyl)-2-($2^4$-((methoxycarbonyl)amino)-$1^5$-methyl-4-oxo-$1^1$H-3-aza-1(4,2)-imidazola-2(1,2)-benzenacyclononaphane-9-yl)pyridine 1-oxide | IC (250 x 30 mm), 80% MeOH:MeCN (2:1)/$CO_2$, 70 ml/min Faster eluting | 614.1 |
| 132 | (R,Z)-5-(5-fluoro-2-(trifluoromethoxy)phenyl)-2-($2^4$-((methoxycarbonyl)amino)-$1^5$-methyl-4-oxo-$1^1$H-3-aza-1(4,2)-imidazola-2(1,2)-benzenacyclononaphane-9-yl)pyridine 1-oxide | OD (250 x 21 mm), 35% MeOH (0.2% DEA)/$CO_2$, 55 ml/min Slower eluting | 614.2 |
| 133 | (R,Z)-2-($1^5$-ethyl-$2^4$-((methoxycarbonyl)amino)-4-oxo-$1^1$H-3-aza-1(4,2)-imidazola-2(1,2)-benzenacyclononaphane-9-yl)-5-(5-fluoro-2-(trifluoromethoxy)phenyl)pyridine 1-oxide | Kromasil-5 (250 x 30 mm), 50% MeOH (0.2% $NH_3H_2O$)/$CO_2$, 70 ml/min Faster eluting | 628.3 |

| Ex | Structure and Name | Chiral Separation SFC Condition | MS (M + H) |
|---|---|---|---|
| 134 | (R,Z)-5-(3-chloro-2,6-difluorophenyl)-2-($2^4$-((ethoxycarbonyl)amino)-$1^5$-methyl-4-oxo-$1^1$H-3-aza-1(4,2)-imidazola-2(1,2)-benzenacyclononaphane-9-yl)pyridine 1-oxide | AD-H (250 x 30 mm), 55% EtOH (0.1% $NH_3H_2O$)/ $CO_2$, 80 ml/min Faster eluting | 596.0 |
| 135 | (R,Z)-5-(3-chloro-2-fluoro-6-(4-(trifluoromethyl)-1H-pyrazol-1-yl)phenyl)-2-($2^4$-((methoxycarbonyl)amino)-$1^5$-methyl-4-oxo-$1^1$H-3-aza-1(4,2)-imidazola-2(1,2)-benzenacyclononaphane-9-yl)pyridine 1-oxide | IC (250 x 21 mm), 55% MeOH (0.2% DEA)/ $CO_2$, 55 ml/min Faster eluting | 698.2 |
| 136 | (R,Z)-5-(3-chloro-2-fluoro-6-(4-(trifluoromethyl)-1H-pyrazol-1-yl)phenyl)-2-($1^5$-ethyl-$2^4$-((methoxycarbonyl)amino)-4-oxo-$1^1$H-3-aza-1(4,2)-imidazola-2(1,2)-benzenacyclononaphane-9-yl)pyridine 1-oxide | (S,S) WHELK-O 1 (250 x 50 mm) 40% MeOH (0.1% $NH_3H_2O$)/ $CO_2$, 60 ml/min Faster eluting | 712.0 |

-continued

| Ex | Structure and Name | Chiral Separation SFC Condition | MS (M + H) |
|---|---|---|---|
| 137 | (R,Z)-5-(2-fluoro-6-(4-(trifluoromethyl)-1H-pyrazol-1-yl)phenyl)-2-(2$^4$-((methoxycarbonyl)amino)-1$^5$-methyl-4-oxo-1$^1$H-3-aza-1(4,2)-imidazola-2(1,2)-benzenacyclononaphane-9-yl)pyridine 1-oxide 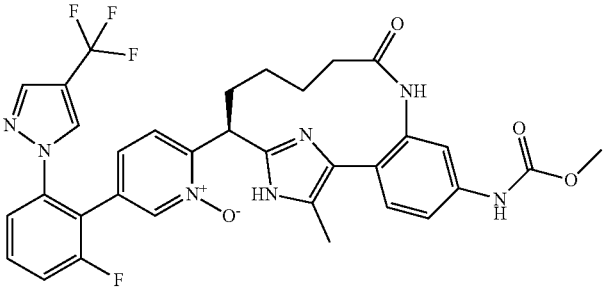 | IC (250 x 21 mm), 55% MeOH (0.2% DEA)/ $CO_2$, 55 ml/min Faster eluting | 664.3 |
| 138 | (R,Z)-2-(1$^5$-ethyl-2$^4$-((methoxycarbonyl)amino)-4-oxo-1$^1$H-3-aza-1(4,2)-imidazola-2(1,2)-benzenacyclononaphane-9-yl)-5-(2-fluoro-6-(4-(trifluoromethyl)-1H-pyrazol-1-yl)phenyl)pyridine 1-oxide 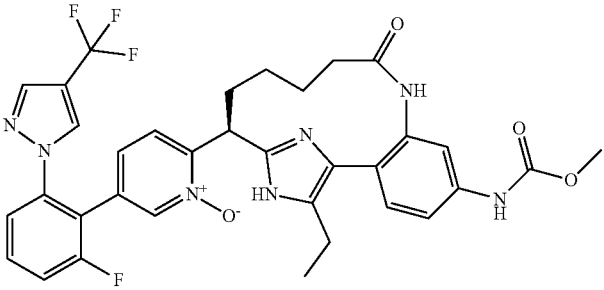 | OD (250 x 30 mm), 40% EtOH (0.1% $NH_3H_2O$)/ $CO_2$, 80 ml/min Slower eluting | 678.3 |
| 139 | (R,Z)-5-(5-chloro-2-(1H-pyrazol-1-yl)phenyl)-2-(2$^4$-((methoxycarbonyl)amino)-1$^5$-methyl-4-oxo-1$^1$H-3-aza-1(4,2)-imidazola-2(1,2)-benzenacyclononaphane-9-yl)pyridine 1-oxide 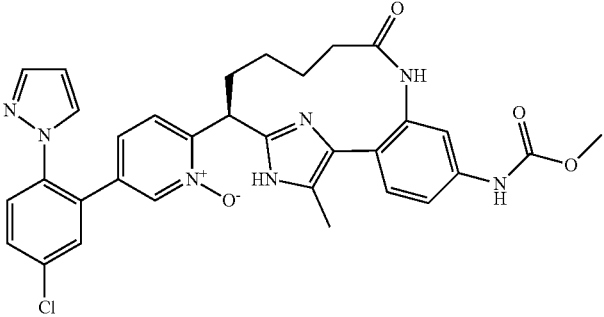 | AS (250 x 30 mm), 45% EtOH (0.1% $NH_3H_2O$)/ $CO_2$, 80 ml/min Slower eluting | 612.0 |

| Ex | Structure and Name | Chiral Separation SFC Condition | MS (M + H) |
|---|---|---|---|
| 140 | (R,Z)-2-(2⁴-((methoxycarbonyl)amino)-1⁵-methyl-4-oxo-1¹H-3-aza-1(4,2)-imidazola-2(1,2)-benzenacyclononaphane-9-yl)-5-(2-(4-methyl-1H-pyrazol-1-yl)phenyl)pyridine 1-oxide | AS (250 x 30 mm), 40% EtOH (0.1% NH$_3$H$_2$O)/ CO$_2$, 60 ml/min Slower eluting | 592.0 |
| 141 | (R,Z)-5-(5-chloro-2-(4-methyl-1H-pyrazol-1-yl)phenyl)-2-(2⁴-((methoxycarbonyl)amino)-1⁵-methyl-4-oxo-1¹H-3-aza-1(4,2)-imidazola-2(1,2)-benzenacyclononaphane-9-yl)pyridine 1-oxide | AS (250 x 30 mm), 40% MeOH (0.1% NH$_3$H$_2$O)/ CO$_2$, 60 ml/min Slower eluting | 626.0 |
| 142 | (R,Z)-2-(2⁵-fluoro-1⁵-methyl-4-oxo-1¹H-3-aza-1(4,2)-imidazola-2(1,2)-benzenacyclononaphane-9-yl)-5-(5-fluoro-2-(1H-tetrazol-1-yl)phenyl)pyridine 1-oxide | (S,S) WHELK-O 1 (250 x 50 mm) 40% MeOH (0.1% NH$_3$H$_2$O)/ CO$_2$, 60 ml/min Slower eluting | 543.1 |

| Ex | Structure and Name | Chiral Separation SFC Condition | MS (M + H) |
|---|---|---|---|
| 143-a | 5-(2,6-difluorophenyl)-2-((5S,9R,Z)-2⁴-((methoxycarbonyl)amino)-1⁵,5-dimethyl-4-oxo-1¹H-3-aza-1(4,2)-imidazola-2(1,2)-benzenacyclononaphane-9-yl)pyridine 1-oxide 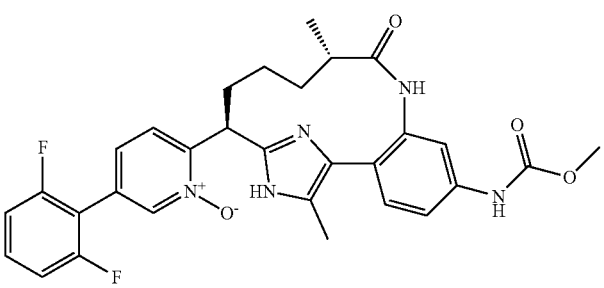 | (R,R) WHELK-O 1 (250 x 30 mm) 40% MeOH (0.2% NH₃H₂O)/ CO₂, 70 ml/min First eluting | 562.1 |
| 143-b | 5-(2,6-difluorophenyl)-2-((5R,9R,Z)-2⁴-((methoxycarbonyl)amino)-1⁵,5-dimethyl-4-oxo-1¹H-3-aza-1(4,2)-imidazola-2(1,2)-benzenacyclononaphane-9-yl)pyridine 1-oxide 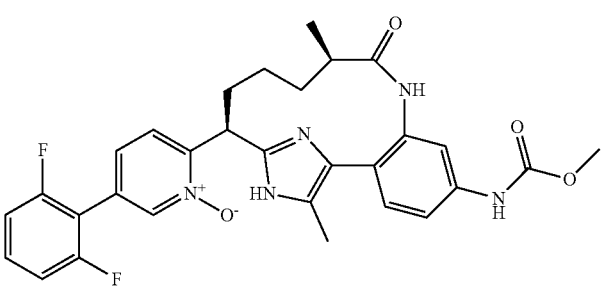 | (R,R) WHELK-O 1 (250 x 30 mm) 40% MeOH (0.2% NH₃H₂O)/ CO₂, 70 ml/min Second eluting | 562.1 |
| 143-c | 5-(2,6-difluorophenyl)-2-((5S,9S,Z)-2⁴-((methoxycarbonyl)amino)-1⁵,5-dimethyl-4-oxo-1¹H-3-aza-1(4,2)-imidazola-2(1,2)-benzenacyclononaphane-9-yl)pyridine 1-oxide 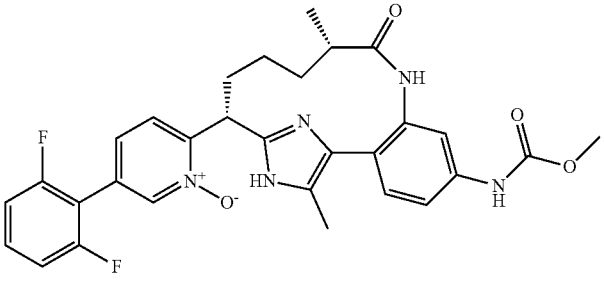 | (R,R) WHELK-O 1 (250 x 30 mm) 40% MeOH (0.2% NH₃H₂O)/ CO₂, 70 ml/min Third eluting | 562.1 |

| Ex | Structure and Name | Chiral Separation SFC Condition | MS (M + H) |
|---|---|---|---|
| 143-d | 5-(2,6-difluorophenyl)-2-((5R,9S,Z)-2⁴-((methoxycarbonyl)amino)-1⁵,5-dimethyl-4-oxo-1¹H-3-aza-1(4,2)-imidazola-2(1,2)-benzenacyclononaphane-9-yl)pyridine 1-oxide 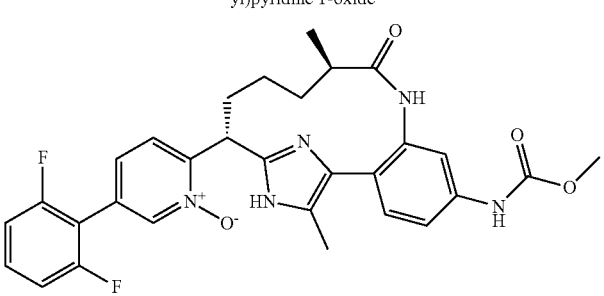 | (R,R) WHELK-O 1 (250 x 30 mm) 40% MeOH (0.2% NH₃H₂O)/ CO₂, 70 ml/min Fourth eluting | 562.1 |
| 144 | 5-(2,6-difluorophenyl)-2-((9R,Z)-1⁵-ethyl-2⁴-((methoxycarbonyl)amino)-5-methyl-4-oxo-1¹H-3-aza-1(4,2)-imidazola-2(1,2)-benzenacyclononaphane-9-yl)pyridine 1-oxide 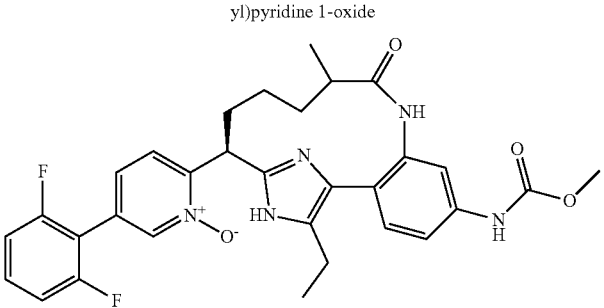 | OZ (250 x 21 mm), 50% MeOH (0.2% NH₃H₂O)/ CO₂, 60 ml/min Faster eluting | 576.1 |
| 145-a | 2-((5R,9R,Z)-15-cyclopropyl-2⁴-((methoxycarbonyl)amino)-5-methyl-4-oxo-1¹H-3-aza-1(4,2)-imidazola-2(1,2)-benzenacyclononaphane-9-yl)-5-(2,6-difluorophenyl)pyridine 1-oxide 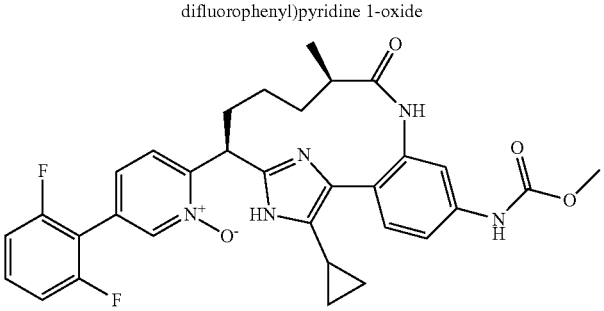 | OZ (250 x 21 mm), 60% MeOH (0.2% NH₃H₂O)/ CO₂, 50 ml/min Faster eluting | 588.3 |

-continued

| Ex | Structure and Name | Chiral Separation SFC Condition | MS (M + H) |
|---|---|---|---|
| 145-b | 2-((5S,9S,Z)-15-cyclopropyl-2⁴-((methoxycarbonyl)amino)-5-methyl-4-oxo-1¹H-3-aza-1(4,2)-imidazola-2(1,2)-benzenacyclononaphane-9-yl)-5-(2,6-difluorophenyl)pyridine 1-oxide | OZ (250 x 21 mm), 60% MeOH (0.2% NH$_3$H$_2$O)/ CO$_2$, 50 ml/min Slower eluting | 588.3 |
| 145-c | 2-((5R,9S,Z)-15-cyclopropyl-2⁴-((methoxycarbonyl)amino)-5-methyl-4-oxo-1¹H-3-aza-1(4,2)-imidazola-2(1,2)-benzenacyclononaphane-9-yl)-5-(2,6-difluorophenyl)pyridine 1-oxide | IC (250 x 30 mm), 65% MeOH (0.2% NH$_3$H$_2$O)/ CO$_2$, 70 ml/min Faster eluting | 588.3 |
| 145-d | 2-((5S,9R,Z)-15-cyclopropyl-2⁴-((methoxycarbonyl)amino)-5-methyl-4-oxo-1¹H-3-aza-1(4,2)-imidazola-2(1,2)-benzenacyclononaphane-9-yl)-5-(2,6-difluorophenyl)pyridine 1-oxide | IC (250 x 30 mm), 65% MeOH (0.2% NH$_3$H$_2$O)/ CO$_2$, 70 ml/min Slower eluting | 588.3 |

-continued

| Ex | Structure and Name | Chiral Separation SFC Condition | MS (M + H) |
|---|---|---|---|
| 146-a | 5-(2-(difluoromethoxy)-6-fluorophenyl)-2-((5R,9R,Z)-1⁵-ethyl-2⁴-((methoxycarbonyl)amino)-5-methyl-4-oxo-1¹H-3-aza-1(4,2)-imidazola-2(1,2)-benzenacyclononaphane-9-yl)pyridine 1-oxide 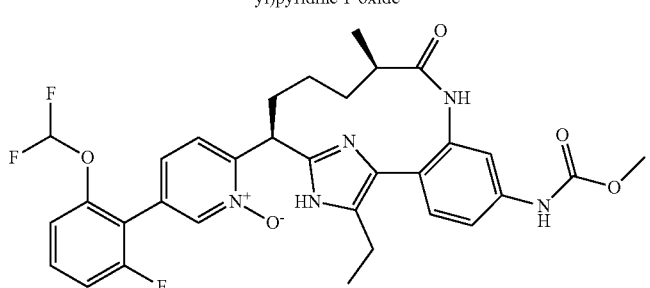 | IC, 250 x 21 mm, 50% MeOH (0.2% NH₄OH)/ CO₂, 60 mL/min First eluting | 624.3 |
| 146-b | 5-(2-(difluoromethoxy)-6-fluorophenyl)-2-((5R,9S,Z)-1⁵-ethyl-2⁴-((methoxycarbonyl)amino)-5-methyl-4-oxo-1¹H-3-aza-1(4,2)-imidazola-2(1,2)-benzenacyclononaphane-9-yl)pyridine 1-oxide 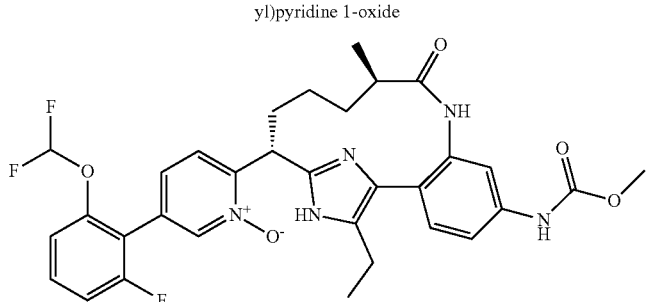 | IC, 250 x 21 mm, 50% MeOH (0.2% NH₄OH)/ CO₂, 60 mL/min First eluting | 624.3 |
| 146-c | 5-(2-(difluoromethoxy)-6-fluorophenyl)-2-((5S,9R,Z)-1⁵-ethyl-2⁴-((methoxycarbonyl)amino)-5-methyl-4-oxo-1¹H-3-aza-1(4,2)-imidazola-2(1,2)-benzenacyclononaphane-9-yl)pyridine 1-oxide 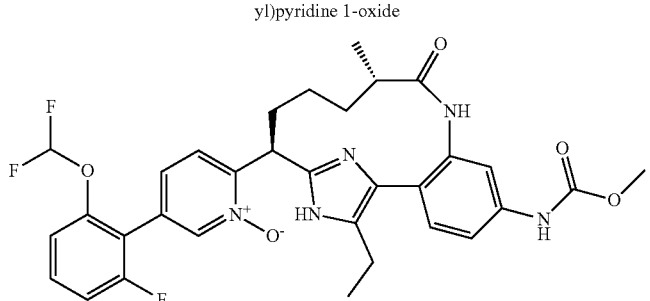 | IC, 250 x 21 mm, 50% MeOH (0.2% NH₄OH)/ CO₂, 60 mL/min First eluting | 624.3 |

-continued

| Ex | Structure and Name | Chiral Separation SFC Condition | MS (M + H) |
|---|---|---|---|
| 146-d | 5-(2-(difluoromethoxy)-6-fluorophenyl)-2-((5S,9S,Z)-1⁵-ethyl-2⁴-((methoxycarbonyl)amino)-5-methyl-4-oxo-1¹H-3-aza-1(4,2)-imidazola-2(1,2)-benzenacyclononaphane-9-yl)pyridine 1-oxide 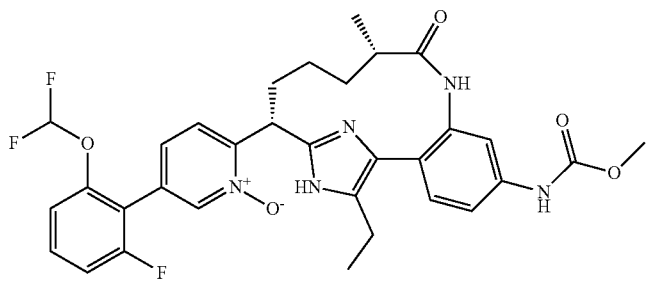 | IC, 250 x 21 mm, 50% MeOH (0.2% NH₄OH)/ CO₂, 60 mL/min First eluting | 624.3 |
| 147 | (R,Z)-5-(2-(difluoromethoxy)-6-fluorophenyl)-2-(2⁴-((methoxycarbonyl)amino)-1⁵,5,5-trimethyl-4-oxo-1¹H-3-aza-1(4,2)-imidazola-2(1,2)-benzenacyclononaphane-9-yl)pyridine 1-oxide 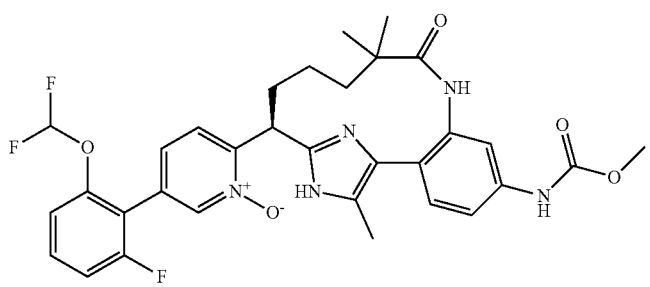 | AD (250 x 30 mm), 40% 2-propanol (0.1% NH₃H₂O)/CO₂, 50 ml/min Faster eluting | 624.3 |
| 148 | (R,Z)-5-(2-(difluoromethoxy)-6-fluorophenyl)-2-(4'-((methoxycarbonyl)amino)-5'-methyl-4'-oxospiro[cyclopropane-1,5'-3-aza-1(4,2)-imidazola-2(1,2)-benzenacyclononaphan]-9'-yl)pyridine 1-oxide 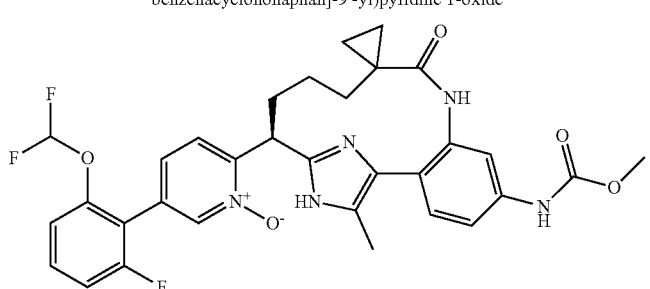 | AS (250 x 30 mm), 50% EtOH (0.1% ammonia)/ CO₂, 80 ml/min Faster Eluting | 622.3 |

-continued

| Ex | Structure and Name | Chiral Separation SFC Condition | MS (M + H) |
|---|---|---|---|
| 149-a | 5-(5-fluoro-2-(trifluoromethoxy)phenyl)-2-((5R,9R,Z)-2$^4$-((methoxycarbonyl)amino)-1$^5$,5-dimethyl-4-oxo-1$^1$H-3-aza-1(4,2)-imidazola-2(1,2)-benzenacyclononaphane-9-yl)pyridine 1-oxide | OD (250 x 21 mm), 43% MeOH (0.2% DEA)/ CO$_2$, 60 ml/min Slower Eluting | 628.1 |
| 149-b | 5-(5-fluoro-2-(trifluoromethoxy)phenyl)-2-((5S,9S,Z)-2$^4$-((methoxycarbonyl)amino)-1$^5$,5-dimethyl-4-oxo-1$^1$H-3-aza-1(4,2)-imidazola-2(1,2)-benzenacyclononaphane-9-yl)pyridine 1-oxide | OD (250 x 21 mm), 43% MeOH (0.2% DEA)/ CO$_2$, 60 ml/min Faster Eluting | 628.1 |
| 149-c | 5-(5-fluoro-2-(trifluoromethoxy)phenyl)-2-((5S,9R,Z)-2$^4$-((methoxycarbonyl)amino)-1$^5$,5-dimethyl-4-oxo-1$^1$H-3-aza-1(4,2)-imidazola-2(1,2)-benzenacyclononaphane-9-yl)pyridine 1-oxide | OD (250 x 30 mm), 37% MeOH (0.2% DEA)/ CO$_2$, 60 ml/min Slower Eluting | 628.1 |

| Ex | Structure and Name | Chiral Separation SFC Condition | MS (M + H) |
|---|---|---|---|
| 149-d | 5-(5-fluoro-2-(trifluoromethoxy)phenyl)-2-((5R,9S,Z)-2⁴-((methoxycarbonyl)amino)-1⁵,5-dimethyl-4-oxo-1¹H-3-aza-1(4,2)-imidazola-2(1,2)-benzenacyclononaphane-9-yl)pyridine 1-oxide | OD (250 x 30 mm), 37% MeOH (0.2% DEA)/ $CO_2$, 60 ml/min Faster Eluting | 628.1 |
| 150-a | 5-(6-(difluoromethoxy)-2,3-difluorophenyl)-2-((5R,9R,Z)-2⁴-((methoxycarbonyl)amino)-1⁵,5-dimethyl-4-oxo-1¹H-3-aza-1(4,2)-imidazola-2(1,2)-benzenacyclononaphane-9-yl)pyridine 1-oxide | AS (250 x 30 mm), 45% EtOH (0.1% $NH_3H_2O$)/ $CO_2$, 80 ml/min Faster Eluting | 628.2 |
| 150-b | 5-(6-(difluoromethoxy)-2,3-difluorophenyl)-2-((5S,9S,Z)-2⁴-((methoxycarbonyl)amino)-1⁵,5-dimethyl-4-oxo-1¹H-3-aza-1(4,2)-imidazola-2(1,2)-benzenacyclononaphane-9-yl)pyridine 1-oxide | AS (250 x 30 mm), 45% EtOH (0.1% $NH_3H_2O$)/ $CO_2$, 80 ml/min Slower Eluting | 628.2 |

| Ex | Structure and Name | Chiral Separation SFC Condition | MS (M + H) |
|---|---|---|---|
| 150-c | 5-(6-(difluoromethoxy)-2,3-difluorophenyl)-2-((5S,9R,Z)-2⁴-((methoxycarbonyl)amino)-1⁵,5-dimethyl-4-oxo-1¹H-3-aza-1(4,2)-imidazola-2(1,2)-benzenacyclononaphane-9-yl)pyridine 1-oxide | AD (250 x 30 mm), 45% EtOH (0.1% NH₃H₂O)/ CO₂, 80 ml/min Faster Eluting | 627.9 |
| 150-d | 5-(6-(difluoromethoxy)-2,3-difluorophenyl)-2-((5R,9S,Z)-2⁴-((methoxycarbonyl)amino)-1⁵,5-dimethyl-4-oxo-1¹H-3-aza-1(4,2)-imidazola-2(1,2)-benzenacyclononaphane-9-yl)pyridine 1-oxide | AD (250 x 30 mm), 45% EtOH (0.1% NH₃H₂O)/ CO₂, 80 ml/min Slower Eluting | 627.9 |
| 151-a | 5-(3-chloro-2,6-difluorophenyl)-2-((7R,9R,Z)-2⁴-((methoxycarbonyl)amino)-1⁵,7-dimethyl-4-oxo-1¹H-3-aza-1(4,2)-imidazola-2(1,2)-benzenacyclononaphane-9-yl)pyridine 1-oxide | AD, 250 x 30 mm, 50% IPA(0.1% NH₃•H₂O)/CO₂, Faster eluting | 595.9 |

| Ex | Structure and Name | Chiral Separation SFC Condition | MS (M + H) |
| --- | --- | --- | --- |
| 151-b | 5-(3-chloro-2,6-difluorophenyl)-2-((7S,9R,Z)-2⁴-((methoxycarbonyl)amino)-1⁵,7-dimethyl-4-oxo-1¹H-3-aza-1(4,2)-imidazola-2(1,2)-benzenacyclononaphane-9-yl)pyridine 1-oxide 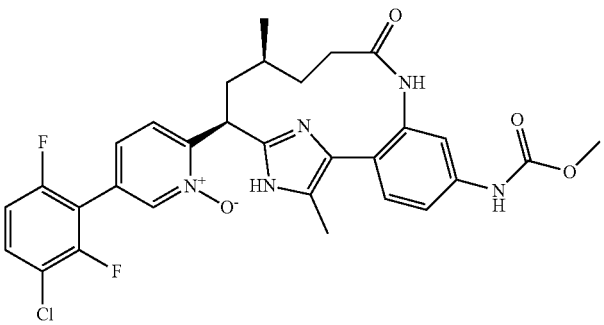 | AD, 250 x 30 mm, 50% IPA(0.1% $NH_3 \cdot H_2O$)/$CO_2$, 80 mL/min Slower eluting | 595.9 |
| 151-c | 5-(3-chloro-2,6-difluorophenyl)-2-((7R,9S,Z)-2⁴-((methoxycarbonyl)amino)-1⁵,7-dimethyl-4-oxo-1¹H-3-aza-1(4,2)-imidazola-2(1,2)-benzenacyclononaphane-9-yl)pyridine 1-oxide 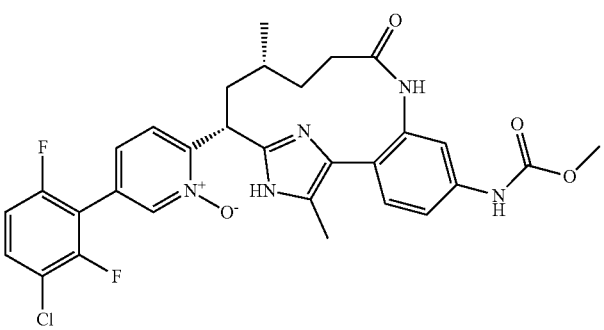 | AD, 250 x 30 mm, 55% EtOH (0.1% $NH_3 \cdot H_2O$)/ $CO_2$, 80 mL/min Faster eluting | 595.9 |
| 151-d | 5-(3-chloro-2,6-difluorophenyl)-2-((7S,9S,Z)-2⁴-((methoxycarbonyl)amino)-1⁵,7-dimethyl-4-oxo-1¹H-3-aza-1(4,2)-imidazola-2(1,2)-benzenacyclononaphane-9-yl)pyridine 1-oxide 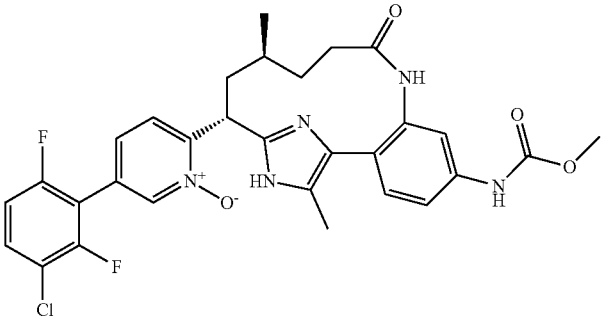 | AD, 250 x 30 mm, 55% EtOH (0.1% $NH_3 \cdot H_2O$)/ $CO_2$, 80 mL/min Slower eluting | 595.9 |

| Ex | Structure and Name | Chiral Separation SFC Condition | MS (M + H) |
|---|---|---|---|
| 152-a | 5-(2-(difluoromethoxy)-6-fluorophenyl)-2-((7R,9R,Z)-2⁴-((methoxycarbonyl)amino)-1⁵,7-dimethyl-4-oxo-1¹H-3-aza-1(4,2)-imidazola-2(1,2)-benzenacyclononaphane-9-yl)pyridine 1-oxide 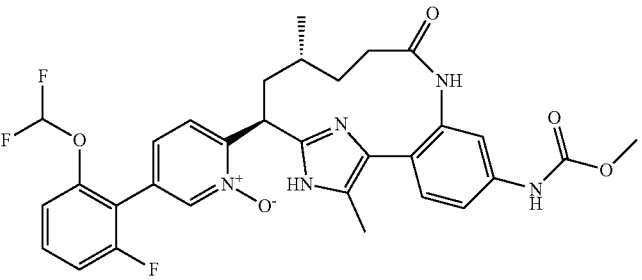 | AD, 250 x 30 mm, 55% EtOH (0.1% NH₃•H₂O)/ CO₂, 80 mL/min Faster eluting | 610.0 |
| 152-b | 5-(2-(difluoromethoxy)-6-fluorophenyl)-2-((7S,9R,Z)-2⁴-((methoxycarbonyl)amino)-1⁵,7-dimethyl-4-oxo-1¹H-3-aza-1(4,2)-imidazola-2(1,2)-benzenacyclononaphane-9-yl)pyridine 1-oxide 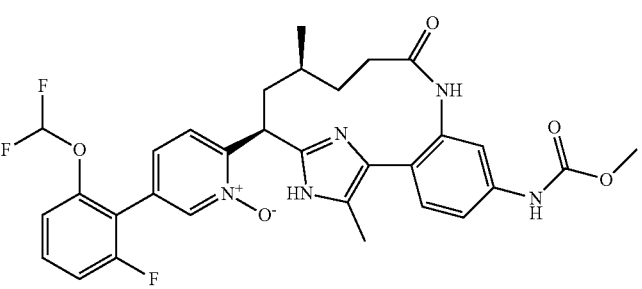 | AD, 250 x 30 mm, 55% EtOH (0.1% NH₃•H₂O)/ CO₂, 80 mL/min Slower eluting | 610.0 |
| 152-c | 5-(2-(difluoromethoxy)-6-fluorophenyl)-2-((7R,9S,Z)-2⁴-((methoxycarbonyl)amino)-1⁵,7-dimethyl-4-oxo-1¹H-3-aza-1(4,2)-imidazola-2(1,2)-benzenacyclononaphane-9-yl)pyridine 1-oxide 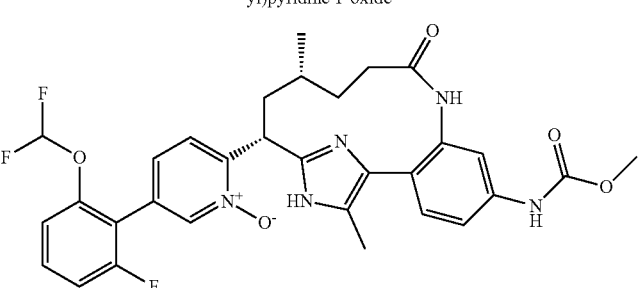 | AD, 250 x 30 mm, 40% IPA(0.1% NH₃•H₂O)/CO₂, 80 mL/min Faster eluting | 610.0 |

-continued

| Ex | Structure and Name | Chiral Separation SFC Condition | MS (M + H) |
|---|---|---|---|
| 152-d | 5-(2-(difluoromethoxy)-6-fluorophenyl)-2-((7S,9S,Z)-2$^4$-((methoxycarbonyl)amino)-1$^5$,7-dimethyl-4-oxo-1$^1$H-3-aza-1(4,2)-imidazola-2(1,2)-benzenacyclononaphane-9-yl)pyridine 1-oxide | AD, 250 x 30 mm, 40% IPA(0.1% NH$_3$•H$_2$O)/CO$_2$, 80 mL/min Slower eluting | 610.0 |
| 153 | (Z)-5-(3-chloro-2,6-difluorophenyl)-2-(1$^4$-((methoxycarbonyl)amino)-7-oxo-2$^1$H-8-aza-2(4,2)-imidazola-1(1,2)-benzena-5(1,2)-cyclopropanacyclooctaphane-3-yl)pyridine 1-oxide | Racemic | 580.0 |
| 154 | 5-(3-chloro-2,6-(difluorophenyl)-2-((5$^1$R,5$^2$R,3R,Z)-1$^4$-((methoxycarbonyl)amino)-2$^5$-methyl-7-oxo-2$^1$H-8-aza-2(4,2)-imidazola-1(1,2)-benzena-5(1,2)-cyclopropanacyclooctaphane-3-yl)pyridine 1-oxide | IC (250 x 21 mm), 55% MeOH (0.2% DEA)/ CO$_2$, 55 ml/min Slower Eluting | 594.0 |

| Ex | Structure and Name | Chiral Separation SFC Condition | MS (M + H) |
|---|---|---|---|
| 155 | 5-(2,6-difluorophenyl)-2-((5$^1$R,5$^2$R,3R,Z)-1$^4$-((methoxycarbonyl)amino)-2$^5$-methyl-7-oxo-2$^1$H-8-aza-2(4,2)-imidazola-1(1,2)-benzena-5(1,2)-cyclopropanacyclooctaphane-3-yl)pyridine 1-oxide | IC (250 x 21 mm), 55% MeOH (0.2% DEA)/ CO$_2$, 55 ml/min Slower Eluting | 560.0 |
| 156 | (Z)-5-(2-(difluoromethyl)-6-fluorophenyl)-2-(1$^4$-((methoxycarbonyl)amino)-2$^5$-methyl-7-oxo-2$^1$H-8-aza-2(4,2)-imidazola-1(1,2)-benzena-5(1,2)-cyclopropanacyclooctaphane-3-yl)pyridine 1-oxide | Racemic | 592.1 |
| 157 | (Z)-5-(3-chloro-6-(difluoromethyl)-2-fluorophenyl)-2-(1$^4$-((methoxycarbonyl)amino)-2$^5$-methyl-7-oxo-2$^1$H-8-aza-2(4,2)-imidazola-1(1,2)-benzena-5(1,2)-cyclopropanacyclooctaphane-3-yl)pyridine 1-oxide | Racemic | 626.2 |

-continued

| Ex | Structure and Name | Chiral Separation SFC Condition | MS (M + H) |
|---|---|---|---|
| 158 | (Z)-5-(6-(difluoromethyl)-2-fluoro-3-methylphenyl)-2-(1⁴-((methoxycarbonyl)amino)-2⁵-methyl-7-oxo-2¹H-8-aza-2(4,2)-imidazola-1(1,2)-benzena-5(1,2)-cyclopropanacyclooctaphane-3-yl)pyridine 1-oxide 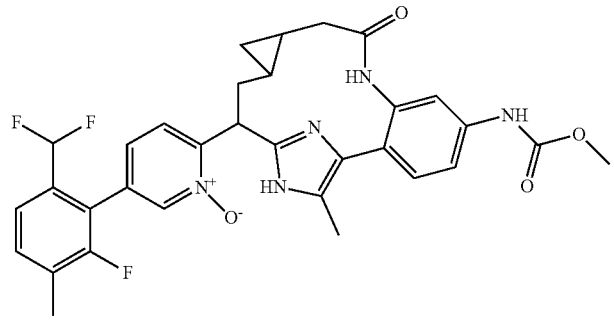 | Racemic | 606.2 |
| 159 | (Z)-5-(3-chloro-6-(difluoromethoxy)-2-fluorophenyl)-2-(1⁴-((methoxycarbonyl)amino)-2⁵-methyl-7-oxo-2¹H-8-aza-2(4,2)-imidazola-1(1,2)-benzena-5(1,2)-cyclopropanacyclooctaphane-3-yl)pyridine 1-oxide 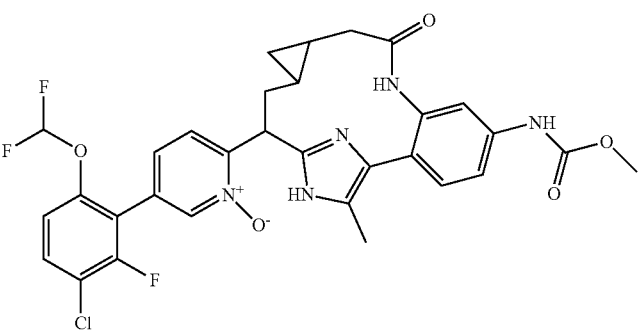 | Racemic | 642.2 |

Example 160 (racemate), 160-a and 160-b (Z)-5-(5-chloro-2-(1H-tetrazol-1-yl)phenyl)-2-(2⁵-fluoro-4-oxo-1¹H-3-aza -1(2,4)-imidazola-2(1,2)-benzenacyclononaphane-9-yl)pyridine 1-oxide

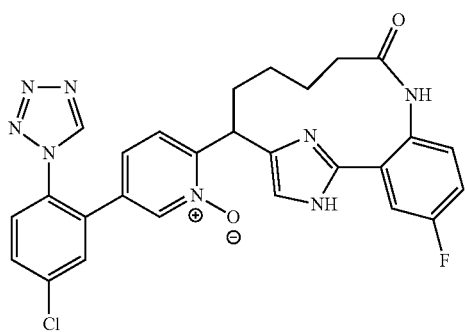 [SMILES: O=C1CCCCC(c2ccc(-c3cc(Cl)ccc3-n3cnnn3)c[n+]2[O-])c2c[nH]c(n2)-c2cc(F)ccc2N1]

Example 160 was prepared from Intermediate 17 and Intermediate 18 by the procedures described in the synthesis of Example 97 and Example 98. The product was purified by reverse phase HPLC. MS (ES⁺) m/z: 545 (M+H).

A sample of racemic Example 160 was subjected to chiral separation by SFC (OJ, 50×4.6 mm; methanol (0.05% diethylamine)/CO₂; 40 mL/min, 40° C.) to give Example 160-a (slower eluting) and Example 160-b (faster eluting). MS (ES⁺) m/z: 545 (M+H).

Example 161 (racemate), 161-a and 161-b (Z)-5-(3-chloro-2-fluoro-6-(1H-tetrazol-1-yl)phenyl)-2-(2⁵-fluoro-4-oxo -1¹H-3-aza-1(2,4)-imidazola-2(1,2)-benzenacyclononaphane-9-yl)pyridine 1-oxide

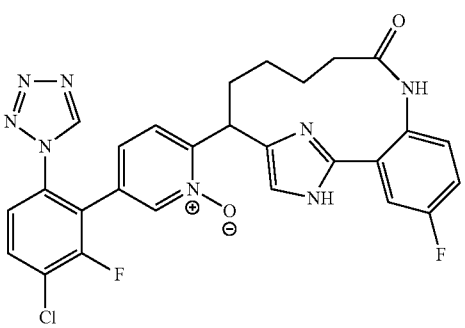 [SMILES: O=C1CCCCC(c2ccc(-c3c(-n4cnnn4)ccc(Cl)c3F)c[n+]2[O-])c2c[nH]c(n2)-c2cc(F)ccc2N1]

Example 161 was prepared by the procedures described in Example 160. It was purified by reverse phase HPLC. MS (ES⁺) m/z: 563 (M+H).

A sample of racemic Example 161 was subjected to chiral separation by SFC (OJ, 50×4.6 mm; ethanol (0.05% diethylamine)/CO$_2$; 4 mL/min, 40° C.) to give Example 161-a (slower eluting) and Example 161-b (faster eluting). MS (ES⁺) m/z: 545 (M+H).

Example 162, 162-a, 162-b (Z)-5-(3-chloro-2,6-difluorophenyl)-2-(2⁵-((methoxycarbonyl)amino)-4-oxo-1¹H-3-aza-1(1,4)-pyrazola-2(1,2)-benzenacyclononaphane-9-yl)pyridine 1-oxide

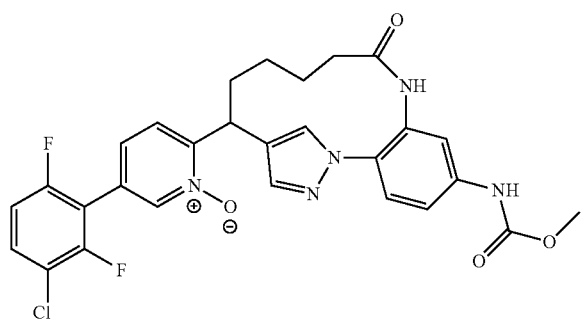 [SMILES: COC(=O)Nc1ccc2c(c1)NC(=O)CCCCC(c1ccc(-c3c(F)ccc(Cl)c3F)c[n+]1[O-])c1cnn-2c1]

162A: Ethyl 1-((2-(trimethylsilyl)ethoxy)methyl)-1H-pyrazole-4-carboxylate

To a solution of ethyl 4-pyrazolecarboxylate (5 g, 35.7 mmol) in DMF (10 mL) at rt was added SEM-Cl (7.6 mL, 42.8 mmol). The mixture was stirred for 10 min. It was diluted with ethyl acetate (50 mL) and washed with 10% aqueous sodium carbonate (10 mL), water (4×30 mL) and brine (20 mL). The organic layer was dried over sodium sulfate, filtered and concentrated under reduced pressure. The residue was purified by flash column chromatography on silica gel (eluting with 0-30% ethyl acetate in hexane) to give the title compound. MS (ES⁺) m/z: 271 (M+H).

162B: N-Methoxy-N-methyl-1-((2-(trimethylsilyl)ethoxy)methyl)-1H-pyrazole-4-carboxamide To a mixture of 162A (4.8 g, 17.75 mmol) and N,O-dimethylhydroxylamine hydrochloride (2.60 g, 26.6 mmol) in THF (40 mL) at 0° C. was added a solution of isopropylmagnesium bromide (2.9 M in 2-methyltetrahydrofurane, 18 mL, 52.2 mmol). It was stirred overnight and allowed to warm to rt. It was quenched with saturated aqueous ammonium chloride (20 mL) and brine (50 mL). The mixture was extracted with ethyl acetate (2×50 mL). The combined organic layers were dried over sodium sulfate, filtered and the filtrated was concentrated under reduced pressure. The residue was purified by flash column chromatography (eluting with 0-100% ethyl acetate in hexane) to give the title compound. MS (ES⁺) m/z: 286 (M+H).

162C: (5-Chloropyridin-2-yl)(1-((2-(trimethylsilyl)ethoxy)methyl)-1H-pyrazol-4-yl)methanone To a solution of 2-bromo-5-chloropyridine (7.2 g, 37.4 mmol) in anhydrous toluene (100 mL) at −78° C. was slowly added n-butyllithium (2.5 M in hexane, 15 mL, 37.5 mmol). It was stirred for 1 h and to the solution was added a solution of 162B (8.7 g, 30.5 mmol) in anhydrous toluene (20 mL). The reaction mixture was stirred for 15 min and was warmed to 0° C. It was stirred for 1 h and quenched with saturated aqueous ammonium chloride. The mixture was extracted with ethyl acetate (2×50 mL). The combined organic layers were dried over sodium sulfate, filtered and the filtrate was concentrated under reduced pressure. The residue was purified by flash column chromatography (eluding with 0-30% ethyl acetate in hexane) to afford the title compound. MS (ES⁺) m/z: 338 (M+H).

162 D: (5-Chloropyridin-2-yl)(1H-pyrazol-4-yl)methanone 162C (5.6 g, 16.57 mmol) was treated with HCl in dioxane (50 mL, 200 mmol) at rt for 1 h. It was concentrated under reduced pressure and the residue was added 100 mL of a mixture of CHCl$_3$/IPA (5:1) and 100 mL of saturated aqueous sodium bicarbonate. The mixture was transferred to a separatory funnel and the organic layer was separated. The aqueous layer was extracted twice with CHCl$_3$/IPA (5:1) (2×50 mL). The combined organic layers were dried over sodium sulfate, filtered and concentrated. The residue was purified by flash column chromatography on silica gel (eluting with 0-3% methanol in DCM) to give the title compound. MS (ES⁺) m/z: 208 (M+H).

162E: Methyl (4-fluoro-3-nitrophenyl)carbamate

To a suspension of sodium hydride (60% wt in mineral oil) (5.5 g, 138 mmol) in anhydrous DMA (60 mL) at 0° C. was added a solution of 4-fluoro-3-nitroaniline (10 g, 64.1 mmol) in DMA (40 mL). It was stirred for 0.5 h and methyl chloroformate (11 mL, 142 mmol) was added. The reaction mixture was stirred for 15 min and was allowed to warm to rt for 1 h. It was quenched with aqueous NaOH (3 N, 50 mL) and the mixture was stirred for 1 h at rt. It was diluted with water (300 mL) and extracted with ethyl acetate (3×200 mL). The combined organic layers were washed with water (4×100 mL), brine (50 mL), dried over sodium sulfate and filtered. The filtrate was concentrated under reduce pressure and the residue was purified by flash column chromatography on silica gel (eluting with 0-5% methanol in DCM) to give the title compound. MS (ES⁺) m/z: 215 (M+H).

162F: Methyl (4-(4-(5-chloropicolinoyl)-1H-pyrazol-1-yl)-3-nitrophenyl)carbamate A mixture of 162D (11.3 g, 46.3 mmol), 162E (11.3 g, 46.3 mmol) and potassium carbonate (14 g, 101 mmol) in DMA (100 mL) was stirred at 100° C. overnight. It was cooled to rt and diluted with ethyl acetate (500 mL), washed with water (4×200 mL). The combined aqueous layers were extracted with ethyl acetate (300 mL). The combined organic layers were washed with brine (2×100 mL), dried over sodium sulfate, filtered and concentrated. The residue was purified by flash column chromatography on silica gel (eluting with 0-7% methanol in DCM) to give a mixture of the desired product and the hydrolysis by-product (1-(4-amino-2-nitrophenyl)-1H-pyrazol-4-yl)(5-chloropyridin-2-yl)methanone.

To a solution of the above mixture in PYRIDINE (50 mL) at 0° C. was added methyl chloroformate (5.68 g, 60.1 mmol). It was stirred for 30 min. Most solvent was removed under reduced pressure. The residue was dissolved in ethyl acetate (200 mL) and washed with 1 N HCl (2×50 mL) and brine (100 mL). The organic layer was dried over sodium sulfate, filtered and concentrated. The residue was purified by flash column chromatography on silica gel (eluting with 0-5% methanol in DCM) to give the title compound. MS (ES+) m/z: 402 (M+H).

162G: Methyl (3-amino-4-(4-(5-chloropicolinoyl)-1H-pyrazol-1-yl)phenyl)carbamate A mixture of 162F (1.68 g, 4.18 mmol), iron (0.934 g, 16.73 mmol) and ammonium chloride (0.447 g, 8.36 mmol) in isopropanol (15 mL) and water (5.00 mL) was stirred at 80° C. for 1 h. It was directly loaded on a silica gel sampler and purified by flash column chromatography on silica gel (eluting with 0-5% methanol in DCM) to the title compound. MS (ES+) m/z: 372 (M+H).

162H: (5-((2-(4-(5-Chloropicolinoyl)-1H-pyrazol-1-yl)-5-((methoxycarbonyl)amino)phenyl)amino)-5-oxopentyl)triphenylphosphonium bromide To a mixture of 162G (1.87 g, 5.03 mmol), (4-carboxybutyl)triphenylphosphonium bromide (2.5 g, 5.64 mmol) in DCM (50.3 mL) was added DIEA (2.5 mL, 14.31 mmol) and HATU (2.3 g, 6.05 mmol). It was stirred for 16 h. It was concentrated under reduced pressure and the residue was purified by flash column chromatography on silica gel (eluting with 0-10% methanol in DCM) to give the title compound. MS (ES+) m/z: 716 (M-Br).

162I: Methyl ((1⁴Z,8E)-9-(5-chloropyridin-2-yl)-4-oxo-1H-3-aza-1(1,4)-pyrazola-2(1,2) -benzenacyclononaphan-8-en-2⁴-yl)carbamate

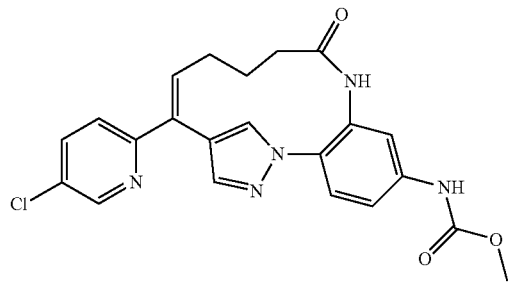 [SMILES: COC(=O)Nc1ccc2c(c1)NC(=O)CCC/C=C(/c1ccc(Cl)cn1)c1cnn-2c1]

To a solution of 162H (4 g, 5.02 mmol) in THF (500 mL) was added potassium tert-butOXIDE (1 M in THF, 21 mL, 21.00 mmol). The mixture was stirred at rt for 16 h. It was quenched with saturated aqueous ammonium chloride, extracted with ethyl acetate (200 mL). The organic layer was dried over sodium sulfate, filtered and concentrated. It was purified by flash column chromatography on silica gel (eluting with 0-6% methanol in DCM) to give the title compound. MS (ES+) m/z: 438 (M+H).

Example 162

Example 162 was prepared from 162I by the procedures described in Example 50. It was purified by reverse phase HPLC to give the racemic product. MS (ES+) m/z: 568.3 (M+H).

A sample of Example 162 was subjected to chiral separation by SFC (Kromasil, 250×30 mm, 50% (2:1 methanol/MeCN) in CO₂; 70 mL/min; 100 bar, 35° C.) to give Example 162-a (slower eluting) and Example 162-b (faster eluting). MS (ES+) m/z: 568 (M+H); ¹H NMR: (500 MHz, DMSO-d₆): δ 9.96 (s, 1H), 9.21 (s, 1H), 8.53 (s, 1H), 8.07 (s, 1H), 7.80 (m, 2H), 7.63 (s, 1H), 7.49 (m, 2H), 7.34 (t, J=9.0 Hz, 1H), 7.16 (d, J=9.0 Hz, 1H), 4.61 (m, 1H), 3.68 (s, 3H), 2.18 (brs, 2H), 2.04 (m, 1H), 1.80-1.60 (m, 2H), 1.40-1.00 (m, 3H).

Example 163

5-(3-chloro-2,6-difluorophenyl)-2-(1¹-methyl-8-oxo-1¹H-9-aza-1(3,4) -pyrazola-2(1,3)-benzenacyclononaphane-3-Y1)pyridine 1-oxide

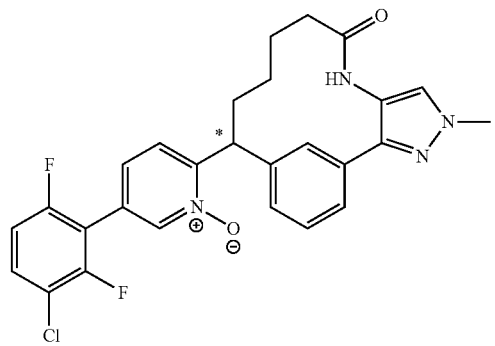 [SMILES: Cn1cc2c(n1)-c1cccc(c1)C(c1ccc(-c3c(F)ccc(Cl)c3F)c[n+]1[O-])CCCCC(=O)N2]

163A: 4-Nitro-1-((2-(trimethylsilyl)ethoxy)methyl)-1H-pyrazole

To a suspension of sodium hydride (7.07 g, 177 mmol, 60% wt in oil) in THF (100 mL) at 0° C. under N₂ was added 4-nitro-1H-pyrazole (10 g, 88 mmol). The mixture was stirred for 0.5 h before SEM-Cl (17.25 mL, 97 mmol) was added. The reaction was stirred at rt for another 1.5 h. It was quenched with aqueous ammonium chloride (sat, 50 mL) and extracted with EtOAc (50 mL×4). The combined organic layers were washed brine (100 mL), dried over sodium sulfate, filtered and concentrated under reduced pressure. The residue was purified by flash column chromatography (SiO₂, petroleum ether:ethyl acetate=100:1 to 10:1, gradient) to give the title compound. ¹H NMR (400 MHz, CDCl₃): δ 8.31 (s, 1H), 8.11 (s, 1H), 5.46 (s, 2H), 3.59-3.68 (m, 2H), 0.99-0.91 (m, 2H), 0.00 (s, 9H).

163B: (5-Chloropyridin-2-yl)(3-(4-nitro-1-((2-(trimethylsilyl)ethoxy)methyl)-1H-pyrazol-5-yl)phenyl)methanone A mixture of Intermediate 2 (975 mg, 3.29 mmol), 163A (500 mg, 2.055 mmol), butyldi-1-adamantylphosphine (111 mg, 0.308 mmol), K₂CO₃ (852 mg, 6.16 mmol), pivalic acid (0.036 mL, 0.308 mmol) and Pd(OAc)₂ (46.1 mg, 0.205 mmol) in DMF (10 mL) under nitrogen was stirred at 120° C. for 6 h. It was cooled to rt and diluted with water (20 mL). The mixture was extracted with EtOAc (20 mL×3). The combined organic layers were washed with brine (10 mL×4), dried over sodium sulfate, filtered and concentrated. The residue was purified by flash column chromatography (SiO₂, petroleum ether: ethyl acetate=50:1 to 10:1) to give the title compound. MS (ES+) m/z: 459.0 (M+H); ¹H NMR (400 MHz, CDCl₃): δ 8.67 (d, J 2.0 Hz, 1H), 8.25-8.34 (m, 3H), 8.10 (d, J=8.2 Hz, 1H), 7.91 (dd, J=2.2, 8.4 Hz, 1H), 7.81 (d, J=7.8 Hz, 1H), 7.65-7.73 (m, 1H), 5.33 (s, 2H), 3.66-3.75 (m, 2H), 0.84-0.93 (m, 2H), 0.04 (s, 9H).

163C: (3-(4-Amino-1-((2-(trimethylsilyl)ethoxy)methyl)-1H-pyrazol-5-yl)phenyl)(5-chloropyridin-2-yl)methanone To a solution of 163B (200 mg, 0.436 mmol) in EtOH (15 mL) was added iron (97 mg, 1.743 mmol) and ammonium chloride (46.6 mg, 0.872 mmol) in water (5 mL). The mixture was stirred at 90° C. for 1 h. It was cooled to rt and diluted with water (20 mL). The mixture was extracted with EtOAc (20 mL×3). The combined organic layers were washed with brine (10 mL×4), dried over sodium sulfate, filtered and concentrated to give the title compound. MS (ES⁺) m/z: 429.1 (M+H); ¹H NMR (400 MHz, CDCl₃): δ 8.66 (d, J=1.8 Hz, 1H), 8.21-8.27 (m, 1H), 8.03-8.12 (m, 2H), 7.84-7.93 (m, 2H), 7.61-7.68 (m, 1H), 7.31 (s, 1H), 5.30-5.41 (m, 2H), 3.61-3.68 (m, 2H), 0.83-0.90 (m, 2H), 0.02-0.06 (m, 9H).

163D: 5-(3-Chloro-2,6-difluorophenyl)-2-(8-oxo-1¹H-9-aza-1(5,4)-pyrazola-2(1,3)-benzenacyclononaphane-3-yl)pyridine 1-oxide

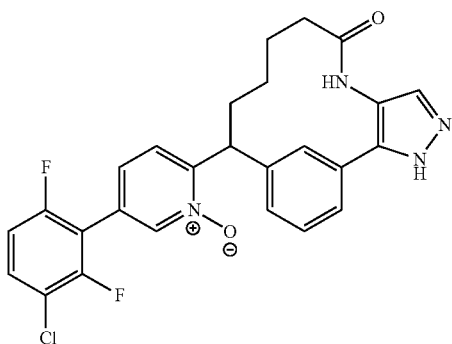 [SMILES: O=C1CCCCC(c2ccc(-c3c(F)ccc(Cl)c3F)c[n+]2[O-])c2cccc(c2)-c2[nH]ncc2N1]

The title compound was prepared from 163C by the procedure described in the synthesis of Example 50. MS (ES⁺) m/z: 495.1 (M+H).

Example 163

To a mixture of 163D and K₂CO₃ (8.38 mg, 0.061 mmol) in DMF (2 mL) was added iodomethane (5.74 mg, 0.040 mmol). It was stirred at 40° C. for 14 h. To the reaction mixture was added water (10 mL) and it was extracted with EtOAc (20 mL×2). The combined organic layers were washed with brine (20 mL), dried over sodium sulfate, filtered and concentrated. The residue was purified by reverse phase HPLC to give the title compounds. MS (ES⁺) m/z: 509.1 (M+H); ¹H NMR (400 MHz, CD₃CN): δ 8.29-8.38 (m, 1H), 7.81 (s, 1H), 7.49-7.73 (m, 4H), 7.41-7.48 (m, 1H), 7.33-7.40 (m, 2H), 7.17 (t, J=9.2 Hz, 1H), 7.04 (d, J=7.5 Hz, 1H), 4.65-4.84 (m, 1H), 3.98 (s, 3H), 2.24-2.28 (m, 2H), 2.03-2.15 (m, 2H), 1.56-1.70 (m, 1H), 1.21-1.33 (m, 2H), 1.02-1.16 (m, 1H).

Example 164

5-(3-chloro-2,6-difluorophenyl)-2-(1¹-methyl-8-oxo-1H-9-aza-1(5,4)-pyrazola-2(1,3)-benzenacyclononaphane-3-Yl)pyridine 1-oxide

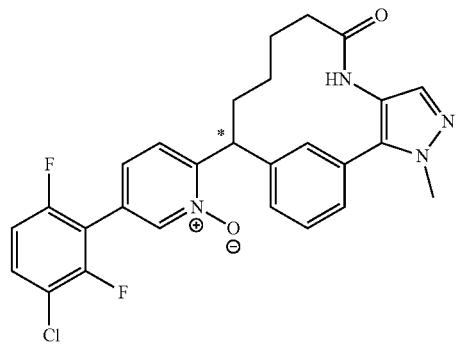 [SMILES: Cn1ncc2c1-c1cccc(c1)C(c1ccc(-c3c(F)ccc(Cl)c3F)c[n+]1[O-])CCCCC(=O)N2]

Example 164 was separated from Example 163 by HPLC. MS (ES⁺) m/z: 509.1 (M+H); ¹H NMR (400 MHz, CD₃CN): δ 8.36 (s, 1H), 7.98 (br. s., 2H), 7.61 (dt, J=6.0, 8.6 Hz, 1H), 7.44-7.57 (m, 4H), 7.34 (t, J=7.7 Hz, 1H), 7.17 (t, J=9.0 Hz, 1H), 6.95 (d, J=7.5 Hz, 1H), 4.81 (dd, J=4.4, 11.2 Hz, 1H), 3.90 (s, 3H), 2.23-2.29 (m, 2H), 2.07-2.15 (m, 2H), 1.52-1.68 (m, 1H), 0.80-1.49 (m, 3H).

Example 165, 465-a, 165-b 5-(5-chloro-2-(4-(trifluoromethyl)-1H-1,2,3-triazol-1-yl)phenyl)-2-(1¹-(difluoromethyl)-8-oxo-1¹H-9-aza-1(5,4)-pyrazola-2(1,3)-benzenacyclononaphane-3-Yl)pyridine 1-oxide

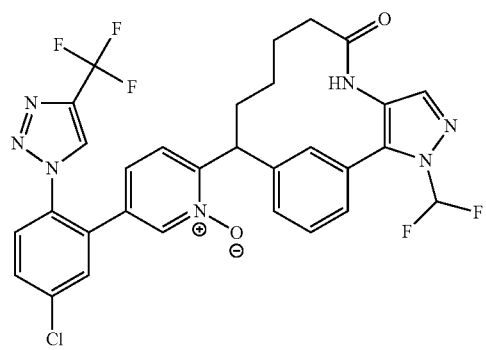 [SMILES: O=C1CCCCC(c2ccc(-c3cc(Cl)ccc3-n3cc(C(F)(F)F)nn3)c[n+]2[O-])c2cccc(c2)-c2c(cnn2C(F)F)N1]

165A: 1-(Difluoromethyl)-4-nitro-1H-pyrazole

A mixture of 4-nitro-1H-pyrazole (2 g, 17.69 mmol), Cs₂CO₃ (5.76 g, 17.69 mmol) and sodium 2-chloro-2,2-difluoroacetate (5.39 g, 35.4 mmol) in DMF (10 mL) was stirred at 120° C. under nitrogen for 2 h. It was cooled to rt and diluted with water (20 mL). The mixture was extracted with EtOAc (70 mL×3). The combined organic layers were washed with water (40 mL) and brine (50 mL), dried over anhydrous sodium sulfate, filtered and concentrated. The residue was purified with flash column chromatography on silica gel (eluting with petroleum ether: ethyl acetate=100:1 to 10:1, gradient) to give the title compound.

Example 165

Example 165 was prepared from 165A by the procedure described in the synthesis of 164D. MS (ES+) m/z: 509.1 (M+H); $^1$H NMR (CD$_3$OD, 400 MHz): δ 8.75 (s, 1H), 8.24 (s, 1H), 7.69-7.81 (m, 4H), 7.58-7.67 (m, 3H), 7.37-7.64 (m, 2H), 7.22 (d, J=8.2 Hz, 1H), 6.98 (d, J=6.8 Hz, 1H), 4.75 (d, J=10.4 Hz, 1H), 2.39-2.52 (m, 1H), 1.95-2.14 (m, 4H), 1.67 (br. s., 1H), 1.24-1.37 (m, 1H), 1.10 (brs, 1H).

A racemic sample of Example 165 was subjected to chiral separation by SFC (AS, 250×30 mm, 30% MeOH (0.1% NH$_3$.H$_2$O)/CO$_2$, 50 mL/min) to afford Example 165-a (slower eluting), Example 165-b (faster eluting). MS (ES+) m/z: 644.2 (M+H).

By using procedures similar to those described above, the following compounds were synthesized and characterized by LCMS

| Ex | Structure and Name | Chiral Separation SFC Condition | MS (M + H) |
|---|---|---|---|
| 166-a | 5-(5-chloro-2-(4-chloro-1H-1,2,3-triazol-1-yl)phenyl)-2-((3S,7R)-1$^1$-(difluoromethyl)-7-methyl-8-oxo-1$^1$H-9-aza-1(5,4)-pyrazola-2(1,3)-benzenacyclononaphane-3-yl)pyridine 1-oxide 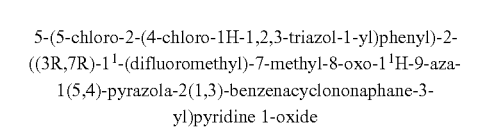 | AD (250 x 30 mm), 40% EtOH (0.1% NH$_3$H$_2$O)/ CO$_2$, 60 ml/min Faster eluting | 624.0 |
| 166-b | 5-(5-chloro-2-(4-chloro-1H-1,2,3-triazol-1-yl)phenyl)-2-((3R,7R)-1$^1$-(difluoromethyl)-7-methyl-8-oxo-1$^1$H-9-aza-1(5,4)-pyrazola-2(1,3)-benzenacyclononaphane-3-yl)pyridine 1-oxide 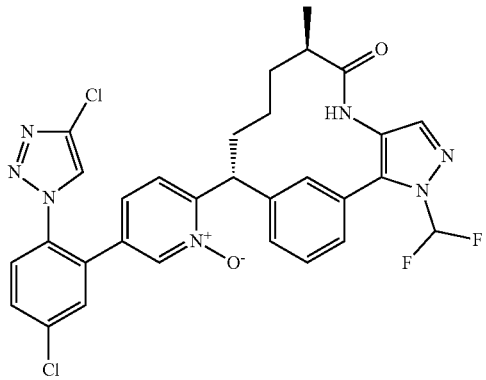 | AD (250 x 30 mm), 40% EtOH (0.1% NH$_3$H$_2$O)/ CO$_2$, 60 ml/min Faster eluting | 624.0 |

| Ex | Structure and Name | Chiral Separation SFC Condition | MS (M + H) |
|---|---|---|---|
| 166-c | 5-(5-chloro-2-(4-chloro-1H-1,2,3-triazol-1-yl)phenyl)-2-((3S,7S)-1¹-(difluoromethyl)-7-methyl-8-oxo-1¹H-9-aza-1(5,4)-pyrazola-2(1,3)-benzenacyclononaphane-3-yl)pyridine 1-oxide | IC (250 x 30 mm), 40% MeOH (0.1% NH₃H₂O)/CO₂, 80 ml/min Faster eluting | 624.0 |
| 166-d | 5-(5-chloro-2-(4-chloro-1H-1,2,3-triazol-1-yl)phenyl)-2-((3R,7S)-1¹-(difluoromethyl)-7-methyl-8-oxo-1¹H-9-aza-1(5,4)-pyrazola-2(1,3)-benzenacyclononaphane-3-yl)pyridine 1-oxide | IC (250 x 30 mm), 40% MeOH (0.1% NH₃H₂O)/CO₂, 80 ml/min Faster eluting | 624.0 |
| 167 | (S)-5-(5-chloro-2-(4-(trifluoromethyl)-1H-pyrazol-1-yl)phenyl)-2-(1¹-(difluoromethyl)-8-oxo-1¹H-9-aza-1(5,4)-pyrazola-2(1,3)-benzenacyclononaphane-3-yl)pyridine 1-oxide | AD (250 x 30 mm), 35% EtOH (0.1% NH₃H₂O)/CO₂, 60 ml/min Slower eluting | 643.2 |

| Ex | Structure and Name | Chiral Separation SFC Condition | MS (M + H) |
|---|---|---|---|
| 168-a | 5-(5-chloro-2-(4-(trifluoromethyl)-1H-pyrazol-1-yl)phenyl)-2-((3S,7R)-1$^1$-(difluoromethyl)-7-methyl-8-oxo-1$^1$H-9-aza-1(5,4)-pyrazola-2(1,3)-benzenacyclononaphane-3-yl)pyridine 1-oxide | IC (250 x 30 mm), 50% EtOH (0.1% NH$_3$H$_2$O)/CO$_2$, 80 ml/min Faster eluting | 657.0 |
| 168-b | 5-(5-chloro-2-(4-(trifluoromethyl)-1H-pyrazol-1-yl)phenyl)-2-((3R,7R)-1$^1$-(difluoromethyl)-7-methyl-8-oxo-1$^1$H-9-aza-1(5,4)-pyrazola-2(1,3)-benzenacyclononaphane-3-yl)pyridine 1-oxide | IC (250 x 30 mm), 50% EtOH (0.1% NH$_3$H$_2$O)/CO$_2$, 80 ml/min Slower eluting | 657.0 |
| 168-c | 5-(5-chloro-2-(4-(trifluoromethyl)-1H-pyrazol-1-yl)phenyl)-2-((3S,7S)-1$^1$-(difluoromethyl)-7-methyl-8-oxo-1$^1$H-9-aza-1(5,4)-pyrazola-2(1,3)-benzenacyclononaphane-3-yl)pyridine 1-oxide | OJ (250 x 30 mm), 25% i-PrOH (0.1% NH$_3$H$_2$O)/CO$_2$, 60 ml/min Slower eluting | 657.0 |

| Ex | Structure and Name | Chiral Separation SFC Condition | MS (M + H) |
|---|---|---|---|
| 168-d | 5-(5-chloro-2-(4-(trifluoromethyl)-1H-pyrazol-1-yl)phenyl)-2-((3R,7S)-1¹-(difluoromethyl)-7-methyl-8-oxo-1¹H-9-aza-1(5,4)-pyrazola-2(1,3)-benzenacyclononaphane-3-yl)pyridine 1-oxide | OJ (250 x 30 mm), 25% i-PrOH (0.1% NH₃H₂O)/CO₂, 60 ml/min Faster eluting | 657.0 |
| 169 | (S)-5-(5-chloro-2-(4-cyano-1H-pyrazol-1-yl)phenyl)-2-(1¹-(difluoromethyl)-8-oxo-1¹H-9-aza-1(5,4)-pyrazola-2(1,3)-benzenacyclononaphane-3-yl)pyridine 1-oxide | OD (250 x 30 mm), 45% EtOH/CO₂, 70 ml/min Slower eluting | 600.0 |
| 170-a | 2-((3S,7R)-1¹-(difluoromethyl)-7-methyl-8-oxo-1¹H-9-aza-1(5,4)-pyrazola-2(1,3)-benzenacyclononaphane-3-yl)-5-(2,3,6-trifluorophenyl)pyridine 1-oxide | AD (250 x 30 mm), 35% EtOH (0.1% ammonia)/CO₂, 80 ml/min Faster eluting | 543.0 |

-continued

| Ex | Structure and Name | Chiral Separation SFC Condition | MS (M + H) |
|---|---|---|---|
| 170-b | 2-((3R,7R)-1¹-(difluoromethyl)-7-methyl-8-oxo-1¹H-9-aza-1(5,4)-pyrazola-2(1,3)-benzenacyclononaphane-3-yl)-5-(2,3,6-trifluorophenyl)pyridine 1-oxide | AD (250 x 30 mm), 35% EtOH (0.1% ammonia)/ $CO_2$, 80 ml/min Slower eluting | 543.0 |
| 171 | (S)-5-(3-chloro-2,6-difluorophenyl)-2-(1¹-(difluoromethyl)-8-oxo-1¹H-9-aza-1(5,4)-pyrazola-2(1,3)-benzenacyclononaphane-3-yl)pyridine 1-oxide | AS (250 x 30 mm), 35% EtOH (0.1% ammonia)/$CO_2$, 80 ml/min Slower eluting | 544.9 |
| 172-a | 5-(2-(4-chloro-1H-1,2,3-triazol-1-yl)phenyl)-2-((3S,7R)-1¹-(difluoromethyl)-7-methyl-8-oxo-1¹H-9-aza-1(5,4)-pyrazola-2(1,3)-benzenacyclononaphane-3-yl)pyridine 1-oxide | AS (250 x 50 mm), 50% MeOH (0.1% ammonia)/$CO_2$, 80 ml/min Faster eluting | 590.0 |

| Ex | Structure and Name | Chiral Separation SFC Condition | MS (M + H) |
|---|---|---|---|
| 172-b | 5-(z2-(4-chloro-1H-1,2,3-triazol-1-yl)phenyl)-2-((3S,7S)-1¹-(difluoromethyl)-7-methyl-8-oxo-1¹H-9-aza-1(5,4)-pyrazola-2(1,3)-benzenacyclononaphane-3-yl)pyridine 1-oxide | AS (250 x 50 mm), 50% MeOH (0.1% ammonia)/CO₂, 80 ml/min Slower eluting | 590.0 |

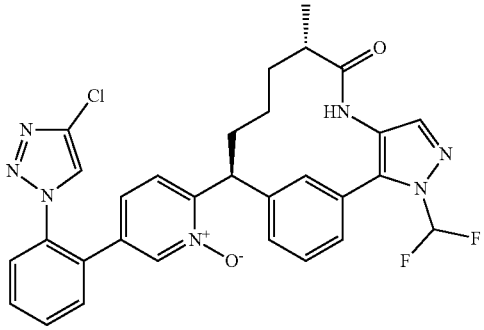

Factor XIa Assay

The effectiveness of a compound of the present invention as an inhibitor of Coagulation Factor XIa can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at rt or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 150 mM NaCl, 5 mM CaCl₂, and 0.1% PEG 8000 (polyethylene glycol; JT Baker or Fisher Scientific). Determinations were made using purified human Factor XIa at a final concentration of 40 pM (Sekisui Diagnostics) and he synthetic substrate, Z-Gly-Pro-Arg-AFC, TFA salt (Sigma #C0980) at a concentration of 100 μM.

Activity assays were performed by diluting a stock solution of substrate at least tenfold to a final concentration ≤0.1 $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m/[S]$, [I]/e, and [I]/e (where [S], [I], and e respectively represent the total concentrations, of substrate, inhibitor and enzyme), the equilibrium constant ($K_i$) for dissociation of the inhibitor from the enzyme can be obtained from the dependence of $V_o/V_i$ on [I] shown in the following equation.

$$V_o/V_i = 1 + [I]/K_i$$

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels.

| Ex. No. | Human FXI$_a$ Ki (nM) |
|---|---|
| 1-a | 22.3 |
| 1-b | 504 |
| 2-a | 0.09 |
| 2-b | 83.1 |
| 3-a | 27.7 |
| 3-b | 0.57 |
| 3-c | 26.3 |
| 3-d | 0.18 |
| 4-a | 0.31 |
| 4-b | 8.40 |
| 5-a | 0.13 |
| 6-a | 0.10 |
| 7-a | 2.40 |
| 8 | 0.41 |
| 9 | 13.6 |
| 10-a | 83.8 |
| 11-a | 0.22 |
| 12 | 593 |
| 13-a | 0.36 |
| 14 | 399 |
| 15 | 41 |
| 16 | >875 |
| 17 | 181 |
| 18 | >875 |
| 19 | 259 |
| 20 | 9.2 |
| 21 | 12.0 |
| 22 | 137 |
| 23 | 18.3 |
| 24 | 2.02 |
| 25 | 708 |
| 26 | 211 |
| 27 | 640 |
| 28 | 0.24 |
| 29 | 7.0 |
| 30 | 0.38 |

| Ex. No. | Human FXI$_a$ Ki (nM) |
|---|---|
| 31 | 0.80 |
| 32 | 0.83 |
| 33 | 0.28 |
| 34 | 1.52 |
| 35 | 0.24 |
| 36-a | 0.26 |
| 37 | 0.13 |
| 38 | 0.11 |
| 39 | 0.26 |
| 40 | 0.46 |
| 41 | 0.19 |
| 42 | 0.44 |
| 43-a | 1.70 |
| 44 | 1.23 |
| 45 | 0.24 |
| 46 | 0.24 |
| 47 | 1.89 |
| 48 | 2.1 |
| 49 | 15.6 |
| 50-a | 0.53 |
| 50-b | 3.50 |
| 50-c | 270 |
| 50-d | 209 |
| 51 | 2.76 |
| 52 | 0.32 |
| 53 | >875 |
| 54 | 839 |
| 55 | >875 |
| 56 | 14.1 |
| 57 | 0.52 |
| 58 | 167 |
| 59 | 8.9 |
| 60 | 342 |
| 61 | 1.4 |
| 62 | 33 |
| 63 | >875 |
| 64 | 164 |
| 65 | 2.9 |
| 66 | 2.1 |
| 67 | 0.55 |
| 68 | 0.52 |
| 69 | 1.87 |
| 70 | 0.37 |
| 71 | 0.47 |
| 72 | 0.50 |
| 73 | 0.34 |
| 74 | 180 |
| 75 | 2.7 |
| 76-a | 0.16 |
| 76-b | 1.37 |
| 76-c | 64 |
| 76-d | 110 |
| 77-a | 0.85 |
| 77-b | 2.31 |
| 79-a | 47.8 |
| 79-b | 0.24 |
| 79-c | 52.2 |
| 79-d | 30.3 |
| 80 | 0.59 |
| 81-a | 0.14 |
| 82 | 3.7 |
| 83 | 2.2 |
| 84 | 0.38 |
| 85-a | >875 |
| 85-b | 6.0 |
| 85-c | 0.97 |
| 85-d | 160 |
| 86-a | 6.34 |
| 86-b | 782 |
| 86-c | 115 |
| 86-d | 1.65 |
| 87-a | 4.1 |
| 88-a | 186 |
| 88-b | 0.75 |
| 88-c | 197 |
| 88-d | 0.57 |
| 89-a | 0.39 |
| 90-a | 3.2 |
| 91-a | 11 |
| 92-a | 0.44 |
| 93-a | 0.89 |
| 94 | 5.1 |
| 95-a | 2.7 |
| 95-b | 30.5 |
| 95-c | 574 |
| 95-d | 2.9 |
| 96-a | 0.53 |
| 97 | 3.3 |
| 98-a | 0.51 |
| 99-a | 0.17 |
| 100-a | 0.33 |
| 101-a | 0.34 |
| 102-a | 0.14 |
| 103-a | 1.7 |
| 104-a | 10.8 |
| 105-a | 0.56 |
| 106-a | 2.54 |
| 107-a | 46 |
| 108-a | 0.18 |
| 109-a | 0.23 |
| 110-a | 0.52 |
| 111-a | 0.19 |
| 112-a | 0.13 |
| 113-a | 0.21 |
| 114-a | 0.17 |
| 114-b | 16.50 |
| 114-c | 0.30 |
| 114-d | 9.96 |
| 115 | 0.53 |
| 116 | 208 |
| 117 | 0.08 |
| 118 | 5.69 |
| 119 | 0.54 |
| 120 | 0.27 |
| 121 | 0.43 |
| 122 | 0.36 |
| 123 | 0.42 |
| 124 | 0.20 |
| 125 | 0.11 |
| 126 | 0.14 |
| 127 | 0.15 |
| 128 | 0.14 |
| 129 | 0.12 |
| 130 | 0.15 |
| 131 | 0.22 |
| 132 | 0.22 |
| 133 | 0.46 |
| 134 | .17 |
| 135 | 198 |
| 136 | 168 |
| 137 | 2.5 |
| 138 | 2.3 |
| 139 | 0.35 |
| 140 | 40 |
| 141 | 0.49 |
| 142 | 0.47 |
| 143-a | 0.33 |
| 143-b | 0.10 |
| 143-c | 1.4 |
| 143-d | 18.6 |
| 144 | 0.46 |
| 145-a | 0.14 |
| 145-b | 45.1 |
| 145-c | 0.29 |
| 145-d | 66.2 |
| 146-a | 0.14 |
| 146-b | 12.1 |
| 146-c | 0.29 |
| 146-d | 73.9 |
| 147 | 0.22 |
| 148 | 2.5 |
| 149-a | 0.17 |
| 149-b | 7.9 |
| 149-c | 0.69 |

-continued

| Ex. No. | Human FXI$_a$ Ki (nM) |
|---|---|
| 149-d | 60.1 |
| 150-a | 0.13 |
| 150-b | 8.49 |
| 150-c | 0.37 |
| 150-d | 20 |
| 151-a | 0.04 |
| 151-b | 3.9 |
| 151-c | 6.05 |
| 151-d | >875 |
| 152-a | 0.09 |
| 152-b | 5.5 |
| 152-c | 43.6 |
| 152-d | 104 |
| 153 | 3.0 |
| 154 | 0.4 |
| 155 | 11.4 |
| 156 | 1.55 |
| 157 | 0.45 |
| 158 | 1.07 |
| 159 | 0.66 |
| 160 | 0.47 |
| 161 | 0.55 |
| 162 | 6.80 |
| 163 | 22.6 |
| 164 | >875 |
| 165 | 0.21 |
| 166-a | 0.14 |
| 166-b | 194.8 |
| 166-c | 9.4 |
| 166-d | >875 |
| 167 | 1.37 |
| 168-a | 11.9 |
| 168-b | >875 |
| 168-c | 9.33 |
| 168-d | 1.3 |
| 169 | 3.8 |
| 170-a | 194.8 |
| 170-b | 9.4 |
| 171 | >875 |
| 172-a | 1.37 |
| 172-b | 11.9 |

Kallikrein Assay

The effectiveness of a compound of the present invention as an inhibitor of Kallikrein can be determined using a relevant purified serine protease, and an appropriate synthetic substrate. The rate of hydrolysis of the chromogenic or fluorogenic substrate by the relevant serine protease was measured both in the absence and presence of compounds of the present invention. Assays were conducted at rt or at 37° C. Hydrolysis of the substrate resulted in release of amino trifluoromethylcoumarin (AFC), which was monitored spectrofluorometrically by measuring the increase in emission at 510 nm with excitation at 405 nm. A decrease in the rate of fluorescence change in the presence of inhibitor is indicative of enzyme inhibition. Such methods are known to one skilled in the art. The results of this assay are expressed as the inhibitory constant, $K_i$.

Kallikrein determinations were made in 50 mM HEPES buffer at pH 7.4 containing 150 mM NaCl, 5 mM CaCl$_2$, and 0.1% PEG 8000 (polyethylene glycol; Fisher Scientific). Determinations were made using purified Human plasma Kallikrein at a final concentration of 0.5 nM (Enzyme Research Laboratories) and the synthetic substrate, Acetyl-K-P-R-AFC (Sigma # C6608) at a concentration of 100 mM.

Activity assays were performed by diluting a stock solution of substrate at least tenfold to a final concentration ≤0.2 $K_m$ into a solution containing enzyme or enzyme equilibrated with inhibitor. Times required to achieve equilibration between enzyme and inhibitor were determined in control experiments. The reactions were performed under linear progress curve conditions and fluorescence increase measured at 405 Ex/510 Em nm. Values were converted to percent inhibition of the control reaction (after subtracting 100% Inhibition value). IC$_{50}$ was determined by inflection point from a four parameter logistic curve fit. Ki was calculated using the Cheng Prusoff equation, Ki=IC$_{50}$/(1+ ([S]/Km)).

The activities shown by this assay indicate that the compounds of the invention may be therapeutically useful for treating or preventing various cardiovascular and/or cerebrovascular thromboembolic conditions in patients suffering from unstable angina, acute coronary syndrome, refractory angina, myocardial infarction, transient ischemic attacks, atrial fibrillation, stroke such as thrombotic stroke or embolic stroke, venous thrombosis, coronary and cerebral arterial thrombosis, cerebral and pulmonary embolism, atherosclerosis, deep vein thrombosis, disseminated intravascular coagulation, and reocclusion or restenosis of recanalized vessels.

| Ex No. | Human plasma Kallikrein Ki (nM) |
|---|---|
| 1-a | 205 |
| 2-a | 2.7 |
| 3-a | 79.8 |
| 3-b | 10.6 |
| 3-c | 660 |
| 3-d | 0.59 |
| 4-a | 3.41 |
| 4-b | 332 |
| 5-a | 3.15 |
| 6-a | 0.29 |
| 7-a | 238 |
| 8 | 1.94 |
| 9 | 379 |
| 11-a | 2.12 |
| 13-a | 1.55 |
| 15 | 89.3 |
| 24 | 34.6 |
| 28 | 1.57 |
| 29 | 132 |
| 30 | 6.77 |
| 31 | 2.68 |
| 32 | 2.95 |
| 33 | 1.67 |
| 34 | 5.01 |
| 35 | 0.70 |
| 36-a | 0.81 |
| 37 | 0.36 |
| 38 | 0.95 |
| 39 | 0.81 |
| 40 | 13.7 |
| 41 | 6.27 |
| 42 | 3.10 |
| 43-a | 7.00 |
| 44 | 2.70 |
| 45 | 0.44 |
| 46 | 1.53 |
| 47 | 5.01 |
| 48 | 1.76 |
| 50-a | 1.89 |
| 50-b | 10.6 |
| 51 | 46.6 |
| 52 | 1.43 |
| 56 | 149.4 |
| 57 | 12.1 |
| 61 | 26.0 |
| 65 | 6.00 |
| 66 | 10.2 |
| 68 | 2.09 |
| 69 | 6.79 |

-continued

| Ex No. | Human plasma Kallikrein Ki (nM) |
|---|---|
| 70 | 2.09 |
| 71 | 0.33 |
| 72 | 2.96 |
| 73 | 1.08 |
| 75 | 8.42 |
| 76-a | 0.53 |
| 76-b | 1.50 |
| 77-a | 1.69 |
| 77-b | 17.3 |
| 79-b | 119 |
| 79-c | 2919 |
| 79-d | 2173 |
| 80 | 13.3 |
| 81-a | 0.46 |
| 82 | 9.58 |
| 83 | 5.47 |
| 84 | 1.85 |
| 85-b | 15.2 |
| 85-c | 2.59 |
| 86-a | 1.29 |
| 86-d | 5.36 |
| 87-a | 12.7 |
| 88-b | 2.67 |
| 88-d | 5.21 |
| 89-a | 13.6 |
| 90-a | 121 |
| 92-a | 26.0 |
| 93-a | 1.92 |
| 94 | 11.3 |
| 95-a | 11.7 |
| 95-d | 10.8 |
| 96-a | 0.60 |
| 97 | 161 |
| 98-a | 0.49 |
| 99-a | 1.21 |
| 100-a | 1.02 |
| 101-a | 3.90 |
| 102-a | 0.43 |
| 103-a | 137 |
| 104-a | 26.3 |
| 105-a | 17.2 |
| 108-a | 1.02 |
| 109-a | 0.77 |
| 110-a | 0.21 |
| 111-a | 0.34 |
| 112-a | 0.26 |
| 113-a | 1.87 |
| 114-a | 0.24 |
| 114-c | 0.78 |
| 115 | 331 |
| 117 | 0.65 |
| 118 | 37.5 |
| 119 | 1.68 |
| 120 | 0.78 |
| 121 | 3.90 |
| 122 | 2.96 |
| 123 | 1.41 |
| 124 | 0.73 |
| 125 | 0.43 |
| 126 | 2.03 |
| 127 | 2.44 |
| 128 | 0.74 |
| 129 | 1.72 |
| 130 | 0.66 |
| 131 | 5.32 |
| 132 | 5.94 |
| 133 | 5.08 |
| 137 | 418 |
| 138 | 665 |
| 139 | 22.2 |
| 141 | 82.8 |
| 142 | 56.7 |
| 143-a | 1.61 |
| 143-b | 0.40 |
| 143-c | 5.92 |

-continued

| Ex No. | Human plasma Kallikrein Ki (nM) |
|---|---|
| 144 | 1.35 |
| 145-a | 0.30 |
| 145-c | 1.10 |
| 146-a | 0.71 |
| 146-c | 3.46 |
| 147 | 3.08 |
| 148 | 37.3 |
| 149-a | 2.02 |
| 149-b | 53.7 |
| 149-c | 7.71 |
| 150-a | 0.51 |
| 150-b | 31.2 |
| 150-c | 1.50 |
| 151-a | 0.16 |
| 151-b | 10.8 |
| 151-c | 29 |
| 152-a | 2.76 |
| 152-b | 114 |
| 153 | 14.4 |
| 156 | 13.6 |
| 157 | 2.04 |
| 158 | 4.92 |
| 159 | 3.50 |
| 160 | 4.00 |
| 161 | 1.35 |
| 165 | 5.76 |
| 166-a | 1.39 |
| 167 | 376 |
| 168-d | 161 |
| 169 | 94.2 |
| 172-a | 376 |

What is claimed is:

1. A compound of the formula:

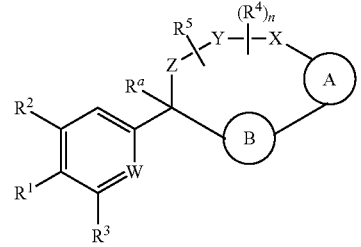

wherein Ⓐ is aryl or heteroaryl, which is optionally substituted with one to three groups independently selected from the group consisting of halo, oxo, cyano, R⁶, OR⁶, C(O)OR⁶, C$_{1-3}$ alkyl-C(O)OR⁶, NR⁶R⁷, NH$_3$⁺, C$_{1-3}$ alkyl-NR⁷R⁸, NHC(O)R⁶, NHC(O)OR⁶, NHC(O)OC$_{3-6}$ cycloalkyl, NHC(O)O—C$_{1-3}$ alkyl-OR⁷, NHC(O)O—C$_{1-3}$ alkyl-C(O)OH, C$_{1-3}$ alkyl-NHC(O)OR⁷, NHC(O)NR⁷R⁸, NHSO$_2$R⁶, C(O)NR⁷R⁸, CH$_2$C(O)NR⁷R⁸ and NHCONH—C$_{1-3}$ alkyl-heterocyclyl; Ⓑ is aryl or heteroaryl, which is optionally substituted with one to three groups independently selected from the group consisting of halo, cyano, oxido, oxo, cyclopropyl, R⁶, OR⁶, C(O)OR⁶, C$_{1-3}$ alkyl- C(O)OR⁶, C(O)NR⁶R⁷ and NR⁶R⁷;

W is N or N⁺O⁻;

Y—X is —C(O)NR⁶—, —C(O)O—, —CHC(O)OR⁷—NR⁶—, —CR⁶R⁷—C(O)NR⁶—, —CHC(O)R⁷—NR⁶—, —CHC(O)OR⁷—CH₂—, —CHC(O)NR⁶R⁷—NR⁶—, —CHCR⁶R⁷OR⁸—NR⁶—, —CHCR⁶R⁷—NR⁶R⁷—NR⁶—, —OC(O)NR⁶—, —NR⁶C(O)NR⁶- or -SO₂NR⁶—;

Z is C₃₋₈ alkylene or C₃₋₈ alkenylene, wherein one or two of the carbon atoms in said alkylene and alkenylene may be replaced with O, NR⁶, C=O, C(O)NR⁶, NR⁶C(O), S, SO or SO₂;

R¹ is aryl, heteroaryl, C₃₋₆ cycloalkyl or heteroalkyl, wherein said aryl, heteroaryl, cycloalkyl and heterocyclyl groups are optionally substituted with one to four substituents independently selected from the group consisting of halo, nitro, cyano, oxo, R⁶, OR⁶, C(O)R⁶, C(O)OR⁶, NR⁶R⁷, C₁₋₃ alkyl-NR⁶R⁷, NHC(O)R⁷, NHC(O)OR⁷, C(NH)NR⁶R⁷, C₃₋₆ cycloalkyl and heteroaryl (which is optionally substituted with halo, cyano, cyclopropyl, C(O)OH, C(O)NR⁶R⁷ or R⁶);

R² is hydrogen, cyano, halo, R⁶ or OR⁶;

R³ is hydrogen, cyano, halo, R⁶ or OR⁶;

each R⁴ is independently C₁₋₆ alkyl, CO₂R⁶, COR⁶ or CONR⁷R⁸, wherein said alkyl is optionally substituted with one to three halo;

R⁵ is hydrogen, halo or C₁₋₆ alkyl;

or one of R⁴ and R⁵ can be taken together with the atoms between them to form a 3 to 6 membered ring;

each R⁶ is independently hydrogen or C₁₋₆ alkyl, which is optionally substituted with one to three groups independently selected from the group consisting of halo and hydroxy;

each R⁷ is independently hydrogen, C₁₋₆ alkyl, heteroaryl or heterocyclyl, wherein said alkyl group is optionally substituted with one to three groups independently selected from the group consisting of halo and hydroxy;

each R⁸ is independently hydrogen or C₁₋₆ alkyl;

R$^a$ is hydrogen, hydroxy or O(C₁₋₆ alkyl);

n is an integer between zero and three;

or a pharmaceutically acceptable salt thereof.

2. The compound of claim 1 of the formula

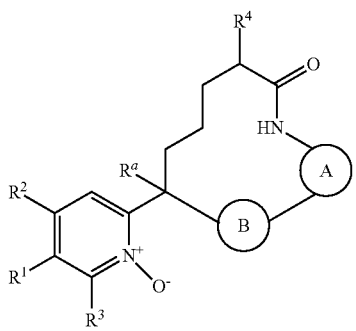

wherein Ⓐ
is aryl or heteroaryl, which is optionally substituted with one to three groups independently selected from the group consisting of halo, oxo, cyano, R⁶, OR⁶, C(O)OR⁶, C₁₋₃ alkyl-C(O)OR⁶, NR⁶R⁷, NH₃⁺, C₁₋₃ alkyl-NR⁷R⁸, NHC(O)R⁶, NHC(O)OR⁶, NHC(O)OC₃₋₆ cycloalkyl, NHC(O)O—C₁₋₃ alkyl-OR⁷, NHC(O)O—C₁₋₃ alkyl-C(O)OH, C₁₋₃ alkyl-NHC(O)OR⁷, NHC(O)NR⁷R⁸, NHSO₂R⁶, C(O)NR⁷R⁸, CH₂C(O)NR⁷R⁸ and NHCONH—C₁₋₃ alkyl-heterocyclyl; Ⓑ is aryl or heteroaryl, which is optionally substituted with one to three groups independently selected from the group consisting of halo, cyano, oxido, oxo, cyclopropyl, R⁶, OR⁶, C(O)OR⁶, C₁₋₃ alkyl-C(O)OR⁶, C(O)NR⁶R⁷ and NR⁶R⁷;

R¹ is aryl, heteroaryl, C₃₋₆ cycloalkyl or heteroalkyl, wherein said aryl, heteroaryl, cycloalkyl and heterocyclyl groups are optionally substituted with one to four substituents independently selected from the group consisting of halo, nitro, cyano, oxo, R⁶, OR⁶, C(O)R⁶, C(O)OR⁶, NR⁶R⁷, C₁₋₃ alkyl-NR⁶R⁷, NHC(O)R⁷, NHC(O)OR⁷, C(NH)NR⁶R⁷, C₃₋₆ cycloalkyl and heteroaryl (which is optionally substituted with halo, cyano, cyclopropyl, C(O)OH, C(O)NR⁶R⁷ or R⁶);

R² is hydrogen, cyano, halo, R⁶ or OR⁶;

R³ is hydrogen, cyano, halo, R⁶ or OR⁶;

R⁴ is C₁₋₆ alkyl, CO₂R⁶, COR⁶ or CONR⁷R⁸, wherein said alkyl is optionally substituted with one to three halo;

R⁶ is hydrogen or C₁₋₆ alkyl, which is optionally substituted with one to three groups independently selected from the group consisting of halo and hydroxy;

R⁷ is hydrogen or C₁₋₆ alkyl, which is optionally substituted with one to three groups independently selected from the group consisting of halo and hydroxy;

R⁸ is hydrogen or C₁₋₆ alkyl;

R$^a$ is hydrogen, hydroxy or O(C₁₋₆ alkyl);

n is an integer between zero and three;

or a pharmaceutically acceptable salt thereof.

3. The compound of claim 1 wherein Ⓑ
is a selected from the group consisting of phenyl, imidazolyl, pyridinyl and pyrimidinyl, wherein said groups are optionally substituted with one to three groups independently selected from the group consisting of halo, oxido, R⁶ and cyclopropyl.or a pharmaceutically acceptable salt thereof.

4. The compound of claim 1 wherein Ⓐ
is phenyl, which is optionally substituted with one to three groups independently selected from the group consisting of halo, C(O)OR⁶ and NHC(O)OR⁶; or a pharmaceutically acceptable salt thereof.

5. The compound of claim 1 wherein R¹ is aryl, which optionally is substituted with one to four substituents independently selected from the group consisting of chloro, fluoro, iodo, methyl, cyclopropyl, OCF₃, OCF₂, CF₃, CF₂, and heteroaryl (which is optionally substituted with halo, cyano, cyclopropyl, C(O)OH, methyl, CF₃ or CF₂); or a pharmaceutically acceptable salt thereof.

6. The compound of any of claim 1 wherein R¹ is phenyl, which optionally is substituted with one to three substituents independently selected from the group consisting of halo, cyclopropyl and tetrazolyl; or a pharmaceutically acceptable salt thereof.

7. The compound of any of claim 1 wherein R$^a$ is hydrogen or hydroxy; or a pharmaceutically acceptable salt thereof.

8. The compound of claim 1 selected from:
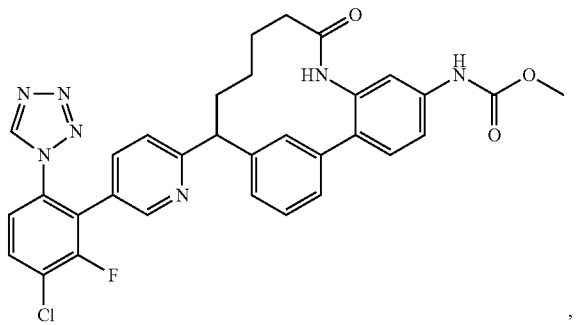
,
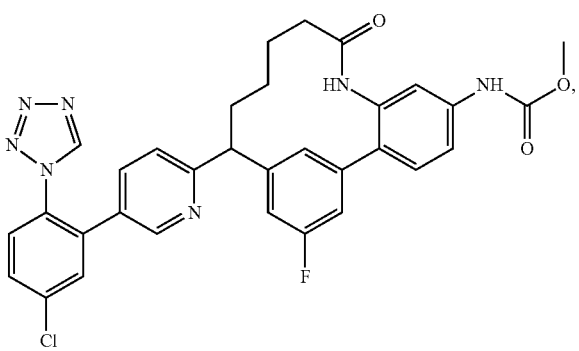
,
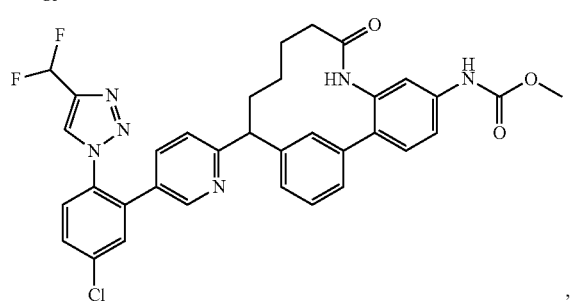
,
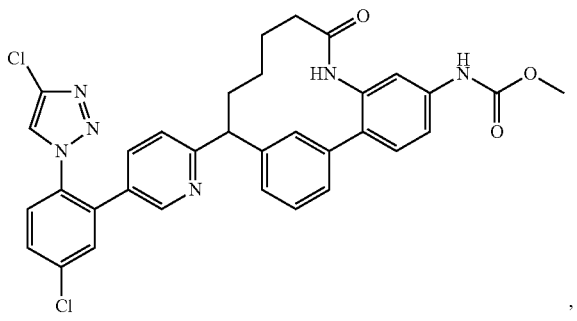
,
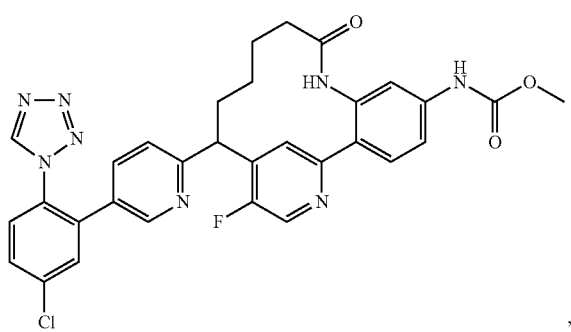
,
-continued
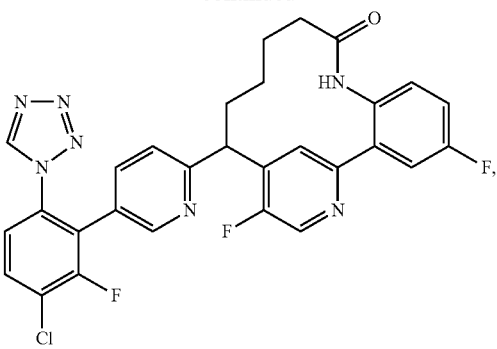
,
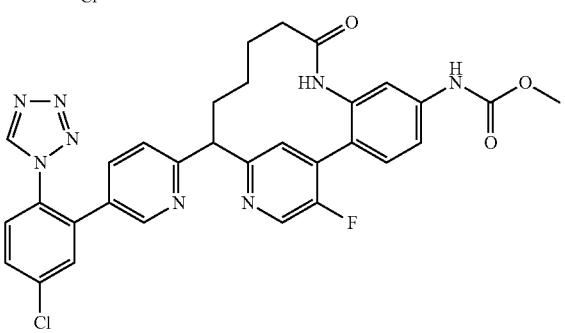
,
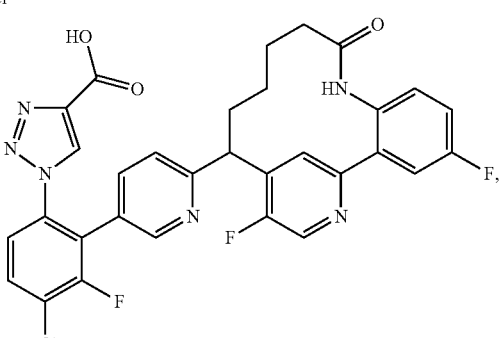
,
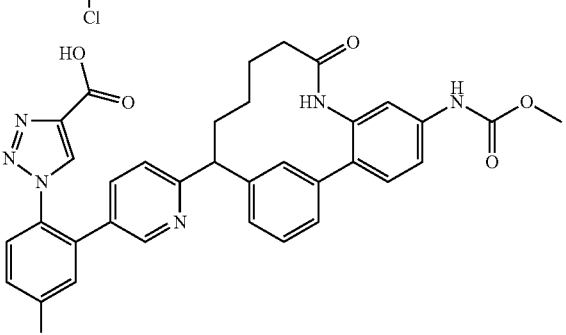
,
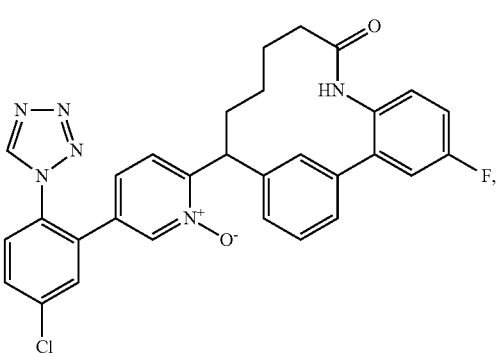
,

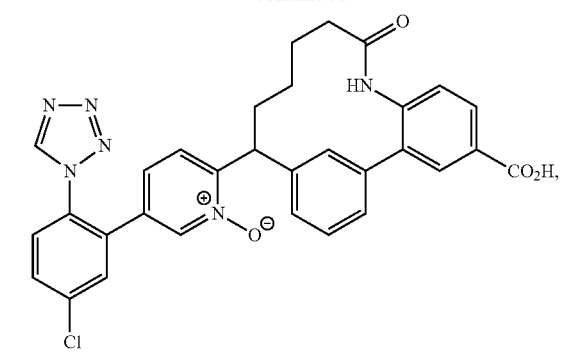,
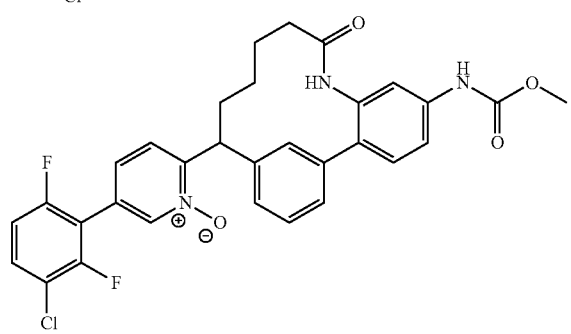,
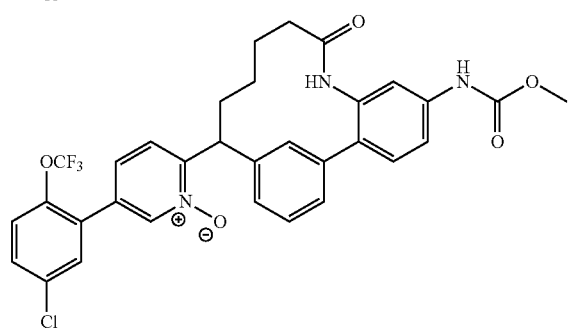,
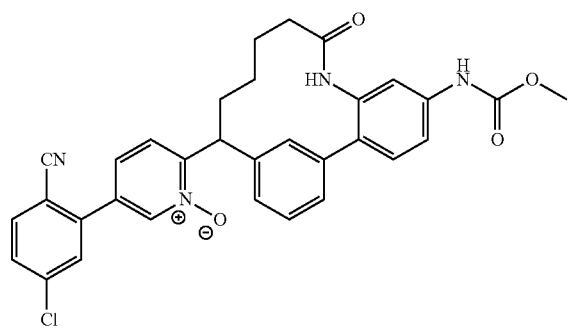,
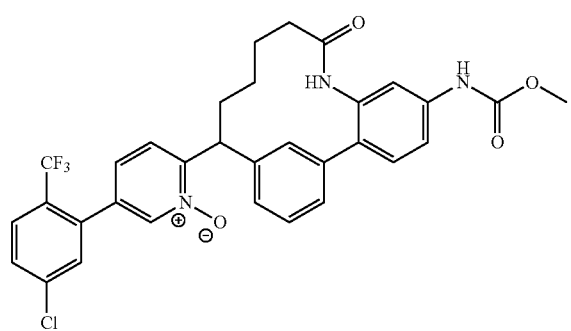,
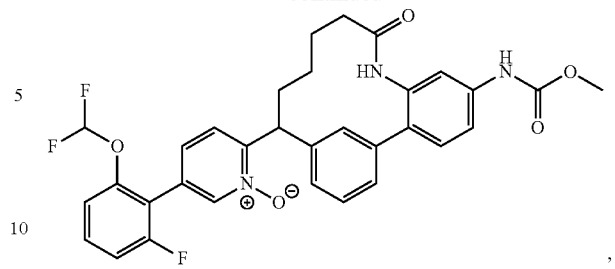,
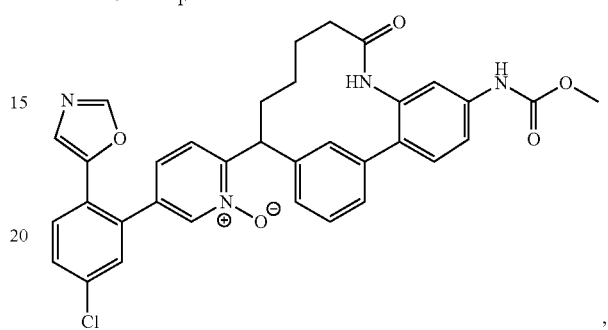,
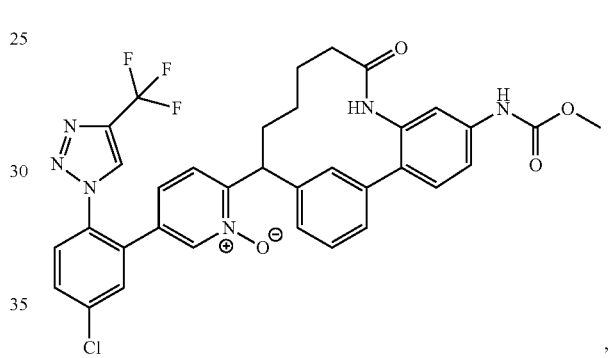,
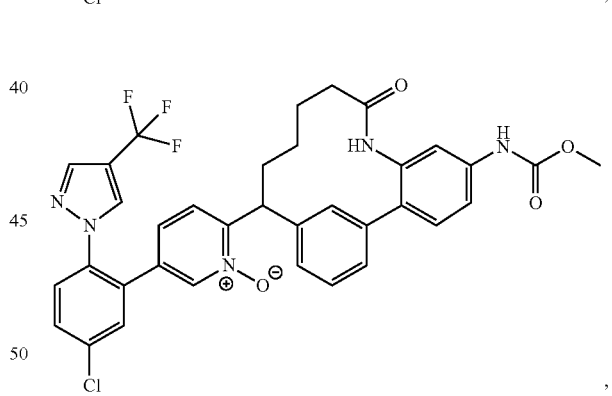,
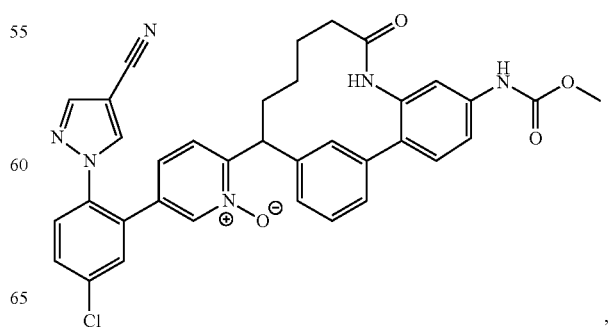, 273
-continued
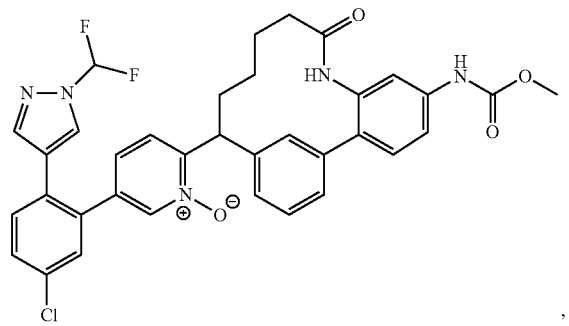
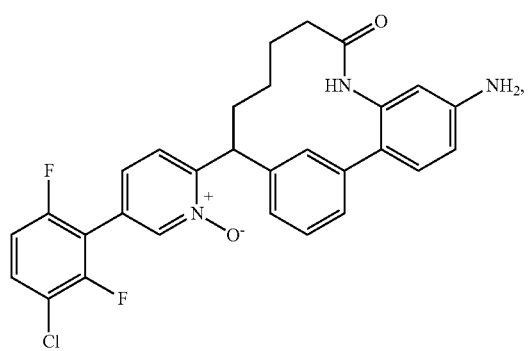
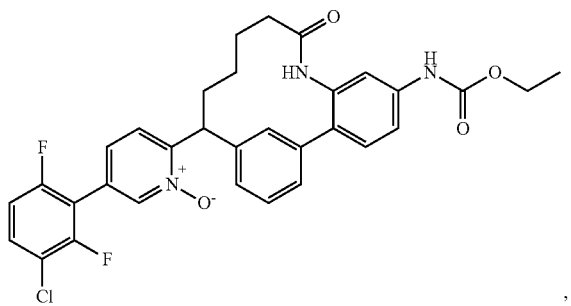
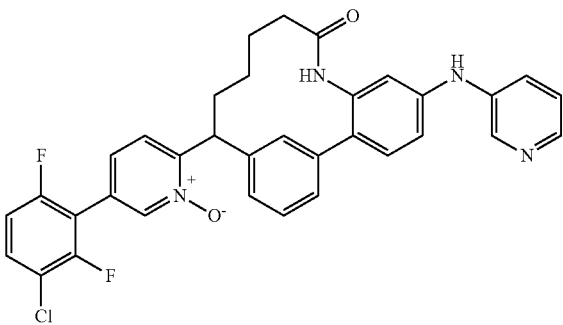
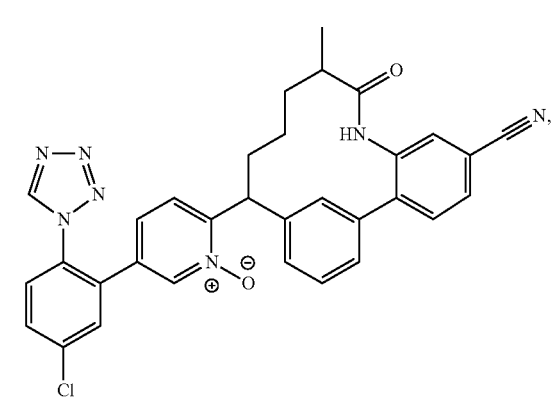
274
-continued
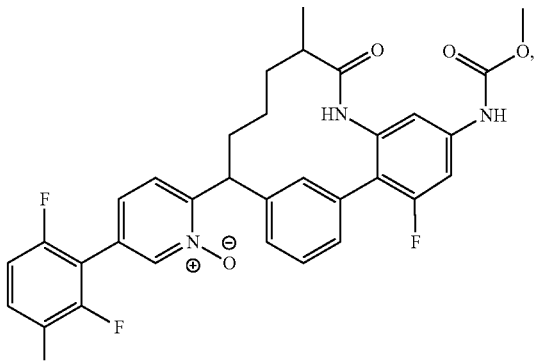
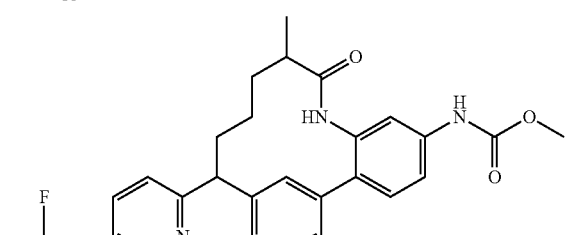
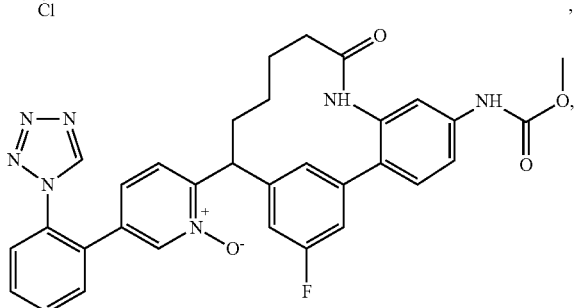
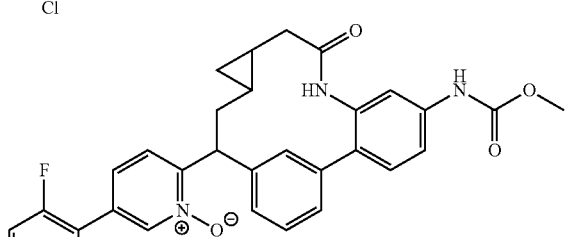
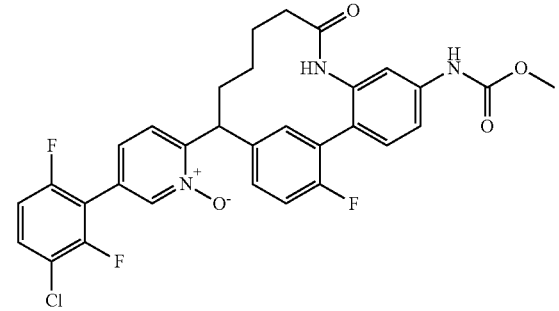

275
-continued
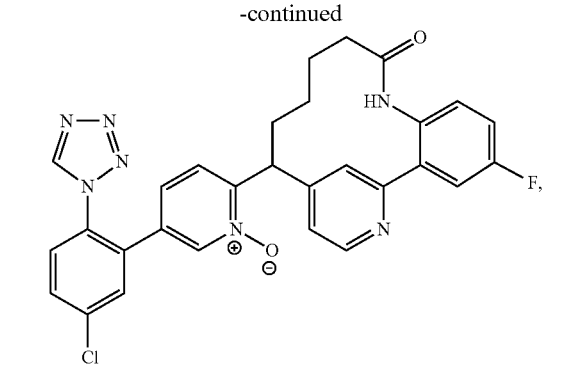
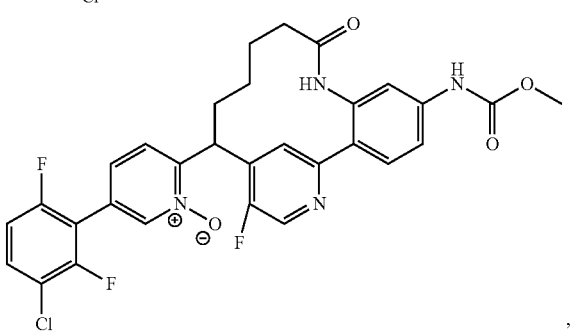
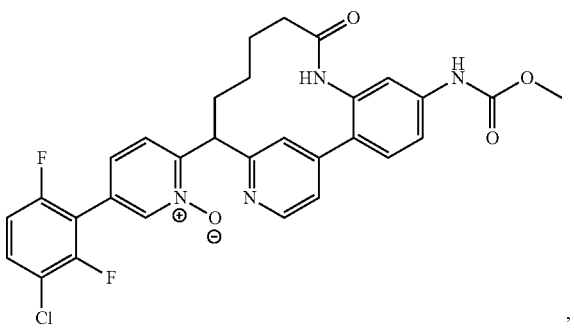
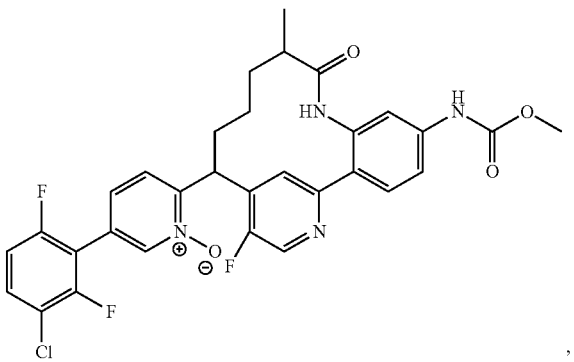
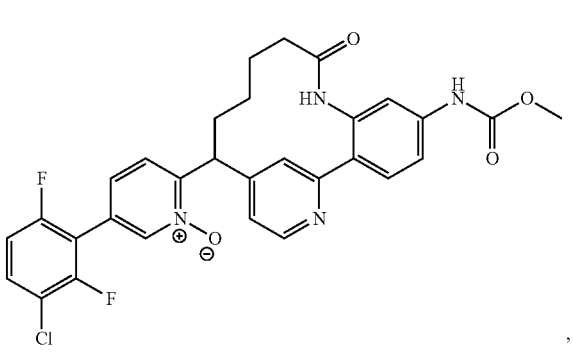 [SMILES: COC(=O)Nc1ccc2c(c1)NC(=O)CCCCC(c1ccc(-c3c(F)ccc(Cl)c3F)c[n+]1[O-])c1cc-2ncc1F]
,
276
-continued
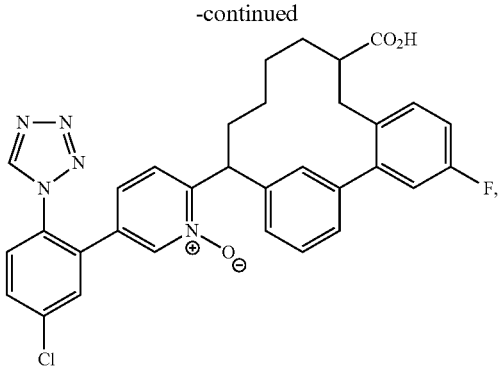
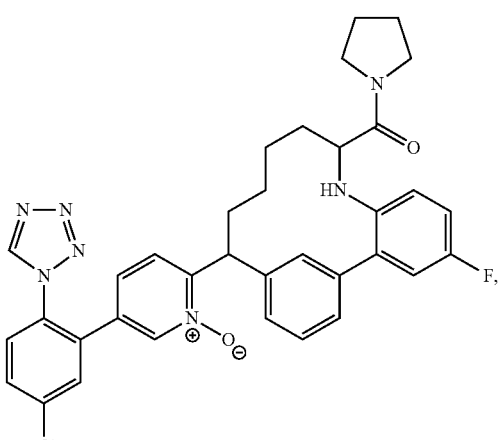
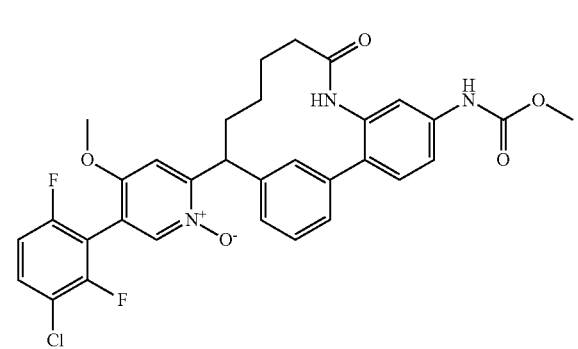
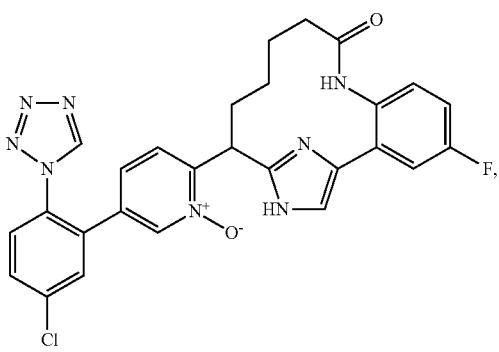
, -continued 279
-continued
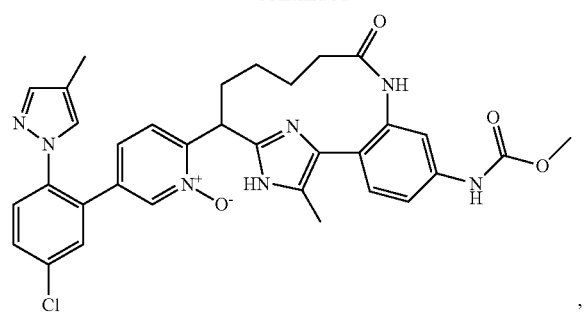
,
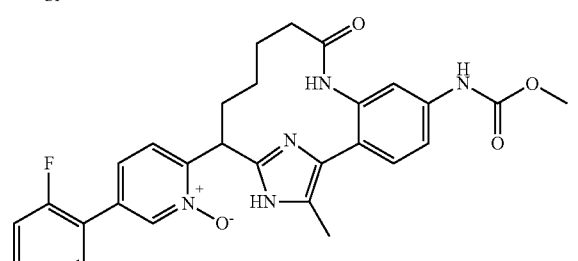
,
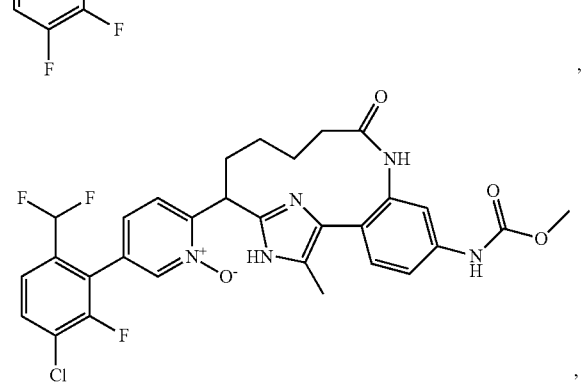
,
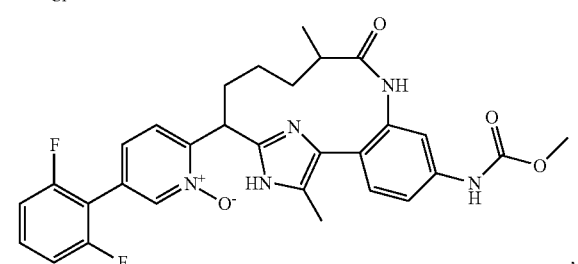
,
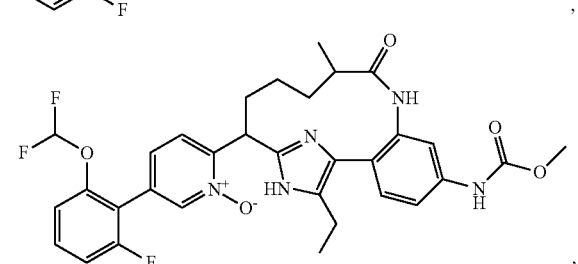
,
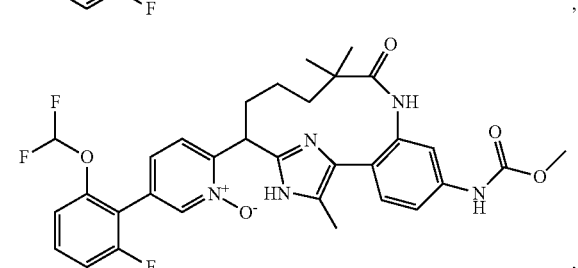
,
280
-continued
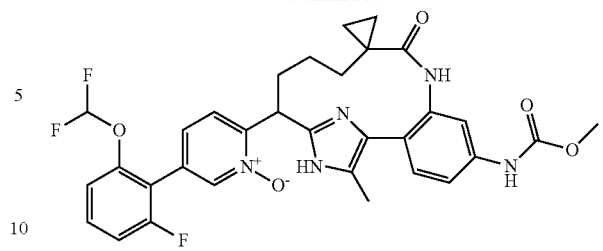
,
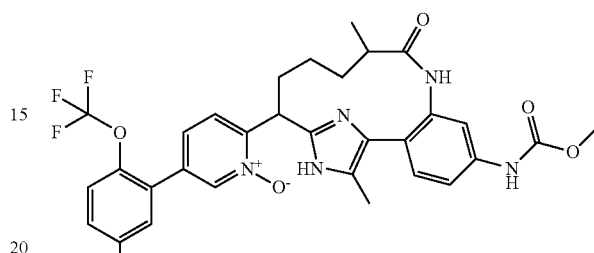
,
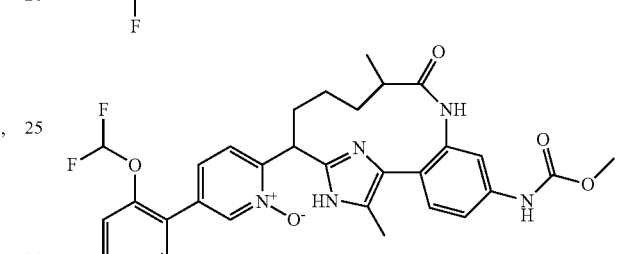
,
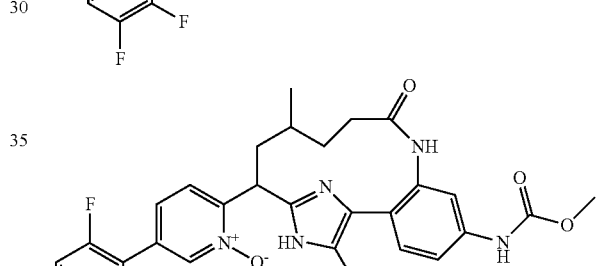
,
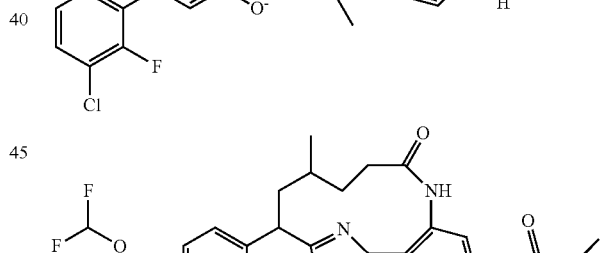
,
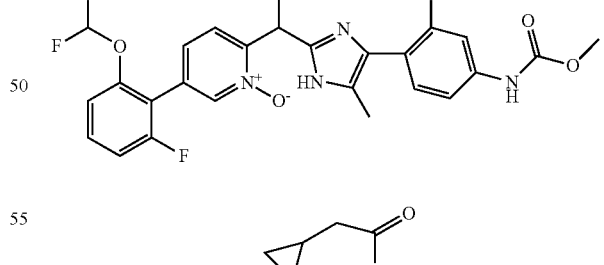
,
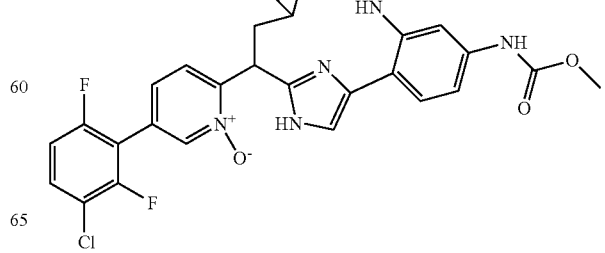
, 281
-continued
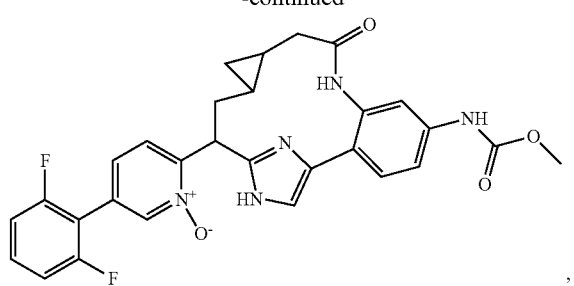
,
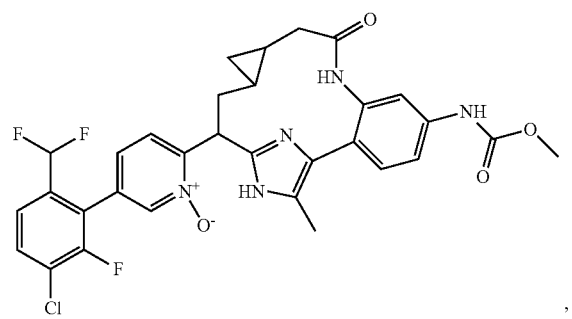
,
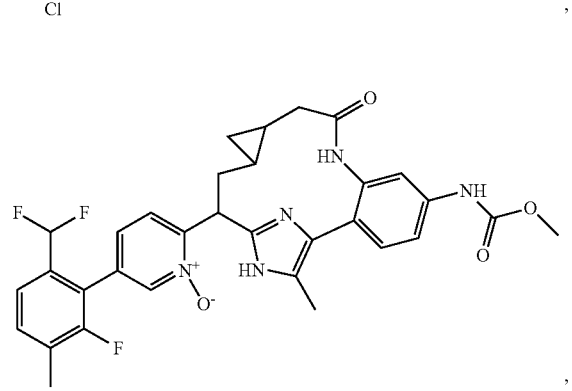
,
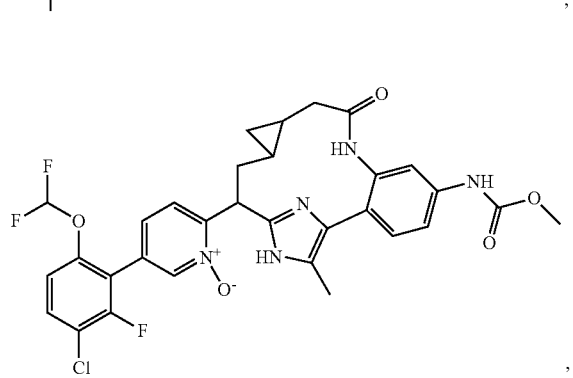
,
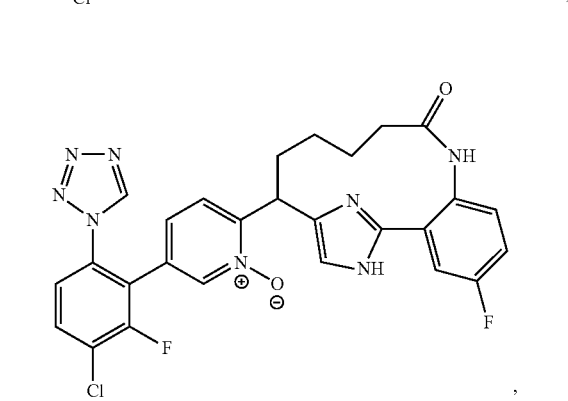
,
282
-continued
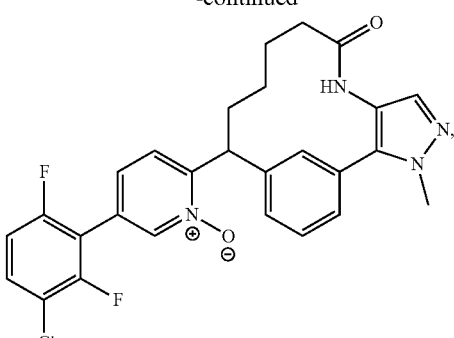
,
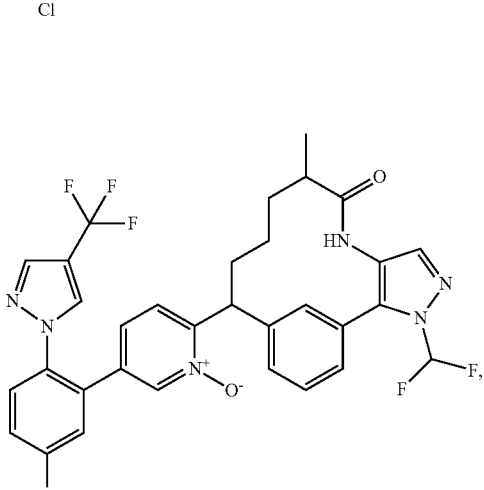
,
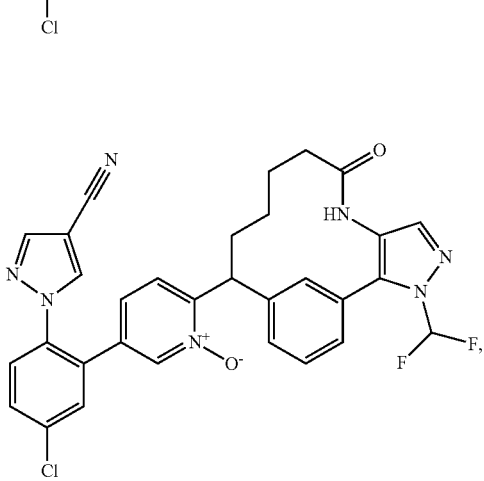
,
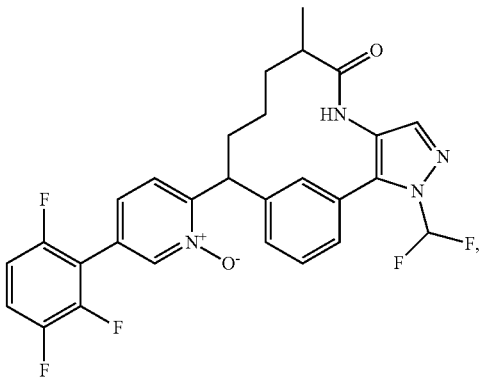
, -continued

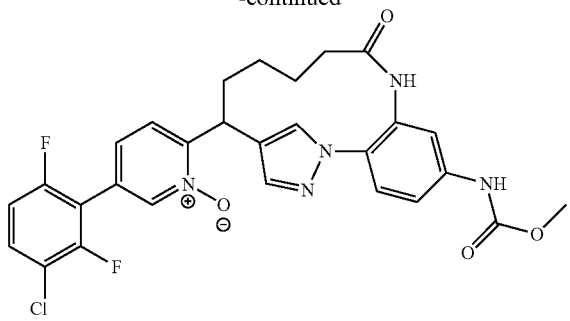

or a pharmaceutically acceptable salt thereof.

9. A pharmaceutical composition comprising a compound of claims 1 or a pharmaceutically acceptable salt thereof and a pharmaceutically acceptable carrier.

10. A method for inhibiting thrombus formation in blood or treating thrombus formation in blood comprising administering a composition of claim 9 to a mammal in need of thereof.

11. A method for preventing thrombus formation in blood comprising administering a composition of claim 9 to a mammal in need thereof.

12. A method of treating venous thromboembolism and pulmonary embolism in a mammal comprising administering a composition of claim 9 to a mammal in need thereof.

13. A method of treating deep vein thrombosis in a mammal comprising administering a composition of claim 9 to a mammal in need thereof.

14. A method of treating thromboembolic stroke in a human comprising administering a composition of claim 9 to a mammal in need thereof.

* * * * *